US009975906B2

(12) United States Patent
Kawasuji et al.

(10) Patent No.: US 9,975,906 B2
(45) Date of Patent: May 22, 2018

(54) TRICYCLIC HETEROCYCLE DERIVATIVES HAVING HIV REPLICATION INHIBITORY EFFECT

(71) Applicant: Shionogi & Co., Ltd., Osaka-shi (JP)

(72) Inventors: Takashi Kawasuji, Toyonaka (JP); Daisuke Taniyama, Toyonaka (JP); Shuichi Sugiyama, Toyonaka (JP); Yoshinori Tamura, Toyonaka (JP)

(73) Assignee: SHIONOGI & CO., LTD., Osaka-shi (JP)

( * ) Notice: Subject to any disclaimer, the term of this patent is extended or adjusted under 35 U.S.C. 154(b) by 0 days. days.

(21) Appl. No.: 15/311,757

(22) PCT Filed: May 15, 2015

(86) PCT No.: PCT/JP2015/063972
§ 371 (c)(1),
(2) Date: Nov. 16, 2016

(87) PCT Pub. No.: WO2015/174511
PCT Pub. Date: Nov. 19, 2015

(65) Prior Publication Data
US 2017/0107234 A1 Apr. 20, 2017

(30) Foreign Application Priority Data

May 16, 2014 (JP) ................. 2014-102007
Jul. 31, 2014 (JP) ................. 2014-156077
Jan. 20, 2015 (JP) ................. 2015-008313

(51) Int. Cl.
| | |
|---|---|
| *C07D 471/06* | (2006.01) |
| *C07D 471/16* | (2006.01) |
| *C07D 487/06* | (2006.01) |
| *C07D 513/06* | (2006.01) |
| *A61K 31/519* | (2006.01) |
| *A61K 31/5513* | (2006.01) |
| *A61K 31/554* | (2006.01) |
| *A61P 31/12* | (2006.01) |
| *A61P 31/18* | (2006.01) |

(52) U.S. Cl.
CPC ......... *C07D 513/06* (2013.01); *C07D 471/06* (2013.01); *C07D 471/16* (2013.01); *C07D 487/06* (2013.01)

(58) Field of Classification Search
CPC combination set(s) only.
See application file for complete search history.

(56) References Cited

U.S. PATENT DOCUMENTS 7,408,063 B2 * 8/2008 Angibaud ............ C07D 471/06
546/79
2013/0203727 A1 8/2013 Babaoglu et al.
(Continued)

FOREIGN PATENT DOCUMENTS

EP 1 593 681 A1 11/2005
EP 3 144 311 A1 3/2017
(Continued)

OTHER PUBLICATIONS

Buchta et al. J. Liebigs. Ann. Chem. 1967, 709, 209-218.*
Jonas Demeulemeester, et al., "LEDGINs, non-catalytic site inhibitors of HIV-1 integrase: a patent review (2006-2014)", Expert Opinion on Therapeutic Patents, vol. 24, No. 6, Total 25 Pages, (2014).
International Search Report dated Aug. 11, 2015 in PCT/JP15/063972 Filed May 15, 2015.
Lee D. Fader, et al., "Discovery of BI 224436, a Noncatalytic Site Integrase Inhibitor (NCINI) of HIV-1" ACS Medicinal Chemistry Letters, vol. 5, No. 4, 2014, pp. 422-427.
Lee D. Fader, et al., "Minimizing the Contribution of Enterohepatic Recirculation to Clearance in Rat for the NCINI Class of Inhibitors of HIV" ACS Medicinal Chemistry Letters, vol. 5, No. 6, 2014, pp. 711-716.
Extended European Search Report dated Nov. 30, 2017 in corresponding European Patent Application No. 15793640.2, filed May 15, 2015, citing documents AO therein, 10 pages.

*Primary Examiner* — Amanda L Aguirre
(74) *Attorney, Agent, or Firm* — Oblon, McClelland, Maier & Neustadt, L.L.P.

(57) ABSTRACT

The present invention provides the following compound having anti-HIV activity of formula:

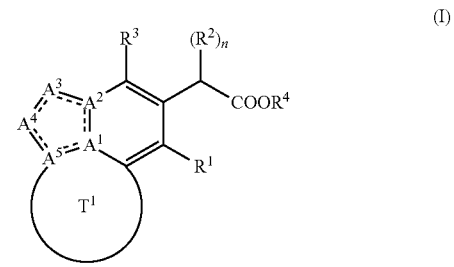

(I)

wherein, $A^1$ is C, $CR^{1A}$ or N;
$A^2$ is C, $CR^{2A}$, or N;
$A^3$ is $CR^{3A}$, $CR^{3A}R^{3B}$, N, $NR^{3C}$, O, S, SO, or $SO_2$;
$A^4$ is $CR^{4A}$, $CR^{4A}R^{4B}$, N, $NR^{4C}$, O, S, SO, or SO2;
$A^5$ is C, $CR^{5A}$, or N;
$T^1$ ring is substituted or unsubstituted monocyclic carbocycle or substituted or unsubstituted monocyclic heterocycle;
$R^1$ is halogen, cyano, nitro or $-X^1-R^{11}$;
$R^2$ is substituted or unsubstituted alkyl and the like;
n is 1 or 2;
$R^3$ is hydrogen, substituted or unsubstituted aromatic carbocyclyl;
$R^4$ is hydrogen or a carboxy protecting group;
the other symbols are as specified in the description.

33 Claims, No Drawings

(56) References Cited

U.S. PATENT DOCUMENTS

| | | |
|---|---|---|
| 2013/0210801 A1 | 8/2013 | Babaoglu et al. |
| 2014/0031338 A1 | 1/2014 | Chasset et al. |
| 2014/0051692 A1 | 2/2014 | Naidu et al. |
| 2014/0249162 A1 | 9/2014 | Son et al. |
| 2014/0249306 A1 | 9/2014 | Iwaki et al. |
| 2015/0361093 A1 | 12/2015 | Tomita et al. |

FOREIGN PATENT DOCUMENTS

| | | |
|---|---|---|
| JP | 2000-505450 A | 5/2000 |
| JP | 2003-510324 A | 3/2003 |
| JP | 2004-256531 A | 9/2004 |
| JP | 2005-516031 A | 6/2005 |
| JP | 2009-503069 A | 1/2009 |
| JP | 2014-511872 A | 5/2014 |
| WO | WO 97/31000 A1 | 8/1997 |
| WO | WO 01/23386 A2 | 4/2001 |
| WO | WO 03/057699 A1 | 7/2003 |
| WO | WO 2006/072636 | 7/2006 |
| WO | WO 2007/018998 A2 | 2/2007 |
| WO | 2007/131350 A1 | 11/2007 |
| WO | 2009/062285 A1 | 5/2009 |
| WO | 2009/062288 A1 | 5/2009 |
| WO | 2009/062289 A1 | 5/2009 |
| WO | 2009/062308 A1 | 5/2009 |
| WO | 2010/130034 A1 | 11/2010 |
| WO | 2010/130842 A1 | 11/2010 |
| WO | 2011/015641 A1 | 2/2011 |
| WO | 2011/076765 A1 | 6/2011 |
| WO | 2012/003497 A1 | 1/2012 |
| WO | 2012/003498 A1 | 1/2012 |
| WO | 2012/033735 A1 | 3/2012 |
| WO | 2012/065963 A2 | 5/2012 |
| WO | 2012/066442 A1 | 5/2012 |
| WO | 2012/102985 A1 | 8/2012 |
| WO | 2012/137181 A1 | 10/2012 |
| WO | 2012/140243 A1 | 10/2012 |
| WO | 2012/145728 A1 | 10/2012 |
| WO | 2013/002357 A1 | 1/2013 |
| WO | 2013/012649 A1 | 1/2013 |
| WO | 2013/025584 A1 | 2/2013 |
| WO | 2013/043553 A1 | 3/2013 |
| WO | 2013/062028 A1 | 5/2013 |
| WO | 2013/073875 A1 | 5/2013 |
| WO | 2013/103724 A1 | 7/2013 |
| WO | 2013/103738 A1 | 7/2013 |
| WO | 2013/123148 A1 | 8/2013 |
| WO | 2013/134113 A1 | 9/2013 |
| WO | 2013/134142 A1 | 9/2013 |
| WO | 2013/157622 A1 | 10/2013 |
| WO | 2013/159064 A1 | 10/2013 |
| WO | 2014/009794 A1 | 1/2014 |
| WO | 2014/028384 A1 | 2/2014 |
| WO | 2014/053665 A1 | 4/2014 |
| WO | 2014/053666 A1 | 4/2014 |
| WO | 2014/057103 A1 | 4/2014 |
| WO | 2014/119636 A1 | 8/2014 |
| WO | WO 2014/159959 A1 | 10/2014 |
| WO | WO 2014/164409 A1 | 10/2014 |
| WO | WO 2014/164467 A1 | 10/2014 |
| WO | WO 2015/126765 A1 | 8/2015 |
| WO | WO 2015/147247 A1 | 10/2015 |
| WO | WO 2015/174511 A1 | 11/2015 |
| WO | WO 2015/179448 A1 | 11/2015 |
| WO | WO 2016/005878 A1 | 1/2016 |
| WO | WO 2016/012930 A1 | 1/2016 |
| WO | WO 2016/033009 A1 | 3/2016 |
| WO | WO 2017/046707 A1 | 3/2017 |
| WO | WO 2017/093930 A1 | 6/2017 |
| WO | WO 2017/093932 A1 | 6/2017 |
| WO | WO 2017/093937 A1 | 6/2017 |
| WO | WO 2017/093938 A1 | 6/2017 |

\* cited by examiner

TRICYCLIC HETEROCYCLE DERIVATIVES HAVING HIV REPLICATION INHIBITORY EFFECT

TECHNICAL FIELD

The present invention relates to a novel compound having an antiviral activity, more particularly, an anti-HIV drug.

BACKGROUND ART

Among viruses, human immunodeficiency virus (hereinafter abbreviated as HIV) that is a type of retrovirus is known to be a cause of acquired immunodeficiency syndrome (hereinafter abbreviated as AIDS). As a therapeutic agent of the AIDS, reverse transcriptase inhibitors (AZT, 3TC, etc.), protease inhibitors (indinavir, etc.), and integrase inhibitors (raltegravir, etc.) are mainly used so far, but problems of side effects such as kidney problems and emergence of resistant viruses have been found, and development of anti-HIV drugs having a mechanism of action different from those is expected.

In addition, in the treatment of AIDS, because resistant viruses easily emerge, it is reported that, multiple drug therapy is currently effective. As the anti-HIV drugs, three types of reverse transcriptase inhibitors, protease inhibitors and integrase inhibitors have been used clinically, but the agents having the same mechanism of action often exhibit cross-resistance, or merely show additive effects, and there is a demand for the development of anti-HIV drugs having a different mechanism of action.

Anti-HIV drugs with a carboxyalkyl type side chain into a six-membered ring nucleus, such as benzene or pyridine, or on their condensed ring, is described in Patent Document 1 to 32 and 36. In particular, five-membered heterocycle condensed with a benzene derivative is described in Patent Document 28 (WO2013/159064), Patent Document 29 (WO2012/145728) etc. Also in Patent Document 16 (WO2012/140243) and Patent Document 36 (WO2014/057103), benzene derivatives having various substituents are described. Moreover anti-HIV drugs having a carboxyalkyl type side chains at 5-membered ring nucleus are described in Patent Document 33 to 35. However, in any of the literature, tricyclic compounds of the present invention are not described.

Furthermore, patents relating to anti-HIV drugs, such as recent integrase inhibitors, have been introduced in Non-patent Document 1.

PRIOR ART DOCUMENTS

Patent Documents

Patent Document 1: WO2007/131350
Patent Document 2: WO2009/062285
Patent Document 3: WO2009/062288
Patent Document 4: WO2009/062289
Patent Document 5: WO2009/062308
Patent Document 6: WO2010/130034
Patent Document 7: WO2010/130842
Patent Document 8: WO2011/015641
Patent Document 9: WO2011/076765
Patent Document 10: WO2012/033735
Patent Document 11: WO2012/003497
Patent Document 12: WO2012/003498
Patent Document 13: WO2012/065963
Patent Document 14: WO2012/066442
Patent Document 15: WO2012/102985
Patent Document 16: WO2012/140243
Patent Document 17: WO2013/012649
Patent Document 18: WO2013/002357
Patent Document 19: WO2013/025584
Patent Document 20: WO2013/043553
Patent Document 21: WO2013/073875
Patent Document 22: WO2013/062028
Patent Document 23: WO2013/103724
Patent Document 24: WO2013/103738
Patent Document 25: WO2013/123148
Patent Document 26: WO2013/134113
Patent Document 27: WO2013/134142
Patent Document 28: WO2013/159064
Patent Document 29: WO2012/145728
Patent Document 30: WO2013/157622
Patent Document 31: WO2014/009794
Patent Document 32: WO2014/028384
Patent Document 33: WO2012/137181
Patent Document 34: WO2014/053665
Patent Document 35: WO2014/053666
Patent Document 36: WO2014/057103
Non-patent Document 1: Expert. Opin. Ther. Patents (2014) 24(6)

Furthermore, the patent applications related to HIV replication inhibitors on the tricyclic benzene derivative have been filed by the present applicant (WO2014/119636, PCT/JP2015/059569).

SUMMARY OF THE INVENTION

Problems to be Solved by the Invention

An object of the present invention is to provide a novel compound having an antiviral activity. Preferably, the present invention provides an anti-HIV drug having an inhibitory effect on HIV replication. More preferably, the present invention also provides an effective new anti-HIV drug against mutant strains and resistant strains of HIV, having the core structure of which differs from that of traditional anti-HIV drugs. Furthermore, the present invention also provides its synthetic intermediates and manufacturing process thereof.

Means for Solving the Problems

As a result of intensive studies, the present inventors have found novel tricyclic indole derivatives useful as HIV replication inhibitors. In addition, the present inventors have found that the compounds of the present invention and the pharmaceutical composition containing the same are useful as an antiviral drugs (examples: antiretroviral drugs, anti-HIV drugs, anti-HTLV-1 (Human T cell leukemia virus type 1: human T-cell leukemia virus type 1) drugs, anti-FIV (Feline immunodeficiency virus: feline AIDS virus) drugs, anti-SIV (Simian immunodeficiency virus: simian AIDS virus) drugs), particularly anti-HIV drugs, anti-AIDS drugs, or therapeutic agents of the related diseases or the like, thereby accomplishing the present invention.

Furthermore, the tricyclic indole derivatives of the present invention encompass the compounds converted N of the indole to C, O, or S etc., the compounds having various heteroatoms on the pyrrole ring, or these various derivatives.

The present invention relates to the following (1) to (46).
(1) A compound represented by the following formula (I):

[Chemical formula 1]

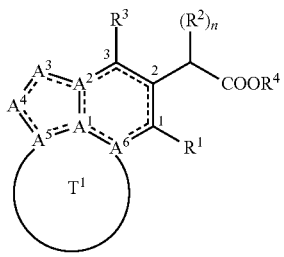

(I)

or its pharmaceutically acceptable salt,
wherein
$A^1$ is C, $CR^{1A}$, or N;
$A^2$ is C, $CR^{2A}$, or N;
$A^3$ is $CR^{3A}$, $CR^{3A}R^{3B}$, N, $NR^{3C}$, O, S, SO, or $SO_2$;
$A^4$ is $CR^{4A}$, $CR^{4A}R^{4B}$, N, $NR^{4C}$, O, S, SO, or $SO_2$;
$A^5$ is C, $CR^{5A}$, or N;
$A^6$ is C, $CR^{6A}$, or N;
$R^{1A}$, $R^{2A}$, $R^{3A}$, $R^{3B}$, $R^{4A}$, $R^{4B}$, $R^{5A}$, and $R^{6A}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocycle oxy, substituted or unsubstituted non-aromatic carbocycle oxy, substituted or unsubstituted aromatic heterocycle oxy, substituted or unsubstituted non-aromatic heterocycle oxy, substituted or unsubstituted aromatic carbocycle thio, substituted or unsubstituted non-aromatic carbocycle thio, substituted or unsubstituted aromatic heterocycle thio, substituted or unsubstituted non-aromatic heterocycle thio, substituted or unsubstituted aromatic carbocycle amino, substituted or unsubstituted non-aromatic carbocycle amino, substituted or unsubstituted aromatic heterocycle amino, substituted or unsubstituted non-aromatic heterocycle amino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylalkylcarbonyl, substituted or unsubstituted non-aromatic carbocyclylalkylcarbonyl, substituted or unsubstituted aromatic heterocyclylalkylcarbonyl, substituted or unsubstituted non-aromatic heterocyclylalkylcarbonyl, substituted or unsubstituted amino, or substituted or unsubstituted carbamoyl;
$R^{3C}$ and $R^{4C}$ are each independently hydrogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; or,
$R^{3A}$ and $R^{3B}$ may be taken together to form oxo, $R^{4A}$ and $R^{4B}$ may be taken together to form oxo;
$R^{3A}$ and $R^{4A}$ may be taken together with an adjacent atom to form substituted or unsubstituted monocyclic carbocycle, or substituted or unsubstituted monocyclic heterocycle, the carbocycle or heterocycle may be further fused to;
$R^{3A}$ and $R^{4C}$ may be taken together with an adjacent atom to form substituted or unsubstituted monocyclic heterocycle, the heterocycle may be further fused to;
$R^{3C}$ and $R^{4A}$ may be taken together with an adjacent atom to form substituted or unsubstituted monocyclic heterocycle, the heterocycle may be further fused to;
$R^{3C}$ and $R^{4C}$ may be taken together with an adjacent atom to form substituted or unsubstituted monocyclic heterocycle, the heterocycle may be further fused to;
$R^{3A}$ and $R^{3B}$ may be taken together with an adjacent atom to form substituted or unsubstituted spiro ring, the spiro ring may be further fused to;
$R^{4A}$ and $R^{4B}$ may be taken together with an adjacent atom to form substituted or unsubstituted spiro ring, the spiro ring may be further fused to;
$R^{4B}$ may be taken together with an atom on the circular arc of $T^1$ ring to form substituted or unsubstituted monocyclic carbocycle or substituted or unsubstituted monocyclic heterocycle, the carbocycle or heterocycle may be further fused to;
$R^{4C}$ may be taken together with an atom on the circular arc of $T^1$ ring to form substituted or unsubstituted monocyclic heterocycle, the heterocycle may be further fused to;
the broken line means the presence or absence of bond, the adjacent broken lines do not exist at the same time,
the carbon atoms on 1st, 2nd, and 3rd position are $sp^2$ carbon;
$T^1$ ring is substituted or unsubstituted monocyclic carbocycle or substituted or unsubstituted monocyclic heterocycle, (1) the carbocycle or heterocycle may be fused with the other substituted or unsubstituted carbocycle or substituted or unsubstituted heterocycle, and/or (2) two atoms which are not adjacent to one another constituting the carbocycle or heterocycle may be bridged by substituted or unsubstituted alkylene, substituted or unsubstituted alkenylene or substituted or unsubstituted alkynylene;
$R^1$ is halogen, cyano, nitro or —$X^1$—$R^{11}$,
$X^1$ is a bond, —O—, —S—, —$NR^{12}$—, —CO—, —SO—, —$SO_2$—, —O—CO—, —CO—O—, —$NR^{12}$—CO—, —CO—$NR^{12}$—, —$NR^{12}$—CO—O—, —$NR^{12}$—CO—$NR^{13}$—, —$NR^{12}$—$SO_2$—, or —$SO_2$—$NR^{12}$—,
$R^{11}$ is a hydrogen atom, substituted or unsubstituted alkyl, substituted or unsubstituted alkenyl, substituted or unsubstituted alkynyl, substituted or unsubstituted carbocyclyl, or substituted or unsubstituted heterocyclyl,
$R^{12}$ and $R^{13}$ are each independently a hydrogen atom, substituted or unsubstituted alkyl, substituted or unsubstituted alkenyl or substituted or unsubstituted alkynyl,
when $X^1$ is —$NR^{12}$—, —CO—$NR^{12}$— or —$SO_2$—$NR^{12}$—, $R^{11}$ and $R^{12}$ may be taken together with an adjacent nitrogen atom to form substituted or unsubstituted heterocyclyl,
when $X^1$ is —$NR^{12}$ 2-CO—$NR^{13}$—, $R^1$ 1 and $R^{13}$ may be taken together with an adjacent nitrogen atom to form substituted or unsubstituted heterocyclyl,
$R^1$ may be taken together with a carbon atom or a nitrogen atom on the circular arc of $T^1$ ring to form substituted or unsubstituted monocyclic carbocycle, or substituted or unsubstituted monocyclic heterocycle, the carbocycle or heterocycle may be further fused to;

$R^2$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyloxy, or substituted or unsubstituted cycloalkenyloxy;

n is 1 or 2;

$R^3$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocycle alkenyl, substituted or unsubstituted non-aromatic carbocycle alkenyl, substituted or unsubstituted aromatic heterocycle alkenyl, substituted or unsubstituted non-aromatic heterocycle alkenyl, substituted or unsubstituted aromatic carbocycle alkynyl, substituted or unsubstituted non-aromatic carbocycle alkynyl, substituted or unsubstituted aromatic heterocycle alkynyl, or substituted or unsubstituted non-aromatic heterocycle alkynyl; and $R^4$ is hydrogen or a carboxy protecting group.

(1') A compound represented by the following formula (I)':

[Chemical formula 2]

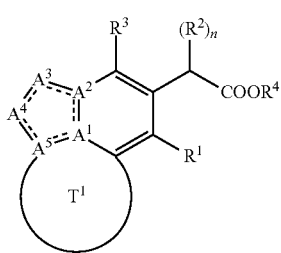

or its pharmaceutically acceptable salt,
wherein
$A^1$ is C, $CR^{1A}$, or N;
$A^2$ is C, $CR^{2A}$, or N;
$A^3$ is $CR^{3A}$, $CR^{3A}R^{3B}$, N, $NR^{3C}$, O, S, SO, or $SO_2$;
$A^4$ is $CR^{4A}$, $CR^{4A}R^{4B}$, N, $NR^{4C}$, O, S, SO, or $SO_2$;
$A^5$ is C, $CR^{5A}$, or N;
$R^{1A}$, $R^{2A}$, $R^{3A}$, $R^{3B}$, $R^{4A}$, $R^{4B}$, and $R^{5A}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylthio, substituted or unsubstituted non-aromatic carbocyclylthio, substituted or unsubstituted aromatic heterocyclylthio, substituted or unsubstituted non-aromatic heterocyclylthio, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted carbonyl, or substituted or unsubstituted carbamoyl;

$R^{3C}$ and $R^{4C}$ are each independently hydrogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; or, $R^{3A}$ and $R^{3B}$ may be taken together to form oxo, $R^{4A}$ and $R^{4B}$ may be taken together to form oxo;

$R^{3A}$ and $R^{4A}$ may be taken together with an adjacent atom to form substituted or unsubstituted monocyclic carbocycle, or substituted or unsubstituted monocyclic heterocycle, the carbocycle or heterocycle may be further fused to;

$R^{3A}$ and $R^{4C}$ may be taken together with an adjacent atom to form substituted or unsubstituted monocyclic heterocycle, the heterocycle may be further fused to;

$R^{3C}$ and $R^{4A}$ may be taken together with an adjacent atom to form substituted or unsubstituted monocyclic heterocycle, the heterocycle may be further fused to;

$R^{3C}$ and $R^{4C}$ may be taken together with an adjacent atom to form substituted or unsubstituted monocyclic heterocycle, the heterocycle may be further fused to;

$R^{3A}$ and $R^{3B}$ may be taken together with an adjacent atom to form substituted or unsubstituted spiro ring, the spiro ring may be further fused to;

$R^{4A}$ and $R^{4B}$ may be taken together with an adjacent atom to form substituted or unsubstituted spiro ring, the spiro ring may be further fused to;

$R^{4B}$ may be taken together with an atom on the circular arc of $T^1$ ring to form substituted or unsubstituted monocyclic carbocycle or substituted or unsubstituted monocyclic heterocycle, the carbocycle or heterocycle may be further fused to;

$R^{4C}$ may be taken together with an atom on the circular arc of $T^1$ ring to form substituted or unsubstituted monocyclic heterocycle, the heterocycle may be further fused to;

the broken line means the presence or absence of bond, the adjacent line do not exist at the same time;

$T^1$ ring is substituted or unsubstituted monocyclic carbocycle, or substituted or unsubstituted monocyclic heterocycle, (1) the carbocycle or heterocycle may be fused with the other substituted or unsubstituted carbocycle or substituted or unsubstituted heterocycle, and/or (2) two atoms which are not adjacent to one another constituting the carbocycle or heterocycle may be bridged by substituted or unsubstituted alkylene, substituted or unsubstituted alkenylene or substituted or unsubstituted alkynylene;

$R^1$ is halogen, cyano, nitro or —$X^1$—$R^{11}$, $X^1$ is a bond, —O—, —S—, —$NR^{12}$—, —CO—, —SO—, —$SO_2$—, —O—CO—, —CO—O—, —$NR^{12}$—CO—, —CO—$NR^{12}$—, —$NR^{12}$—CO—O—, —$NR^{12}$—CO—$NR^{13}$—, —$NR^{12}$—$SO_2$—, or —$SO_2$—$NR^{12}$—, $R^{11}$ is a hydrogen atom, substituted or unsubstituted alkyl, substituted or unsubstituted alkenyl, substituted or unsubstituted alkynyl, substituted or unsubstituted carbocyclyl, or substituted or unsubstituted heterocyclyl, $R^{12}$ and $R^{13}$ are each independently a hydrogen atom, substituted or unsubstituted alkyl, substituted or unsubstituted alkenyl or substituted or unsubstituted alkynyl, when $X^1$ is —$NR^{12}$—, —CO—$NR^{12}$— or —$SO_2$—$NR^{12}$—, $R^{11}$ and $R^{12}$ may be taken together with an adjacent nitrogen atom to form substituted or unsubstituted heterocyclyl, when $X^1$ is —$NR^{12}$—CO—$NR^{13}$—, —$R^{11}$ and $R^{12}$ may be taken together with an adjacent nitrogen atom to form substituted or unsubstituted heterocyclyl;

$R^2$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyloxy, or substituted or unsubstituted cycloalkenyloxy;

n is 1 or 2;

$R^3$ is hydrogen, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or non-cyclic group; and $R^4$ is hydrogen or a carboxy protecting group).

(1") A compound represented by the following formula (I)':

[Chemical formula 3]

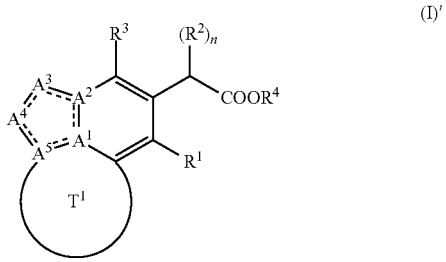

or its pharmaceutically acceptable salt,
wherein
$A^1$ is C, $CR^{1A}$, or N;
$A^2$ is C, $CR^{2A}$, or N;
$A^3$ is $CR^{3A}$, $CR^{3A}R^{3B}$, N, $NR^{3C}$, O, S, SO, or $SO_2$;
$A^4$ is $CR^{4A}$, $CR^{4A}R^{4B}$, N, $NR^{4C}$, O, S, SO, or $SO_2$;
$A^5$ is C, $CR^{5A}$, or N;
$R^{1A}$, $R^{2A}$, $R^{3A}$, $R^{3B}$, $R^{4A}$, $R^{4B}$, and $R^{5A}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylthio, substituted or unsubstituted non-aromatic carbocyclylthio, substituted or unsubstituted aromatic heterocyclylthio, substituted or unsubstituted non-aromatic heterocyclylthio, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylalkylcarbonyl, substituted or unsubstituted non-aromatic carbocyclylalkylcarbonyl, substituted or unsubstituted aromatic heterocyclylalkylcarbonyl, substituted or unsubstituted non-aromatic heterocyclylalkylcarbonyl, or substituted or unsubstituted carbamoyl;

$R^{3C}$ and $R^{4C}$ are each independently hydrogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; or, $R^{3A}$ and $R^{3B}$ may be taken together to form oxo, $R^{4A}$ and $R^{4B}$ may be taken together to form oxo;

$R^{3A}$ and $R^{4A}$ may be taken together with an adjacent atom to form substituted or unsubstituted monocyclic carbocycle, or substituted or unsubstituted monocyclic heterocycle, the carbocycle or heterocycle may be further fused to;

$R^{3A}$ and $R^{4C}$ may be taken together with an adjacent atom to form substituted or unsubstituted monocyclic heterocycle, the heterocycle may be further fused to;

$R^{3C}$ and $R^{4A}$ may be taken together with an adjacent atom to form substituted or unsubstituted monocyclic heterocycle, the heterocycle may be further fused to;

$R^{3C}$ and $R^{4C}$ may be taken together with an adjacent atom to form substituted or unsubstituted monocyclic heterocycle, the heterocycle may be further fused to;

$R^{3A}$ and $R^{3B}$ may be taken together with an adjacent atom to form substituted or unsubstituted spiro ring, the spiro ring may be further fused to;

$R^{4A}$ and $R^{4B}$ may be taken together with an adjacent atom to form substituted or unsubstituted spiro ring, the spiro ring may be further fused to;

$R^{4B}$ may be taken together with an atom on the circular arc of $T^1$ ring to form substituted or unsubstituted monocyclic carbocycle, or substituted or unsubstituted monocyclic heterocycle, the carbocycle or heterocycle may be further fused to;

$R^{4C}$ may be taken together with an atom on the circular arc of $T^1$ ring to form substituted or unsubstituted monocyclic heterocycle, the heterocycle may be further fused to; the broken line means the presence or absence of bond, the adjacent broken lines do not exist at the same time;

$T^1$ ring is substituted or unsubstituted monocyclic carbocycle, or substituted or unsubstituted monocyclic heterocycle, (1) the carbocycle or heterocycle may be fused with the other substituted or unsubstituted carbocycle or substituted or unsubstituted heterocycle, and/or (2) two atoms which are not adjacent to one another constituting the carbocycle or heterocycle may be bridged by substituted or unsubstituted alkylene, substituted or unsubstituted alkenylene, or substituted or unsubstituted alkynylene;

$R^1$ is halogen, cyano, nitro or —$X^1$—$R^{11}$,
$X^1$ is a bond, —O—, —S—, —$NR^{12}$—, —CO—, —SO—, —$SO_2$—, —O—CO—, —CO—O—, —$NR^{12}$—CO—, —CO—$NR^{12}$—, —$NR^{12}$—CO—O—, —$NR^{12}$—CO—$NR^{13}$—, —$NR^{12}$—$SO_2$—, or —$SO_2$—$NR^{12}$—,
$R^{11}$ is a hydrogen atom, substituted or unsubstituted alkyl, substituted or unsubstituted alkenyl, substituted or unsubstituted alkynyl, substituted or unsubstituted carbocyclyl, or substituted or unsubstituted heterocyclyl,
$R^{12}$ and $R^{13}$ are each independently a hydrogen atom, substituted or unsubstituted alkyl, substituted or unsubstituted alkenyl or substituted or unsubstituted alkynyl, when $X^1$ is —$NR^{12}$—, —CO—$NR^{12}$—, or —$SO_2$—$NR^{12}$—, $R^{11}$ and $R^{12}$ may be taken together with an adjacent nitrogen atom to form substituted or unsubstituted heterocyclyl, when $X^1$ is —$NR^{12}$—CO—$NR^{13}$—, $R^{11}$ and $R^{12}$ may be taken together with an adjacent nitrogen atom to form substituted or unsubstituted heterocyclyl;

$R^2$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyloxy, or substituted or unsubstituted cycloalkenyloxy;

n is 1 or 2;

$R^3$ is hydrogen, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or non-cyclic group;

and $R^4$ is hydrogen or a carboxy protecting group).

(2) The compound or its pharmaceutically acceptable salt according to the above (1), (1') or (1"), represented by any one of the following formula:

[Chemical formula 4]

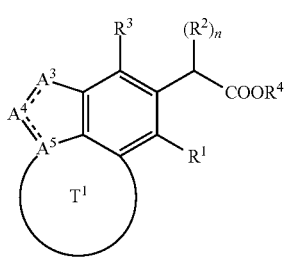

(I-A)

wherein each symbol is as defined in the above (1), (1') or (1").

(3) The compound or its pharmaceutically acceptable salt according to the above (1), (1') or (1"), wherein at least one of the following conditions 1) to 3) is fulfilled:
1) $A^3$ is N, $NR^{3C}$, O, S, SO, or $SO_2$:
2) $A^4$ is N, $NR^{4C}$, O, S, SO, or $SO_2$:
3) $A^5$ is N.

(4) The compound or its pharmaceutically acceptable salt according to the above (1), (1'), (1") or (2), $A^3$ is $CR^{3A}$; $A^4$ is $CR^{4A}$; and $A^5$ is N.

(5) The compound or its pharmaceutically acceptable salt according to the above (1), (1'), (1") or (2), $A^3$ is N or $NR^{3C}$; $A^4$ is $CR^{4A}$; and $A^5$ is C.

(6) The compound or its pharmaceutically acceptable salt according to the above (1), (1'), (1") or (2), $A^3$ is N or $NR^{3C}$; $A^4$ is $CR^{4A}$; and $A^5$ is C or N.

(7) The compound or its pharmaceutically acceptable salt according to the above (1), (1'), (1") or (2), $A^3$ is O or S; $A^4$ is $CR^{4A}$ or N; and $A^5$ is C.

(8) The compound or its pharmaceutically acceptable salt according to the above (1), (1'), or (1"), represented by formula (I-A):

[Chemical formula 5]

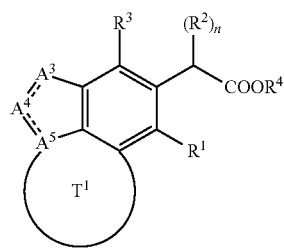

(I-A)

wherein each symbol is independently as defined in the above (1), (1') or (1").

(9) The compound or its pharmaceutically acceptable salt according to the above (8), represented by any one of the following formula:

[Chemical formula 6]

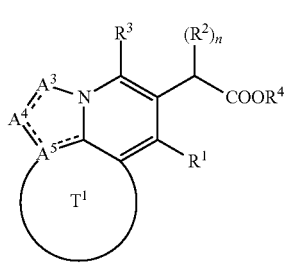

(I-B)

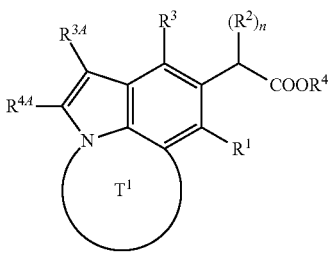

(I-A-1)

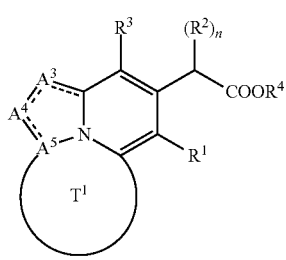

(I-C)

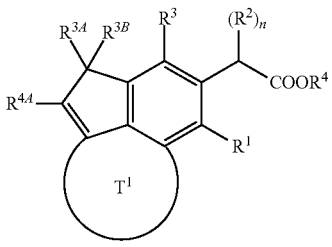

(I-A-2)

-continued
(I-A-3)
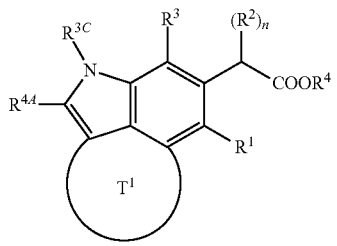
(I-A-4)
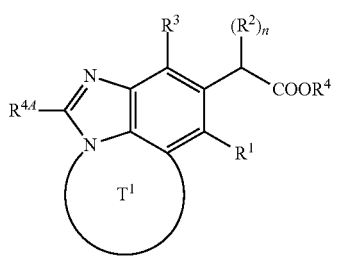
(I-A-5)
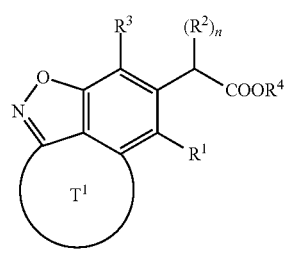
(I-A-6)
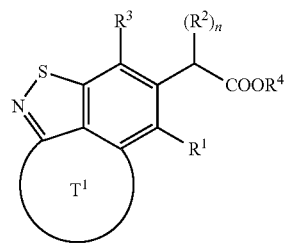
(I-A-5')
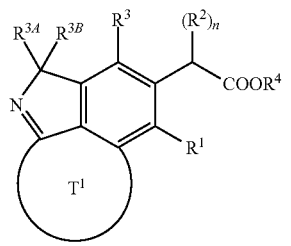
(I-A-6')
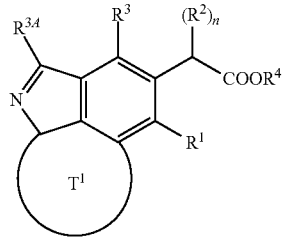
-continued
(I-A-7)
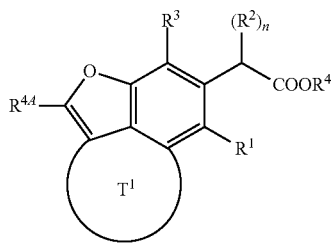
(I-A-8)
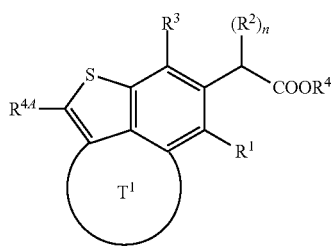
(I-A-9)
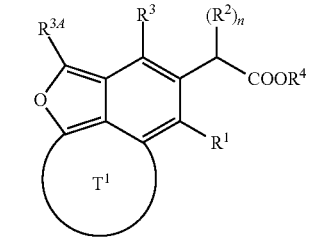
(I-A-10)
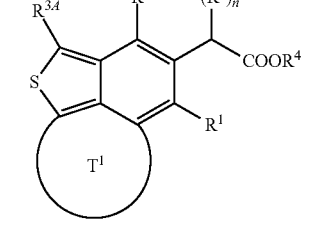
wherein each symbol is independently as defined in the above (1), (1') or (1").
(10) The compound or its pharmaceutically acceptable salt according to the above (1), (1') or (1"), represented by the following formula (I-B):
[Chemical formula 7]
(I-B)
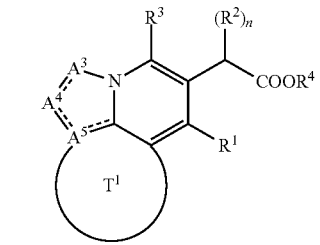
wherein each symbol is independently as defined in the above (1), (1') or (1").

(11) The compound or its pharmaceutically acceptable salt according to the above (10), represented by any one of the following formula:

[Chemical formula 8]

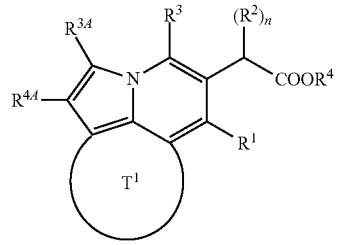
(I-B-1)

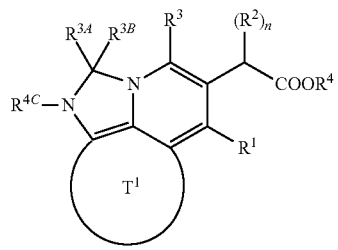
(I-B-2)

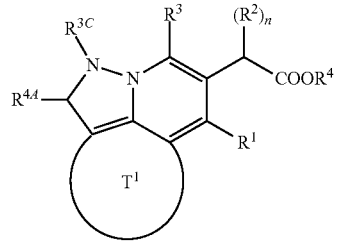
(I-B-3)

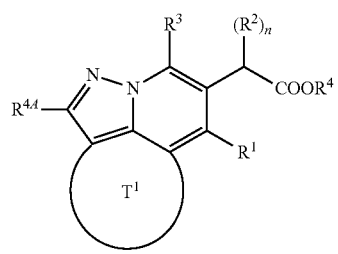
(I-B-4)

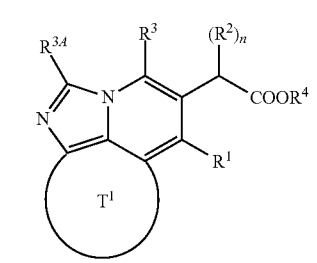
(I-B-5)

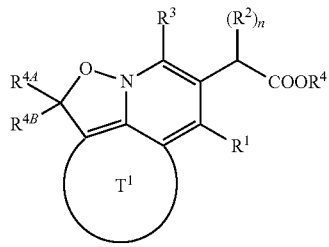
(I-B-6)

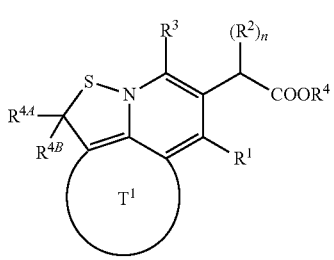
(I-B-7)

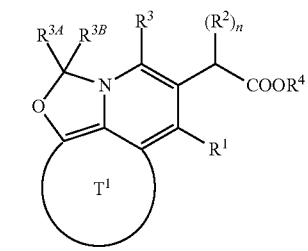
(I-B-8)

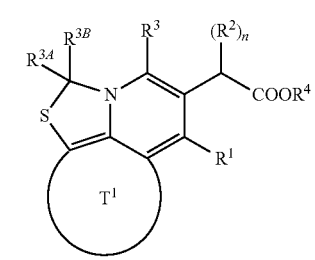
(I-B-9)

wherein each symbol is independently as defined in the above (1), (1') or (1").

(12) The compound or its pharmaceutically acceptable salt according to the above (1), (1') or (1"), represented by the following formula (I-C):

[Chemical formula 9]

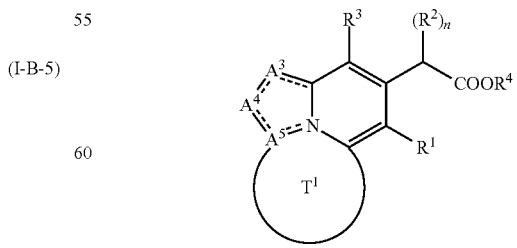
(I-C)

wherein each symbol is independently as defined in the (1), (1') or (1").

(13) The compound or its pharmaceutically acceptable salt according to the above (12), represented by any one of the following formula:

[Chemical formula 10]

(I-C-1)
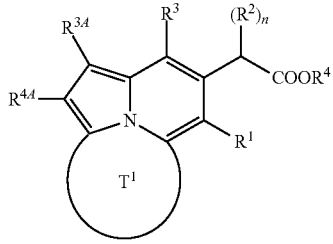

(I-C-2)
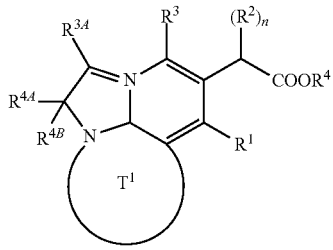

(I-C-3)
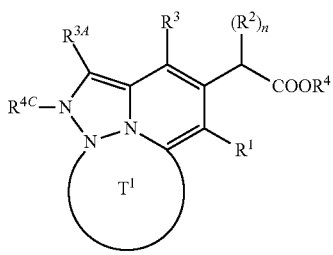

(I-C-4)
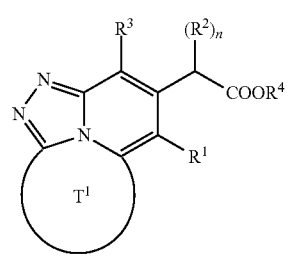

(I-C-5)
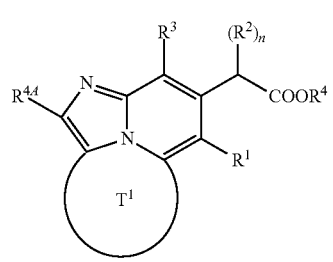

(I-C-6)
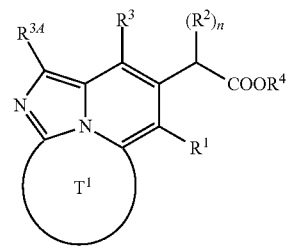

wherein each symbol is independently as defined in the above (1), (1') or (1").

(14) The compound or its pharmaceutically acceptable salt according to any one of the above (1), (1'), (1"), (2) to (13), wherein $T^1$ ring is any one of the following structure:

[Chemical formula 11]

(T¹-1)
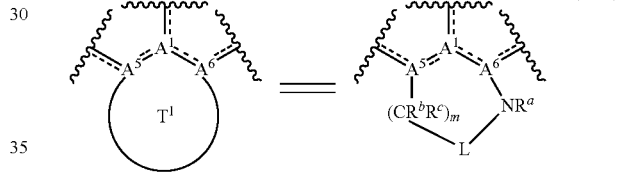

(T¹-2)
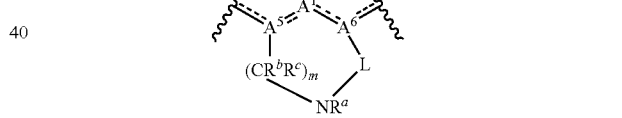

wherein $A^1$, $A^5$ and $A^6$ are as defined in the above (1), (1') or (1");

$R^a$ is hydrogen, substituted or unsubstituted alkyl, substituted or unsubstituted alkenyl, substituted or unsubstituted carbocyclyl, substituted or unsubstituted heterocyclyl, —$COR^{a1}$, —$SOR^{a2}$, or —$SO_2R^{a3}$ ($R^{a1}$, $R^{2a}$, and $R^{a3}$ are each independently hydrogen, substituted or unsubstituted alkyl, substituted or unsubstituted alkenyl, substituted or unsubstituted carbocyclyl, or substituted or unsubstituted heterocyclyl;

m is an integer of 0 to 5;

L is —$SO_2$—, —SO—, —CO—, or —$CR^bR^c$—; and $R^b$ and $R^c$ are each independently hydrogen, substituted or unsubstituted alkyl, substituted or unsubstituted alkenyl, substituted or unsubstituted carbocyclyl, substituted or unsubstituted heterocyclyl, or $R^b$ and $R^c$ may be taken together to form oxo.

(14') The compound or its pharmaceutically acceptable salt according to any one of the above (1), (1'), (1"), (2) to (13), wherein $T^1$ ring is any one of the following structures:

[Chemical formula 12]

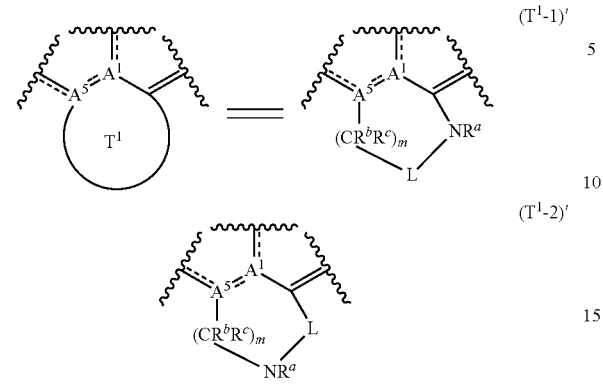

(T¹-1)'

(T¹-2)' wherein $A^1$ and $A^5$ are as defined in the above (1') or (1");

$R^a$ is hydrogen, substituted or unsubstituted alkyl, substituted or unsubstituted alkenyl, substituted or unsubstituted carbocyclyl, substituted or unsubstituted heterocyclyl, —$COR^{a1}$, —$SOR^{a2}$, or —$SO_2R^{a3}$ ($R^{a1}$, $R^{a2}$, and $R^{a3}$ are each independently hydrogen, substituted or unsubstituted alkyl, substituted or unsubstituted alkenyl, substituted or unsubstituted carbocyclyl, or substituted or unsubstituted heterocyclyl;

m is an integer of 0 to 5;

L is —$SO_2$—, —SO—, —CO—, or —$CR^bR^c$—; and $R^b$ and $R^c$ are each independently hydrogen, substituted or unsubstituted alkyl, substituted or unsubstituted alkenyl, substituted or unsubstituted carbocyclyl, substituted or unsubstituted heterocyclyl, or $R^b$ and $R^c$ may be taken together to form oxo.

(15) The compound or its pharmaceutically acceptable salt according to any one of the above (1), (1'), (1"), (2) to (13), wherein $T^1$ ring is any one of the following structures:

[Chemical formula 13]

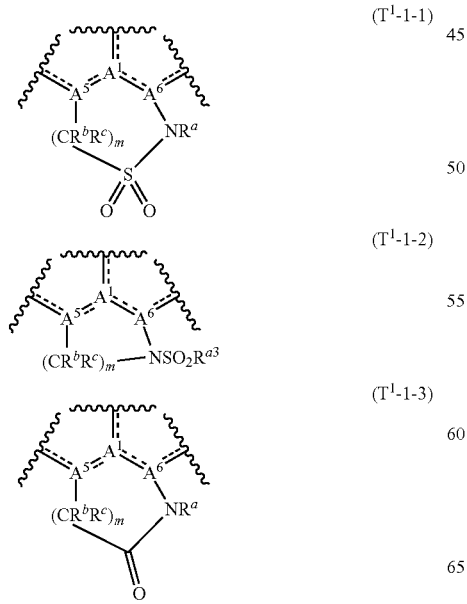

(T¹-1-1)

(T¹-1-2)

(T¹-1-3)

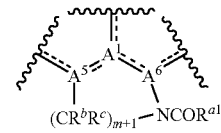

(T¹-1-4)

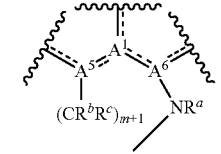

(T¹-1-5)

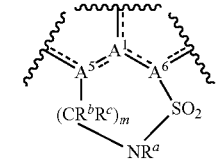

(T¹-2-1)

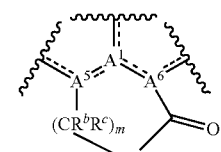

(T¹-2-2)

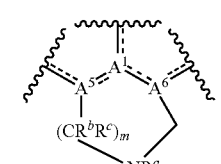

(T¹-2-3)

(15') The compound or its pharmaceutically acceptable salt according to any one of the above (1), (1'), (1"), (2) to (13), wherein $T^1$ ring is any one of the following structures:

[Chemical formula 14]

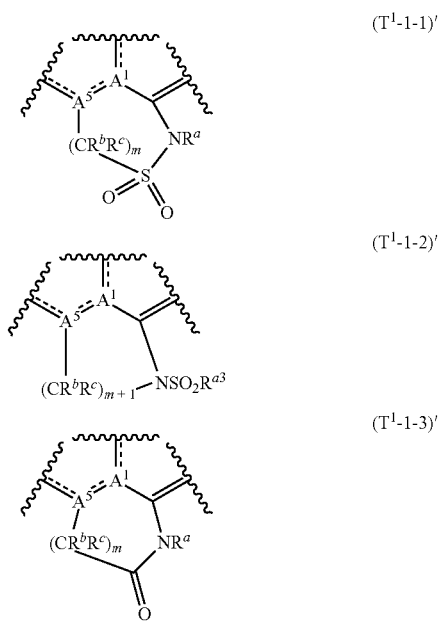

(T¹-1-1)'

(T¹-1-2)'

(T¹-1-3)'

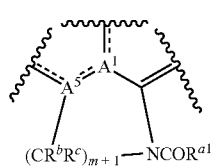 (T¹-1-4)'
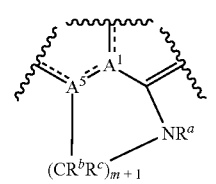 (T¹-1-5)'
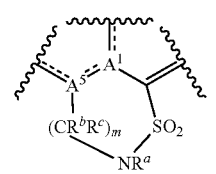 (T¹-2-1)'
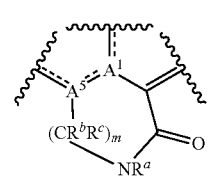 (T¹-2-2)'
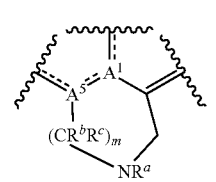 (T¹-2-3)'
(16) The compound or its pharmaceutically acceptable salt according to the above (1), (1') or (1") represented by any one of the following formula:
[Chemical formula 15]
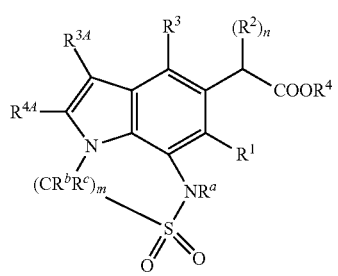 (I-A-1-1)
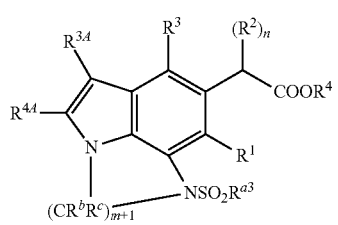 (I-A-1-2)
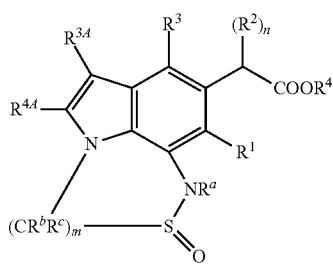 (I-A-1-3)
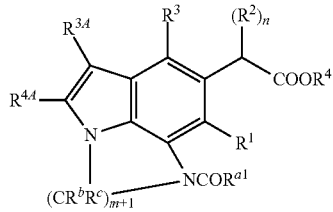 (I-A-1-4)
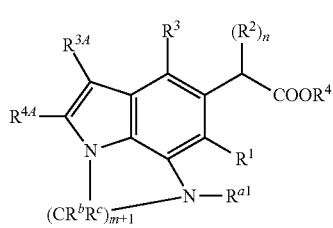 (I-A-1-5)
[Chemical formula 16]
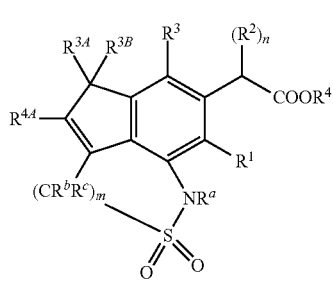 (I-A-2-1)
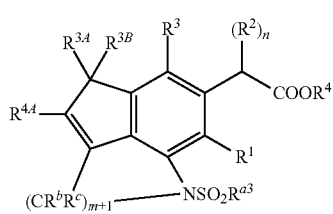 (I-A-2-2)
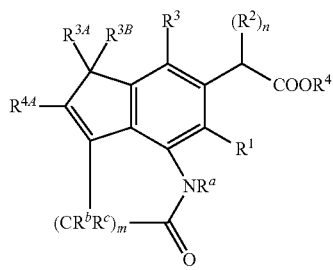 (I-A-2-3)

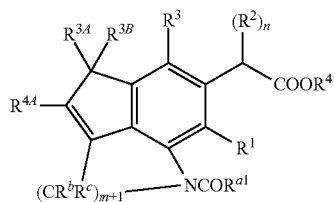
(I-A-2-4)
[Chemical formula 17]
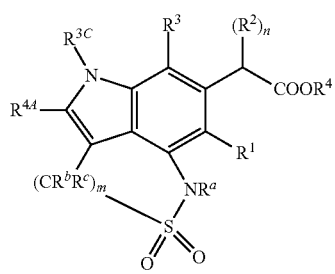
(I-A-3-1)
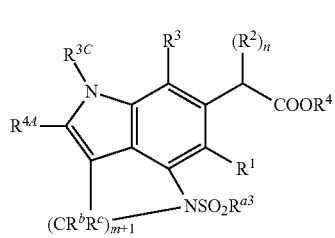
(I-A-3-2)
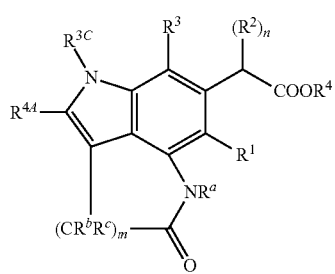
(I-A-3-3)
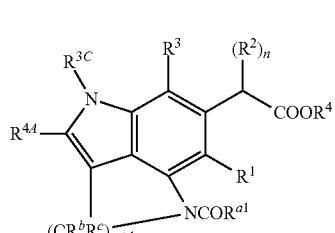
(I-A-3-4)
[Chemical formula 18]
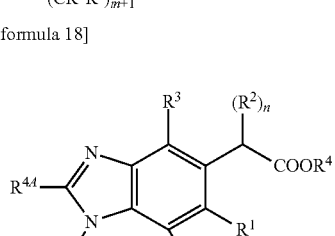
(I-A-4-1)
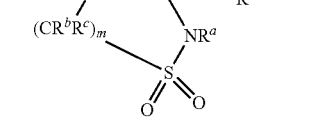
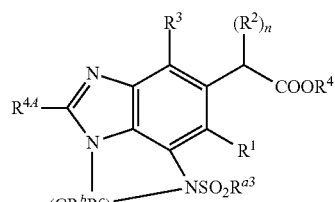
(I-A-4-2)
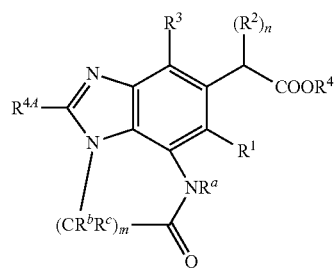
(I-A-4-3)
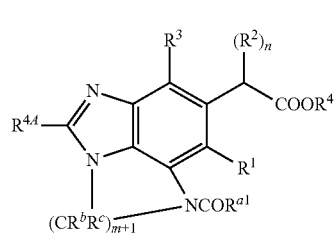
(I-A-4-4)
[Chemical formula 19]
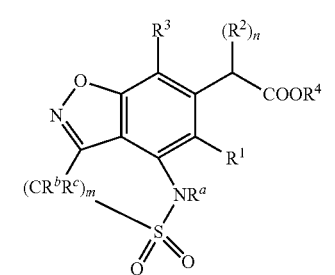
(I-A-5-1)
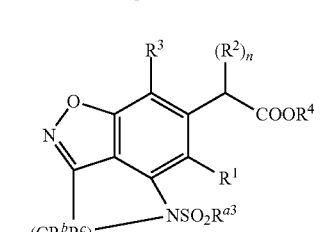
(I-A-5-2)
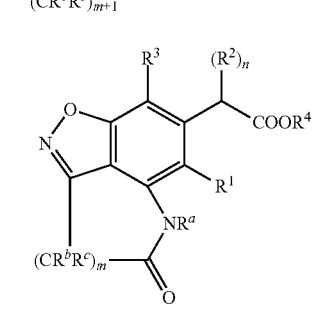
(I-A-5-3)

(I-A-5-4)
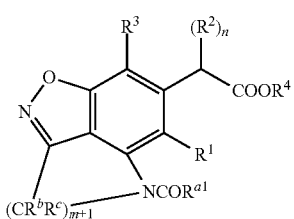
[Chemical formula 20]
(I-A-5'-1)
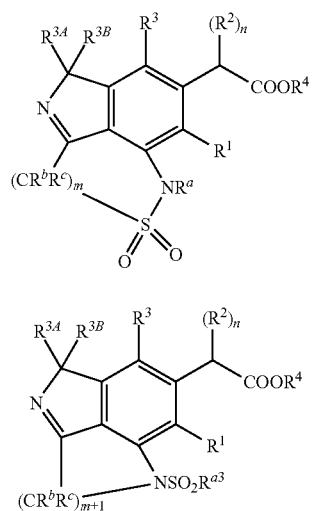
(I-A-5'-2)
(I-A-5'-3)
(I-A-5'-4)
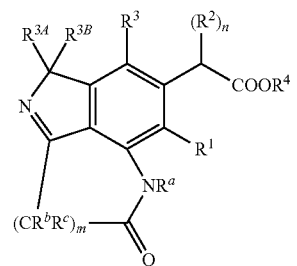
[Chemical formula 21]
(I-A-6-1)
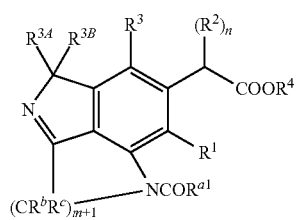
(I-A-6-2)
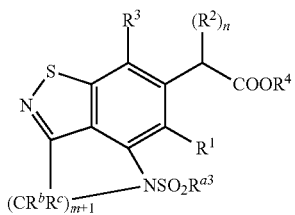
(I-A-6-3)
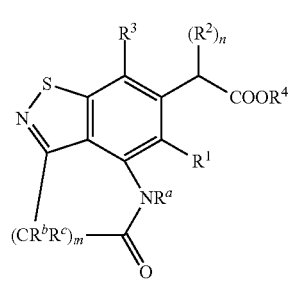
(I-A-6-4)
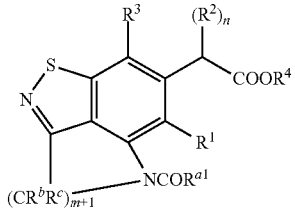
[Chemical formula 22]
(I-A-6'-1)
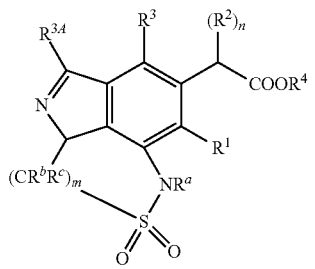
(I-A-6'-2)
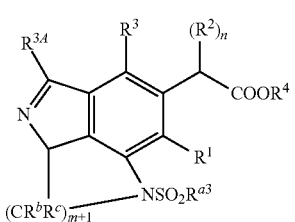
(I-A-6'-3)
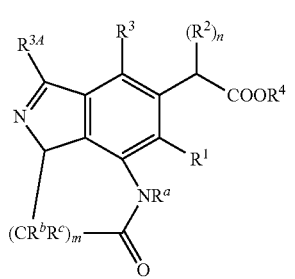

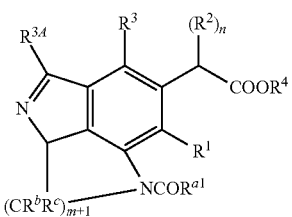
(I-A-6'-4)
[Chemical formula 23]
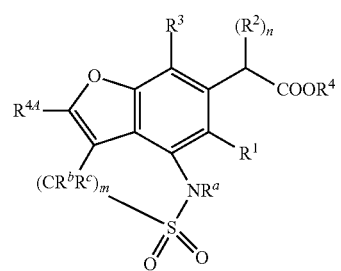
(I-A-7-1)
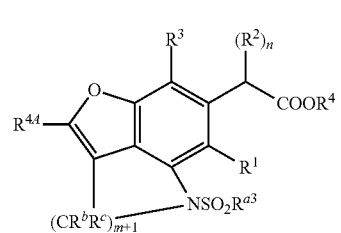
(I-A-7-2)
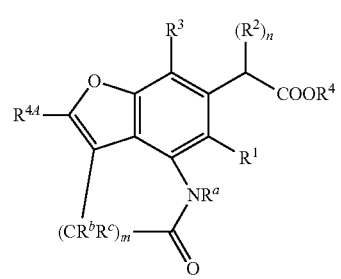
(I-A-7-3)
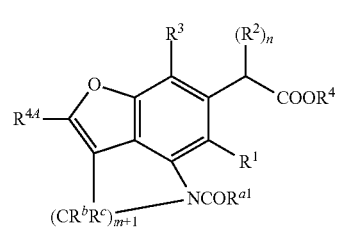
(I-A-7-4)
[Chemical formula 24]
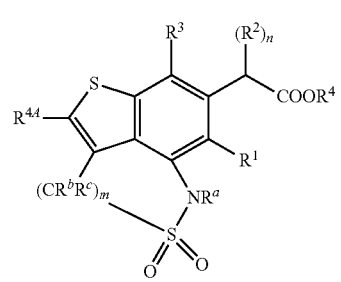
(I-A-8-1)
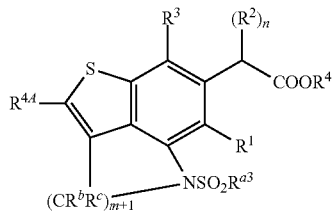
(I-A-8-2)
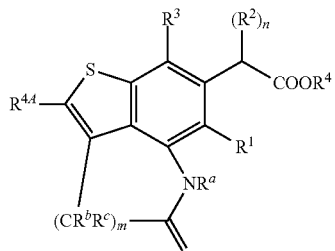
(I-A-8-3)
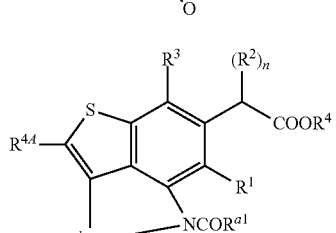
(I-A-8-4)
[Chemical formula 25]
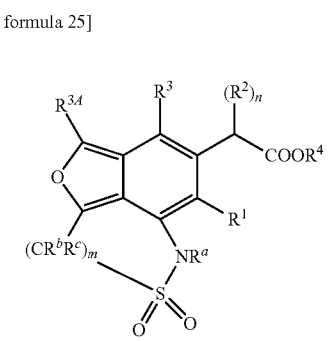
(I-A-9-1)
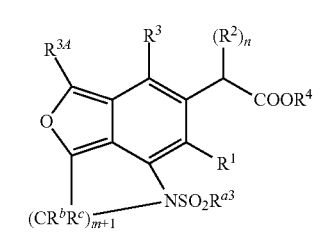
(I-A-9-2)
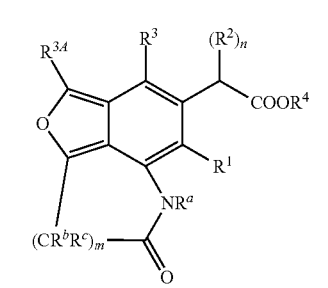
(I-A-9-3)

-continued
(I-A-9-4)
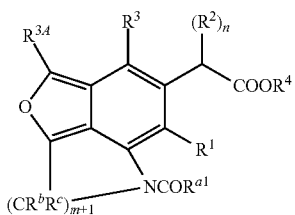
[Chemical formula 26]
(I-A-10-1)
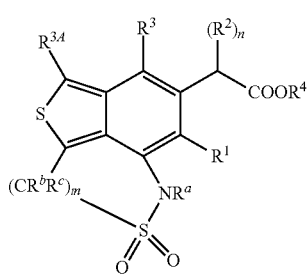
(I-A-10-2)
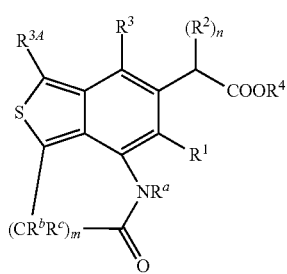
(I-A-10-3)
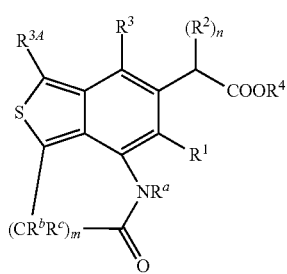
(I-A-10-4)
wherein each symbol is as defined above.
(17) The compound or its pharmaceutically acceptable salt according to the above (1), (1') or (1") represented by any one of the following formula:
[Chemical formula 27]
(I-B-1-1)
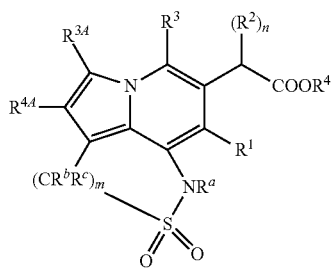
(I-B-1-2)
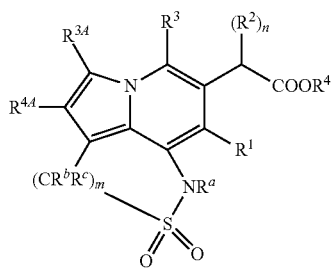
(I-B-1-3)
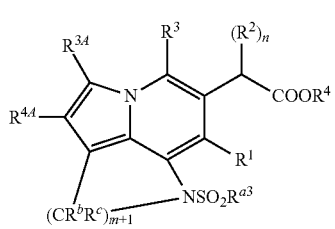
(I-B-1-4)
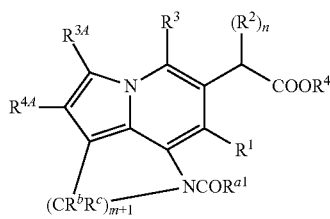
[Chemical formula 28]
(I-B-2-1)
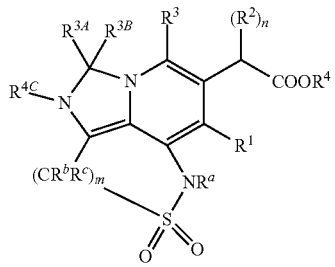

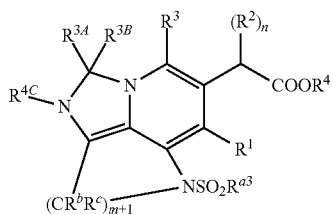
(I-B-2-2)
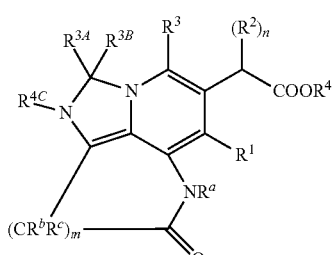
(I-B-2-3)
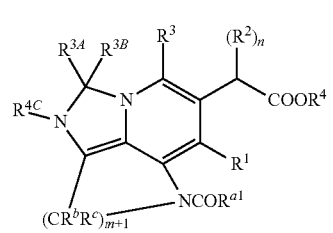
(I-B-2-4)
[Chemical formula 29]
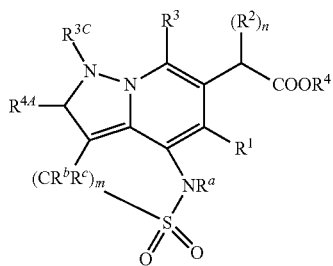
(I-B-3-1)
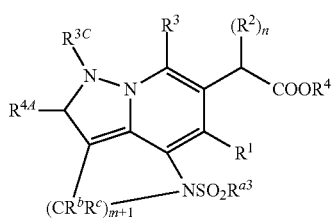
(I-B-3-2)
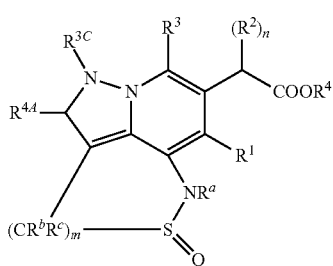
(I-B-3-3)
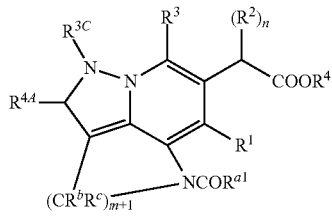
(I-B-3-4)
[Chemical formula 30]
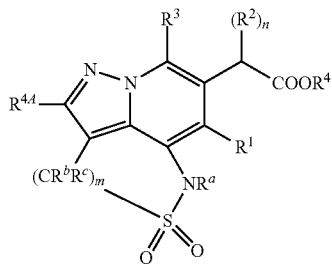
(I-B-4-1)
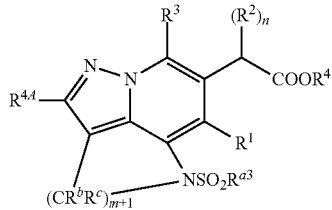
(I-B-4-2)
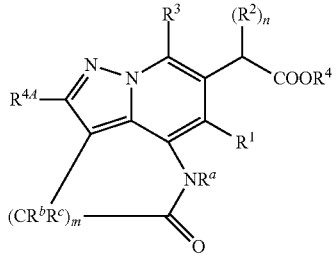
(I-B-4-3)
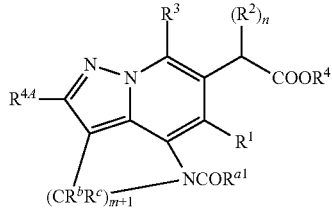
(I-B-4-4)
[Chemical formula 31]
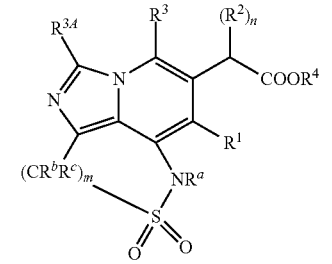
(I-B-5-1)

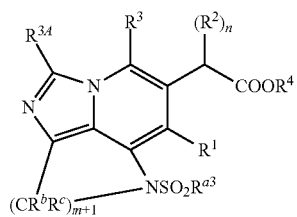
(I-B-5-2)
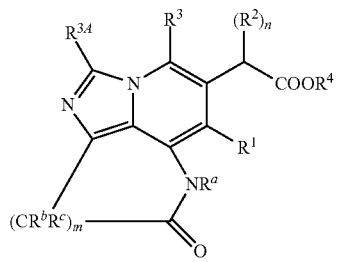
(I-B-5-3)
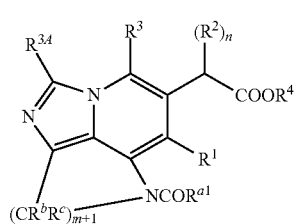
(I-B-5-4)
[Chemical formula 32]
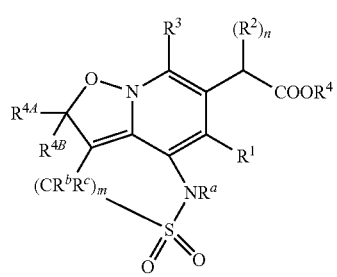
(I-B-6-1)
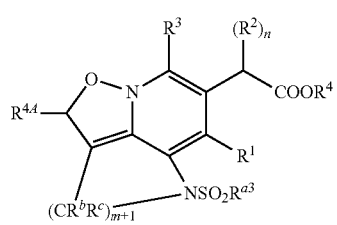
(I-B-6-2)
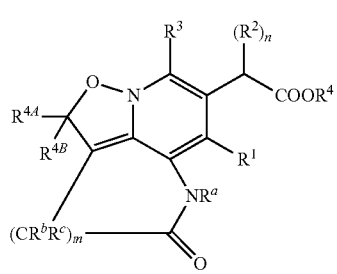
(I-B-6-3)
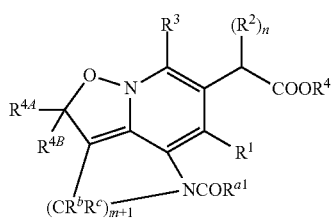
(I-B-6-4)
[Chemical formula 33]
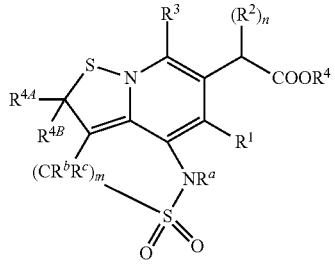
(I-B-7-1)
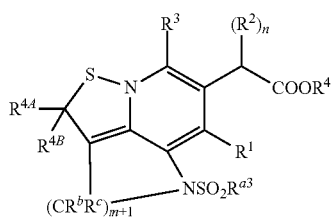
(I-B-7-2)
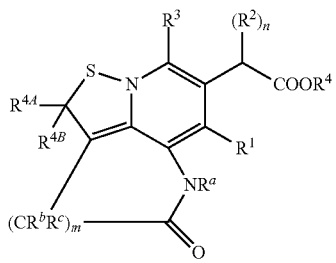
(I-B-7-3)
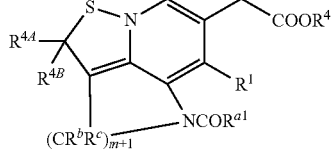
(I-B-7-4)
[Chemical formula 34]
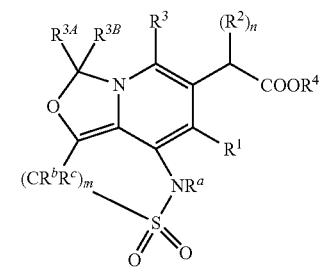
(I-B-8-1)

-continued
(I-B-8-2)
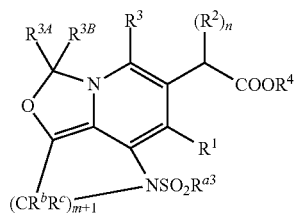
(I-B-8-3)
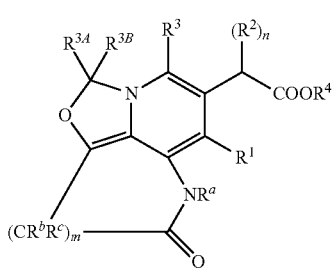
[Chemical formula 35]
(I-B-9-1)
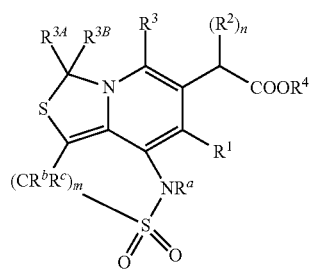
(I-B-9-2)
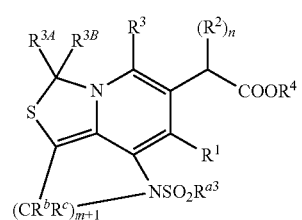
(I-B-9-3)
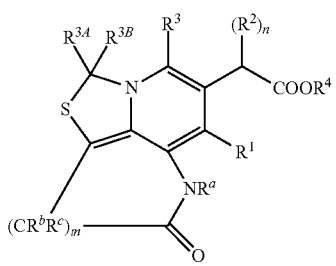
-continued
(I-B-8-4)
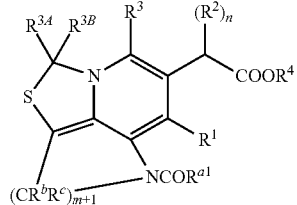
wherein each symbol is as defined above.
(18) The compound or its pharmaceutically acceptable salt according to the above (1), (1') or (1") represented by any one of the following formula:
[Chemical formula 36]
(I-B-9-4)
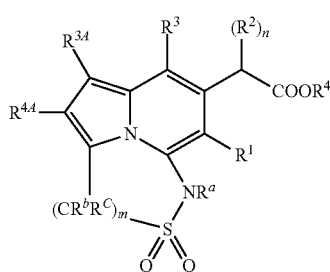
(I-C-1-1)
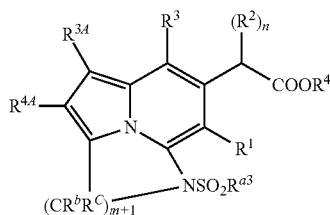
(I-C-1-2)
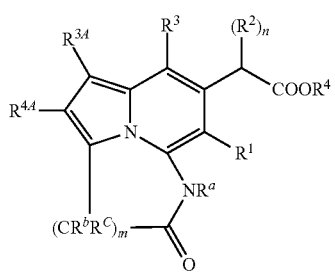
(I-C-1-3)
(I-C-1-4)
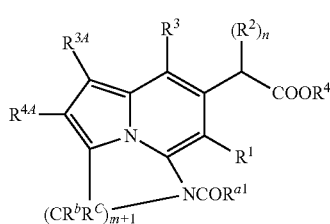

[Chemical formula 37]
(I-C-2-1)
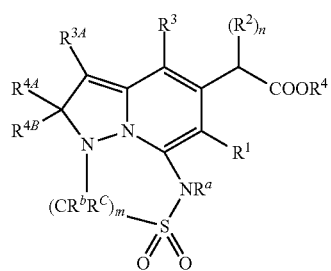
(I-C-2-2)
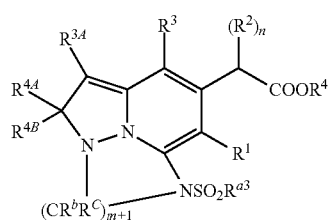
(I-C-2-3)
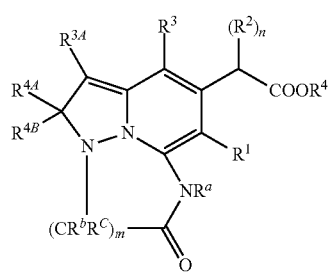
(I-C-2-4)
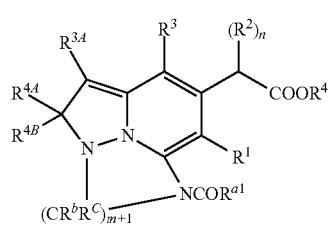
[Chemical formula 38]
(I-C-3-1)
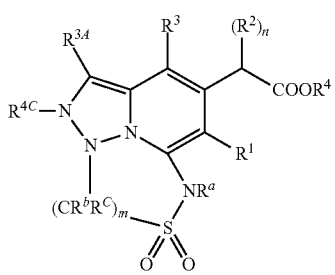
(I-C-3-2)
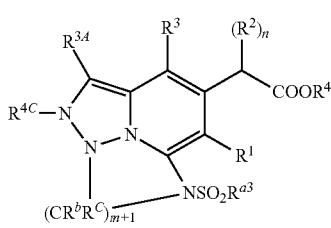
(I-C-3-3)
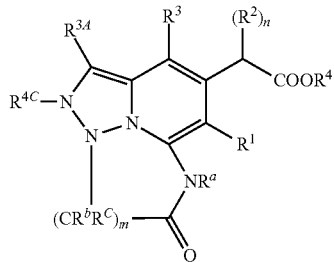
(I-C-3-4)
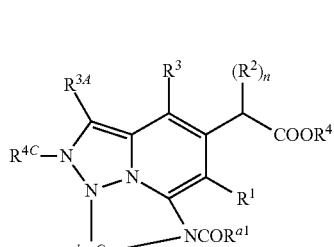
[Chemical formula 39]
(I-C-4-1)
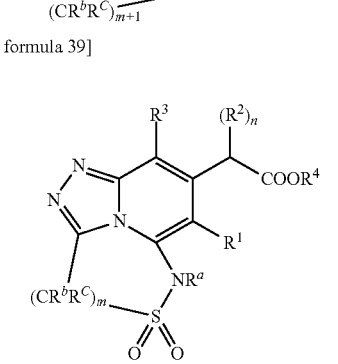
(I-C-4-2)
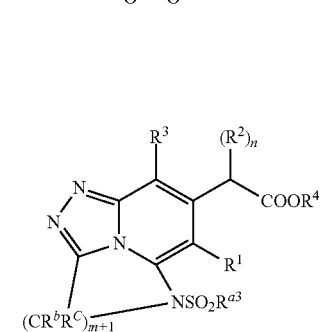
(I-C-4-3)
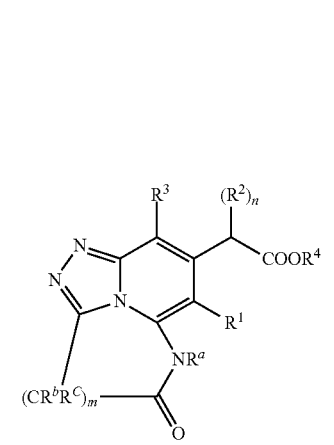

-continued (I-C-4-4)
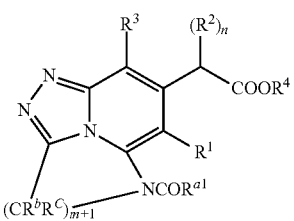

[Chemical formula 40]

(I-C-5-1)
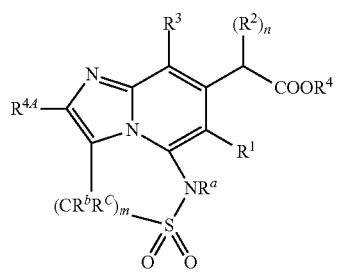

(I-C-5-2)
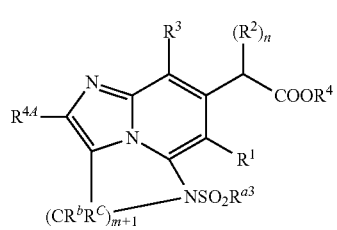

(I-C-5-3)
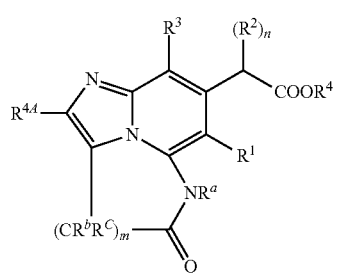

(I-C-5-4)
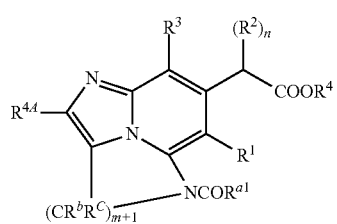

[Chemical formula 41]

(I-C-6-1)
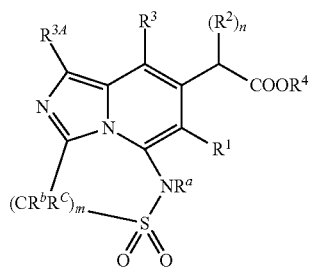

-continued (I-C-6-2)
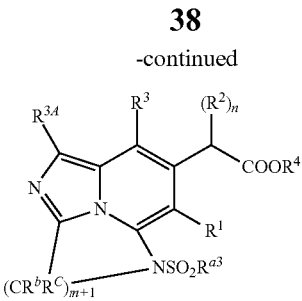

(I-C-6-3)
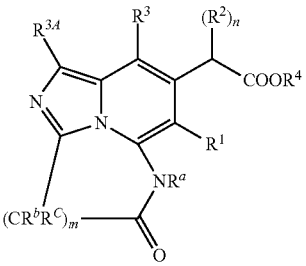

(I-C-6-4)
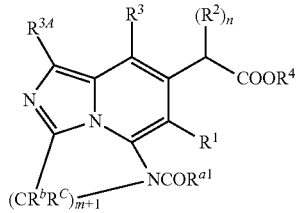

(19) The compound or its pharmaceutically acceptable salt according to any one of the above (8) to (13), wherein $T^1$ ring is the structure represented by the formula ($T^1$-2-1), ($T^1$-2-2) or ($T^1$-2-3) described in the above (15).

(20) The compound or its pharmaceutically acceptable salt according to any one of the above (1), (1'), (1''), (2) to (19), wherein $R^1$ is alkyl.

(21) The compound or its pharmaceutically acceptable salt according to any one of the above (1), (1'), (1''), (2) to (19), wherein n is 1, and $R^2$ is alkyloxy.

(22) The compound or its pharmaceutically acceptable salt according to any one of the above (1), (1'), (1''), (2) to (19), wherein $R^4$ is hydrogen.

(23) The compound or its pharmaceutically acceptable salt according to any one of the above (1), (1'), (1''), (2) to (19), $R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

(24) The compound or its pharmaceutically acceptable salt according to any one of the above (1), (1'), (1''), (2) to (19), wherein $R^1$ is alkyl; n is 1, $R^2$ is alkyloxy; $R^4$ is hydrogen; and $R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

(25) The compound or its pharmaceutically acceptable salt according to any one of the above (14) to (19), wherein $R^1$ is alkyl; n is 1, $R^2$ is alkyloxy; $R^4$ is hydrogen; $R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; m is an integer of 0 to 3; and $R^b$ and $R^c$ are each independently hydrogen or alkyl.

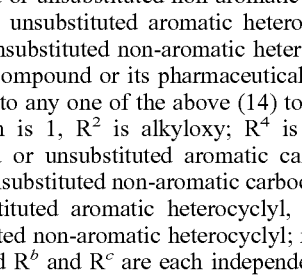

(26) The compound or its pharmaceutically acceptable salt according to the above (1), (1') or (1") represented by the following formula:

[Chemical formula 42]

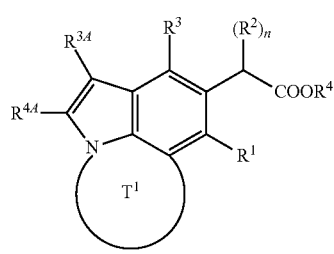

(I-A-1)

wherein $R^1$ is alkyl; n is 1, $R^2$ is alkyloxy; $R^4$ is hydrogen; $R^3$ is substituted or unsubstituted aromatic carbocyclyl or substituted or unsubstituted non-aromatic carbocyclyl, $R^{3A}$ is hydrogen, $R^{4A}$ is substituted or unsubstituted aromatic heterocyclyl, and $T^1$ ring is substituted or unsubstituted monocyclic heterocycle.

Preferable example of the compound (I-A-1) is the compound (I-A-1-1) to (I-A-1-5) described in the above (16), more preferably the compound described in the following (27) to (31).

(27) The compound or its pharmaceutically acceptable salt according to the above (26) represented by the following formula:

[Chemical formula 43]

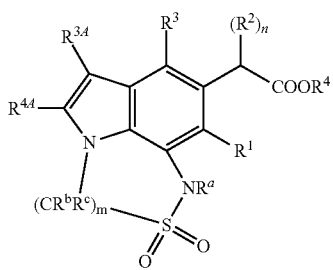

(I-A-1-1)

wherein $R^1$ is alkyl; n is 1, $R^2$ is alkyloxy; $R^4$ is hydrogen; $R^3$ is substituted or unsubstituted aromatic carbocyclyl or substituted or unsubstituted non-aromatic carbocyclyl, $R^{3A}$ is hydrogen, $R^{4A}$ is substituted or unsubstituted aromatic heterocyclyl, m is 1, $R^b$ and $R^c$ is hydrogen, and $R^a$ is hydrogen or alkyl.

(28) The compound or its pharmaceutically acceptable salt according to the above (26) represented by the following formula:

[Chemical formula 44]

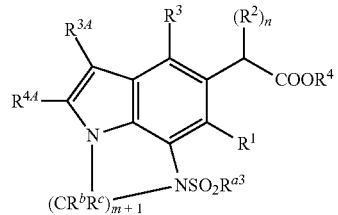

(I-A-1-2)

wherein $R^1$ is alkyl; n is 1, $R^2$ is alkyloxy; $R^4$ is hydrogen; $R^3$ is substituted or unsubstituted aromatic carbocyclyl or substituted or unsubstituted non-aromatic carbocyclyl, $R^{3A}$ is hydrogen, $R^{4A}$ is substituted or unsubstituted aromatic heterocyclyl, m is 1, $R^b$ is each independently hydrogen or alkyl, $R^c$ is hydrogen, and $R^{a3}$ is alkyl.

(29) The compound or its pharmaceutically acceptable salt according to the above (26) represented by the following formula:

[Chemical formula 44]

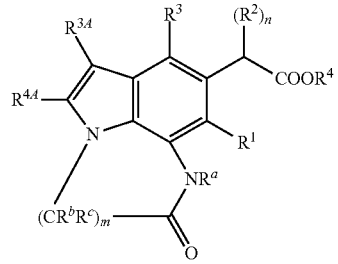

(I-A-1-3)

wherein $R^1$ is alkyl; n is 1, $R^2$ is alkyloxy; $R^4$ is hydrogen; $R^3$ is substituted or unsubstituted aromatic carbocyclyl or substituted or unsubstituted non-aromatic carbocyclyl, $R^{3A}$ is hydrogen, $R^{4A}$ is substituted or unsubstituted aromatic heterocyclyl, m is 1, and $R^a$ is hydrogen or alkyl.

(30) The compound or its pharmaceutically acceptable salt according to the above (26) represented by the following formula:

[Chemical formula 45]

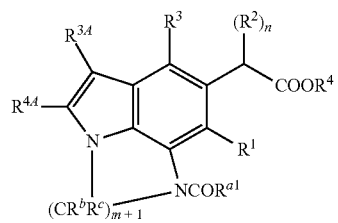

(I-A-1-4)

wherein $R^1$ is alkyl; n is 1, $R^2$ is alkyloxy; $R^4$ is hydrogen; $R^3$ is substituted or unsubstituted aromatic carbocyclyl or substituted or unsubstituted non-aromatic carbocyclyl, $R^{3A}$ is hydrogen, $R^{4A}$ is substituted or unsubstituted aromatic heterocyclyl, m is 1, and $R^{a1}$ is hydrogen or alkyl.

(31) The compound or its pharmaceutically acceptable salt according to the above (26) represented by the following formula:

[Chemical formula 46]

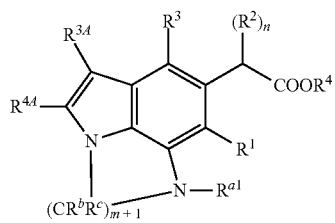

(I-A-1-5)

wherein $R^1$ is alkyl; n is 1, $R^2$ is alkyloxy; $R^4$ is hydrogen; $R^3$ is substituted or unsubstituted aromatic carbocyclyl or substituted or unsubstituted non-aromatic carbocyclyl, $R^{3A}$ is hydrogen, $R^{4A}$ is substituted or unsubstituted aromatic heterocyclyl, m is 1, and $R^{a1}$ is hydrogen or alkyl.

(32) A pharmaceutical composition comprising the compound or its pharmaceutically acceptable salt according to any one of the above (1), (1'), (1"), (2) to (31).

(33) The pharmaceutical composition according to the above (32), having anti-virus activity.

(34) The pharmaceutical composition according to the above (32), having anti-HIV activity.

(35) A method of treating or preventing a HIV infectious disease, which comprises administering the compound or its pharmaceutically acceptable salt according to any one of the above (1), (1'), (1"), (2) to (31).

(36) Use of the compound or its pharmaceutically acceptable salt according to any one of the above (1), (1'), (1"), (2) to (31), for manufacturing a therapeutic or prophylactic agent for a HIV infectious disease.

(37) The compound or its pharmaceutically acceptable salt according to any one of the above (1), (1'), (1"), (2) to (31) for treating or preventing a HIV infectious disease.

(38) A pharmaceutical composition comprising the compound or its pharmaceutically acceptable salt according to any one of the above (1), (1'), (1"), (2) to (31), for the oral administration.

(39) The pharmaceutical composition according to (38), which is a tablet, powder, granule, capsule, pill, film, suspension, emulsion, elixir, syrup, lemonade, spirit, aromatic water, extract, decoction or tincture.

(40) The pharmaceutical composition according to (39), which is a sugarcoated tablet, film-coated tablet, enteric-coated tablet, sustained-release tablet, troche tablet, sublingual tablet, buccal tablet, chewable tablet, orally dispersing tablet, dry syrup, soft capsule, micro capsule or sustained-release capsule.

(41) A pharmaceutical composition comprising the compound or its pharmaceutically acceptable salt according to any one of the above (1), (1'), (1"), (2) to (31), for parenteral administration.

(42) The pharmaceutical composition according to (41) for dermal, subcutaneous, intravenous, intraarterial, intramuscular, intraperitoneal, transmucosal, inhalation, transnasal, ophthalmic, inner ear, or vaginal administration.

(43) The pharmaceutical composition according to (41) or (42), which is injection, infusion, eye drop, nose drop, ear drop, aerosol, inhalation, lotion, impregnation, liniment, mouthwash, enema, ointment, plaster, jelly, cream, patch, cataplasm, external powder or suppository.

(44) A pharmaceutical composition comprising the compound or its pharmaceutically acceptable salt according to any one of the above (1), (1'), (1"), (2) to (31), for a pediatric or geriatric patient.

(45) A pharmaceutical composition comprising a combination of the compound or its pharmaceutically acceptable salt according to any one of the above (1), (1'), (1"), (2) to (31), and a reverse transcriptase inhibitor, a protease inhibitor, integrase inhibitor or the other anti-HIV drug.

(46) A pharmaceutical composition comprising the compound or its pharmaceutically acceptable salt according to any one of the above (1), (1'), (1"), (2) to (31), for a combination treatment with a reverse transcriptase inhibitor, a protease inhibitor, integrase inhibitor, or the other anti-HIV drug.

The present invention moreover provides the following invention.

A method for treatment or prevention of viral infection (example: HIV infection) characterized by administering to a human the above compound or its pharmaceutically acceptable salt.

The above compound or its pharmaceutically acceptable salt, for the treatment or prevention of viral infection (example: HIV infection).

Effects of the Invention

The compound of the present invention has a replication inhibitory activity on a virus, particularly HIV (example: HIV-1), a mutant virus thereof and a resistant virus thereof. Accordingly, the compound of the present invention is useful in the prevention or treatment of viral infections (example: AIDS) and the like. Moreover, the present invention provides a synthetic intermediate for an antiviral drug.

MODE FOR CARRYING OUT THE INVENTION

Each meaning of terms used herein is described below. Each term, alone or in combination with another word, is used in the same meaning.

"Halogen" includes a fluorine atom, a chroline atom, a bromine atom, and an iodine atom. A fluorine atom and a chlorine atom are especially preferable.

"Alkyl" includes C1 to C15, preferably C1 to C10, more preferably C1 to C6, and further preferably C1 to C4 linear or branched hydrocarbon group. For example, it includes methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.

A preferred embodiment of "alkyl" is methyl, methyl, ethyl, n-propyl, isopropyl, n-butyl, isobutyl, sec-butyl, tert-butyl, or n-pentyl. A more preferred embodiment is methyl, ethyl, n-propyl, isopropyl, or tert-butyl.

"Alkenyl" includes a C2 to C15, preferably C2 to C10, more preferably C2 to C6 and further preferably C2 to C4 linear or branched hydrocarbon group having one or more double bond(s) at any position(s). For example, it includes vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

A preferred embodiment of "alkenyl" is vinyl, allyl, propenyl, isopropenyl or butenyl.

"Alkynyl" includes a C2 to C10, preferably C2 to C8, more preferably C2 to C6 and further preferably C2 to C4 linear or branched hydrocarbon group having one or more triple bond(s) at any position(s). For example, it includes ethynyl, propynyl, butynyl, pentynyl, hexynyl, heptynyl, octynyl, nonynyl, decynyl and the like. These may have further a double bond at any available position.

A preferred embodiment of "alkynyl" is ethynyl, propynyl, butynyl, or pentynyl.

"Alkylene" includes a C1 to C15, preferably C1 to C10, more preferably C1 to C10, further preferably C1 to C4 linear or branched divalent hydrocarbon group having one or more double bond(s) at any position(s). For example, it includes methylene, ethylene, trimethylene, propylene, tetramethylene, pentamethylene, hexamethylene and the like.

"Alkenylene" includes a C2 to C15, preferably C2 to C10, more preferably C2 to C6 and further preferably C2 to C4 linear or branched bivalent hydrocarbon group having one or more triple bond(s) at any position(s). For example, it includes vinylene, propenylene, butenylene, pentenylene and the like.

"Alkynylene" includes a C2 to C15, preferably C2 to C10, more preferably C2 to C6 and further preferably C2 to C4 linear or branched divalent hydrocarbon group having one or more double bond(s) at any position(s). Furthermore, it may have double bond(s) at any position(s). For example, it includes ethynylene, propynylene, butynylene, pentynylene, hexynylene and the like.

"Carbocycle" includes a hydrocarbon group, which is monocyclic or polycyclic having two or more rings. In addition, the "carbocycle" also includes a fused ring, a spiro ring and a crosslinked ring. Constituent atom(s) of fused ring, the spiro ring and the crosslinked ring may include heteroatom(s). "Monocyclic carbocycle" means monocyclic carbocycle, it includes aromatic carbocycle and non-aromatic carbocycle.

As "monocyclic aromatic carbocycle", benzene ring is exemplified.

As "monocyclic non-aromatic carbocycle", the monocyclic non-aromatic carbocycle consisting of C3 to C16 is preferred, more preferably C3 to C12, and further preferably C4 to C8. For example, cycloalkane, cycloalkene or the like is exemplified.

As "cycloalkane", cyclopropane, cyclobutane, cyclopentane, cyclohexane, cyclohepta ne, cyclooctane, cyclononane or the like is exemplified.

As "cycloalkene", cyclopropene, cyclobutene, cyclopentene, cyclohexene, cycloheptene, cyclohexadiene or the like is exemplified.

"Heterocycle" means a ring, which is monocyclic or polycyclic having two or more rings, containing one or more, preferably 1 to 4, and same or different of heteroatom(s) selected independently from O, S and N. In addition, the "heterocycle" also includes a fused ring, a spiro ring and a crosslinked ring. Constituent atom(s) of the fused ring, the spiro ring and the crosslinked ring may not include heteroatom(s). "Monocyclic heterocycle" means monocyclic heterocycle, and includes aromatic heterocycle and non-aromatic heterocycle. "Heterocycle" which is polycyclic having two or more rings, includes a fused ring wherein a heterocycle which is monocyclic or polycyclic having two or more rings, is fused with a ring of the above "carbocycle".

"Heterocycle" is preferably 5 to 7-membered or 8 to 12-membered ring.

As "monocyclic aromatic heterocycle", 5 to 6-membered aromatic heterocycle is exemplified.

As "monocyclic non-aromatic heterocycle", 5 to 10-membered non-aromatic heterocycle is exemplified.

"Carbocycle" and "heterocycle" also includes a ring having a crosslinked ring or a spiro ring. "Crosslinked ring" means a ring having a crosslinked structure in which two atoms, which are not adjacent to one another, constituting the ring is bridged by alkylene, alkenylene, alkynylene or the like.

[Chemical formula 47]

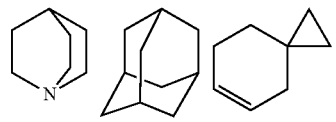

"Carbocyclyl" means a monocyclic or polycyclic having two or more rings hydrocarbon group, and includes a fused cyclic group, a spiro cyclic group and a crosslinked cyclic group. Carbocyclyl includes aromatic carbocyclyl and non-aromatic carbocyclyl.

"Heterocyclyl" means a cyclic group, which is monocyclic or polycyclic having two or more rings, containing one or more, preferably 1 to 4, and same or different of heteroatom(s) selected independently from O, S and N. In addition, "heterocyclyl" includes a fused cyclic group, a spiro cyclic group and a crosslinked cyclic group. Constituent atom(s) of the fused cyclic group, the spiro cyclic group and the crosslinked cyclic group may not include heteroatom(s). "Heterocyclyl" includes aromatic heterocyclyl and non-aromatic heterocyclyl. "Heterocyclyl" which is polycyclic having two or more rings includes a fused cyclic group wherein a heterocycle which is monocyclic or polycyclic having two or more rings, is fused with a ring of the above "carbocycle". "Heterocyclyl" is preferably 5 to 7-membered.

"Aromatic carbocycle" includes a cyclic aromatic hydrocarbon ring which is monocyclic or polycyclic having two or more rings. For example, benzene ring, naphthalene ring, anthracene ring, phenanthrene ring or the like is exemplified.

An embodiment of "aromatic carbocycle" includes benzene ring, naphthalene ring. Another embodiment thereof includes benzene ring.

"Aromatic carbocyclyl" means a cyclic hydrocarbon group which is monocyclic or polycyclic having two or more rings. For example, phenyl, naphthyl, anthryl, phenanthryl or the like is exemplified.

A preferred embodiment of "aromatic carbocyclyl" includes phenyl.

"Non-aromatic carbocycle" includes a cyclic saturated hydrocarbon ring or a cyclic unsaturated non-aromatic hydrocarbon ring, which is monocyclic or polycyclic having two or more rings. "Non-aromatic carbocycle" which is polycyclic having two or more rings, includes a fused ring wherein a non-aromatic carbocycle, which is monocyclic or polycyclic having two or more rings, is fused with a ring of the above "aromatic carbocycle".

In addition, "non-aromatic carbocycle" also includes a ring having a bridge or a ring to form a spiro ring.

[Chemical formula 48]

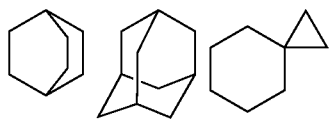

Monocyclic non-aromatic carbocycle is preferably C3 to C16, more preferably C3 to C12, and further preferably C3 to C8. For example, cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclohexadiene or the like is exemplified.

Non-aromatic carbocycle which is polycyclic having two or more rings includes, for example, indane, indene, acenaphthalene, tetrahydronaphhalene, fluorine and the like.

"Non-aromatic carbocyclyl" means a cyclic saturated hydrocarbon group or a cyclic unsaturated non-aromatic hydrocarbon, which is monocyclic or polycyclic having two or more rings. Non-aromaic carbocyclyl which is polycyclic having two or more rings includes a fused cyclic group wherein a non-aromatic carbocyclyl, which is monocyclic or polycyclic having two or more rings, is fused with a ring of the above "aromatic carbocyclyl".

In addition, the "non-aromatic carbocyclyl" also includes a group having a bridge or a group to form a spiro ring as follows:

[Chemical formula 49]

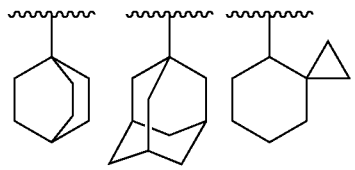

Monocyclic non-aromatic carbocyclyl is preferably C3 to C16, more preferably C3 to C12, and further preferably C4 to C8. For example, cycloalkyl, cycloalkenyl or the like is exemplified.

"Cycloalkyl" is preferably C3 to C10, more preferably C3 to C7, and includes cyclopropyl, cyclobutyl, cyclopentyl, cyclohexyl, cycloheptyl, cyclooctyl, cyclononyl, cyclodecyl and the like.

"Cycloalkenyl" includes cyclopropenyl, cyclobutenyl, cyclopentenyl, cyclohexenyl, cycloheptenyl, cyclohexadienyl and the like.

Non-aromatic carbocyclyl which is polycyclic having two or more rings includes, for example, indanyl, indenyl, acenaphthyl, tetrahydronaphthyl, fluorenyl, dihydroindenyl and the like.

"Aromatic heterocycle" means an aromatic ring, which is monocyclic or polycyclic having two or more rings, containing one or more and same or different of heteroatom(s) selected independently from O, S and N.

"Aromatic heterocycle", which is polycylic having two or more rings, includes a fused ring wherein an aromatic heterocycle, which is monocyclic or polycyclic having two or more rings, is fused with a ring of the above "aromatic carbocycle".

Monocyclic aromatic heterocycle is preferably 5- to 8-membered, more preferably 5- or 6-membered. For example, pyrrole, imidazole, pyrazole, pyridine, pyridazine, pyrimidine, pyrazine, triazole, triazine, tetrazole, furan, thiophen, isoxazole, oxazole, oxadiazole, isothiazole, thiazole, thiadiazole or the like is exemplified.

Bicyclic aromatic heterocycle includes, for example, indoline, isoindoline, indazoline, indolidine, quinoline, isoquinoline, cinnoline, phthalazine, quinazoline, naphthyridine, quinoxaline, purine, puteridine, benzimidazole, benzisoxazole, benzoxazole, benzoxadiazole, benzoisothiazole, benzothiazole, benzothiazole, benzofuran, isobenzofuran, benzothiophen, benzotriazole, imidazopyridine, triazolopyridine, imidazothiazole, pyrradinopyridazine, oxazolopyridine, thiazolopyridine and the like.

Aromatic heterocycle which is polycyclic having three or more rings includes, for example, carbazole, acridine, xanthene, phenothiazine, phenoxathiine, phenoxazine, dibenzofuran and the like.

"Aromatic heterocyclyl" means an aromatic cyclic group, which is monocyclic or polycyclic having two or more rings, containing one or more and same or different of heteroatom(s) selected independently from O, S and N.

Aromatic heterocyclyl, which is polycyclic having two or more rings, includes a fused cyclic group wherein an aromatic heterocyclyl which is monocyclic or polycyclic having two or more rings is fised with the ring of the above "aromatic carbocyclyl".

Monocyclic aromatic heterocyclyl is preferably 5 to 10-membered, more preferably 5- or 6-membered. For example, pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl or the like is exemplified.

Bicyclic aromatic heterocyclyl is preferably 8 to 18-membered ring. For example, it includes indolyl, isoindolyl, indazolyl, indolidinyl, quinolinyl, isoquinolinyl, cinnnolinyl, phthalazinyl, quinazolinyl, naphthylidinyl, quinoxalinyl, prynyl, puteriinyl, banzmidazolyl, benzisooxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazine, oxzolopyridyl, thiazolopyridyl and the like.

Aromatic heterocyclyl, which is polycyclic having three or more rings, is preferably 11 to 26-membered ring. For example, it includes carbazolyl, acridinyl, xanthenyl, phenothiazinyl, phenoxathiinyl, phenoxazinyl, dibenzofuryl and the like.

"Non-aromatic heterocycle" includes a non-aromatic ring, which is monocyclic or polycyclic having two or more rings, containing one or more and same or different of heteroatom(s) independently selected from O, S and N.

"Non-aromatic heterocycle", which is polycyclic having two or more rings, includes a fused ring wherein a non-aromatic heterocycle, which is monocyclic or polycyclic having two or more ring(s), is fused with a ring of the above "aromatic carbocycle", "non-aromatic carbocycle", and/or "aromatic heterocycle".

In addition, the "non-aromatic heterocycle" also includes a ring having a bridge or a ring to form a spiro ring as follows.

[Chemical formula 50]

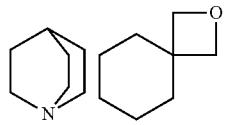

Monocyclic non-aromatic heterocycle is preferably 3 to 8-membered, more preferably 5 or 6-membered ring. For example, it includes dioxane, thiirane, oxyrane, oxetane, oxathiorane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyran, dihydrothiazoline, tetrahydrothiazoline, tetrahydroisothiazoline, dihydrooxadine, hexahydroazepine, tetrahydrodiazepine, tetrahydropyridazine, hexahydropyrimidine, dioxolane, dioxazine, aziridine, dioxoline, oxepane, thiolane, thiazie and the like.

Non-aromatic heterocycle which is polycyclic having two or more rings includes, for example, indoline, isoindoline, chromane, isochromane and the like.

"Non-aromatic heterocyclyl" means a non-aromatic cyclic group, which is monocyclyl or polycyclyl having two or more rings, containing one or more and same or different heteroatom(s) independently selected from O, S and N.

"Non-aromatic heterocyclyl" which is polycyclic having two or more rings, includes a fused cyclic group wherein a non-aromatic heterocyclyl, which is monocyclic or polycyclic having two or more rings, is fused with a ring of the above "aromatic carbocyclyl", "non-aromatic carbocyclyl", and/or "aromatic heterocyclyl".

In addition, the "non-aromatic heterocyclyl" also includes a group having a bridge or a group to form a spiro ring as follows.

[Chemical formula 51]

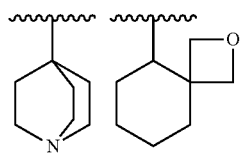

Monocyclic non-aromatic heterocyclyl is preferably 3 to 8-membered, more preferably 5 or 6-membered ring. For example, it includes dioxanyl, thiiranyl, oxyranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidinyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxadinyl, hexahidroazepinyl, tetrahydrodiazepinyl, tetrahydropyridazinyl, hexahydropyrimidinyl, dioxolanyl, dioxadinyl, aziridinyl, dioxolinyl, oxepanyl, thiolanyl, thiinyl, thiazinyl and the like.

Non-aromatic heterocyclyl which is polycyclic having two or more rings includes, for example, indolinyl, isoindolinyl, chromanyl, isochromanyl, dihydrobenzofuryl, benzodioxolyl, benzodioxanyl, benzomorpholinyl and the like.

"Hydroxyalkyl" means a group wherein hydrogen atom(s) attached to a carbon atom(s) of the above "alkyl" is replaced with one or more hydroxyl group(s). For example, it includes hydroxymethyl, 1-hydroxyethyl, 2-hydroxyethyl, 1-hydroxypropyl, 2-hydroxypropyl, 1,2-hydroxyethyl and the like.

A preferred embodiment of "hydroxyalkyl" is hydroxymethyl.

"Alkyloxy" means a group wherein the above "alkyl" is bonded to an oxygen atom. For example, it includes methoxy, ethoxy, n-propyloxy, isopropyloxy, n-butyloxy, tert-butyloxy, isobutyloxy, sec-butyloxy, pentyloxy, isopentyloxy, hexyloxy and the like.

A preferred embodiment of "alkyloxy" is methoxy, ethoxy, n-propyloxy, isopropyloxy, tert-butyloxy or the like.

"Alkenyloxy" means a group wherein the "alkenyl" is bonded to an oxygen atom. For example, it includes vinyloxy, allyloxy, 1-propenyloxy, 2-butenyloxy, 2-petenyloxy, 2-hexenyloxy, 2-heptenyloxy, 2-octenyloxy and the like.

"Alkynyloxy" means a group wherein the above "alkynyl" is bonded to an oxygen atom. For example, it includes ethynyloxy, 1-propynyloxy, 2-propynyloxy, 2-buthynyloxy, 2-pentynyloxy, 2-hexynyloxy, 2-heptynyloxy, 2-octynyloxy and the like.

"Haloalkyl" means a group wherein one or more "halogen" described above is bonded to the above "alkyl". For example, it includes monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropane-2-yl and the like.

A preferred embodiment of "haloalkyl" is trifluoromethyl, trichloromethyl or the like.

"Haloalkyloxy" means a group wherein the above "haloalkyl" is bonded to an oxygen atom. For example, it includes monofluoromethoxy, monofuluoroethoxy, trifluoromethoxy, trichloromethoxy, trifluoroethoxy, trichloroethoxy and the like.

A preferred embodiment of "haloalkyloxy" is trifluoromethoxy or trichloromethoxy.

"Alkyloxyalkyl" means a group wherein the above "alkyloxy" is bonded to the above "alkyl". For example, it includes methoxymethyl, methoxyethyl, ethoxylmethyl and the like.

"Alkyloxyalkyloxy" means a group wherein the above "alkyloxy" is bonded to the above "alkyloxy". For example, it includes methoxymethoxy, methoxyethoxy, ethoxymethoxy, ethoxyethoxy and the like.

"Alkylcarbonyl" means a group wherein the above "alkyl" is bonded to a carbonyl group. For example, it includes methylcarbonyl, ethylcarbonyl, propylcarbonyl, isopropylcarbonyl, tert-butylcarbonyl, isobutylcarbonyl, sec-butylcarbonyl, pentylcarbonyl, isopentylcarbonyl, hexylcarbonyl and the like.

A preferred embodiment of "alkylcarbonyl" is methylcarbonyl, ethylcarbonyl, or n-propylcarbonyl.

"Alkenylcarbonyl" means a group wherein the above "alkenyl" is bonded to a carbonyl group. For example, it includes ethylenylcarbonyl, propenylcarbonyl and the like.

"Alkynylcarbonyl" means a group wherein the above "alkynyl" is bonded to a carbonyl group. For example, it includes ethynylcarbonyl, propynylcarbonyl and the like.

"Monoalkylamino" means a group wherein a hydrogen atom attached to a nitrogen atom of an amino group is replaced with the above "alkyl". For example, it includes methylamino, ethylamino, isopropylamino and the like.

A preferred embodiment of "monoalkylamino" is methylamino or ethylamino.

"Dialkylamino" means a group wherein two hydrogen atoms attached to a nitrogen atom of an amino group are replaced with two "alkyl" described above. These two alkyl groups may be the same or different. For example, it includes dimethylamino, diethylamino, N, N-diisopropylamino, N-methyl-N-ethylamino, N-isopropyl-N-ethylamino and the like.

A preferred embodiment of "dialkylamino" is dimethylamino or diethylamino.

"Alkylsulfonyl" means a group wherein the above "alkyl" is bonded to a sulfonyl group. For example, it includes methylsulfonyl, ethylsulfonyl, propylsulfonyl, isopropylsulfonyl, tert-butylsulfonyl, isobutylsulfonyl, sec-butylsulfonyl and the like.

A preferred embodiment of "alkylsulfonyl" is methylsulfonyl or ethylsulfonyl.

"Alkenylsulfonyl" means a group wherein the above "alkenyl" is bonded to a sulfonyl group. For example, it includes ethylenylsulfonyl, propenylsulfonyl and the like.

"Alkynylsulfonyl" means a group wherein the above "alkynyl" is bonded to a sulfonyl group. For example, it includes ethynylsulfonyl, propynylsulfonyl and the like.

"Monoalkylcarbonylamino" means a group wherein a hydrogen atom attached to a nitrogen atom of an amino group is replaced with the above "alkylcarbonyl". For example, it includes methylcarbonylamino, ethylcarbonylamino, propylcarbonylamino, isopropylcarbonylamino, tert-butylcarbonylamino, isobutylcarbonylamino, sec-butylcarbonylamino and the like.

A preferred embodiment of "monoalkylcarbonylamino" is methylcarbonylamino or ethylcarbonylamino.

"Dialkylcarbonylamino" means a group wherein two hydrogen atoms attached to a nitrogen atom of an amino group is replaced with the above "alkylcarbonyl". These two alkylcarbonyl groups may be the same or different. For example, it includes dimethylcarbonylamino, diethylcarbonylamino, N, N-diisopropylcarbonylamino and the like.

A preferred embodiment of "dialkylcarbonylamino" is dimethylcarbonylamino or diethylcarbonylamino.

"Monoalkylsulfonylamino" means a group wherein a hydrogen atom attached to a nitrogen atom of an amino group is replaced with the above "alkylsulfonyl". For example, it includes methylsulfonylamino, ethylsulfonylamino, propylsulfonylamino, isopropylsulfonylamino, tert-butylsulfonylamino, isobutylsulfonylamino, sec-butylsulfonylamino and the like.

A preferred embodiment of "monoalkylsulfonylamino" is methylsulfonylamino or ethylsulfonylamino.

"Dialkylsulfonylamino" means a group wherein two hydrogen atoms attached to a nitrogen atom of an amino group are replaced with the above "alkylsulfonyl". These two alkylsulfonyl groups may be the same or different. For example, it includes dimethylsulfonylamino, diethylsulfonylamino, N, N-diisopropylsulfonylamino and the like.

A preferred embodiment of "dialkylcarbonylamino" is dimethylsulfonylamino or diethylsulfonylamino.

"Alkylimino" means a group wherein a hydrogen atom attached to a nitrogen atom of an imino group is replaced with the above "alkyl". For example, it includes methylimino, ethylimino, n-propylimino, isopropylimino and the like.

"Alkenylimino" means a group wherein a hydrogen atom attached to a nitrogen atom of an imino group is replaced with the above "alkenyl". For example, it includes ethylenylimino, propenylimino and the like.

"Alkynylimino" means a group wherein a hydrogen atom attached to a nitrogen atom of an imino group is replaced with the above "alkynyl". For example, it includes ethynylimino, propynylimino and the like.

"Alkylcarbonylimino" means a group wherein a hydrogen atom attached to a nitrogen atom of an imino group is replaced with the above "alkylcarbonyl". For example, it includes methylcarbonylimino, ethylcarbonylimino, n-propylcarbonylimino, isopropylcarbonylimino and the like.

"Alkenylcarbonylimino" means a group wherein a hydrogen atom attached to a nitrogen atom of an imino group is replaced with the above "alkenylcarbonyl". For example, it includes ethylenylcarbonylimino, propenylcarbonylimino and the like.

"Alkynylcarbonylimino" means a group wherein a hydrogen atom attached to a nitrogen atom of an imino group is replaced with the above "alkynylcarbonyl". For example, it includes ethynylcarbonylimino, propynylcarbonylimino and the like.

"Alkyloxyimino" means a group wherein a hydrogen atom attached to a nitrogen atom of an imino group is replaced with the above "alkyloxy". For example, it includes methyloxyimino, ethyloxyimino, n-propyloxyimino, isopropyloxyimino and the like.

"Alkenyloxyimino" means a group wherein a hydrogen atom attached to a nitrogen atom of an imino group is replaced with the above "alkenyloxy". For example, it includes ethylenyloxyimino, propenyloxyimino and the like.

"Alkynyloxyimino" means a group wherein a hydrogen atom attached to a nitrogen atom of an imino group is replaced with the above "alkynyloxy". For example, it includes ethynyloxyimino, propynyloxyimino and the like.

"Alkylcarbonyloxy" means a group wherein the above "alkylcarbonyl" is bonded to an oxygen atom. For example, it includes methylcarbonyloxy, ethylcarbonyloxy, propylcarbonyloxy, isopropylcarbonyloxy, tert-butylcarbonyloxy, isobutylcarbonyloxy, sec-butylcarbonyloxy and the like.

A preferred embodiment of "alkylcarbonyloxy" is methylcarbonyloxy or ethylcarbonyloxy.

"Alkenylcarbonyloxy" means a group wherein the above "alkenylcarbonyl" is bonded to an oxygen atom. For example, it includes ethylenylcarbonyloxy, propenylcarbonyloxy and the like.

"Alkynylcarbonyloxy" means a group wherein the above "alkynylcarbonyl" is bonded to an oxygen atom. For example, it includes ethynylcarbonyloxy, propynylcarbonyloxy and the like.

"Alkylsulfonyloxy" means a group wherein the above "alkylsulfonyl" is bonded to an oxygen atom. For example, it includes methylsulfonyloxy, ethylsulfonyloxy, propylsulfonyloxy, isopropylsulfonyloxy, tert-butylsulfonyloxy, isobutylsulfonyloxy, sec-butylsulfonyloxy and the like.

A preferred embodiment of "alkylsulfonyloxy" is methylsulfonyloxy or ethylsulfonyloxy.

"Alkenylsulfonyloxy" means a group wherein the above "alkenylsulfonyl" is bonded to an oxygen atom. For example, it includes ethylenylsulfonyloxy, propenylsulfonyloxy and the like.

"Alkynylsulfonyloxy" means a group wherein the above "alkynylsulfonyl" is bonded to an oxygen atom. For example, it includes ethynylsulfonyloxy, propynylsulfonyloxy and the like.

"Alkyloxycarbonyl" means a group wherein the above "alkyloxy" is bonded to a carbonyl group. For example, it includes methyloxycarbonyl, ethyloxycarbonyl, propyloxycarbonyl, isopropyloxycarbonyl, tert-butyloxycarbonyl, isobutyloxycarbonyl, sec-butyloxycarbonyl, pentyloxycarbonyl, isopentyloxycarbonyl, hexyloxycarbonyl and the like.

A preferred embodiment of "alkyloxycarbonyl" is methyloxycarbonyl, ethyloxycarbonyl, or propyloxycarbonyl.

"Alkenyloxycarbonyl" means a group wherein the above "alkenyloxy" is bonded to a carbonyl group. For example, it includes ethylenyloxycarbonyl, propenyloxycarbonyl and the like.

"Alkynyloxycarbonyl" means a group wherein the above "alkynyloxy" is bonded to a carbonyl group. For example, it includes ethynyloxycarbonyl, propynyloxycarbonyl and the like.

"Alkylsulfanyl" means a group wherein a hydrogen atom attached to a sulfur atom of an sulfanyl group is replaced with the above "alkyl". For example, it includes methylsulfanyl, ethylsulfanyl, n-propylsulfanyl, isopropylsulfanyl and the like.

"Alkenylsulfanyl" means a group wherein a hydrogen atom attached to a sulfur atom of a sulfanyl group is replaced with the above "alkenyl". For example, it includes ethylenylsulfanyl, propenylsulfanyl and the like.

"Alkynylsulfanyl" means a group wherein a hydrogen atom attached to a sulfur atom of a sulfanyl group is replaced with the above "alkynyl". For example, it includes ethynylsulfanyl or propynylsulfanyl and the like.

"Alkylsulfinyl" means a group wherein the above "alkyl" is bonded to a sulfinyl group. For example, it includes methylsulfinyl, ethylsulfinyl, n-propylsulfinyl, isopropylsulfinyl and the like.

"Alkenylsulfinyl" means a group wherein the above "alkenyl" is bonded to a sulfinyl group. For example, it includes ethylenylsulfinyl, propenylsulfinyl and the like.

"Alkynylsulfinyl" means a group wherein the above "alkynyl" is bonded to a sulfinyl group. For example, it includes ethynylsulfinyl, propynylsulfinyl and the like.

"Monoalkylcarbamoyl" means a group wherein a hydrogen atom attached to a nitrogen atom of carbamoyl group is replaced with the above "alkyl". For example, it includes methylcarbamoyl, ethylcarbamoyl and the like.

"Dialkylcarbamoyl" means a group wherein two hydrogen atoms attached to a nitrogen atom of a carbamoyl group are replaced with the above "alkyl". These two alkyl groups may be the same or different. For example, it includes dimethylcarbamoyl, diethylcarbamoyl and the like.

"Monoalkylsulfamoyl" means a group wherein a hydrogen atom attached to a nitrogen atom of a sulfamoyl group is replaced with the above "alkyl". For example, it includes methylsulfamoyl, dimethylsulfamoyl and the like.

"Dialkylsulfamoyl" means a group wherein two hydrogen atoms attached to a nitrogen atom of a sulfamyl group are replaced with the above "alkyl". These two alkyl groups may be the same or different. For example, it includes dimethylcarbamoyl, diethylcarbamoyl and the like.

"Trialkylsilyl" means a group wherein three "alkyl" groups described above are bonded to a silicon atom. These three alkyl may be the same or different. For example, it includes trimethylsilyl, triethylsilyl, tert-butyldimethylsilyl and the like.

The alkyl part of "aromatic carbocyclylalkyl", "non-aromatic carbocyclylalkyl", "aromatic heterocyclylalkyl", "non-aromatic heterocyclylalkyl", "aromatic carbocyclylalkyloxy", "non-aromatic carbocyclylalkyloxy", "aromatic heterocyclylalkyloxy", "non-aromatic heterocyclylalkyloxy", "aromatic carbocyclylalkylsulfanyl", "non-aromatic carbocyclylalkylsulfanyl", "aromatic heterocyclylalkylsulfanyl", "non-aromatic heterocyclylalkylsulfanyl", "aromatic carbocyclylalkyloxycarbonyl", "non-aromatic carbocyclylalkyloxycarbonyl", "aromatic heterocyclylalkyloxycarbonyl", "non-aromatic heterocyclylalkyloxycarbonyl", "aromatic carbocyclylalkyloxyalkyl", "non-aromatic carbocyclylalkyloxyalkyl", "aromatic heterocyclylalkyloxyalkyl", "non-aromatic heterocyclylalkyloxyalkyl", "aromatic carbocyclylalkylamino", "non-aromatic carbocyclylalkylamino", "aromatic heterocyclylalkylamino" and "non-aromatic heterocyclylalkylamino" is also same as the above "alkyl".

"Aromatic carbocyclylalkyl" or "aralkyl" means an alkyl substituted with one or more "aromatic carbocyclyl" described above. For example, it includes benzyl, phenethyl, phenylpropynyl, benzhydryl, trityl, naphthylmethyl, a group of the formula:

[Chemical formula 52]

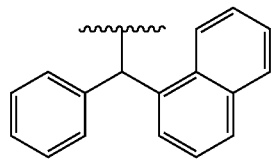

and the like.

A preferred embodiment of "aromatic carbocyclylalkyl" is benzyl, phenethyl, or benzhydryl.

"Non-aromatic carbocyclylalkyl" means an alkyl substituted with one or more "non-aromatic carbocyclyl" described above. In addition, "non-aromatic carbocyclylalkyl" also includes "non-aromatic carbocyclylalkyl" wherein the alkyl part is substituted with the above "aromatic carbocyclyl". For example, it includes cyclopropylmethyl, cyclobutylmethyl, cyclopentylmethyl, cyclohexylmethyl, a group of the formula:

[Chemical formula 53]

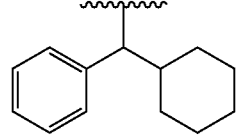

and the like.

"Aromatic heterocyclylalkyl" means an alkyl substituted with one or more "aromatic heterocyclyl" described above. In addition, "aromatic heterocyclylalkyl" also includes "aromatic heterocyclylalkyl" wherein the alkyl part is substituted with the above "aromatic carbocyclyl" and/or "non-aromatic carbocyclyl". For example, it includes pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl, groups of the formula:

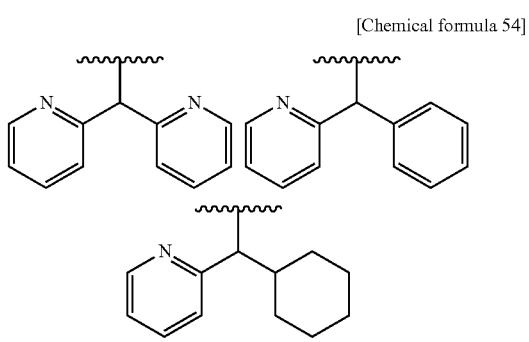

and the like.

"Non-aromatic heterocyclylalkyl" means an alkyl substituted with one or more "non-aromatic heterocyclyl" described above. In addition, "non-aromatic heterocyclylalkyl" also includes "non-aromatic heterocyclylalkyl" wherein the alkyl part is substituted with the above "aromatic carbocyclyl", "non-aromatic carbocyclyl" and/or "aromatic heterocyclyl". For example, it includes tetrahydropyranylmethyl, morpholinylethyl, piperidinylmethyl, piperazinylmethyl, groups of the formula:

[Chemical formula 55]

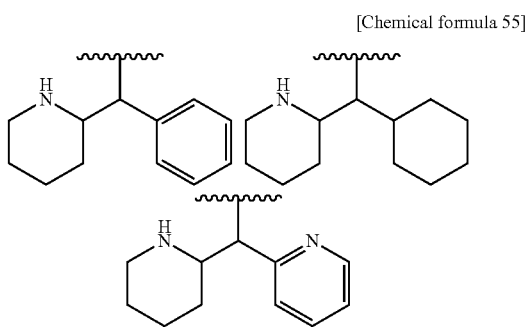

and the like.

"Aromatic carbocyclylalkyloxy" means an alkyloxy substituted with one or more "aromatic carbocyclyl" described above. For example, it includes benzyloxy, phenetyloxy, phenylpropyloxy, benzhydryloxy, trityloxy, naphthylmethyloxy, a group of the formula:

[Chemical formula 56]

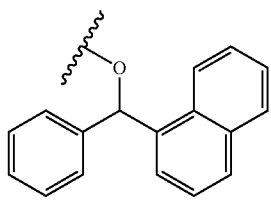

and the like.

"Non-aromatic carbocyclylalkyloxy" means an alkyloxy substituted with one or more "non-aromatic carbocyclyl" described above. In addition, "non-aromatic carbocyclylalkyloxy" includes "non-aromatic carbocyclylalkyloxy" wherein the alkyl part is substituted with the above "aromatic carbocyclyl". For example, it includes cyclopropylmethyloxy, cyclobutylmethyloxy, cyclopentylmethyloxy, cyclohexylmethyloxy, a group of the formula:

[Chemical formula 57]

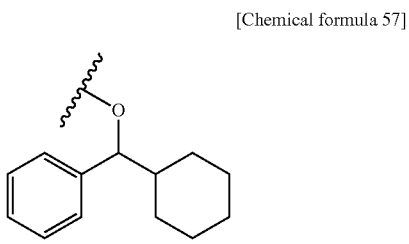 [SMILES: *OC(c1ccccc1)C1CCCCC1]

and the like.

"Aromatic heterocyclylalkyloxy" means alkyloxy substituted with one or more "aromatic heterocyclyl" described above. In addition, "aromatic heterocyclylalkyloxy" also includes "aromatic heterocyclylalkyloxy" wherein the alkyl group is substituted with the above "aromatic carbocyclyl" and/or "non-aromatic carbocyclyl". For example, it includes pyridylmethyloxy, furanylmethyloxy, imidazolylmethyloxy, indolylmethyloxy, benzothiophenylmethyloxy, oxazolylmethyloxy, isoxazolylmethyloxy, thiazolylmethyloxy, isothiazolylmethyloxy, pyrazolylmethyloxy, isopyrazolylmethyloxy, pyrrolidinylmethyloxy, benzoxazolylmethyloxy, groups of the formula:

[Chemical formula 58]

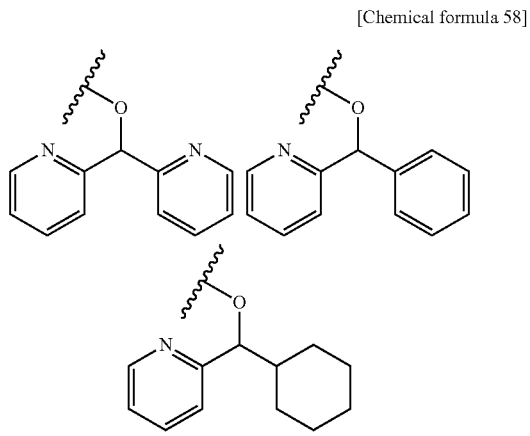

and the like.

"Non-aromatic heterocyclylalkyloxy" means an alkyloxy substituted with one or more "non-aromatic heterocyclyl" described above. In addition, "non-aromatic heterocyclylalkyloxy" also includes "non-aromatic heterocyclylalkyloxy" wherein the alkyl part is substituted with the above "aromatic carbocyclyl", "non-aromatic carbocyclyl" and/or "aromatic heterocyclyl". For example, it includes tetrahydropyranylmethyloxy, morpholinylethyloxy, piperidinylmethyloxy, piperazinylmethyloxy, groups of the formula:

[Chemical formula 59]

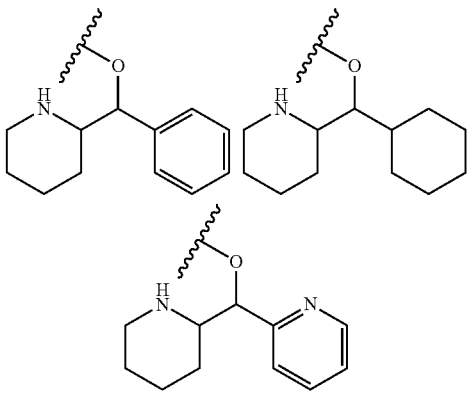

and the like.

"Aromatic carbocyclylalkylsulfanyl" means an alkylsulfanyl substituted with one or more "aromatic carbocyclyl" described above. For example, it includes benzylsulfanyl, phenethylsulfanyl, phenylpopynylsulfanyl, benzhydrylsulfanyl, tritylsulfanyl, naphthylmethylsulfanyl and the like.

"Non-aromatic carbocyclylalkylsulfanyl" means an alkylsulfanyl substituted with one or more "non-aromatic carbocyclyl" described above. In addition, "non-aromatic carbocyclylalkylsulfanyl" also includes "non-aromatic carbocyclylalkylsulfanyl" wherein the alkyl part is substituted with the above "aromatic carbocyclyl". For example, it includes cyclopropylmethylsulfanyl, cyclobutylmethylsulfanyl, cyclopentylmethylsulfanyl, cyclohexylmethylsulfanyl and the like.

"Aromatic heterocyclylalkylsulfanyl" means an alkyl sulfanyl substituted with one or more "aromatic heterocyclyl" described above. In addition, "aromatic heterocyclylalkylsulfanyl" also includes "aromatic heterocyclylalkylsulfanyl" wherein the alkyl part is substituted with the above "aromatic carbocyclyl" and/or "non-aromatic carbocyclyl". For example, it includes pyridylmethylsulfanyl, furanylmethylsulfanyl, imidazolylmethylsulfanyl, indolylmethylsulfanyl, benzothiophenylmethylsulfanyl, oxazolylmethylsulfanyl, isoxazolylmethylsulfanyl, thiazolylmethylsulfanyl, isothiazolylmethylsulfanyl, pyrazolylmethylsulfanyl, isopyrazolylmethylsulfanyl, pyrrolidinylmethylsulfanyl, benzoxazolylmethylsulfanyl and the like.

"Non-aromatic heterocyclylalkylsulfanyl" means an alkylsulfanyl substituted with one or more "non-aromatic heterocyclyl" described above. In addition, "non-aromatic heterocyclylalkylsulfanyl" also includes "non-aromatic heterocyclylalkylsulfanyl" wherein the alkyl part is substituted with the above "aromatic carbocyclyl", "non-aromatic carbocyclyl" and/or "aromatic heterocyclyl". For example, it includes tetrahydropyranylmethylsulfanyl, morpholinylethylsulfanyl, piperidinylmethylsulfanyl, piperazinylmethylsulfanyl and the like.

"Aromatic carbocyclylalkyloxycarbonyl" means an alkyloxycarbonyl substituted with one or more "aromatic carbocyclyl" described above. For example, it includes benzyloxycarbonyl, phenethyloxycarbonyl, phenylpropynyloxycarbonyl, benzhydryloxycarbonyl, tryryloxycarbo nyl, naphthylmethyloxycarbonyl, a group of the formula:

[Chemical formula 60]

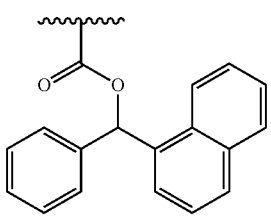

and the like.

"Non-aromatic carbocyclylalkyloxycarbonyl" means an alkyloxycarbonyl substituted with one or more "non-aromatic carbocyclyl" described above. In addition, "non-aromatic carbocyclylalkyloxycarbonyl" also includes "non-aromatic carbocyclylalkyloxycarbonyl" wherein the alkyl part is substituted with the above "aromatic carbocyclyl". For example, it includes cyclopropylmethyloxycarbonyl, cyclobutylmethyloxycarbonyl, cyclopentylmethyloxycarbonyl, cyclohexylmethyloxycarbonyl, a group of the formula:

[Chemical formula 61]

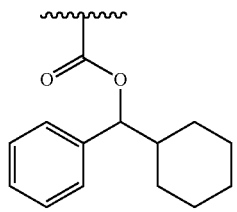

and the like.

"Aromatic heterocyclylalkyloxycarbonyl" means an alkylocycarbonyl substituted with one or more "aromatic heterocyclyl" described above. In addition, "aromatic heterocyclylalkyloxycarbonyl" also includes "aromatic heterocyclylalkyloxycarbonyl" wherein the alkyl part is substituted with the above "aromatic carbocyclyl" and/or "non-aromatic carbocyclyl". For example, it includes pyridylmethyloxycarbonyl, furanylmethyloxycarbonyl, imidazolylmethyloxycarbonyl, indolylmethyloxycarbonyl, benzothiophenylmethyloxycarbonyl, oxazolylmethyloxycarbonyl, isoxazolylmethyloxycarbonyl, thiazolylmethyloxycarbonyl, isothiazolylmethyloxycarbonyl, pyrazolylmethyloxycarbonyl, isopyrazolylmethyloxycarbonyl, pyrrolidinylmethyloxycarbonyl, benzoxazolylmethyloxycarbonyl, groups of the formula:

[Chemical formula 62]

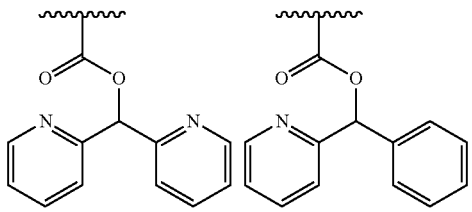

-continued

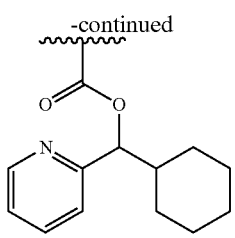

and the like.

"Non-aromatic heterocyclylalkyloxycarbonyl" means an alkyloxycarbonyl substituted with one or more "non-aromatic heterocyclyl" described above. In addition, "non-aromatic heterocyclylalkyloxycarbonyl" also includes "non-aromatic heterocyclylalkyloxycarbonyl" wherein the alkyl part is substituted with the above "aromatic carbocyclyl", "non-aromatic carbocyclyl" and/or "aromatic heterocyclyl". For example, it includes tetrahydropyranylmethyloxy, morpholinylethyloxy, piperidinylmethyloxy, piperazinylmethyloxy, groups of the formula:

[Chemical formula 63]

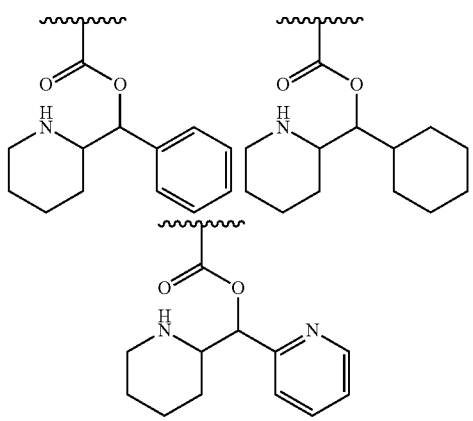

and the like.

"Aromatic carbocyclylalkyloxyalkyl" means an alkyloxyalkyl substituted with one or more "aromatic carbocyclyl" described above. For example, it includes benzyloxymethyl, phenethyloxymethyl, phenylpropynyloxymethyl, benzhydryloxymethyl, trityloxymethyl, naphthylmethyloxymethyl, a group of the formula:

[Chemical formula 64]

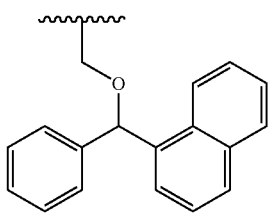

and the like.

"Non-aromatic carbocyclylalkyloxyalkyl" means an alkyloxyalkyl substituted with one or more "non-aromatic carbocyclyl" described above. In addition, "non-aromatic carbocyclylalkyloxyalkyl" also includes "non-aromatic carbocyclylalkyloxyalkyl" wherein the alkyl part bonded to the non-aromatic carbocycle is substituted with the above "aromatic carbocyclyl". For example, it includes cyclopropylmethyloxymethyl, cyclobutylmethyloxymethyl, cyclopentylmethyloxymethyl, cyclohexylmethyloxymethyl, a group of the formula:

[Chemical formula 65]

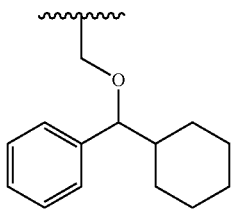

and the like.

"Aromatic heterocyclylalkyloxyalkyl" means an alkyloxyalkyl substituted with one or more "aromatic heterocyclyl" described above. In addition, "aromatic heterocyclylalkyloxyalkyl" also includes "aromatic heterocyclylalkyloxyalkyl" wherein the alkyl part bonded to the aromatic heterocycle is substituted with the above "aromatic carbocyclyl" and/or "non-aromatic carbocyclyl". For example, it includes pyridylmethyloxymethyl, furanylmethyloxymethyl, imidazolylmethyloxymethyl, indolylmethyloxymethyl, banzothiophenylmethyloxymethyl, oxazolylmethyloxymethyl, isoxazolylmethyloxymethyl, thiazolylmethyloxymethyl, isothiazolylmethyloxymethyl, pyrazolylmethyloxymethyl, isopyrazolylmethyloxymethyl, pyrrolidinylmethyloxymethyl, benzoxazolylmethyloxymethyl, groups of the formula:

[Chemical formula 66]

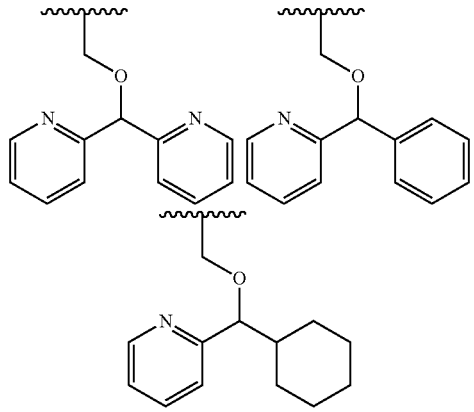

and the like.

"Non-aromatic heterocyclylalkyloxyalkyl" means an alkyloxyalkyl substituted with one or more "non-aromatic heterocyclyl" described above. In addition, "non-aromatic heterocyclylalkyloxy" also includes "non-aromatic heterocyclylalkyloxyalkyl" wherein the alkyl part bonded to the non-aromatic heterocycle is substituted with the above "aromatic carbocyclyl", "non-aromatic carbocyclyl" and/or "aromatic heterocyclyl". For example, it includes tetrahydropyranylmethyloxymethyl, morpholinylethyloxymethyl, piperidinylmethyloxymethyl, piperazinylmethyloxymethyl, groups of the formula:

[Chemical formula 67]

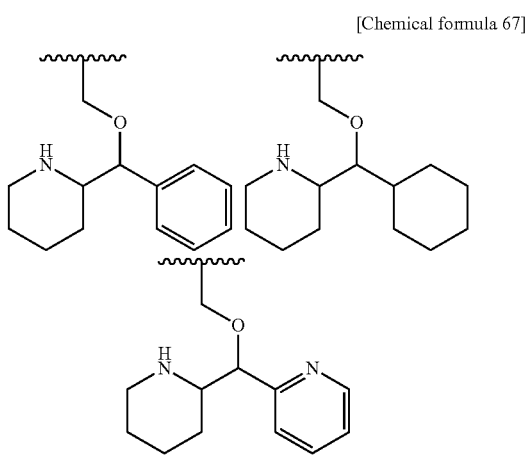

and the like.

"Aromatic carbocyclylalkylamino" means a group wherein one or two hydrogen atom(s) attached to a nitrogen atom of an amino group is(are) replaced with the above "aromatic carbocyclylalkyl". For example, it includes benzylamino, phenethylamino, phenylpropynylamino, benzhydrylamino, tritylamino, naphthylmethylamino, dibenzylamino and the like.

"Non-aromatic carbocyclylalkylamino" means a group wherein one or two hydrogen atom(s) attached to a nitrogen atom of an amino group is(are) replaced with the above "non-aromatic carbocyclylalkyl". For example, it includes cyclopropylmethylamino, cyclobutylmethylamino, cyclopentylmethylamino, cyclohexylmethylamino and the like.

"Aromatic heterocyclylalkylamino" means a group wherein one or two hydrogen atom(s) attached to a nitrogen atom of an amino group is(are) replaced with the above "aromatic heterocyclylalkyl". For example, it includes pyridylmethylamino, furanylmethylamino, imidazolylmethylamino, indolylmethylamino, benzothiophenylmethylamino, oxazolylmethylamino, isoxazolylmethylamino, thiazolylmethylamino, isothiazolylmethylamino, pyrazolylmethylamino, isopyrazolylmethylamino, pyrrolidinylmethylamino, benzoxazolylmethylamino and the like.

"Non-aromatic heterocyclylalkylamino" means a group wherein one or two hydrogen atom(s) attached to a nitrogen atom of an amino group is(are) replaced with the above "non-aromatic heterocyclylalkyl". For example, it includes tetrahydropyranylmethylamino, morpholinylethylamino, piperidinylmethylamino, piperazinylmethylamino and the like.

The "aromatic carbocycleoxy" part of "aromatic carbocycleamino", "aromatic carbocyclylcarbonyl", "aromatic carbocycleoxycarbonyl", "aromatic carbocyclylcarbonylamino", "aromatic carbocyclesulfanyl", and "aromatic carbocycle sulfonyl" is same as the above "aromatic carbocyclyl".

"Aromatic carbocycle oxy" means a group wherein "aromatic carbocycle" is bonded to an oxygen atom. For example, it includes phenyloxy, naphthyloxy and the like.

"Aromatic carbocycle amino" means a group wherein one or two hydrogen atom(s) attached to a nitrogen atom of an amino group is(are) replaced with "aromatic carbocycle". For example, it includes phenylamino, naphthylamino and the like.

"Aromatic carbocyclylcarbonyl" means a group wherein "aromatic carbocycle" is bonded to a carbonyl group. For example, it includes phenylcarbonyl, naphthylcarbonyl and the like.

"Aromatic carbocycle oxycarbonyl" means a group wherein the above "aromatic carbocycle oxy" is bonded to a carbonyl group. For example, it includes phenyloxycarbonyl, naphthyloxycarbonyl and the like.

"Aromatic carbocyclylcarbonylamino" means a group wherein one or two hydrogen atom attached to a nitrogen atom of an amino group is(are) replaced with the above "aromatic carbocyclylcarbonyl". For example, it includes phenylcarbonylamino, naphthylcarbonylamino and the like.

"Aromatic carbocycle sulfanyl" means a group wherein a hydrogen atom attached to a sulfur atom of a sulfanyl group is replaced with "aromatic carbocycle". For example, it includes phenylsulfanyl, naphthylsulfanyl and the like.

"Aromatic carbocycle sulfonyl" means a group wherein "aromatic carbocycle" is bonded to a sulfonyl group. For example, it includes phenylsulfonyl, naphthylsulfonyl and the like.

The "non-aromatic carbocycle" part of "non-aromatic carbocycle oxy", "non-aromatic carbocycle amino", "non-aromatic carbocyclylcarbonyl", "non-aromatic carbocycle oxycarbonyl", "non-aromatic carbocyclylcarbonylamino", "non-aromatic carbocycle sulfanyl", and "non-aromatic carbocycle sulfonyl" is same as the above "non-aromatic carbocyclyl".

"Non-aromatic carbocycle oxy" means a group wherein "non-aromatic carbocycle" is bonded to an oxygen atom. For example, it includes cyclopropyloxy, cyclohexyloxy, cyclohexenyloxy and the like.

"Non-aromatic carbocycle amino" means a group wherein one or two hydrogen atom(s) attached to a nitrogen atom of an amino group is(are) replaced with "non-aromatic carbocycle". For example, it includes cyclopropylamino, cyclohexylamino, cyclohexenylamino and the like.

"Non-aromatic carbocyclylcarbonyl" means a group wherein "non-aromatic carbocycle" is bonded to a carbonyl group. For example, it includes cyclopropylcarbonyl, cyclohexylcarbonyl, cyclohexenylcarbonyl and the like.

"Non-aromatic carbocycle oxycarbonyl" means a group wherein the above "non-aromatic carbocycle oxy" is bonded to a carbonyl group. For example, it includes cyclopropyloxycarbonyl, cyclohexyloxycarbonyl, cyclohexenyloxycarbonyl and the like.

"Non-aromatic carbocyclylcarbonylamino" means a group wherein one or two hydrogen atom(s) attached to a nitrogen atom of an amino group is(are) replaced with the above "non-aromatic carbocyclylcarbonyl". For example, it includes cyclopropylcarbonylamino, cyclohexylcarbonylamino, cyclohexenylcarbonylamino and the like.

"Non-aromatic carbocycle sulfanyl" means a group wherein a hydrogen atom attached to a sulfur atom of a sulfanyl group is replaced with "non-aromatic carbocycle". For example, it includes cyclopropylsulfanyl, cyclohexylsulfanyl, cyclohexenylsulfanyl and the like.

"Non-aromatic carbocycle sulfonyl" means a group wherein "non-aromatic carbocycle" is bonded to a sulfonyl group. For example, it includes cyclopropylsulfonyl, cyclohexylsulfonyl, cyclohexenylsulfonyl and the like.

The "aromatic heterocycle" part of "aromatic heterocycle oxy", "aromatic heterocycle amino", "aromatic heterocyclylcarbonyl", "aromatic heterocycle oxycarbonyl", "aromatic heterocyclylcarbonyl amino", "aromatic heterocycle sulfanyl", and "aromatic heterocycle sulfonyl" is same as the above "aromatic heterocyclyl".

"Aromatic heterocycle oxy" means a group wherein "aromatic heterocycle" is bonded to an oxygen atom. For example, it includes pyridyloxy, oxazolyloxy and the like.

"Aromatic heterocycle amino" means a group wherein one or two hydrogen atom attached to a nitrogen atom of an amino group is(are) replaced with "aromatic heterocycle". For example, it includes pyridylamino, oxazolylamino and the like.

"Aromatic heterocyclylcarbonyl" means a group wherein "aromatic heterocycle" is bonded to a carbonyl group. For example, it includes pyridylcarbonyl, oxazolylcarbonyl and the like.

"Aromatic heterocycle oxycarbonyl" means a group wherein the above "aromatic heterocycle oxy" is bonded to a carbonyl group. For example, it includes pyridyloxycarbonyl, oxazolyloxycarbonyl and the like.

"Aromatic heterocyclylcarbonylamino" means a group wherein one or two hydrogen atom attached to a nitrogen atom of an amino group is(are) replaced with the above "aromatic heterocyclylcarbonyl". For example, it includes pyridylcarbonylamino, oxazolylcarbonylamino and the like.

"Aromatic heterocycle sulfanyl" means a group wherein a hydrogen atom attached to a sulfur atom of a sulfanyl group is replaced with "aromatic heterocycle". For example, it includes pyridylsulfanyl, oxazolylsulfanyl and the like.

"Aromatic heterocycle sulfonyl" means a group wherein "aromatic heterocycle" is bonded to a sulfonyl group. For example, it includes pyridylsulfonyl, oxazolylsulfonyl and the like.

The "non-aromatic heterocycle" part of "non-aromatic heterocycle oxy", "non-aromatic heterocycle amino", "non-aromatic heterocyclylcarbonyl", "non-aromatic heterocycle oxycarbonyl", "non-aromatic heterocyclylcarbonylamino", "non-aromatic heterocycle sulfanyl", and "non-aromatic heterocycle sulfonyl" is same as the above "non-aromatic heterocyclyl".

"Non-aromatic heterocycle oxy" means a group wherein "non-aromatic heterocycle" is bonded to an oxygen atom. For example, it includes piperidinyloxy, tetrahydrofuryloxy and the like.

"Non-aromatic heterocycle amino" means a group wherein a hydrogen atom attached a nitrogen atom of an amino group is replaced with "non-aromatic heterocycle". For example, it includes piperidinylamino, tetrahydrofurylamino and the like.

"Non-aromatic heterocyclylcarbonyl" means a group wherein "non-aromatic heterocycle" is bonded to a carbonyl group. For example, it includes piperidinylcarbonyl, tetrahydrofurylcarbonyl and the like.

"Non-aromatic heterocycle oxycarbonyl" means a group wherein the above "non-aromatic heterocycle oxy" is bonded to a carbonyl group. For example, it includes piperidinyloxycarbonyl, tetrahydrofuryloxycarbonyl and the like.

"Non-aromatic heterocyclylcarbonylamino" means a group wherein one or two hydrogen atom attached to a nitrogen atom of an amino group is(are) replaced with the above "non-aromatic heterocyclylcarbonyl". For example, it includes piperidinylcarbonylamino, tetrahydrofurylcarbonylamino and the like.

"Non-aromatic heterocycle sulfanyl" means a group wherein a hydrogen atom attached to a sulfur atom of a sulfanyl group is replaced with the above "non-aromatic heterocycle". For example, it includes piperidinylsulfanyl, tetrahydrofurylsulfanyl and the like.

"Non-aromatic heterocycle sulfonyl" means a group wherein "non-aromatic heterocycle" is bonded to a sulfonyl group. For example, it includes piperidinylsulfonyl, tetrahydrofurylsulfonyl and the like.

The substituents of "substituted or unsubstituted alkyl", "substituted or unsubstituted alkenyl", "substituted or unsubstituted alkynyl", "substituted or unsubstituted haloalkyl", "substituted or unsubstituted alkyloxy", "substituted or unsubstituted alkenyloxy", "substituted or unsubstituted alkynyloxy", "substituted or unsubstituted haloalkyloxy", "substituted or unsubstituted alkylcarbonyl", "substituted or unsubstituted alkenylcarbonyl", "substituted or unsubstituted alkynylcarbonyl", "substituted or unsubstituted monoalkylamino", "substituted or unsubstituted dialkylamino", "substituted or unsubstituted alkylsulfonyl", "substituted or unsubstituted alkenylsulfonyl", "substituted or unsubstituted alkynylsulfonyl", "substituted or unsubstituted monoalkylcarbonylamino", "substituted or unsubstituted dialkylcarbonylamino", "substituted or unsubstituted monoalkylsulfonylamino", "substituted or unsubstituted dialkylsulfonylamino", "substituted or unsubstituted alkylimino", "substituted or unsubstituted alkenylimino", "substituted or unsubstituted alkynylimino", "substituted or unsubstituted alkylcarbonylimino", "substituted or unsubstituted alkenylcarbonylimino", "substituted or unsubstituted alkynylcarbonylimino", "substituted or unsubstituted alkyloxyimino", "substituted or unsubstituted alkenyloxyimino", "substituted or unsubstituted alkynyloxyimino", "substituted or unsubstituted alkylcarbonyloxy", "substituted or unsubstituted alkenylcarbonyloxy", "substituted or unsubstituted alkynylcarbonyloxy", "substituted or unsubstituted alkylsulfonyloxy", "substituted or unsubstituted alkenylsulfonyloxy", "substituted or unsubstituted alkynylsulfonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfanyl", "substituted or unsubstituted alkenylsulfanyl", "substituted or unsubstituted alkynylsulfanyl", "substituted or unsubstituted alkylsulfinyl", "substituted or unsubstituted alkenylsulfinyl", "substituted or unsubstituted alkynylsulfinyl", "substituted or unsubstituted monoalkylcarbamoyl", "substituted or unsubstituted dialkylcarbamoyl", "substituted or unsubstituted monoalkylsulfamoyl", "substituted or unsubstituted dialkylsulfamoyl", "substituted or unsubstituted alkylene", "substituted or unsubstituted alkenylene" and "substituted or unsubstituted alkynylene" and the like include the following Substiutuent group. A carbon atom at any position(s) may be bonded to the same or different and one or more group(s) selected from the following Substituent group. The substituent(s) is(are) preferably 1 to 4, more preferably 1 to 3.

Substituent group: halogen, hydroxy, carboxy, formyl, formyl oxy, sulfanyl, sulfino, sulfo, thioformyl, thiocarboxy, dithiocarboxy, thiocarbamoyl, cyano, nitro, nitroso, azido, hydradino, ureido, amidino, guanidino, trialkylsilyl, alkyloxy, alkenyloxy, alkynyloxy, haloalkyloxy, alkyl carbonyl, alkenyl carbonyl, alkynyl carbonyl, alkylsulfonyl, alkenyl sulfonyl, alkynyl sulfonyl, alkylcarbonyloxy, alkenylcarbonyloxy, alkynylcarbonyloxy, alkylsulfonyloxy, alkenylsulfonyloxy, alkynylsulfonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, substituted or unsubstituted amino, substituted or unsubstituted imino, substituted or unsubstituted carbamoyl, substituted or unsubstituted sulfamoyl substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocycle oxy, substituted or unsubstituted non-aromatic carbocycle oxy, substituted or unsubstituted aromatic heterocycle oxy, substituted or unsubstituted non-aromatic heterocycle oxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocycle oxycarbonyl, substituted or unsubstituted non-aromatic carbocycle oxycarbonyl, substituted or unsubstituted aromatic heterocycle oxycarbonyl, substituted or unsubstituted non-aromatic heterocycle oxycarbonyl, substituted or unsubstituted aromatic carbocyclylalkyloxy, substituted or unsubstituted non-aromatic carbocyclylalkyloxy, substituted or unsubstituted aromatic heterocyclylalkyloxy, substituted or unsubstituted non-aromatic heterocyclylalkyloxy, substituted or unsubstituted aromatic carbocyclylalkylsulfanyl, substituted or unsubstituted non-aromatic carbocyclylalkylsulfanyl, substituted or unsubstituted aromatic heterocyclylalkylsulfanyl, substituted or unsubstituted non-aromatic heterocyclylalkylsulfanyl, substituted or unsubstituted aromatic carbocyclylalkyloxycarbonyl, substituted or unsubstituted non-aromatic carbocyclylalkyloxycarbonyl, substituted or unsubstituted aromatic heterocyclylalkyloxycarbonyl, substituted or unsubstituted non-aromatic heterocyclylalkyloxycarbonyl, substituted or unsubstituted aromatic carbocycle sulfanyl, substituted or unsubstituted non-aromatic carbocycle sulfanyl, substituted or unsubstituted aromatic heterocycle sulfanyl, substituted or unsubstituted non-aromatic heterocycle sulfanyl, substituted or unsubstituted non-aromatic carbocycle sulfonyl, substituted or unsubstituted aromatic carbocycle sulfonyl, substituted or unsubstituted aromatic heterocycle sulfonyl, and substituted or unsubstituted non-aromatic heterocycle sulfonyl.

The substituents on the ring of "aromatic carbocycle", "non-aromatic carbocycle", "aromatic heterocycle", and "non-aromatic heterocycle" in "substituted or unsubstituted aromatic carbocyclyl", "substituted or unsubstituted non-aromatic carbocyclyl", "substituted or unsubstituted aromatic heterocyclyl", "substituted or unsubstituted non-aromatic heterocyclyl", "substituted or unsubstituted aromatic carbocycle oxy", "substituted or unsubstituted non-aromatic carbocycle oxy", "substituted or unsubstituted aromatic heterocycle oxy", "substituted or unsubstituted non-aromatic heterocycle oxy", "substituted or unsubstituted aromatic carbocycle amino", "substituted or unsubstituted non-aromatic carbocycle amino", "substituted or unsubstituted aromatic heterocycle amino", "substituted or unsubstituted non-aromatic heterocycle amino", "substituted or unsubstituted aromatic carbocyclylcarbonyl", "substituted or unsubstituted non-aromatic carbocyclylcarbonyl", "substituted or unsubstituted aromatic heterocyclylcarbonyl", "substituted or unsubstituted non-aromatic heterocyclylcarbonyl", "substituted or unsubstituted aromatic carbocycle oxycarbonyl", "substituted or unsubstituted non-aromatic carbocycle oxycarbonyl", "substituted or unsubstituted aromatic heterocycle oxycarbonyl", "substituted or unsubstituted non-aromatic heterocycle oxycarbonyl", "substituted or unsubstituted aromatic carbocycle sulfanyl", "substituted or unsubstituted non-aromatic carbocycle sulfanyl", "substituted or unsubstituted aromatic heterocycle sulfanyl", "substituted or unsubstituted non-aromatic heterocycle sulfanyl", "substituted or unsubstituted aromatic carbocycle sulfonyl", "substituted or unsubstituted non-aromatic carbocycle sulfonyl", "substituted or unsubstituted aromatic heterocycle sulfonyl", and "substituted or unsubstituted non-aromatic heterocycle sulfonyl", and the substituents on the ring of "carbocycle" and "heterocycle", include the following Substituent group. An atom at any position(s) on the ring may be bonded to the same or different and one or more group(s) selected from the following Substituent Group. The substituent(s) is(are) preferably 1 to 4, more preferably 1 to 3 group(s). Substituent Group: halogen, hydroxy, carboxy, formyl, formyl oxy, sulfanyl, sulfino, sulfo, thioformyl, thiocarboxy, dithiocarboxy, thiocarbamoyl, cyano, nitro, nitroso, azido, hydradino, ureido, amidino, guanidino, trialkylsilyl, alkyl, alkenyl, alkynyl, haloalkyl, hydroxyalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, alkylsulfonyl, alkenylsulfonyl, alkynylsulfonyl, alkylcarbonyloxy, alkenylcarbonyloxy, alkynylcarbonyloxy, alkylsulfonyloxy, alkenylsulfonyloxy, alkynylsulfonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, substituted or unsubstituted amino, substituted or unsubstituted imino, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocycle oxy, substituted or unsubstituted non-aromatic carbocycle oxy, substituted or unsubstituted aromatic heterocycle oxy, substituted or unsubstituted non-aromatic heterocycle oxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocycle oxycarbonyl, substituted or unsubstituted non-aromatic carbocycle oxycarbonyl, substituted or unsubstituted aromatic heterocycle oxycarbonyl, substituted or unsubstituted non-aromatic heterocycle oxycarbonyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, substituted or unsubstituted aromatic carbocyclylalkyloxy, substituted or unsubstituted non-aromatic carbocyclylalkyloxy, substituted or unsubstituted aromatic heterocyclylalkyloxy, substituted or unsubstituted non-aromatic heterocyclylalkyloxy, substituted or unsubstituted aromatic carbocyclylalkylsulfanyl, substituted or unsubstituted non-aromatic carbocyclylalkylsulfanyl, substituted or unsubstituted aromatic heterocyclylalkylsulfanyl, substituted or unsubstituted non-aromatic heterocyclylalkylsulfanyl, substituted or unsubstituted aromatic carbocyclylalkyloxycarbonyl, substituted or unsubstituted non-aromatic carbocyclylalkyloxycarbonyl, substituted or unsubstituted aromatic heterocyclylalkyloxycarbonyl, substituted or unsubstituted non-aromatic heterocyclylalkyloxycarbonyl, substituted or unsubstituted aromatic carbocyclylalkyloxyalkyl, substituted or unsubstituted non-aromatic carbocyclylalkyloxyalkyl, substituted or unsubstituted aromatic heterocyclylalkyloxyalkyl, substituted or unsubstituted non-aromatic heterocyclylalkyloxyalkyl, substituted or unsubstituted aromatic carbocycle sulfanyl, substituted or unsubstituted non-aromatic carbocycle sulfanyl, substituted or unsubstituted aromatic heterocycle sulfanyl, substituted or unsubstituted non-aromatic heterocycle sulfanyl, substituted or unsubstituted aromatic carbocycle sulfonyl, substituted or unsubstituted non-aromatic carbocycle sulfonyl, substituted or unsubstituted aromatic heterocycle sulfonyl, and substituted or unsubstituted non-aromatic heterocycle sulfonyl.

In addition, "substituted or unsubstituted", "non-aromatic carbocyclyl" and "substituted or unsubstituted non-aromatic heterocycly,optionally substituted with "oxo".

[Chemical formula 68]

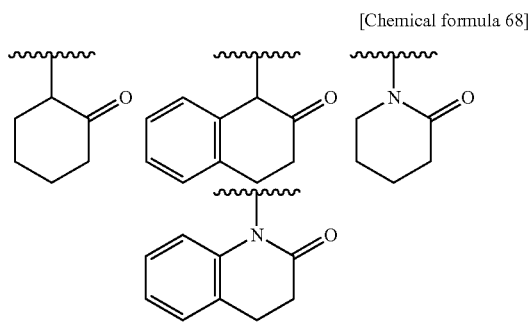

In addition, "substituted or unsubstituted non-aromatic carbocyclyl" and "substituted or unsubstituted non-aromatic heterocyclyl" include a case forming a bridge by alkylene, alkenylene or alkynylene, or a spiro ring with the other ring, for example cycloalkane, cycloalkene, cycloalkyne, oxylane, oxetane, thiirane and the like.

[Chemical formula 69]

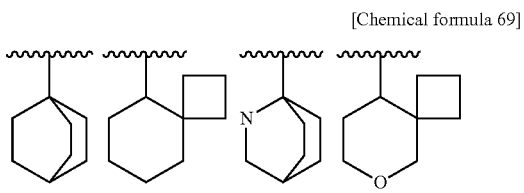

The non-aromatic carbocycle and non-aromatic heterocycle part of the above "substituted or unsubstituted non-aromatic carbocycle oxy", "substituted or unsubstituted non-aromatic heterocycle oxy", "substituted or unsubstituted non-aromatic carbocyclylcarbonyl", "substituted or unsubstituted non-aromatic heterocyclylcarbonyl", "substituted or unsubstituted non-aromatic carbocycle oxycarbonyl", "substituted or unsubstituted non-aromatic heterocycle oxycarbonyl", "substituted or unsubstituted non-aromatic carbocyclylalkyl", "substituted or unsubstituted non-aromatic heterocyclylalkyl", "substituted or unsubstituted non-aromatic carbocyclylalkyloxy", "substituted or unsubstituted non-aromatic heterocyclylalkyloxy", "substituted or unsubstituted non-aromatic carbocyclylalkylsulfanyl", "substituted or unsubstituted non-aromatic heterocyclylalkylsulfanyl", "substituted or unsubstituted non-aromatic carbocyclylalkyloxycarbonyl", "substituted or unsubstituted non-aromatic heterocyclylalkyloxycarbonyl", "substituted or unsubstituted non-aromatic carbocyclylalkyloxyalkyl", "substituted or unsubstituted non-aromatic heterocyclylalkyloxyalkyl", "substituted or unsubstituted non-aromatic carbocycle sulfanyl", "substituted or unsubstituted non-aromatic heterocycle sulfanyl", "substituted or unsubstituted non-aromatic carbocycle sulfonyl", "substituted or unsubstituted non-aromatic heterocycle sulfonyl", "substituted or unsubstituted carbocycle" and "substituted or unsubstituted heterocycle" may be optionally substituted with "oxo" as above.

"Substituted or unsubstituted amino" includes an amino optionally substituted with one or two group(s) selected from the following Substituent Group.

Substituent Group: hydroxy, cyano, alkyl, alkenyl, alkynyl, haloalkyl, haloalkenyl, haloalkynyl, alkyloxy, alkenyloxy, alkynyloxy, haloalkyloxy, haloalkenyloxy, haloalkynyloxy, alkylcarbonyl, alkenylcarbonyl, alkynylcarbonyl, haloalkylcarbonyl, haloalkenylcarbonyl, haloalkynylcarbonyl, alkylsulfonyl, haloalkylsulfonyl, substituted or unsubstituted carbamoyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, substituted or unsubstituted non-aromatic heterocyclylalkyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylalkylcarbonyl, substituted or unsubstituted non-aromatic carbocyclylalkylcarbonyl, substituted or unsubstituted aromatic heterocyclylalkylcarbonyl, substituted or unsubstituted non-aromatic heterocyclylalkylcarbonyl, substituted or unsubstituted aromatic carbocyclylalkyloxycarbonyl, substituted or unsubstituted non-aromatic carbocyclylalkyloxycarbonyl, substituted or unsubstituted aromatic heterocyclylalkyloxycarbonyl, and substituted or unsubstituted non-aromatic heterocyclylalkyloxycarbonyl.

An embodiment of "substituted or unsubstituted amino" includes amino, methylamino, dimethylamino, ethylamino, diethylamino, ethylmethylamino, cyclocpropylamino, cyclohexylamino, benzylamino, acetylamino, benzoylamino, methylsulfonylamino, tetrahydropyranylamino, tetrahydrofuranylamino, morpholinoamino, morpholinylamino, piperidinylamino, piperazinylamino and the like. Another embodiment thereof includes amino, methylamino, dimethylamino, ethylmethylamino, diethylamino, acetylamino, methylsulfonylamino, tetrahydropyranylamino, tetrahydrofuranylamino, morpholinoamino, piperidinylamino and the like.

"Substituted or unsubstituted imino" includes an imino optionally substituted with a group selected from the following Substituent Group.

Substituent Group: hydroxy, alkyl, alkenyl, alkynyl, haloalkyl, haloalkenyl, haloalkynyl, alkyloxy, alkenyloxy, alkynyloxy, haloalkyloxy, haloalkenyloxy, haloalkynyloxy, alkylcarbonyl, alkenylcarbonyl, alkynylcarbonyl, haloalkylcarbonyl, haloalkenylcarbonyl, haloalkynylcarbonyl, amino, alkylamino, haloalkylamino, substituted or unsubstituted aromatic carbocyclyl, substituted or unsubstituted non-aromatic carbocyclyl, substituted or unsubstituted aromatic heterocyclyl, and substituted or unsubstituted non-aromatic heterocyclyl.

An embodiment of "substituted or unsubstituted imino" includes imino, methylimino, ethylimino, cyclopropylimino, cyclohexylimino, acetylimino, tetrahydropyranylimino, tetrahydrofuranylimino, morpholinoimino, morpholinylimino, piperidinylimino, piperazinylimino and the like.

"Substituted or unsubstituted carbamoyl" includes a carbamoyl optionally substituted with one or two group(s) selected from the following Substituent Group.

Substituent Group: hydroxy, cyano, amino, alkyl, alkenyl, alkynyl, haloalkyl, haloalkenyl, haloalkynyl, hydroxyalkyl, alkylamino, alkylcarbonyl, alkenylcarbonyl, alkynylcarbonyl, alkylsulfonyl, alkylcarbonylamino, alkenylcarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, and substituted or unsubstituted non-aromatic heterocyclylalkyl.

An embodiment of "substituted or unsubstituted carbamoyl" includes carbamoyl, N-methylcarbamoyl, N, N-dimethylcarbamoyl, N-ethyl-N-methylcarbamoyl, N, N-diethylcarbamoyl, N-n-propylaminocarbamoyl, N-isopropylcarbamoyl, N-morpholino carbamoyl, N-tetrahydrofuranylcarbamoyl, N-piperidylcarbamoyl, N-tetrahydropyranylcarbamoyl, N-benzylcarbamoyl, N-acetylcarbamoyl, N-methylsulfonylcarbamoyl, N-(2,2,2-trifuluoroethyl)carbamoyl, N-(2-hydroxy-1-methylethyl)carbamoyl and the like. Another embodiment thereof includes carbamoyl, N-methylcarbamoyl, N,N-dimethylcarbamoyl, N-n-propylaminocarbamoyl, N-isopropylcarbamoyl, N-morpholinocarbamoyl, N-tetrahydrofuranylcarbamoyl, N-piperidylcarbamoyl, N-tetrahydropyranylcarbamoyl, N-methylsulfonylcarbamoyl, N-(2,2,2-trifluoroethyl)carbamoyl, N-(2-hydroxy-1-methylethyl)carbamoyl and the like.

"Substituted or unsubstituted sulfamoyl" includes an aminosulfonyl optionally substituted with one or two group(s) selected from the following Substituent Group.
Substituent Group: alkyl, alkenyl, alkynyl, haloalkyl, haloalkenyl, haloalkynyl, hydroxyalkyl, alkylcarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalkyl, substituted or unsubstituted non-aromatic carbocyclylalkyl, substituted or unsubstituted aromatic heterocyclylalkyl, and substituted or unsubstituted non-aromatic heterocyclylalkyl.

An embodiment of "substituted or unsubstituted sulfamoyl" includes sulfamoyl, N-methyl sulfamoyl, N,N-dimethyl sulfamoyl, N-ethyl-N-methylsulfamoyl, N,N-diethylsulfamoyl, N-n-propylaminosulfamoyl, N-isopropylsulfamoyl, N-morpholinosulfamoyl, N-tetrahydrofuranylsulfamoyl, N-pyperidylsulfamoyl, N-tetrahydropyranylsulfamoyl, N-benzylsulfamoyl, N-acetylsulfamoyl, N-methylsulfonylsulfamoyl and the like. Another embodiment includes sulfamoyl, N-methylsulfamoyl, N, N-dimethylsulfamoyl, N-n-propylaminosulfamoyl, N-isopropylsulfamoyl, N-morpholinosulfamoyl, N-tetrahydrofranylsulfamoyl, N-piperidylsulfamoyl, N-tetrahydropyranylsulfamoyl, N-methylsulfonylsulfamoyl and the like.

"Non-cyclic group" is preferably other than hydrogen atom. An example thereof is substituted or unsubstituted alkyl, substituted or unsubstituted alkenyl, substituted or unsubstituted alkynyl, substituted or unsubstituted alkoxy, substituted or unsubstituted alkylamino, or substituted or unsubstituted alkylthio. The substituent(s) thereof include the same or different 1 to 4, preferably 1 to 2 groups selected from the Substituent Group A. The bonding atom in "non-cyclic group" to the benzene ring of the core structure does not form a ring, and may be bonded to arbitrary ring.

Substituent Group A: aryl optionally substituted with Substituent Group B, cycloalkyl optionally substituted with Substituent Group B, heterocyclyl (preferably 5- to 7-membered ring) optionally substituted with Substituent Group B.
Substituent Group B: halogen, hydroxy, alkyl or alkyloxy.

The present invention provides a variety of compounds encompassed by the following compounds (I) or (I)'.

[Chemical formula 70]

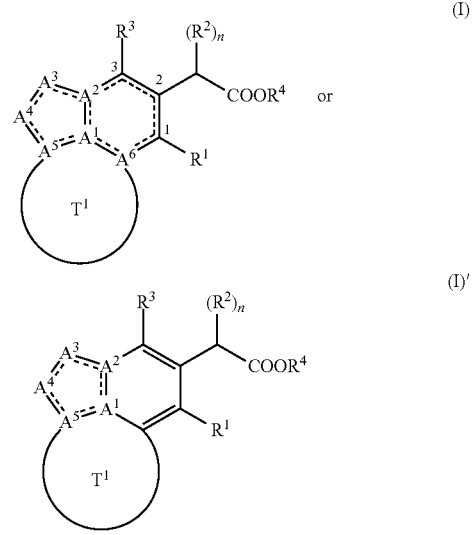

The compound (I) or (I)' has a basic skeleton of the tricyclic structure which is a [6+5]-membered ring fused with a ring represented by $T^1$. The basic skeleton can have various substitutents unless generated a bad effect to the anti HIV replication inhibitory activity as a main activity, and may form further fused rings and the like.

Preferred embodiment of the compound (I) includes the compound (I)'.

Preferred embodiments of each group are exemplified as below.

$R^1$ is halogen, cyano, nitro or $—X^1—R^{11}$ $X^1$ is a bond, $—O—$, $—S—$, $—NR^{12}—$, $—CO—$, $—SO—$, $—SO_2—$, $—O—CO—$, $—CO—O—$, $—NR^{12}—CO—$, $—CO—NR^{12}—$, $—NR^{12}—CO—O—$, $—NR^{12}—CO—NR^{13}—$, $—NR^{12}—SO_2—$ or $—SO_2—NR^{12}—$, $R^{11}$ is a hydrogen atom, substituted or unsubstituted alkyl, substituted or unsubstituted alkenyl, substituted or unsubstituted alkynyl, substituted or unsubstituted carbocyclyl, or substituted or unsubstituted heterocyclyl, $R^{12}$ and $R^{13}$ are each independently a hydrogen atom, substituted or unsubstituted alkyl, substituted or unsubstituted alkenyl or substituted or unsubstituted alkynyl, When $X^1$ is $—NR^{12}—$, $—CO—NR^{12}—$ or $—SO^2—NR^{12}—$, $R^{11}$ and $R^{12}$ may be taken together with an adjacent nitrogen atom to form substituted or unsubstituted heterocyclyl, when $X^1$ is $—NR^{12}—CO—NR^{13}—$, $R^{11}$ and $R^{13}$ may be taken together with an adjacent nitrogen atom to form substituted or unsubstituted heterocyclyl.

$R^1$ is preferably a hydrogen atom, substituted or unsubstituted alkyl, or substituted or unsubstituted alkenyl, more preferably a hydrogen atom or alkyl, further preferably linear or branched alkyl having C1 to C4, particularly preferably methyl. The substituent of "substituted or unsubstituted" in $R^1$ includes hydroxy, alkoxy, halogen, halogenated alkyl, halogenated alkoxy, amino, alkylamino and the like.

$R^2$ is each independently substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyloxy, or substituted or unsubstituted cycloalkenyloxy. It is preferably substituted or unsubstituted alkyl, substituted or unsubstituted alkenyl, substituted or unsubstituted alkyl oxy, or substituted or unsubstituted alkenyloxy, more preferably substituted or unsubstituted alkyloxy, substituted or unsubstituted alkenyloxy, particularly preferably alkyloxy. Alkyloxy is preferably linear or branched alkyloxy having C1 to C6, more preferably t-butyloxy. The substituent of "substituted or unsubstituted" in $R^2$ includes hydroxy, alkoxy, halogen, halogenated alkyl, halogenated alkoxy, amino, alkylamino and the like.

n is 1 or 2, preferably 1.

When n is 1, $R^2$ preferably takes the following steric structure.

[Chemical formula 71]

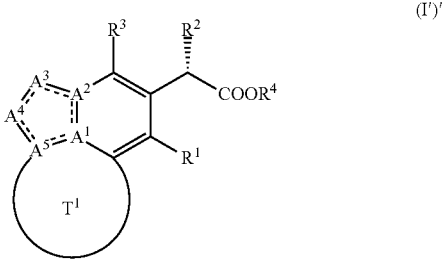

(I')'

$R^3$ is hydrogen, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or non-cyclic group, preferably substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, more preferably substituted or unsubstituted aromatic carbocyclyl. The substituent on these ring are exemplified by the following $R^{31}$ to $R^{35}$.

$R^3$ is preferably substituted or unsubstituted aromatic carbocyclyl or non-aromatic cyclyl, preferably 5 to 7-membered ring, and may be fused and have a bridged structure. The part of fused ring is 5 to 10-membered, may be monocyclic or bicyclic. Substituted or unsubstituted aromatic carbocyclyl includes the benzene ring exemplified by the following formula.

[Chemical formula 72]

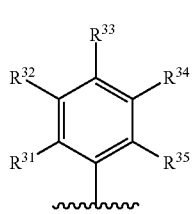

$R^{31}$, $R^{32}$, $R^{33}$, $R^{34}$ and $R^{35}$ are each independently, preferably a hydrogen atom, halogen, hydroxy, amino, alkyl, cycloalkyl, alkenyl, alkynyl, haloalkyl, alkyloxy, alkenyloxy, alkynyloxy haloalkyl, haloalkyloxy, carboxy, carbamoyl, or alkylamino, more preferably a hydrogen atom, halogen, hydroxy, amino, alkyl or alkyl oxy, further preferably hydrogen, fuluoro, chloro, bromo, hydroxy, amino, methyl, ethyl or methyloxy, particularly preferably hydrogen, halogen, hydroxy, methyl or ethyl.

$R^{31}$ and $R^{32}$, $R^{32}$ and $R^{33}$, $R^{33}$ and $R^{34}$, and $R^{34}$ and $R^{35}$ may be each independently taken together with an adjacent atom to form substituted or unsubstituted aromatic carbocycle, substituted or unsubstituted non-aromatic carbocycle, substituted or unsubstituted aromatic heterocycle or substituted or unsubstituted non-aromatic heterocycle. These rings are preferably 5 to 8-membered, more preferably 5 or 6-membered, further preferably 6-membered. The two groups which are not adjacent to each other in $R^{31}$, $R^{32}$, $R^{33}$, $R^{34}$ and $R^{35}$ may be taken together to form a bridged structure. The bridged structure includes substituted or unsubstituted alkylene or substituted or unsubstituted alkenylene. The substituent of "substituted or unsubstituted" is preferably alkyl, cycloalkyl, cycloalkylalkyl, alkoxy, alkoxyalkyl, halogen, halogenated alkyl, amino, alkylamino, hydroxy, oxo, carboxy, carbamoyl or phenyl, more preferably halogen, alkyl, alkoxy, amino, hydroxy and/or oxo, further preferably methyl, ethyl, F, Br, amino, hydroxy and the like.

$R^3$ may be more preferably fused with one or two carbocycle or heterocycle (e.g., 5 to 7-membered ring). More preferred example is cyclyl exemplified as below. The ring of carbocycle, heterocycle, phenyl, non-aromatic carbocycle, or the following cyclyl may be the same or different 1 to 4 substituents (e.g., halogen, hydroxy, alkoxy, amino, mono- or di-alkylamino, alkyl, halogenated alkyl, hydroxyalkyl, aminoalkyl, oxo, cyano).

Non-cyclic group in $R^3$ is preferably other than hydrogen. Examples thereof are substituted or unsubstituted alkyl, substituted or unsubstituted alkenyl, substituted or unsubstituted alkynyl, substituted or unsubstituted alkoxy, substituted or unsubstituted alkylamino, or substituted or unsubstituted alkylthio. The substituents of "substituted or unsubstituted" are the same or different 1 to 4, preferably 1 to 2 group(s) selected from the above Substituent Group A. The bonding atom to the benzene ring of the core structure in the non-cyclic group does not constitute a ring, and may be bonded to an arbitrary ring. Non-cyclic group in $R^3$ is preferably alkenyl, cycloalkyl alkyl, cycloalkyl oxy or the like.

Another embodiment of non-cyclic group in $R^3$ is alkenyl, substituted or unsubstituted aromatic carbocycle alkenyl, substituted or unsubstituted non-aromatic carbocycle alkenyl, substituted or unsubstituted aromatic heterocycle alkenyl, substituted or unsubstituted non-aromatic heterocycle alkenyl, substituted or unsubstituted aromatic carbocycle alkynyl, substituted or unsubstituted non-aromatic carbocycle alkynyl, substituted or unsubstituted aromatic heterocycle alkynyl, or substituted or unsubstituted non-aromatic heterocycle alkynyl, more preferably alkenyl, cycloalkyl alkenyl or the like. The substituents of "substituted or unsubstituted" are the same or different 1 to 4, preferably 1 to 2, group(s) selected from the above Substituent Group A.

$R^3$ is more preferable the following group.

[Chemical formula 73]

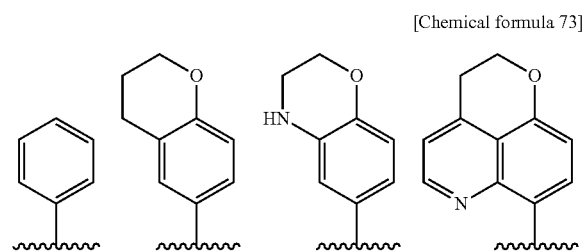

[Chemical formula 74]

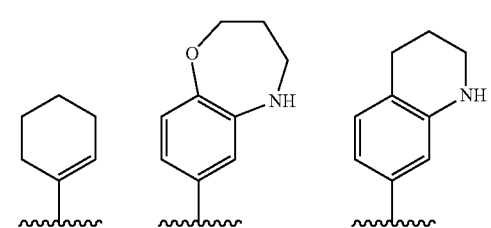

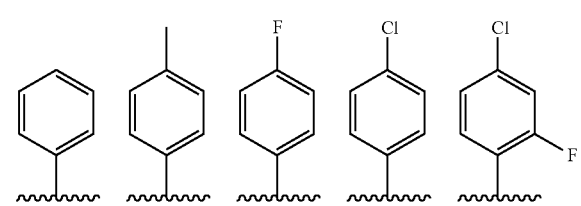

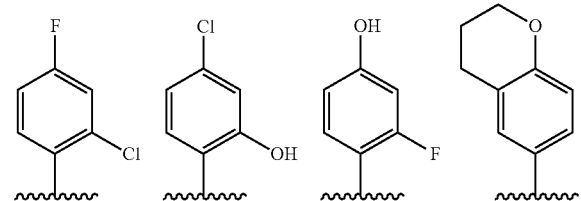

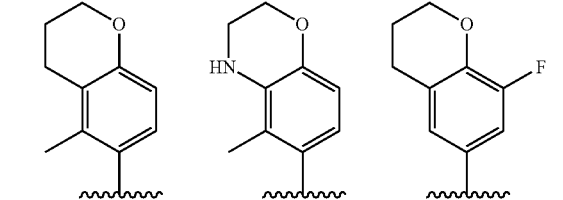

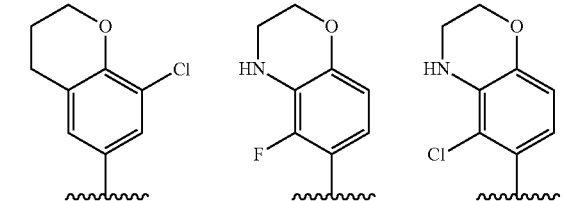

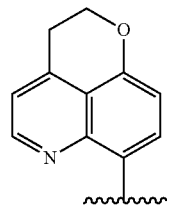

[Chemical formula 75]

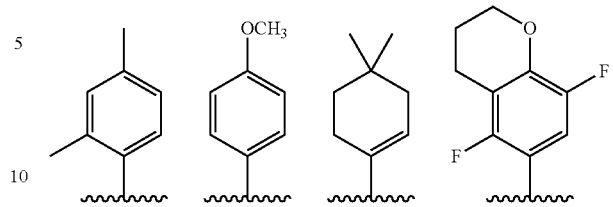

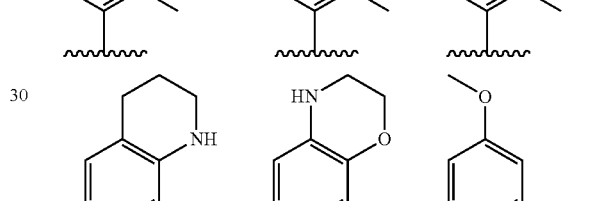

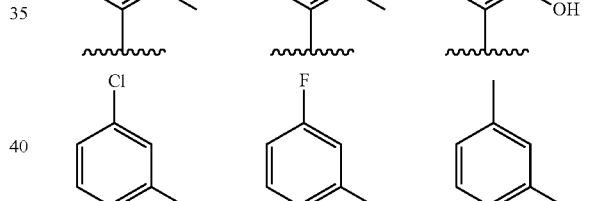

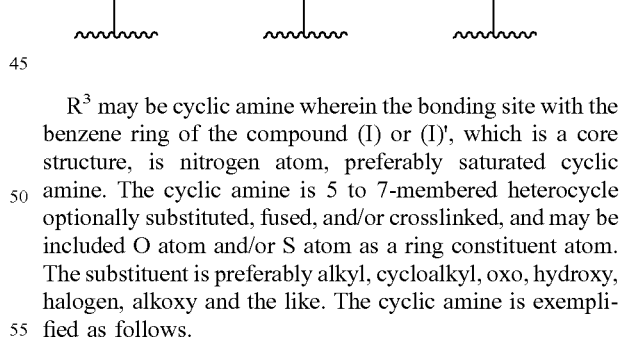

$R^3$ may be cyclic amine wherein the bonding site with the benzene ring of the compound (I) or (I)', which is a core structure, is nitrogen atom, preferably saturated cyclic amine. The cyclic amine is 5 to 7-membered heterocycle optionally substituted, fused, and/or crosslinked, and may be included O atom and/or S atom as a ring constituent atom. The substituent is preferably alkyl, cycloalkyl, oxo, hydroxy, halogen, alkoxy and the like. The cyclic amine is exemplified as follows.

[Chemical formula 76]

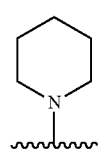

(1)

(2) 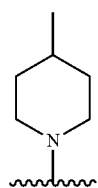

(3) 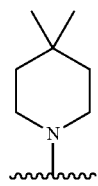

(4) 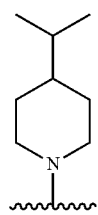

(5) 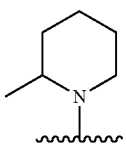

(6) 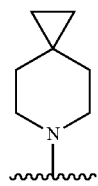

(7) 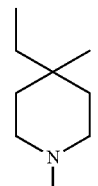

(8) 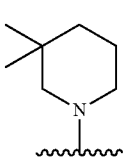

(9) 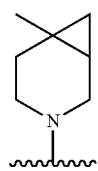

(10) 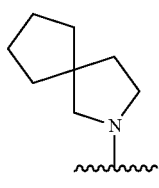

(11) 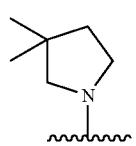

(12) 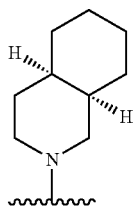

(13) 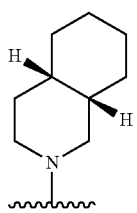

(14) 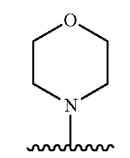

(15) 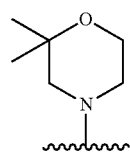

(16) 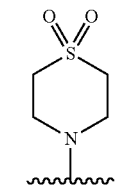

$R^3$ may be substituted or unsubstituted non-aromatic carbocyclyl having one or two double bond in the ring or substituted or unsubstituted non-aromatic heterocyclyl having one or two double bonds in the ring. The carbocyclyl or heterocyclyl is preferably 5 to 7-membered ring. The substituent is preferably alkyl, cycloalkyl, oxo, hydroxy, halogen, alkoxy or the like.

[Chemical formula 77]

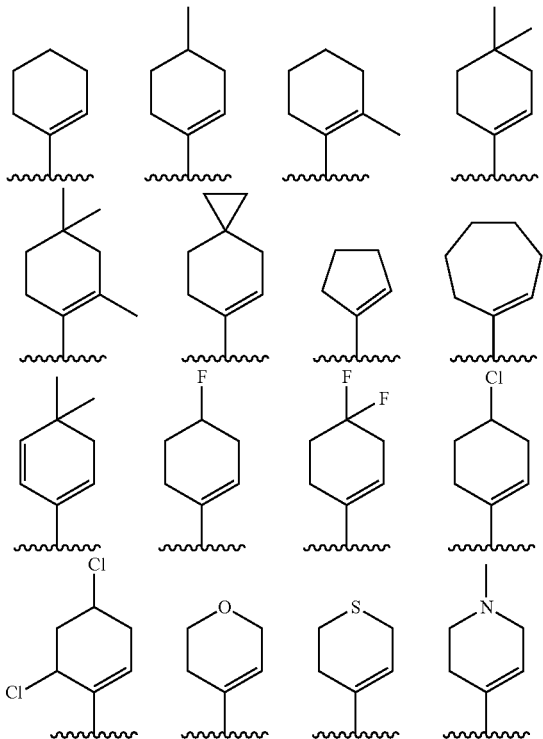

Moreover, $R^3$ may be selected from the following groups.

[Chemical formula 78]

One embodiment of the isomers of the compound (I) or (I)' includes stereoisomers identified by the direction of $R^3$ ring, but the present invention includes all of those isomers and racemics.

$R^4$ is hydrogen, a carboxy protecting group or, substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl or the like, preferably hydrogen. The compound, wherein $R^4$ is other than hydrogen and is converted to hydrogen by hydrolysis or deprotection of a carboxy protecting group, is particularly useful as a synthetic intermediate. Also the compound, wherein $R^4$ is other than hydrogen and can be converted to hydrogen inside the body, is useful as a prodrug. Examples of carboxy protecting groups are preferably alkyl (example: methyl, ethyl, t-butyl), aralkyl (example: benzyl), more preferably C1 to C4 alkyl.

$A^1$ is C, $CR^{1A}$, or N, preferably C or N, more preferably C. $A^2$ is C, $CR^{2A}$, or N, preferably C.

$A^3$ is $CR^{3A}$, $CR^{3A}R^{3B}$, N, $NR^{3C}$, O, S, SO, or $SO_2$, preferably $CR^{3A}$. $R^{3A}$ is preferably hydrogen or alkyl, more preferably hydrogen or C1 to C6 alkyl.

$A^4$ is $CR^{4A}$, $CR^{4A}R^{4B}$, N, $NR^{4C}$, O, S, SO, or $SO_2$, preferably $CR^{4A}$. $R^{4A}$ is preferably hydrogen, alkyl, substituted or unsubstituted amino, substituted or unsubstituted carbamoyl, substituted or unsubstituted phenyl, or substituted or unsubstituted heterocyclyl (example: 4 to 6-membered ring). The substituents of "substituted or unsubstituted amino" include alkyl, halogenated alkyl, carbamoyl, alkyl carbamoyl, alkyl carbonyl, alkyloxycarbonyl, aromatic carbocyclyl optionally substituted with Substituent Group A, non-aromatic carbocyclyl optionally substituted with Substituent Group A, aromatic heterocyclyl optionally substituted with Substituent Group A, non-aromatic heterocyclyl optionally substituted with Substituent Group A, aromatic carbocyclylalkyl optionally substituted with Substituent Group A, aromatic carbocyclylalkyl optionally substituted with Substituent Group A, aromatic heterocyclylalkyl optionally substituted with Substituent Group A, non-aromatic heterocyclylalkyl optionally substituted with Substituent Group A, aromatic carbocyclylalkylcarbonyl optionally substituted with Substituent Group A, non-aromatic carbocyclylalkylcarbonyl optionally substituted with Substituent Group A, aromatic heterocyclylalkylcarbonyl optionally substituted with Substituent Group A, non-aromatic heterocyclylalkyl carbonyl optionally substituted with Substituent Group A, aromatic carbocyclylalkyloxycarbonyl optionally substituted with Substituent Group A, non-aromatic carbocyclylalkyloxycarbonyl optionally substituted with Substituent Group A, aromatic heterocyclylalkyloxycarbonyl optionally substituted with Substituent Group A, non-aromatic heterocyclylalkyloxycarbonyl optionally substituted with Substituent Group A. The substitutents of "substituted or unsubstituted phenyl or heterocyclyl" include Substituent Group A: alkyl, alkenyl, alkynyl, alkoxy, hydroxy, alkoxyalkyl, hydroxyalkyl, halogen, halogenated alkyl, halogenated alkoxy, amino, alkylamino, aminoalkyl, carbamoyl, alkylcarbamoyl, benzyl, halogenated benzyl.

$R^{4A}$ is more preferably hydrogen, alkyl, substituted or unsubstituted phenyl, or substituted or unsubstituted heterocyclyl (example: 4- to 6-membered ring). The substituents of "substituted or unsubstituted" includes alkyl, alkenyl, alkynyl, alkoxy, hydroxy, alkoxyalkyl, hydroxyalkyl, halogen, halogenated alkyl, halogenated alkoxy, amino, alkylamino, aminoalkyl, carbamoyl, alkylcarbamoyl, benzyl, halogenated benzyl.

$A^5$ is C, $CR^{5A}$, or N, preferably N or C.

$A^6$ is C, $CR^{6A}$, or N, preferably N or C, more preferably C.

In $A^1$ to $A^5$, N atoms are preferably up to three.

$R^{1A}$, $R^{2A}$, $R^{3A}$, $R^{3B}$, $R^{4A}$, $R^{4B}$, $R^{5A}$, and $R^{6A}$ are each independently selected from the group consisting of hydrogen, halogen, hydroxy, carboxy, formyl, formyloxy, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocycle oxy, substituted or unsubstituted non-aromatic carbocycle oxy, substituted or unsubstituted aromatic heterocycle oxy, substituted or unsubstituted non-aromatic heterocycle oxy, substituted or unsubstituted aromatic carbocycle thio, substituted or unsubstituted non-aromatic carbocycle thio, substituted or unsubstituted aromatic heterocycle thio, substituted or unsubstituted non-aromatic heterocycle thio, substituted or unsubstituted aromatic carbocycle amino, substituted or unsubstituted non-aromatic carbocycle amino, substituted or unsubstituted aromatic heterocycle amino, substituted or unsubstituted non-aromatic heterocycle amino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylalkylcarbonyl, substituted or unsubstituted non-aromatic carbocyclylalkylcarbonyl, substituted or unsubstituted aromatic heterocyclylalkylcarbonyl, substituted or unsubstituted non-aromatic heterocyclylalkylcarbonyl, substituted or unsubstituted amino, and substituted or unsubstituted carbamoyl.

Moreover, $R^{3A}$ and $R^{3B}$ may be taken together to form oxo, $R^{4A}$ and $R^{4B}$ may be taken together to form oxo.

The substituents of "substituted or unsubstituted" include same or different 1 to 4, preferably 1 to 2, substitutent(s) selected from alkyl, alkoxy, hydroxy, halogen, halogenated alkyl, halogenated alkoxy, amino, alkylamino, substituted or unsubstituted phenyl (example of a substituent: alkyl, alkoxy, hydroxy, halogen), substituted or unsubstituted phenyloxy (example of a substituent: alkyl, alkoxy, hydroxy, halogen), substituted or unsubstituted benzyloxy (example of a substituent: alkyl, alkoxy, hydroxy, halogen), and substituted or unsubstituted heterocyclyl (example: 4- to 6-membered ring, (example of a substituent: alkyl, alkoxy, hydroxy, halogen, heterocyclyl)).

Preferred examples of $R^{1A}$, $R^{2A}$, $R^{3A}$, $R^{3B}$, $R^{4A}$, $R^{4B}$, and $R^{5A}$ are each independently hydrogen, alkyl, substituted or unsubstituted phenyl, or substituted or unsubstituted heterocyclyl (example: 4 to 6-membered ring). Preferred examples of the substituents of "substituted or unsubstituted" include alkyl, alkenyl, alkynyl, alkoxy, hydroxy, alkoxyalkyl, hydroxyalkyl, halogen, halogenated alkyl, halogenated alkoxy, amino, alkylamino, carbamoyl, alkylcarbamoyl, benzyl, halogenated benzyl, phenyl, halogenated phenyl, heterocyclyl, alkylheterocyclyl.

$R^{6A}$ is preferably hydrogen.

Examples of $R^{1A}$, $R^{2A}$, $R^{3A}$, $R^{3B}$, $R^{4A}$, $R^{4B}$, and $R^{5A}$ include the following groups. Particularly preferably, $R^{4A}$ is the following groups.

[Chemical formula 79]

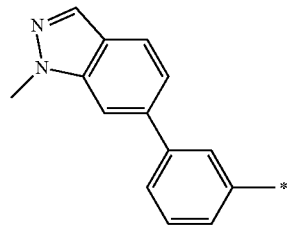

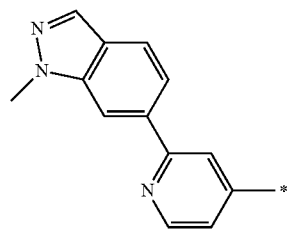

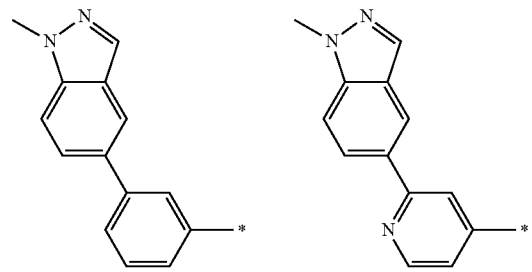

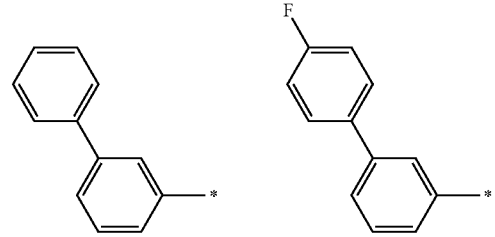

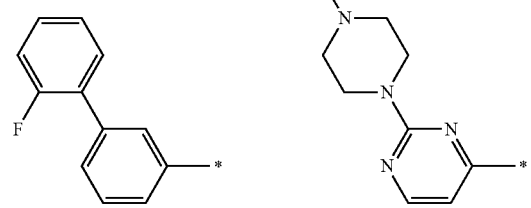

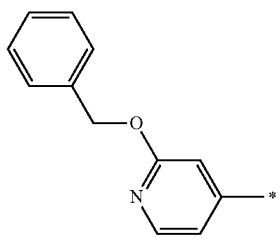

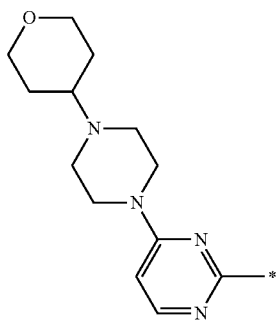 [SMILES: Cc1nccc(N2CCN(C3CCOCC3)CC2)n1]

$R^{3C}$ and $R^{4C}$ are each independently hydrogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, preferably each independently hydrogen or alkyl. Preferred example of the substituents of "substituted or unsubstituted" include alkyl, alkenyl, alkynyl, alkoxy, hydroxy, alkoxyalkyl, hydroxyalkyl, halogen, halogenated alkyl, halogenated alkoxy, amino, alkylamino, carbamoyl, alkylcarbamoyl, benzyl, halogenated benzyl.

$R^{3A}$ and $R^{4A}$ may be taken together with an adjacent atom to form substituted or unsubstituted monocyclic carbocycle or substituted or unsubstituted monocyclic heterocycle. The carbocycle or heterocycle may be further fused to. For example, the compound (I) is represented by the following structure.

[Chemical formula 80]

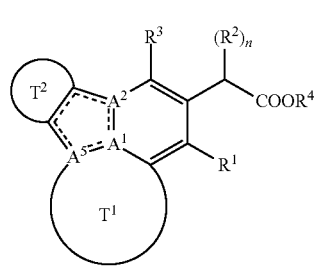
(I-P-1)

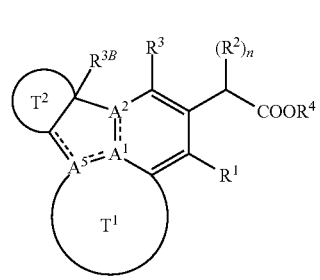
(I-P-2)

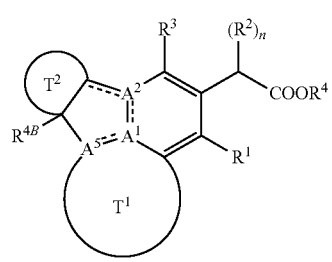
(I-P-3)

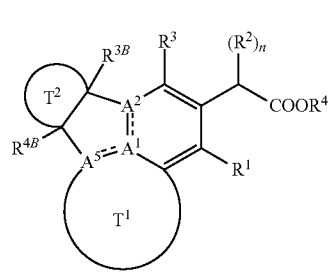
(I-P-4)

wherein $T^2$ ring is substituted or unsubstituted monocyclic carbocycle or substituted or unsubstituted monocyclic heterocycle, the carbocycle or heterocycle may be further fused to.

$R^{3A}$ and $R^{4C}$ may be taken together with an adjacent atom to form substituted or unsubstituted monocyclic heterocycle, the heterocycle may be further fused to. For example, the compound (I) is represented by the following structure.

[Chemical formula 81]

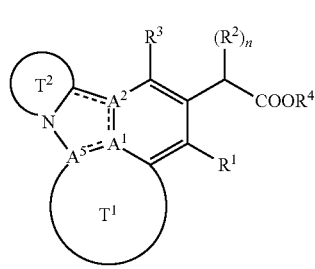
(I-Q-1)

Preferred embodiment of the above any one of $T^2$ ring is represented as follows.

[Chemical formula 84]

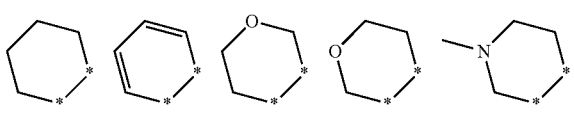

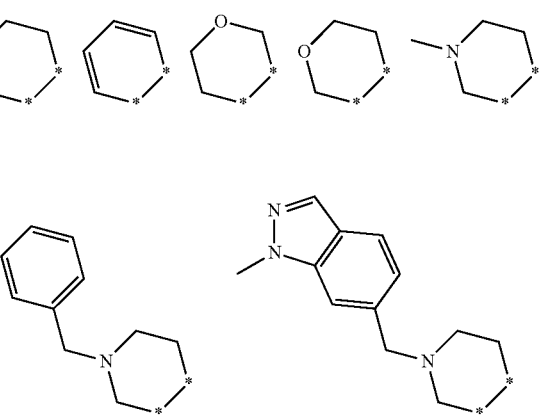

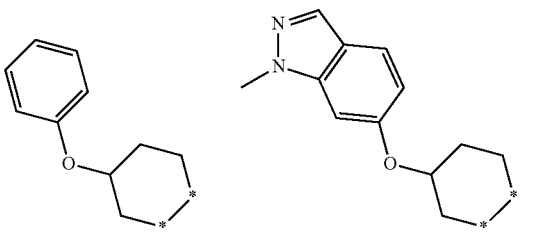

wherein a star mark means a position binding to the mother skeleton, and is C or N atom.

$R^{3A}$ and $R^{3B}$ may be taken together with an adjacent atom to form a substituted or unsubstituted spiro ring, the spiro ring may be further fused to. For example, the compound (I) is represented by the following structure.

[Chemical formula 85]

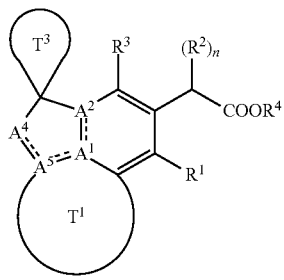

(I-T-1)

wherein $T^3$ ring is substituted or unsubstituted monocyclic carbocycle or substituted or unsubstituted monocyclic heterocycle, the carbocycle or heterocycle may be further fused to.

$R^{4A}$ and $R^{4B}$ may be taken together with an adjacent atom to form a substituted or unsubstituted spiro ring, the spiro ring may be further fused to. For example, the compound (I) is represented by the following structure.

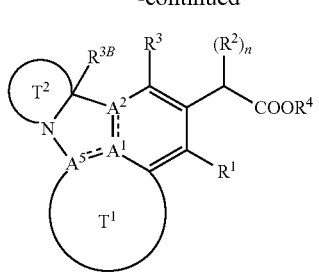

(I-Q-2)

wherein $T^2$ ring is substituted or unsubstituted monocyclic heterocycle, the heterocycle may be further fused to.
$R^{3C}$ and $R^{4A}$ may be taken together with an adjacent atom to form substituted or unsubstituted monocyclic heterocycle, the heterocycle may be further fused to. For example, the compound (I) is represented by the following structure.

[Chemical formula 82]

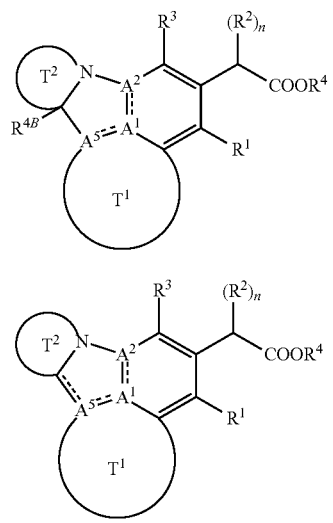

(I-R-1)

(I-R-2)

wherein $T^2$ ring is substituted or unsubstituted monocyclic heterocycle, the heterocycle may be further fused to.
$R^{3C}$ and $R^{4C}$ may be taken together with an adjacent atom to form substituted or unsubstituted monocyclic heterocycle, the heterocycle may be further fused to. For example, the compound (I) is represented by the following structure.

[Chemical formula 83]

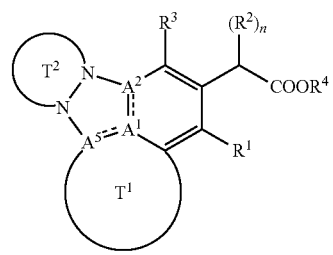

(I-S-1)

wherein $T^2$ ring is substituted or unsubstituted monocyclic heterocycle, the heterocycle may be further fused to.

[Chemical formula 86]

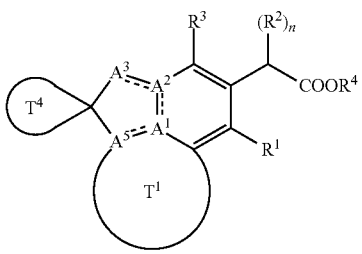

(I-V-1)

wherein T⁴ ring is substituted or unsubstituted monocyclic carbocycle or substituted or unsubstituted monocyclic heterocycle, the carbocycle or heterocycle may be further fused to.

$R^{4B}$ may be taken together with a carbon atom or nitrogen atom on the arc of T¹ ring to form substituted or unsubstituted monocyclic carbocycle, or substituted or unsubstituted monocyclic heterocycle. The carbocycle or heterocycle may be further fused to. For example, the compound (I) is represented by the following structure.

[Chemical formula 87]

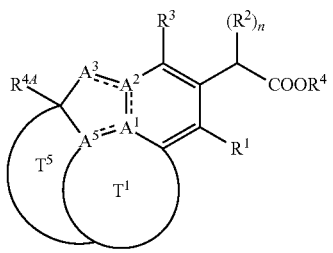

(I-W-1)

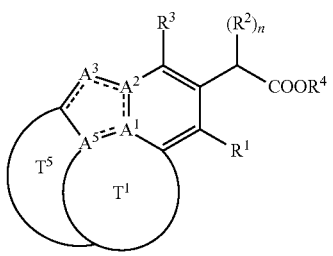

(I-W-2)

wherein T⁵ ring is substituted or unsubstituted monocyclic carbocycle, or substituted or unsubstituted monocyclic heterocycle, the carbocycle or heterocycle may be further fused to.

$R^{4C}$ may be taken together with a carbon atom or nitrogen atom on the arc of T¹ ring to form a substituted or unsubstituted monocyclic heterocycle, the heterocycle may be further fused to. For example, the compound (I) is represented by the following structure.

[Chemical formula 88]

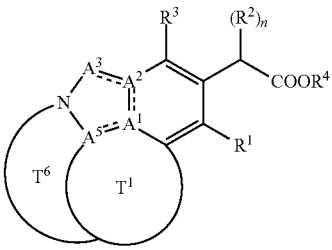

(I-X-1)

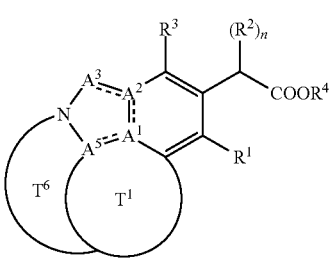

(I-X-2)

wherein T⁶ ring is substituted or unsubstituted monocyclic heterocycle, the heterocycle may be fused to.

In each compound having T² to T⁶ ring, (A¹, A²) is preferably (C, C), (C, N) or (N, C). A⁵ is preferably N or C.

$R^1$ may be taken together with a carbon atom or nitrogen atom on the arc of T¹ ring to form substituted or unsubstituted monocyclic carbocycle or substituted or unsubstituted monocyclic heterocycle, the carbocycle or heterocycle may be further fused to. For example, the compound (I) is represented by the following structure.

[Chemical formula 89]

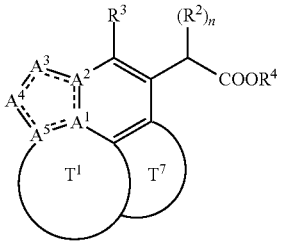

(I-Y-1)

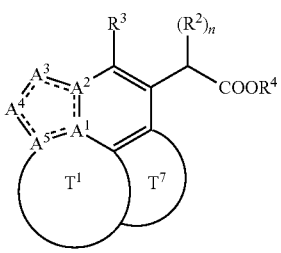

(I-Y-2)

wherein T⁷ ring is substituted or unsubstituted monocyclic carbocycle or substituted or unsubstituted monocyclic heterocycle, the carbocycle or heterocycle may be further fused to.

In the compound (I) and (I)', the broken line means the presence or absence of bond, the adjacent broken lines are not presence at the same time, the carbon atoms at 1 st, 2nd, 3rd positions are sp² carbon. As a preferred embodiment thereof, the broken line was bonded between A¹ and A², and A³ and A⁴.

The constituent atom of T¹ ring at a para position from R³ is carbon atom.

T¹ ring is preferably substituted or unsubstituted 5 to 12-membered ring, more preferably 5 to 10-membered ring. T¹ ring is further preferably 5 to 8-membered ring. T¹ ring is preferably heterocycle, more preferably non-aromatic heterocycle, the constituent atom of the heterocycle preferably includes one to two nitrogen atom(s), or one to two nitrogen atom(s) and one sulfur atom.

T² ring is preferably substituted or unsubstituted 5 to 12-membered ring, more preferably 5 to 10-membered ring, further preferably 5 to 8-membered heterocycle.

T³ ring and T⁴ ring are each independently preferably substituted or unsubstituted 3 to 9-membered ring, more preferably 5 to 7-membered non-aromatic carbocycle or non-aromatic heterocycle.

T⁵ ring and T⁶ ring are each independently preferably substituted or unsubstituted 5 to 20-membered ring, more preferably 5 to 15-membered ring, further preferably 5 to 10-membered ring.

T⁷ ring is preferably substituted or unsubstituted 5 to 12-membered ring, more preferably 5 to 10-membered ring, further preferably 5 to 8-membered heterocycle.

When monocyclic carbocycles or monocyclic heterocycles in T¹ ring, T² ring, T³ ring, T⁴ ring, T⁵ ring, T⁶ ring, and T⁷ ring are each independently further fused to, the fused ring preferably includes substituted or unsubstituted 5 to 12-membered ring, more preferably 5 to 10-membered ring, further preferably 5 to 8-membered monocyclic carbocycle or heterocycle. The substituents on the monocyclic carbocycle or monocyclic heterocycle includes the same or different one to four, preferably one to two, substituent(s) each independently selected from oxo, hydroxy, halogen, amino, alkylamino, substituted or unsubstituted alkyl, substituted or unsubstituted alkenyl, substituted or unsubstituted alkynyl, —COR$^{a1}$, —SOR$^{a2}$, —SO₂R$^{a3}$(R$^{a1}$, R$^{a2}$, and R$^{a3}$ are each independently hydrogen, substituted or unsubstituted alkyl, substituted or unsubstituted alkenyl, substituted or unsubstituted carbocyclyl, or substituted or unsubstituted heterocyclyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylthio, substituted or unsubstituted non-aromatic carbocyclylthio, substituted or unsubstituted aromatic heterocyclylthio, substituted or unsubstituted non-aromatic heterocyclylthio, substituted or unsubstituted alkylcarbonyl, substituted or unsubstituted alkenylcarbonyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylthiocarbonyl, substituted or unsubstituted non-aromatic carbocyclylthiocarbonyl, substituted or unsubstituted aromatic heterocyclylthiocarbonyl, substituted or unsubstituted non-aromatic heterocyclylthiocarbonyl, substituted or unsubstituted aromatic carbocyclylcarbonyloxy, substituted or unsubstituted non-aromatic carbocyclyl carbonyloxy, substituted or unsubstituted aromatic heterocyclylcarbonyloxy, substituted or unsubstituted non-aromatic heterocyclylcarbonyloxy, substituted or unsubstituted aromatic carbocyclylamino, substituted or unsubstituted non-aromatic carbocyclyl amino, substituted or unsubstituted aromatic heterocyclyl amino, substituted or unsubstituted non-aromatic heterocyclyl amino, formyl, and substituted or unsubstituted carbamoyl, substituted or unsubstituted formylalkyl, substituted or unsubstituted carbamoylalkyl, or the after defined R$^a$, R$^b$, and R$^c$. The substituents of "substituted or unsubstituted" include the same or different 1 to 4, preferably 1 to 2 substituent(s) selected from alkyl, alkenyl, alkynyl, alkoxy, hydroxy, alkoxyalkyl, hydroxyalkyl, halogen, halogenated alkyl, halogenated alkoxy, amino, alkylamino, substituted or unsubstituted phenyl (example of a substituent: alkyl, alkoxy, hydroxy, halogen), substituted or unsubstituted phenyloxy (example of a substituent: alkyl, alkoxy, hydroxy, halogen), substituted or unsubstituted benzyloxy (example of a substituent: alkyl, alkoxy, hydroxy, halogen), substituted or unsubstituted heterocyclyl (e.g., 4 to 6-membered, (example of a substituent: alkyl, alkoxy, hydroxy, halogen)), substituted or unsubstituted heterocyclylalkyl, substituted or unsubstituted heterocyclyloxy, and substituted or unsubstituted heterocyclyl amino.

The two atoms, which is not adjacent to each other, constituting monocyclic carbocycle or heterocycle in T¹ ring may be bridged by substituted or unsubstituted alkylene, substituted or unsubstituted alkenylene or substituted or unsubstituted alkynylene. The substituents of the alkylene, alkenylene or alkynylene include methyl, ethyl, halogen, hydroxy, alkoxy, halogenated alkyl, halogenated alkoxy, amino, methyl amino, carbamoyl, phenyl and the like.

T¹ ring preferably includes the structure represented as follows.

[Chemical formula 90]

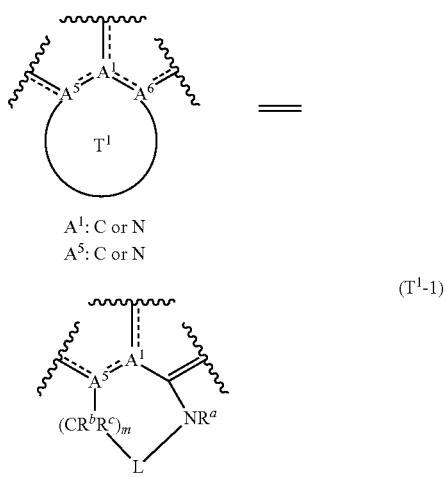

A¹: C or N
A⁵: C or N (T¹-1)

-continued

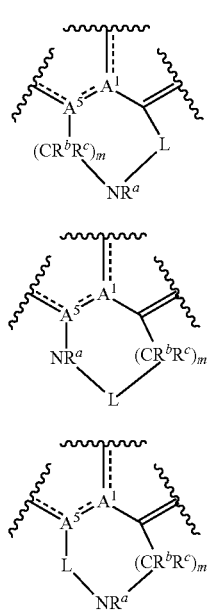

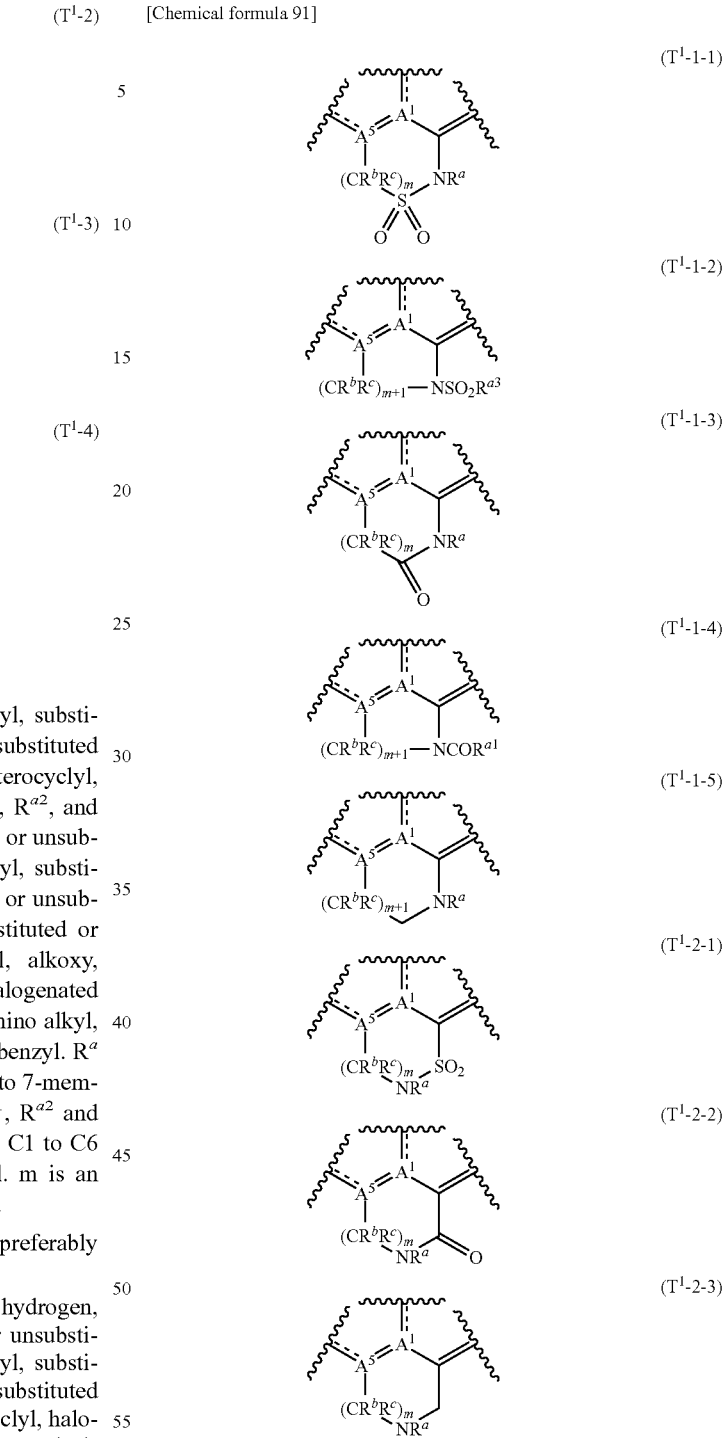

T¹ ring is more preferably (T¹-1) or (T¹-2).

R$^a$ is hydrogen, substituted or unsubstituted alkyl, substituted or unsubstituted alkenyl, substituted or unsubstituted carbocyclyl, substituted or unsubstituted heterocyclyl, —COR$^{a1}$, —SOR$^{a2}$, or —SO$_2$R$^{a3}$ (wherein R$^{a1}$, R$^{a2}$, and R$^{a3}$ are each independently hydrogen, substituted or unsubstituted alkyl, substituted or unsubstituted alkenyl, substituted or unsubstituted carbocyclyl, or substituted or unsubstituted heterocyclyl). The substituents of "substituted or unsubstituted" include alkyl, alkenyl, alkynyl, alkoxy, hydroxy, alkoxyalkyl, hydroxyalkyl, halogen, halogenated alkyl, halogenated alkoxy, amino, alkylamino, amino alkyl, carbamoyl, alkylcarbamoyl, benzyl, halogenated benzyl. R$^a$ is preferably hydrogen, C1 to C6 alkyl, phenyl, 5 to 7-membered heterocyclyl, —COR$^{a1}$, or —SO$_2$R$^{a3}$. R$^{a1}$, R$^{a2}$ and R$^{a3}$ are each independently preferably hydrogen, C1 to C6 alkyl, phenyl, or 5 to 7-membered heterocyclyl. m is an integer of 0 to 5, preferably an integer of 1 to 3.

L is —SO$_2$—, —SO—, —CO—, or —CR$^b$R$^c$—, preferably —SO$_2$—, —CO—, or —CH$_2$—.

R$^b$ and R$^c$ are each independently preferably hydrogen, substituted or unsubstituted alkyl, substituted or unsubstituted alkenyl, substituted or unsubstituted alkynyl, substituted or unsubstituted alkyloxy, substituted or unsubstituted carbocyclyl, substituted or unsubstituted heterocyclyl, halogen, hydroxy, amino, alkylamino, substituted or unsubstituted carbamoyl, R$^b$ and R$^c$ may be taken together to form oxo. The substituents of "substituted or unsubstituted" include halogen, hydroxy, alkoxy, halogenated alkyl, halogenated alkoxy, amino, alkylamino, carbamoyl, alkylcarbamoyl, phenyl, halogenated phenyl, heterocyclyl (e.g., 5 to 7-membered).

R$^b$ and R$^c$ are each independently preferably oxo or C1 to C6 alkyl.

T¹ ring includes more preferably the structure represented as follows.

wherein A¹ is preferably C, A⁵ is preferably N or C, the preferred embodiments of the other symbols are as defined above.

The compound (I) includes a compound comprising any combination selected from the above mentioned preferred embodiments of R¹ to R⁴ and n, the above mentioned preferred embodiments of A¹ to A⁶, and the above mentioned preferred embodiments of T¹ to T⁷ ring. More preferred embodiments of the compound (I) include the above mentioned the compound (I-A), (I-B) and (I-C).

Preferred embodiments of the compound (I-A) include the above mentioned the compound (I-A-1), (I-A-2), (I-A-3), (I-A-4), (I-A-5), (I-A-6), (I-A-5'), (I-A-6'), (I-A-7), (I-A-8), (I-A-9), and (I-A-10), more preferably the compound (I-A-1), (I-A-3), (I-A-4), (I-A-5), and (I-A-8), more preferably the compound (I-A-1-1), (I-A-1-2), (I-A-1-3), (I-A-1-4), (I-A-1-5), (I-A-2-1), (I-A-2-2), (I-A-2-3), (I-A-2-4), (I-A-3-1), (I-A-3-2), (I-A-3-3), (I-A-3-4), (I-A-4-1), (I-A-4-2), (I-A-4-3), (I-A-4-4), (I-A-5-1), (I-A-5-2), (I-A-5-3), (I-A-5-4), (I-A-6-1), (I-A-6-2), (I-A-6-3), (I-A-6-4), (I-A-5'-1), (I-A-5'-2), (I-A-5'-3), (I-A-5'-4), (I-A-6'-1), (I-A-6'-2), (I-A-6'-3), (I-A-6'-4), (I-A-7-1), (I-A-7-2), (I-A-7-3), (I-A-7-4), (I-A-8-1), (I-A-8-2), (I-A-8-3), (I-A-8-4), (I-A-9-1), (I-A-9-2), (I-A-9-3), (I-A-9-4), (I-A-10-1), (I-A-10-2), (I-A-10-3), and (I-A-10-4). Particularly preferable is the compound (I-A-1-1), (I-A-1-2), (I-A-1-3), (I-A-1-4), (I-A-1-5).

The other symbols of these compound or preferred embodiments of the substituents are as defined above.

Preferred embodiment of the compound (I-B) include the above mentioned compound (I-B-1), (I-B-2), (I-B-3), (I-B-4), (I-B-5), (I-B-6), (I-B-7), (I-B-8), and (I-B-9), more preferably the compound (I-B-3) and (I-B-4), further preferably the compound (I-B-1-1), (I-B-1-2), (I-B-1-3), (I-B-1-4), (I-B-2-1), (I-B-2-2), (I-B-2-3), (I-B-2-4), (I-B-3-1), (I-B-3-2), (I-B-3-3), (I-B-3-4), (I-B-4-1), (I-B-4-2), (I-B-4-3), (I-B-4-4), (I-B-5-1), (I-B-5-2), (I-B-5-3), (I-B-5-4), (I-B-6-1), (I-B-6-2), (I-B-6-3), (I-B-6-4), (I-B-7-1), (I-B-7-2), (I-B-7-3), (I-B-7-4), (I-B-8-1), (I-B-8-2), (I-B-8-3), (I-B-8-4), (I-B-9-1), (I-B-9-2), (I-B-9-3), and (I-B-9-4).

The other symbols of these compound or preferred embodiments of the substituents are as defined above.

Preferred embodiment of the compound (I-C) include the above mentioned compound (I-C-1), (I-C-2), (I-C-3), (I-C-4), (I-C-5) and (I-C-6), more preferably the compound (I-C-1-1), (I-C-1-2), (I-C-1-3), (I-C-1-4), (I-C-2-1), (I-C-2-2), (I-C-2-3), (I-C-2-4), (I-C-3-1), (I-C-3-2), (I-C-3-3), (I-C-3-4), (I-C-4-1), (I-C-4-2), (I-C-4-3), (I-C-4-4), (I-C-5-1), (I-C-5-2), (I-C-5-3), (I-C-5-4), (I-C-6-1), (I-C-6-2), (I-C-6-3), and (I-C-6-4). The other symbols of these compound or preferred embodiments of the substituents are as defined above.

Moreover, in the above preferred compound, the present invention includes a compound wherein the part of $T^1$ ring is the structure represented by the above formula ($T^1$-2-1), ($T^1$-2-2), ($T^1$-2-3), ($T^1$-3) or ($T^1$-4). The other symbols of these compound or preferred embodiments of the substituents are as defined above.

The compound of the present invention has a strong HIV replication inhibition activity. More preferably, it is excellent in various useful pharmacokinetics and/or safety and the like as a pharmaceutical. These profiles are remarkably improved by devising, for example, the type or position of heteroatoms on the ring or the type or position of substituents on the ring.

The compound of the present invention includes all possible isomers, preferably stereo isomers (e.g., keto-enol isomers, imine-enamine isomers, diastereo isomers, atropisomers, optical isomers, rotamers etc.), racemates or mixtures thereof. Although these isomers are often easily separated by optical resolution, crystallization, chromatographic separation and the like, these may be displayed in the same flat structural. Also, when these isomers can be separated by chromatographic separation, they are distinguishable by a peak time (RT).

One or more hydrogens, carbons and/or other atoms of the compounds represented by the formula (I) may be substituted by an isotope of hydrogen, carbon and/or the other atom. Examples of the isotope include hydrogen, carbon, nitrogen, oxygen, phosphorus, sulfur, fluorine, iodine and chlorine, like $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$. The compound represented by the formula (I) also includes compounds substituted with the isotope. The compound substituted with the isotope is also useful as a pharmaceutical, and includes all radiolabeled materials of the compounds represented by the formula (I). Also, a "radiolabeling method" for producing the "radiolabeled material" is also included in the present invention, and it is useful as a research and/or diagnostic tool in metabolism pharmacokinetic studies and binding assays.

The radiolabeled material of the compound represented by the formula (I) can be prepared by a method well known in the art. For example, a tritium-labeled compound represented by the formula (I) can be prepared, for example, by introducing tritium into a particular compound represented by the formula (I) by catalytic dehalogenation using tritium. This method includes reacting a precursor, in which the compound represented by the formula (I) is properly substituted with halogen, with tritium gas, in the presence of an appropriate catalyst, for example, Pd/C, in the presence or absence of a base. As the appropriate method for preparing other tritium-labeled compound, document of Isotopes in the Physical and Biomedical Sciences, Vol. 1, Labeled Compounds (Part A), Chapter 6 (1987) can be referred. A $^{14}C$-labeled compound can be prepared by using a raw material having a $^{14}C$ carbon.

Examples of the pharmaceutically acceptable salt of the compound represented by the formula (I) include salts of the compound represented by the formula (I) with an alkali metal (e.g., lithium, sodium, potassium, etc.), an alkaline earth metal (e.g., calcium, barium, etc.), magnesium, a transition metal (e.g., zinc, iron, etc.), ammonia, an organic base (e.g., trimethylamine, triethylamine, dicyclohexylamine, ethanolamine, diethanolamine, triethanolamine, meglumine, diethanolamine, ethylenediamine, pyridine, picoline, quinolone, etc.) and an amino acid, or salts with an inorganic acid (e.g., hydrochloric acid, sulfuric acid, nitric acid, carbonic acid, hydrobromic acid, phosphoric acid, hydroiodic acid, etc.) and an organic acid (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid, etc.). Examples include, particularly, salts with hydrochloric acid, sulfuric acid, phosphoric acid, tartaric acid, or methanesulfonic acid, and the like. These salts can be formed by a method usually carried out.

The compound of the present invention can be produced, for example, according to the general synthesis method described below. In addition, extraction, purification and the like may be performed by a treatment performed in a normal experiment of organic chemistry. The synthesis of the compound of present invention can be carried out while referring to the method known in the art. The present invention also provides intermediates and final compounds in the following general synthetic methods. The type of substituent(s) in each compound and preferred embodiments are as defined above.

(General Synthesis Method)

The compound (I) can be synthesized by appropriately combining known reactions to the person skilled in the art using compounds known to the public or commercially available reagents. Preferably, a reaction for forming fused ring, a reaction for forming side chains, reduction reaction, oxidation reaction, hydrolysis reaction, Friedel-Crafts reaction, coupling reaction, protecting reaction, deprotection reaction and the like may be performed as appropriate using benzene derivatives or pyridine derivatives having leaving group(s) such as halogen, nitro group(s), (substituted) amino group(s), (protected) amino group(s), alkyl group(s), (protected) hydroxy group(s), ester group(s) or the like as starting materials. Also each substituent(s) ($R^3$, —C($R^2$)n-COOR$^4$, $R^1$) on the 6-membered mother skeleton may be present in the compounds of the starting material, or be introduced after forming a $T^1$ ring.

As reaction solvents, for example, DMF, THF, dioxane, DME, tetrahydrofuran, acetone, acetonitrile, alcohol (eg. methanol, ethanol), ethyl acetate, DMSO, dichloromethane, dichloroethane, toluene, chloroform, benzene, toluene, xylene, water or a mixture selected from thereof can be used as appropriate. As bases, for example, pyridine, lutidine, triethylamine, potassium carbonate, sodium carbonate, cesium carbonate, sodium hydride, N, N-diisopropylethylamine or the like can be used as appropriate.

[1] A Reaction Forming $T^1$ Ring $T^1$ ring is preferably formed after synthesized a bicyclic benzene derivative or pyridine derivative. In one embodiment, when $T^1$ ring is $T^1$-1, the compound (I-X) including the compound(I) or the intermediate(s) thereof can be synthesized through the following steps. The said reaction, for example, may be performed according to the method described in WO2004/094430.

[Chemical formula 92]

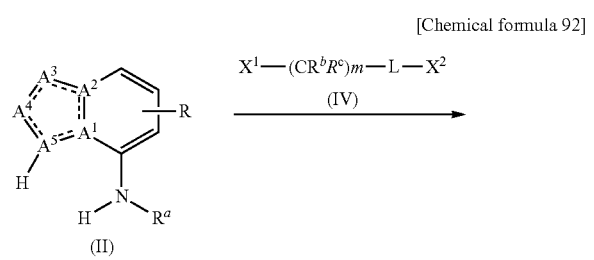

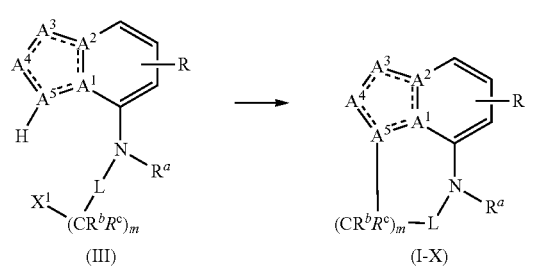

wherein R means one to three substituent(s) selected from the group consisting of $R^3$, —C($R^2$)nCOO$^4$, $R^1$, a combination thereof, and the substituent that can be introduced these substituent(s) in the compound (I); $X^1$ is a leaving group (eg. a halogen atom) or an aldehyde group, or $X^1$ may be taken together with an adjacent one (CR$^b$R$^c$) to form olefin or acetylene; $X^2$ is a leaving group (eg. a halogen atom); the other symbols are as defined above.

When the compound (I-X) is the compound (I), the compound (I-X) is represented by the following formula.

[Chemical formula 93]

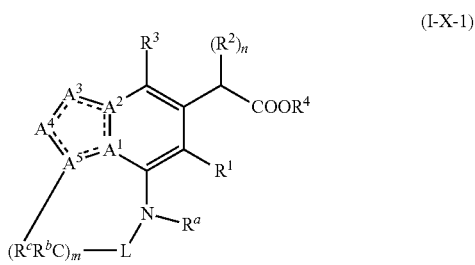

The above reactions in detail are as follows.

(1) In the case that L is C=O or SO$_2$:

(Step 1)

The compound (III) can be obtained by reacting the compound (II) with the compound (IV) in the presence of base (e.g., pyridine) and suitable reagent(s) (e.g., DMAP) if necessary, in a solvent (e.g., dichloromethane), at a suitable temperature (e.g., 0° C. to 100° C., preferably room temperature), for suitable time (e.g., a few minutes to several ten hours).

(Step 2)

The compound (I-X) can be obtained by reacting the compound (III) in the presence of deprotonating agents (eg. sodium hydride), in a solvent (e.g., DMF), at a suitable temperature (e.g., 0° C. to 150° C., preferably about 100° C.), when A$^5$ is N.

The compound (I-X) can be obtained by performing the intramolecular Friedel-Crafts reaction using the compound (III), wherein $X^1$—(CR$^b$R$^c$)— is Cl-C(O)—, in the presence of Lewis acid (e.g., aluminium chloride, titanium tetraisopropoxide (IV)), when A$^5$ is C.

(2) In the case that L is —(CR$^b$R$^c$)—:

(2-1) When A$^5$ is N, the compound (II) is reacted in the presence of bases (e.g., potassium carbonate), in a solvent (e.g., DMF), at a suitable temperature (e.g., 0° C. to 100° C., preferably room temperature) in Step 1. In Step 2, the compound (I-X) can be obtained by reacting the compound (III) in the presence of deprotonating reagents (e.g., sodium hydride) if necessary, at suitable temperature (e.g., room temperature to 100° C.).

(2-2) When A$^5$ is C, the compound (III) is obtained by reacting the compound (II), preferably wherein R$^a$ is —COR$^{a1}$, —SOR$^{a2}$, or —SO$_2$R$^{a3}$, in the presence of bases (e.g., potassium carbonate), in a solvent (e.g., DMF, acetonitrile), at a suitable temperature (e.g., 00° C. to 100° C., preferably room temperature) in Step 1. In Step 2, for example, the compound (I-X) can be obtained by performing the intramolecular Friedel-Crafts reaction using the compound (III), wherein $X^1$—(CR$^b$R$^c$)— is Cl—C(O)—, and Lewis acid (e.g., aluminum chloride, titanium chloride (IV)).

[2] Synthesis of the Compound (I-A-1)

[Chemical formula 94]

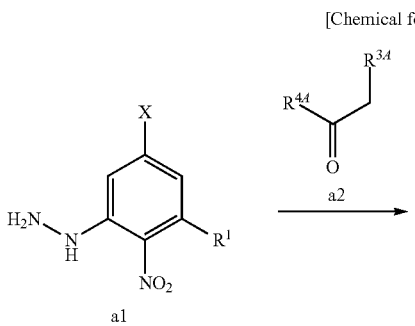

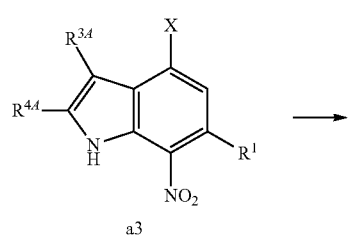

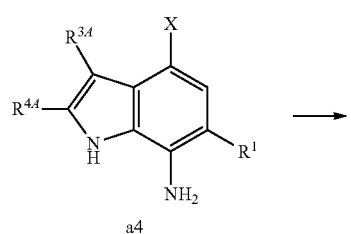

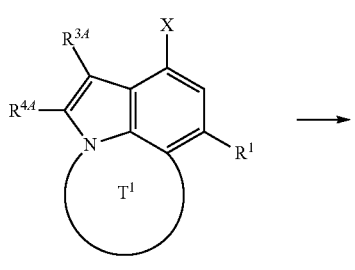

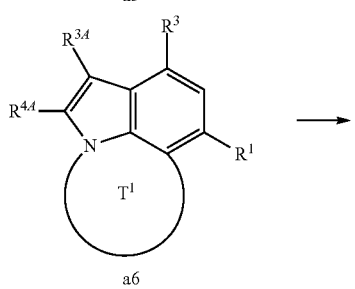

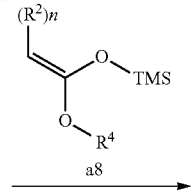

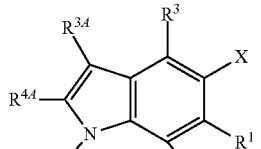

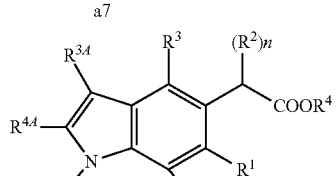

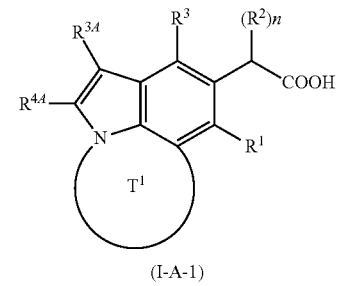

wherein X is each independently a leaving group such as halogen; the other symbols are as defined above.

(Step 1)

The compound a3 is obtained by reacting the compound a1 and the compound a2 according to the indole synthesis of Fischer.

(Step 2)

The compound a4 is obtained by reducing the compound a3.

The reduction is preferably performed by refluxing iron powder and ammonium chloride or tin (II) chloride in ethanol.

(Step 3)

The compound a5 is obtained by putting the compound a4 to the reaction forming $T^1$ ring described above [1].

(Step 4)

For example, the compound a6 is obtained by reacting the compound a5 with a boron reagent ($R^3$-boronic acid) in the presence of a transition metal reagent and ligand (e.g., $Pd_2(dba)_3$/RuPhos) and base (e.g., sodium carbonate), in a solvent (e.g., mixture of dioxane and water), at a suitable temperature (e.g., reflux temperature).

(Step 5)

For example, the compound a7 is obtained by reacting the compound a6 with NBS in a solvent (e.g., DMF, dichloromethane), preferably at room temperature to under ice-cooling.

(Step 6)

The compound a9 is obtained by reacting the compound a7 and the compound a8 according to a coupling reaction with silyl enol ether having a methyl group (Journal of the American Chemical Society, 2004, 126, 5182-5191.).

(Step 7)

The compound (I-A-1) is obtained by reaction the compound a9 in the presence of bases (e.g., sodium hydrate), in a solvent (e.g., THF, a mixture of methanol and water), at a suitable temperature (e.g., about 50° C.). The compound (I-A-1) can be also converted into a variety of carboxylic acid equivalents or carboxylic acid by methods known to those skilled person in the art.

[2-1] Alternative Synthetic Method of the Compound (I-A-1) Type

[Chemical formula 95]

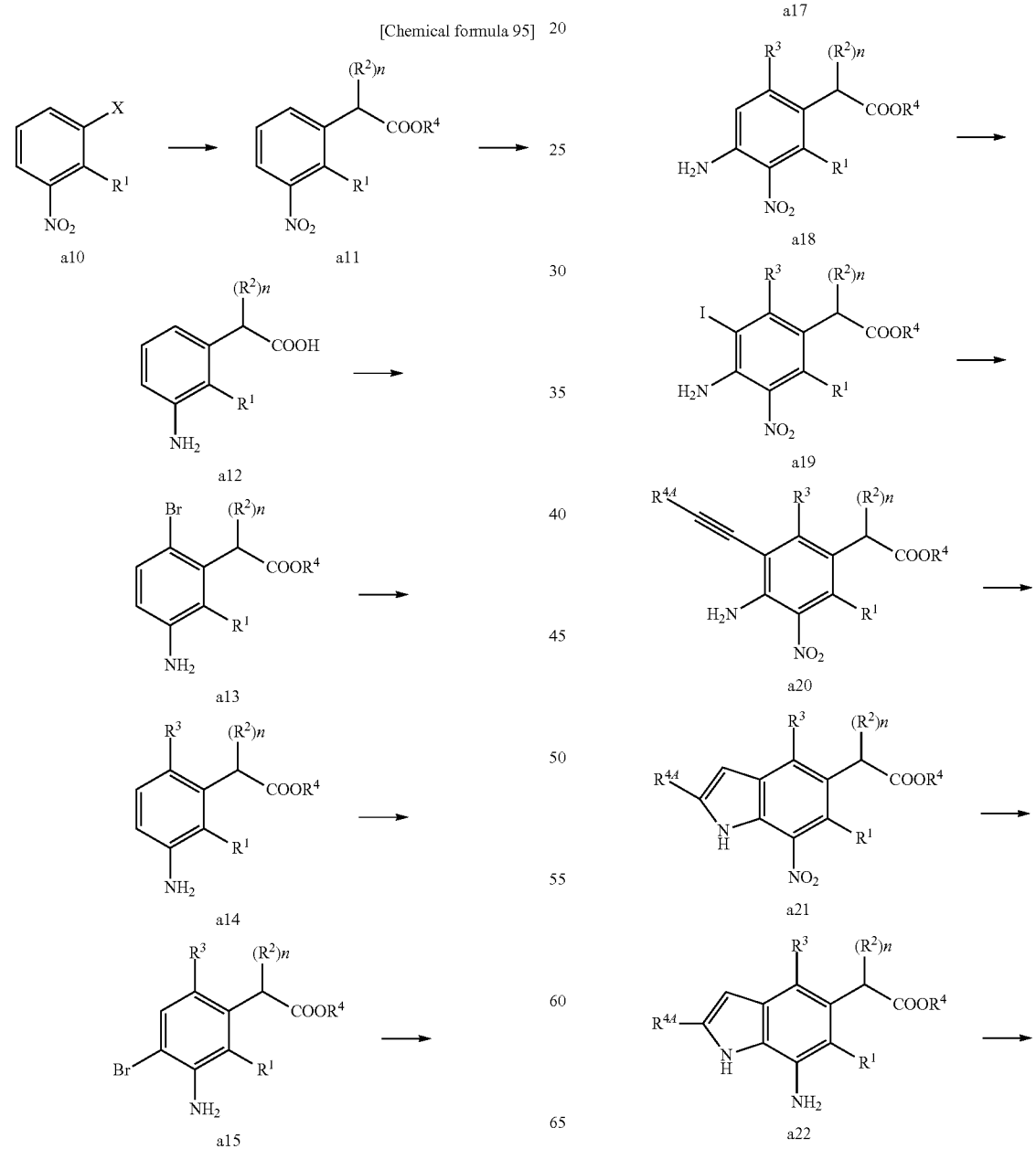

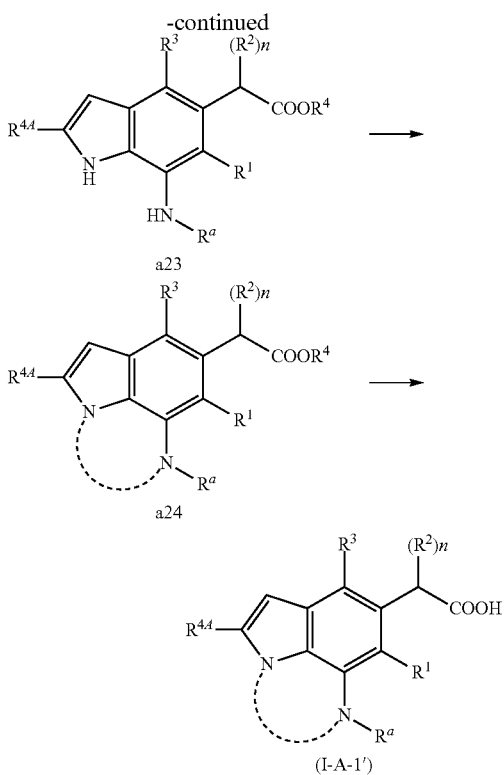

wherein each symbol are as defined above.

(Step 1)

The compound a11 can be obtained by reacting the compound a10 in DMF, DMA, THF, dioxane and the like or a mixture thereof, with a phosphine, such as tri-t-butylphosphine, tricyclohexylphosphine, triphenylphosphine or the like, a catalyst, such as dibenzylideneacetone palladium, palladium acetate, dichlorobistriphenylphosphine palladium and the like, zinc fluoride and silyl enol ether added, at 50° C. to 150° C., preferably at 70° C. to 130° C., for 0.1 to 8 hours, preferably 0.5 to 2 hours.

(Step 2)

The compound a12 can be obtained by reacting the compound a11 in a solvent such as acetic acid, hydrochloric acid, sulfuric acid or the like or a mixture thereof, with a reductant such as zinc, iron, tin chloride or the like added, at −20° C. to 80° C., preferably 0° C. to 60° C., for 0.1 to 8 hours, preferably 0.5 to 2 hours. Or the compound a12 can be obtained by reacting the compound a11 in a solvent such as methanol, ethyl acetate, acetic acid or the like, or a mixture thereof, with a catalyst such as Pd/X, Pd(OH)$_2$, Raney-Ni or the like added, under hydrogen atmosphere, at −30° C. to 80° C., preferably 0° C. to 50° C., for 0.1 to 8 hours, preferably 0.5 to 2 hours.

(Step 3)

The compound a13 can be obtained by reacting the compound a12 in a solvent such as dichloromethane, chloroform, dichloriethane or the like or a mixture thereof, with a brominating reagent such as bromine or NBS added, at −50° C. to 50° C., preferably −30° C. to 30° C., for 0.1 to 4 hours, preferably 0.5 to 1 hour.

(Step 4)

The compound a14 can be obtained by reacting the compound a13 in a solvent such as DMF, DMA, THF, dioxane, water or the like or a mixture thereof, with an aqueous solution of a base such as $K_2CO_3$, $Na_2CO_3$, $K_3PO_4$ or the like, a boronic acid or a borate synthesized in a known method or commercially available and a catalyst such as $PdCl_2(dtbpf)$, $Pd(PPh_3)_4$, $PdCl_2(dppf)$ or the like added, at 50° C. to 150° C., preferably 70° C. to 130° C., for 0.1 to 8 hours, preferably 0.5 to 2 hours.

(Step 5)

The compound a15 can be obtained in the same manner as Step 3.

(Step 6)

The compound a16 can be obtained by reacting the compound a15 in a solvent such as dichloromethane, chloroform, dichloroethane or the like or a mixture thereof, with an oxidant such as mCPBA, peracetic acid or the like added, at 0° C. to 120° C., preferably 30° C. to 90° C., for 0.1 to 10 hours, preferably 0.5 to 4 hours.

(Step 7)

The compound a17 can be obtained by reacting the compound a16 in a solvent such as toluene, DMF, DMA, THF, dioxane and the like or a mixture thereof, with a phosphine such as BINAP, xantphos or the like, a catalyst such as dibenzylideneacetone palladium, palladium acetate or the like, a bese such as cesium carbonate, potassium carbonate or the like and acetoamide added, at 50° C. to 150° C., preferably 70° C. to 130° C., for 0.1 to 8 hours, preferably 0.5 to 2 hours.

(Step 8)

The compound a18 can be obtained by reacting the compound a17 in a solvent such as methanol, ethanol or the like or a mixture thereof, with a base such as cesium carbonate, potassium carbonate or the like, at 50° C. to 150° C., preferably 70° C. to 130° C., for 0.1 to 10 hours, preferably 0.5 to 4 hours.

(Step 9)

The compound a19 can be obtained by reacting the compound a18 in a solvent such as methanol, ethanol or the like or a mixture thereof, with an iodinating reagent such as iodine or NIS added, at −50° C. to 50° C., preferably −30° C. to 30° C., for 0.1 to 4 hours, preferably 0.5 to 1 hour.

(Step 10)

The compound a20 can be obtained by reacting the compound a19 in a solvent such as DMF, DMA, THF, dioxane or the like or a mixture thereof, with a base such as $Et_3N$, DIPEA or the like, substituted alkyne synthesized in a known method or commercially available, and a catalyst such as $PdCl_2(PPh_3)_4$, $Pd(PPh_3)_4$, $PdCl_2(dppf)$ added, at 50° C. to 150° C., preferably 70° C. to 130° C., for 0.1 to 8 hours, preferably 0.5 to 2 hours.

(Step 11)

The compound a21 can be obtained by reacting the compound a20 in a solvent such as DMF, THF or the like or a mixture thereof, with a base such as t-BuOK, potassium carbonate or the like added, at −20° C. to 80° C., preferably 0° C. to 60° C., for 0.1 to 4 hours, preferably 0.5 to 1 hour.

(Step 12)

The compound a22 can be obtained in the same manner as Step 2.

(Step 13)

The compound a23 can be obtained by reacting the compound a22 in a solvent such as dichloromethane, DMF, DMA or the like or a mixture thereof, with a base such as cesium carbonate, pyridine, $Et_3N$ or the like, an alkylation reagent synthesized in a known method or commercially available such as methle iodide, MsCl, AcCl, MeNCO or the like, a sulfonylation reagent, acid chloride, and isocyanate added, at −50° C. to 50° C., preferably −30° C. to 30° C., for 0.1 to 4 hours, preferably 0.5 to 1 hour.

(Step 14)

The compound a24 can be obtained by reacting the compound a23 in a solvent such as DMF, DMA, THF or the like or a mixture thereof, with a base such as cesium carbonate, potassium carbonate or the like, an alkylation reagent synthesized in a known method or commercially available such as 1,2-dibromoethane, 1,3-dibromopropane, chloroacetylchloride, chloromethyl sulfonyl chloride or the like, acid chloride or sulfonyl chloride or the like added, at −20° C. to 80° C., preferably 00° C. to 60° C., for 0.1 to 8 hours, preferably 0.5 to 2 hours.

(Step 15)

The compound (I-A-1') can be obtained by reacting the compound a24 in a solvent such as methanol, THF, dioxane or the like or a mixture thereof, with a base such as sodium hydrate aqueous solution, sodium hydrate aqueous solution, potassium hydrate aqueous solution, lithium hydrate aqueous solution or the like added, at 10° C. to 110° C., preferably 30° C. to 90° C., for 0.1 to 8 hours, preferably 0.5 to 1 hour.

[2-2] Alternative Synthetic Method of the Compound (I-A-1) Type

[Chemical formula 96]

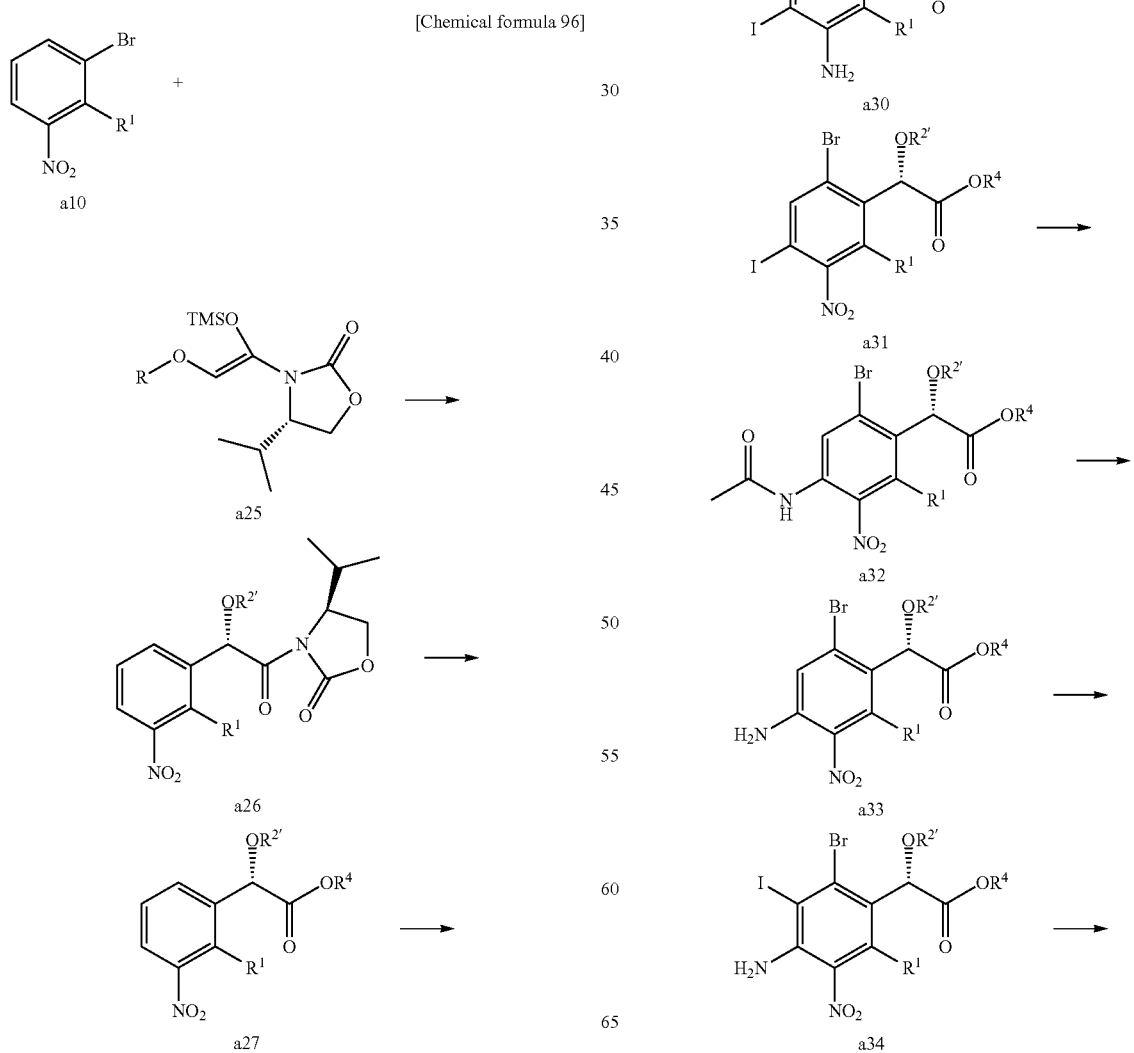

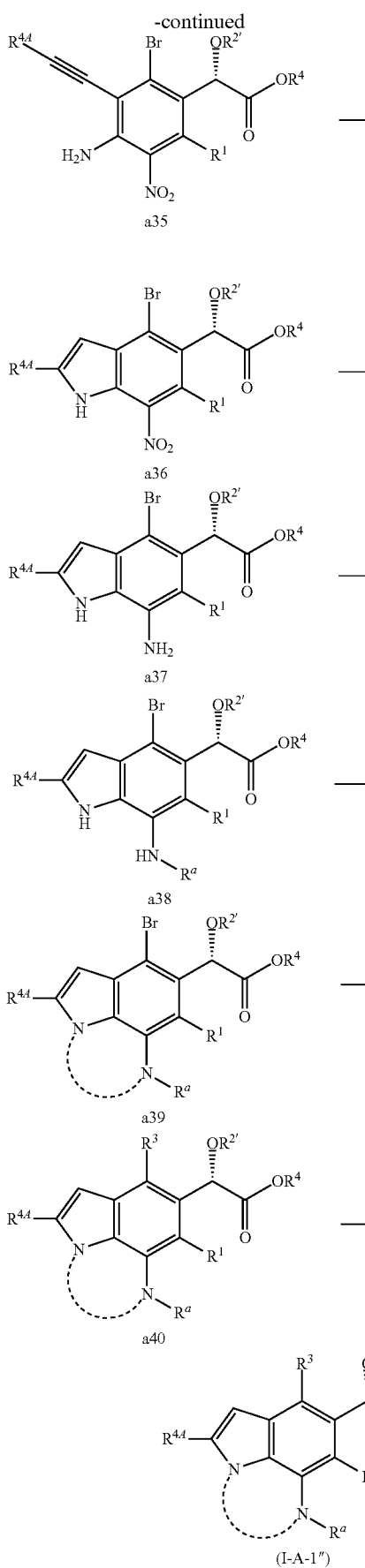

wherein $R^{2'}$ is substituted or unsubstituted alkyl, substituted or unsubstituted alkenyl, substituted or unsubstituted alkynyl, or substituted or unsubstituted non-aromatic carbocycle; the other symbols are as defined above.

(Step 1)

It can be carried out according to Step 1 in the synthesis of the compound (I-A-1').

(Step 2)

The carboxylic acid derivative can be obtained by reacting the compound a26 in a mixture of THF-water, with a mixture of hydrogen peroxide and lithium hydrate aqueous solution added, at −20° C. to 10° C., preferably −10° C. to 10° C., for 0.1 to 5 hours, preferably 0.1 to 1 hour. The compound a27 can be obtained by reacting the obtained carboxylic acid derivative in a solvent of DMF, DME, THF or the like, with a base such as potassium carbonate, sodium carbonate or the like, and an alkyl halide such as benzyl bromide, methyl iodide, at 0° C. to 100° C. preferably 20° C. to 50° C., for 0.5 to 24 hours, preferably 1 to 5 hours. Or the compound a27 can be obtained by esterifying with diphenyl diazomethane/diethylether solution or the like added.

(Step 3-16)

It can be carried out according to Step 2, 3, 9, 6, 7, 8, 9, 10, 11, 12, 13, 14, 4, 15 in the synthesis of the compound (I-A-1')

[2-3] Alternative Synthetic Method of the Compound (I-A-1) Type

[Chemical formula 97]

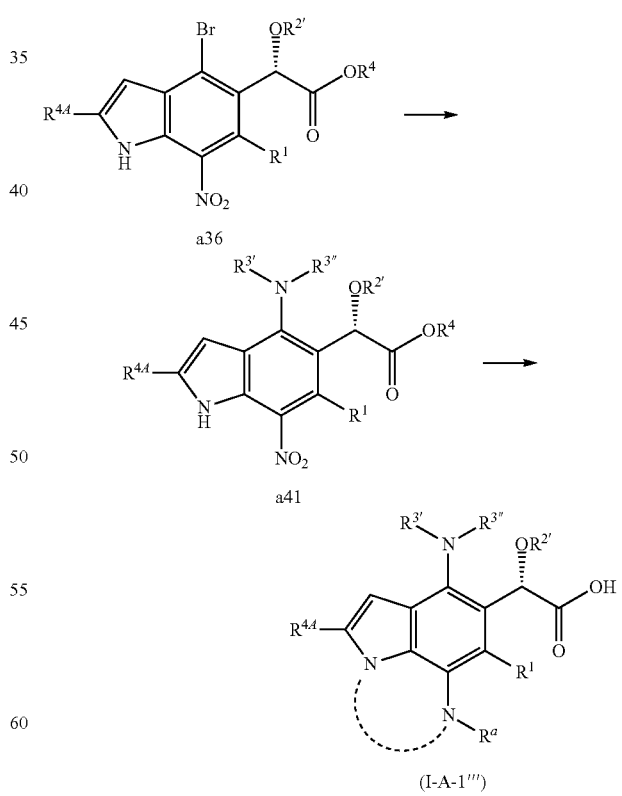

wherein $R^{3h}$ and $R^{3'''}$ is taken together with an adjacent nitrogen atom to form non-aromatic heterocycle; the other symbols are as defined above.

(Step 1)

The compound a41 can be obtained by reacting the compound a36 under solvent free condition or in a solvent such as DMSO, DMF, acetonitrile, methanol butanol or the like, with a base such as ammonium, a cyclic amine, a base such as potassium carbonate, triethylamine, ethyl diisopropylamine, potassium t-butoxide or the like, at 0° C. to 200° C., preferably 50° C. to 150° C., for 1 to 72 hours, preferably 1 to 24 hours.

(Step 2)

It can be carried out according to Step a compound 12, 13, 14, 15 in a synthesis of the compound (I-A-1').

[2-4] Alternative Synthetic Method of the Compound (I-1) Type

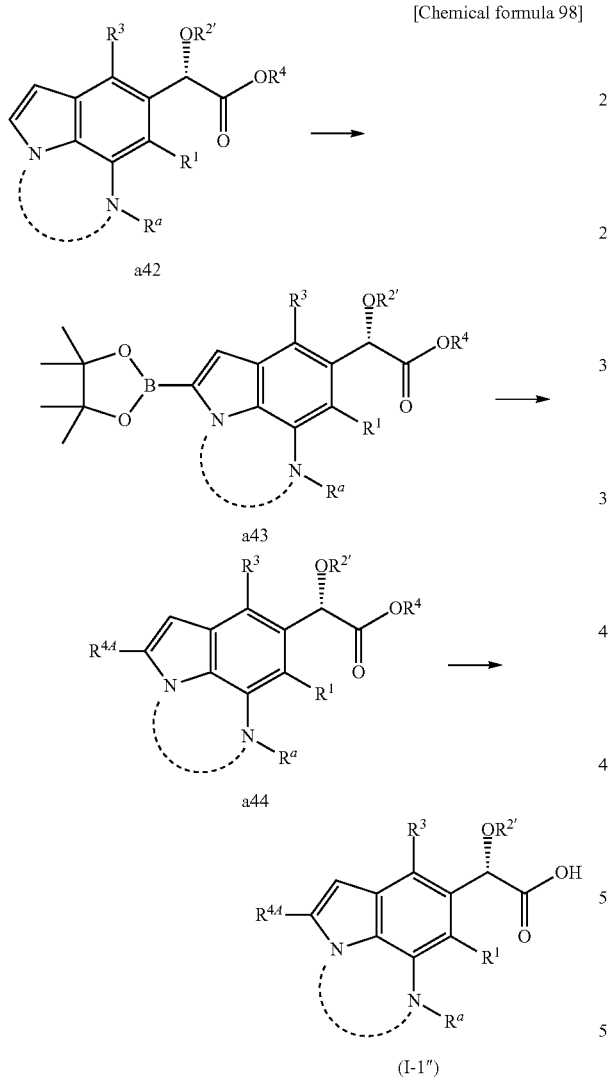

[Chemical formula 98]

wherein each symbol is as defined above.

(Step 1)

The compound a 43 can be obtained by reacing the compound a42 in a solvent such as hexane, THF, DMF or the like or a mixture thereof, with 4,4'-di-tert-butyl-2,2'-bipyridine, bispinacoldiborone, and an iridium catalyst such as 1,5-cyclooctadiene methoxy iridium or the like added, at 50° C. to 150° C., preferably 70° C. to 130° C., for 0.1 to 8 hours, preferably 0.5 to 2 hours.

(Step 2)

The compound a44 can be obtained by reacting the compound a43 in a solvent such as DMF, DMA, THF, dioxane, water or the like or a mixture thereof, with a aqueous solution of base such as $K_2CO_3$, $Na_2CO_3$, $K_3PO_4$ or the like, alkenyl halide, aryl halide, alkyl halide, and a catalyst such as $PdCl_2(dtbpf)$, $Pd(PPh_3)_4$, $PdCl_2(dppf)$ or the like added, at 50° C. to 15° C., preferably 70° C. to 130° C., for 0.1 to 8 hours, preferably 0.5 to 2 hours.

(Step 3)

The compound (I-A-1") can be obtained by reacting the compound a44 in a solvent such as methanol, THF, dioxane or the like or a mixture thereof, with a base such as sodium hydrate aqueous solution, potassium hydrate aqueous solution, lithium hydrate aqueous solution or the like added, at 10° C. to 110° C., preferably 30° C. to 90° C., for 0.1 to 8 hours, preferably 0.5 to 1 hour.

[3] Synthesis of the Compound (I-A-3)

[Chemical formula 99]

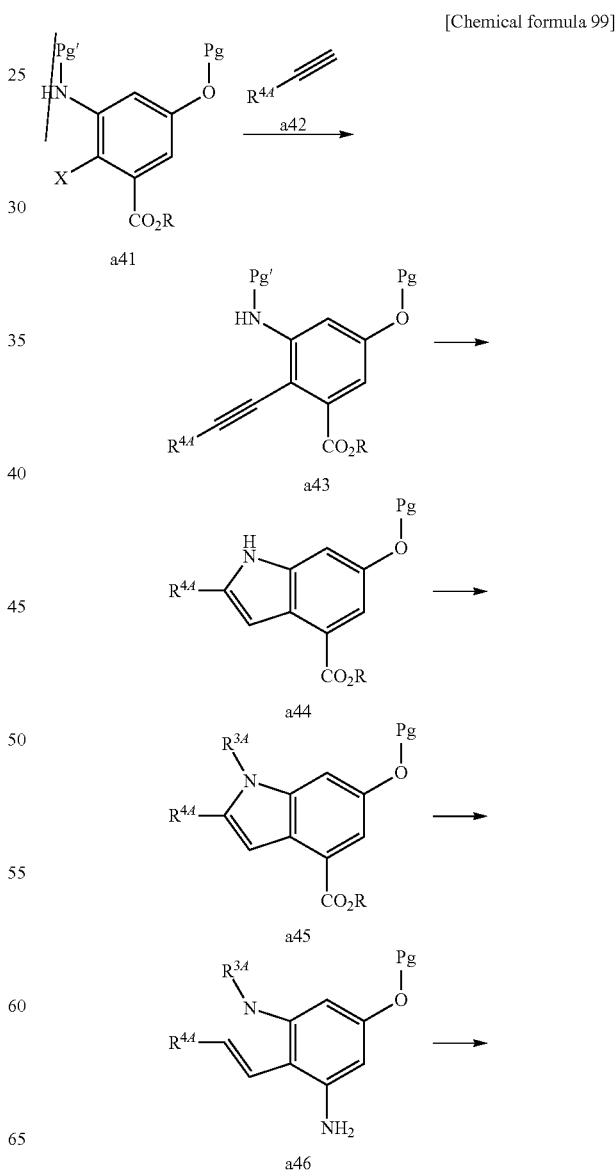

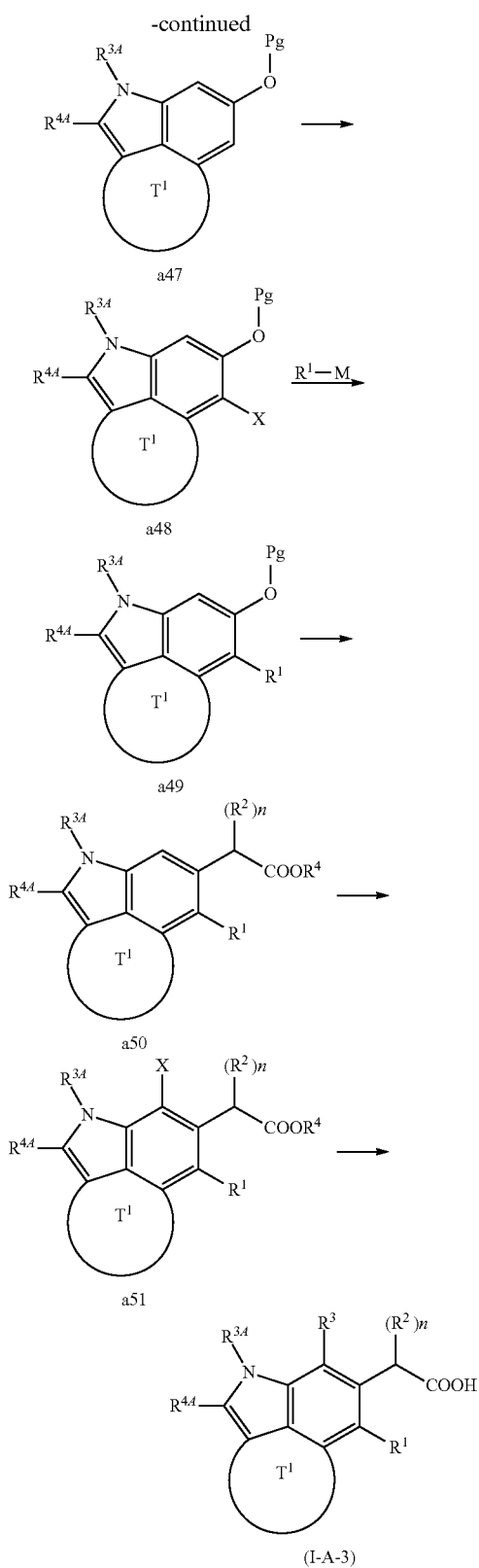

wherein each symbol is as defined above,
wherein Pg is a hydroxy protecting group (e.g., SEM group, benzyl group); Pg' is an amino protecting group (e.g., Ac); X is a leaving group (e.g., I, Br); R is a carboxy protecting group; the other symbols are as defined above.

(Step 1)

The compound a43 can be obtained by putting the compound a41 and the compound a42 to the Sonogashira coupling reaction.

(Step 2)

The compound a44 can be obtained by reacting the compound a43 in the presence of a base (e.g., TBAF, potassium tert-butoxide), in a solvent (e.g., THF), at a suitable temperature (e.g., 0° C. to 100° C., preferably about 70° C.).

(Step 3)

The compound a45 can be obtained by reacting the compound a44 with an alkylating reagent having $R^{3A}$ (e.g., methyl iodide in the case that $R^{3A}$ is methyl group), in the presence of a base (e.g., cesium carbonate), in a solvent (e.g., acetonitrile), at a suitable temperature (e.g., from room temperature to about 60° C.).

(Step 4)

The ester group of the compound a45 is hydrolyzed into a carboxyl group by reacting the compound a45 in the presence of a base (e.g., sodium hydrate), in a solvent (e.g., THF, a mixture of methanol and water), at a suitable temperature (e.g., from room temperature to about 50° C.). Thereafter, the compound a46 can be obtained by subsequently converting the carboxyl group to an amino group, e.g., by Curtius reaction with DPPA etc.

(Step 5)

The compound a47 can be obtained by putting the compound a46 to the reaction forming $T^1$ ring described above [1].

(Step 6)

The compound a48 can be obtained by reacting the compound a47 with a halogenating reagent (e.g., NIS), in a solvent (e.g., DMF, dichloromethane), at a suitable temperature (e.g., under ice cooling to reflux temperature).

(Step 7)

The compound a49 can be obtained by reacting the compound a48 with $R^1$-M (e.g., $R^1$-botanic acid), in the presence of a suitable transition metal and ligand to be used in a coupling reaction (e.g., $Pd_2(dba)_3$, RuPhos) and a base (e.g., potassium phosphate), in a solvent (e.g., dioxane), a suitable temperature (e.g., from about 50° C. to reflux temperature).

(Step 8)

The compound a50 can be obtained by deprotecting a hydroxyl protecting group of the compound a49, and then conducting according to Step 4 in the synthesis of the compound (I-A-7), and then conducting according to Step 6 in the synthesis of the compound (I-A-1).

(Step 9)

The compound a51 can be obtained by reacting the compound a50 with a halogenating reagent (e.g., NIS), in a solvent (e.g., DMF, dichloromethane), at a suitable temperature (e.g., under ice-cooling to reflux temperature).

(Step 10)

It can be carried out according to Step 4, 7 in the synthesis of the compound (I-A-1).

[4] Synthesis of the Compound (I-A-4)

[Chemical formula 100]

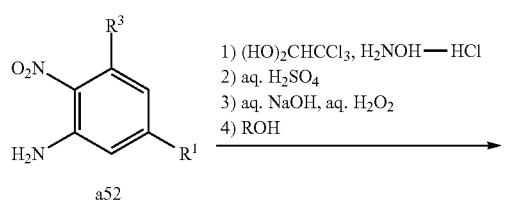

a52

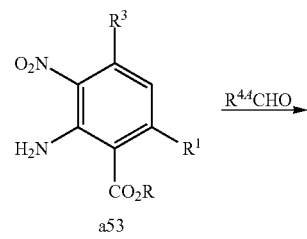

a53

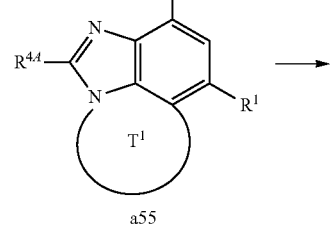

a54

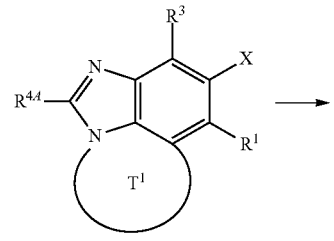

a55

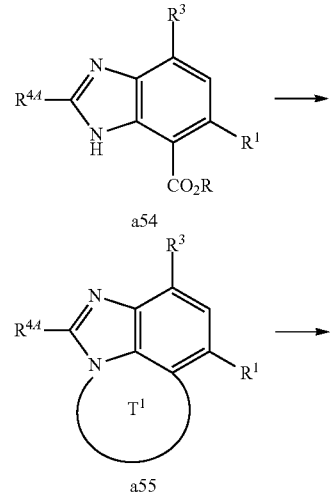

a56

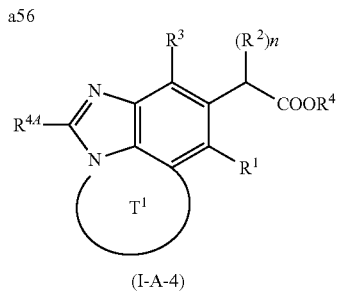

(I-A-4)

wherein R is alkyl or the like; the other symbols are as defined above.

(Step 1)

The compound a53 can be obtained by reacting the compound a52, for example, according to the synthesis method described in Journal of Organic Chemistry, 2013, 78(17), 8217-8231.

(Step 2)

The compound a54 can be obtained by reacting the compound a53 with $R^{4.4}$—CHO, for example, according to the synthesis method described in Angewandte Chemie, International Edition, 2012, 51(46), 11589-11593.

(Step 3)

For example, it can be carried out according to Step 4, 5 in the synthesis of the compound (I-B-5).

(Step 4)

The compound a56 can be obtained by reacting the compound a55 with a halogenating reagent (e.g., NIS), in a solvent (e.g., DMF, dichloromethane), at a suitable temperature (e.g., under ice-cooling to reflux temperature).

(Step 5)

It can be carried out according to Step 6, 7 in the synthesis of the compound (I-A-1).

[5] Synthesis of the Compound (I-A-7)

[Chemical formula 101]

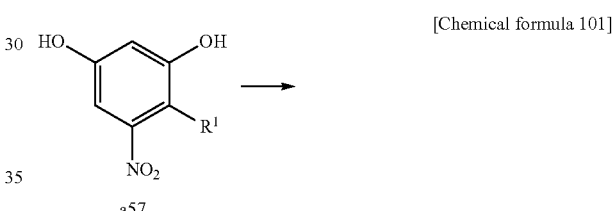

a57

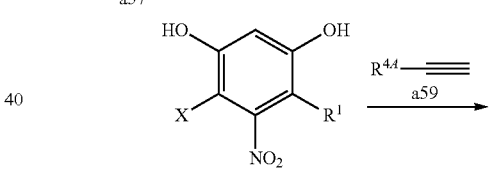

a58

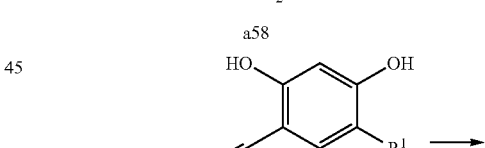

a60

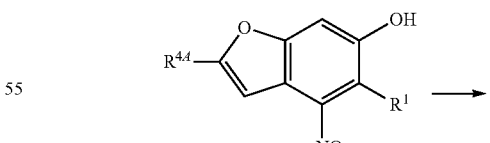

a61

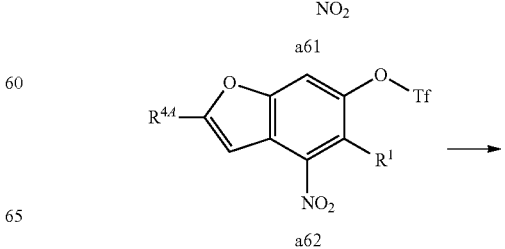

a62

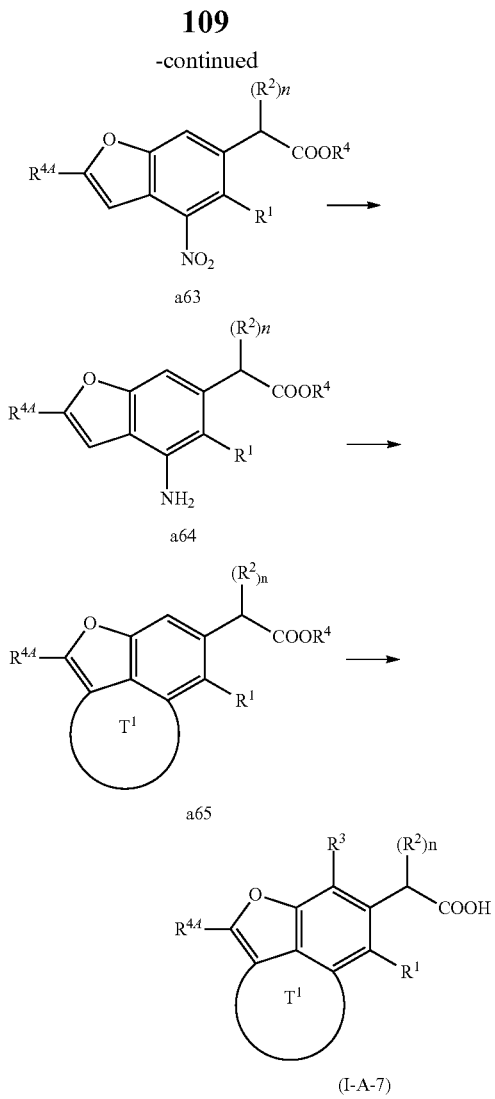

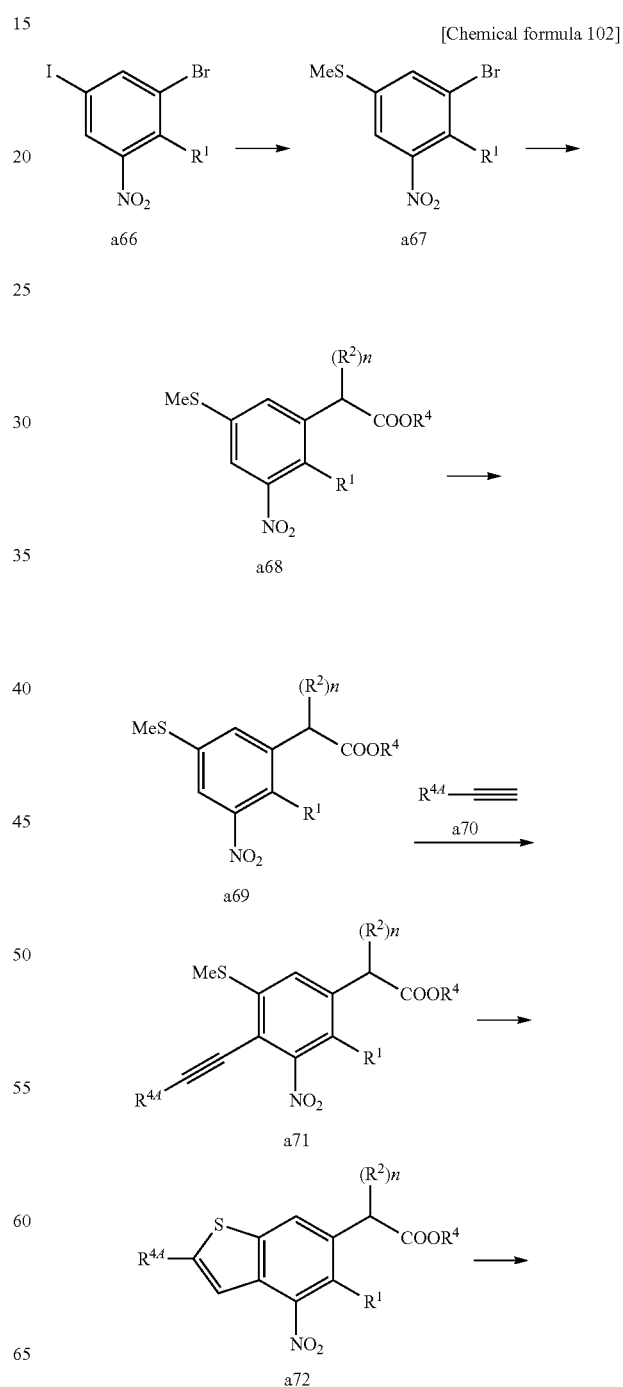

(Step 5-6)

It can be carried out according to Step 6, 2 in the synthesis of the compound (I-A-1).

(Step 7)

It can be carried out according to the formation reaction of $T^1$ ring described above [1].

(Step 8)

It can be carried out according to Steps 5, 4, 7 in the synthesis of the compound (I-A-1).

[6] Synthesis of the compound (I-A-8)

[Chemical formula 102]

wherein each symbol is as defined above.

(Step 1)

The compound a58 can be obtained by reacting the compound a57 with a halogenating reagent (e.g., NIS), in a solvent (e.g., DMF, dichloromethane), at a suitable temperature (e.g., under ice-cooling to reflux temperature).

(Step 2)

The compound a60 can be obtained by putting the compound a58 and a compound a59 to the Sonogashira coupling reaction.

(Step 3)

The compound a61 can be obtained by reacting the compound a60 in the presence of a transition metal catalyst (e.g., palladium or copper), in a solvent (e.g., dioxane, THF, toluene), preferably from room temperature to reflux temperature.

(Step 4)

The compound a62 can be obtained by reacting the compound a61 with trifluoromethanesulfonic acid anhydride, in a presence of a base (e.g., pyridine), in a solvent (e.g., dichloromethane), at a suitable temperature (e.g., under ice-cooling).

-continued

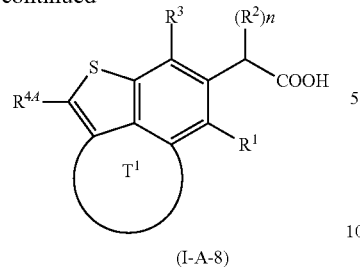

(I-A-8)

wherein each symbol is as defined above.

(Step 1)
The compound a67 can be obtained by introducing a methylthio group into the compound a66. As the reaction conditions, 1) a coupling reaction of dimethyl sulfide with a transition metal (Tetrahedron Letters, 2006, 47(29), 5059-5062), or 2) a thiophenol formation by a coupling reaction with a thioacetate salt and a transition metal and subsequent methylation with a methylation reagent (Beilstein Journal of Organic Chemistry, 2013, 9, 467-475) are exemplified.

(Step 2)
It can be carried out according to Step 6 in the synthesis of the compound (I-A-1).

(Step 3)
The compound a69 can be obtained by reacting the compound a68 with a halogenating reagent (e.g., NIS), in a solvent (e.g., DMF, dichloromethane), at a suitable temperature (e.g., under ice-cooling to reflux temperature).

(Step 4)
The compound a71 can be obtained by putting the compound a69 and the compound a70 to the Sonogashira coupling reaction.

(Step 5)
The compound a72 can be obtained by conducting dehalogenation by catalytic reduction after the formation of thiazole ring via a halonium cation using the compound a71 according to the method described in Journal of Organic Chemistry, 2002, 67(6), 1905-1909.

(Step 6)
It can be carried out according to Steps 6 to 10 in the synthesis of the compound (I-A-7).

[7] Synthesis of the Compound (I-B-1)

[Chemical formula 103]

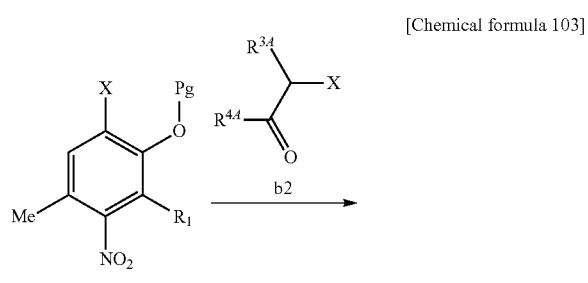

-continued

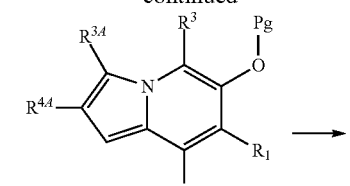

b4

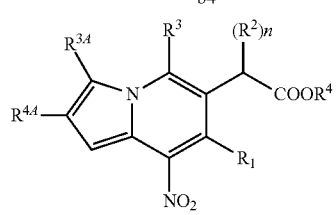

b5

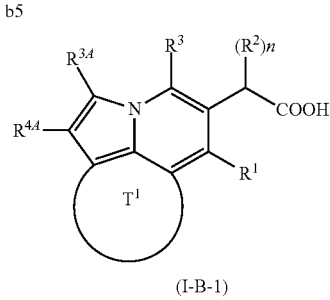

(I-B-1)

wherein each symbol is as defined above.

(Step 1)
The compound b3 can be obtained by reacting the compound b1 and the compound b2, for example according to the method described in Journal of Heterocycle Chemistry, 2013, 50(3), 638-644.

(Step 2)
It can be carried out according to Step 4 in the synthesis of the compound (I-A-1).

(Step 3)
It can be carried out according to Step 2, 3 in the synthesis of the compound (I-B-5).

(Step 4)
It can be carried out according to Step 2 in the synthesis of the compound (I-A-1), subsequent the $T^1$ ring forming reaction according to Step 7 in the synthesis of the compound (I-A-1).

[8] Synthesis of the Compound (I-B-4)

[Chemical formula 104]

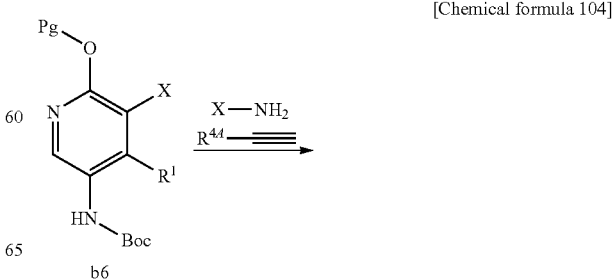

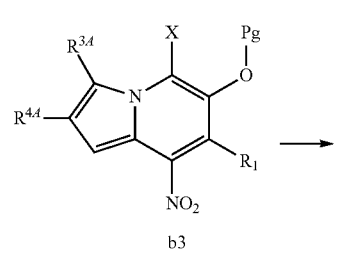

b3

113

-continued

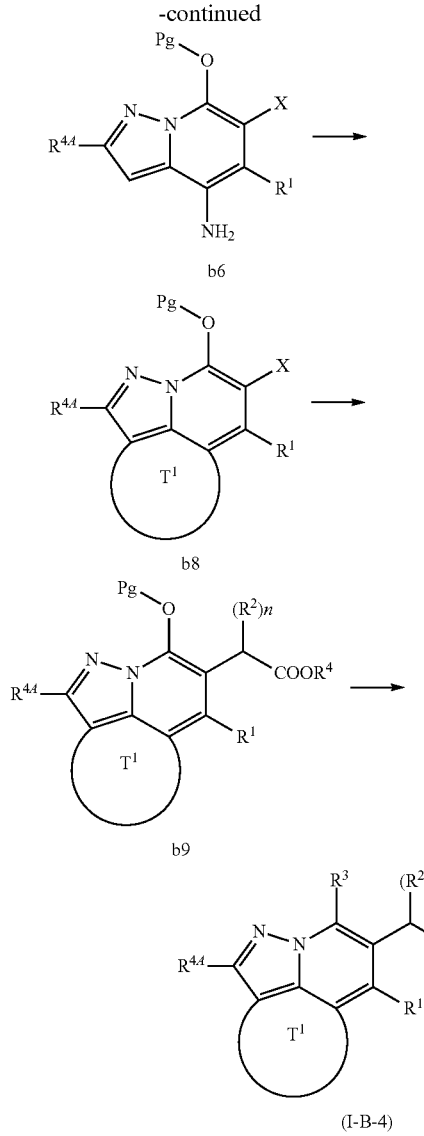

b6 b8 b9

(I-B-4)

wherein each symbol is as defined above.

(Step 1)

The compound (2) can be obtained by reacting the compound (1), X—NH$_2$ (X is a leaving group (eg. ArSO$_3$—, (O$_2$N)$_2$ PhO—) and an acetylene group having R$^{4A}$ group, according to the method described in Bioorganic & Medicinal Chemistry Letters, 2013, 23(19), 5311-5316. Pg (: hydroxy protecting group) is preferably benzyl.

(Step 2)

It can be carried out according to the T$^1$ ring forming reaction described above.

(Step 3)

It can be carried out according to Step 6 in the synthesis of the compound (I-A-1).

(Step 4)

It can be carried out according to Step 4 in the synthesis of the compound (I-A-7) and Step 4, 7 in the synthesis of the compound (I-A-1) after deprotection the hydroxy protecting group (Pg).

114

[9] Synthesis of the Compound (I-B-5)

[Chemical formula 105]

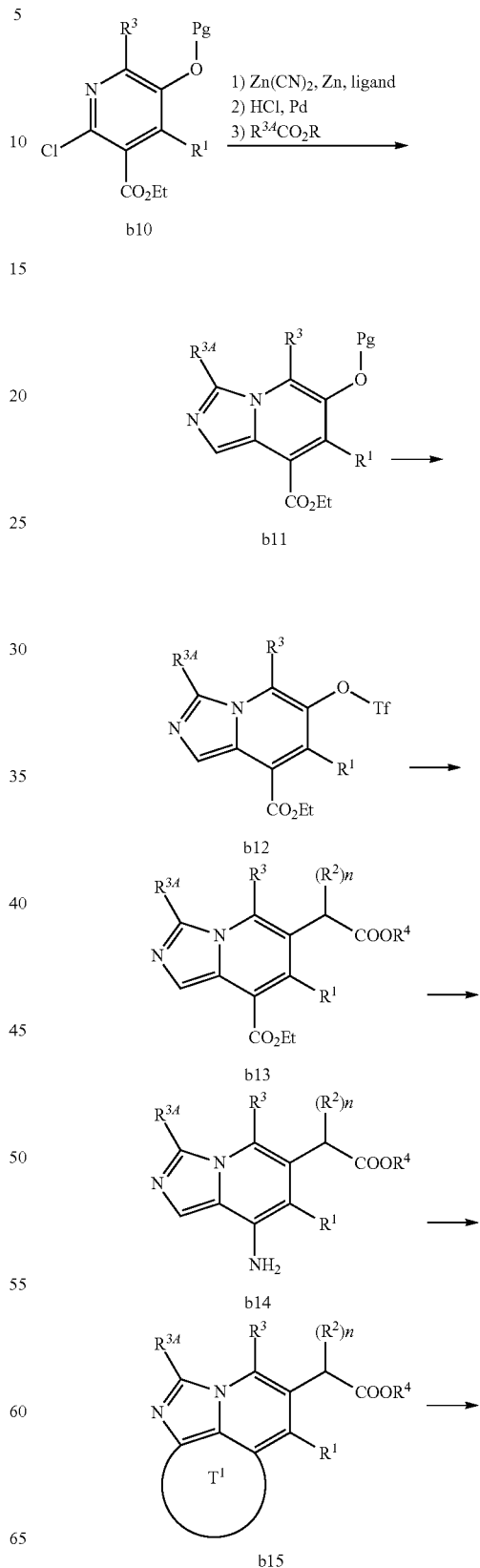

b10 b11 b12 b13 b14 b15

-continued

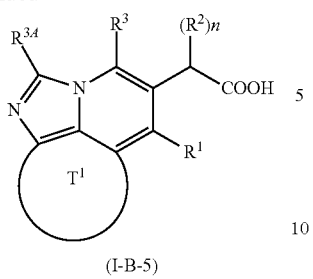

(I-B-5)

wherein each symbol is as defined above.

(Step 1)

The compound b11 can be obtained by reacting the compound b10, for example, according to the method in WO2004/046133.

(Step 2)

It can be carried out according to Step 4 in the synthesis of the compound (I-A-7) after deprotection of the hydroxy protecting group (Pg).

(Step 3)

It can be carried out according to Step 6 in the synthesis of the compound (I-A-1).

(Step 4)

The ester group of the compound b13 is converted to carboxyl group by hydrolysis in the presence of a base (e.g., sodium hydrate), in a solvent (e.g., THF, a mixture of methanol and water), at a suitable temperature (e.g., from room temperature to about 50° C.). Thereafter, subsequently the compound b14 can be obtained by converting a carboxyl group to an amino group by Curtius reaction using DPPA, for example.

(Step 5)

It can be carried out according to the $T^1$ ring forming reaction described above.

(Step 6)

It can be carried out according to Step 7 in the synthesis of the compound (I-A-1).

[10] Synthesis of the Compound (I-C-5)

[Chemical formula 106]

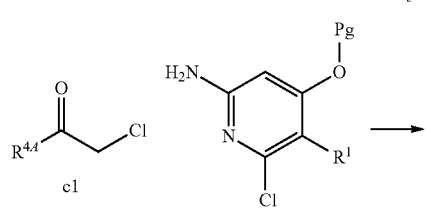

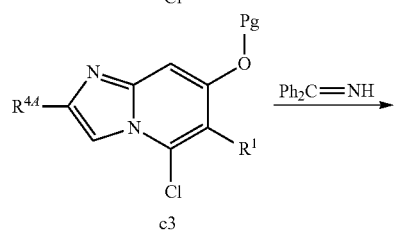

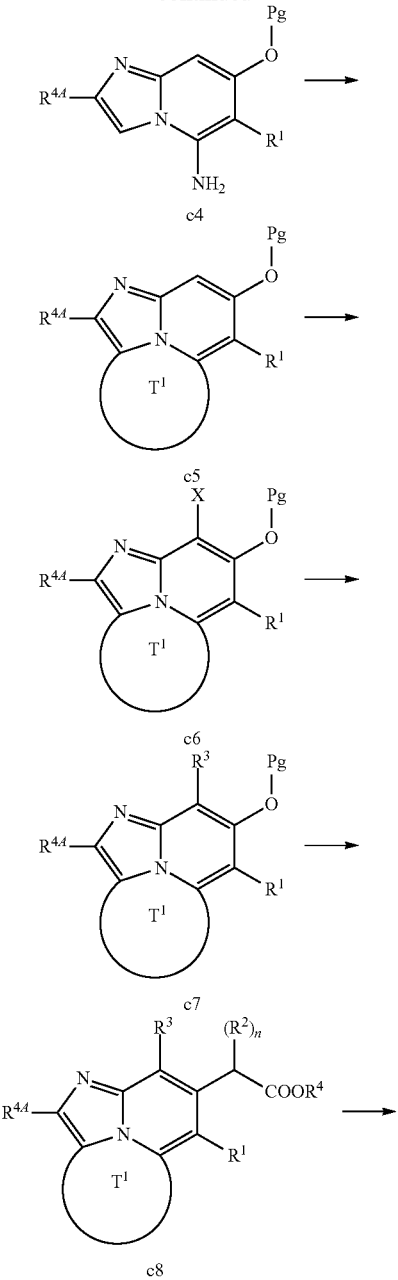

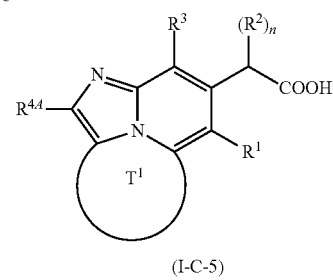

(I-C-5)

wherein each symbol is as defined above.

(Step 1)

The compound c3 can be obtained by reacting the compound c1 and the compound c2, for example, according to the method described in Journal of Medicinal Chemistry, 1987, 30(11), 2047-51, in a solvent (e.g., ethanol), at a suitable temperature (e.g., room temperature to reflux temperature).

(Step 2)

For example, according to the method described in WO2006/036816, the compound c3 is reacted with diphenyl imine using a suitable transition metal, ligand, base, and solvent for a coupling reaction (e.g., palladium acetate, BINAP, cesium carbonate and toluene), at a suitable temperature (e.g., about 100° C. to reflux temperature). After that, the compound c4 can be obtained by conducting deprotection of a diphenylmethyl group from an amino group under acidic condition (eg. dilute hydrochloric acid), in a solvent (e.g., THF), at a suitable temperature (e.g., room temperature to reflux temperature).

(Step 3)

It can be carried out according to the $T^1$ ring forming reaction described above.

(Step 4)

The compound c6 can be obtained by reacting the compound c5 with a halogenating reagent (e.g., NIS), in a solvent (e.g., DMF, dichloromethane), at a suitable temperature (e.g., under ice-cooling to reflux temperature).

(Step 5)

It can be carried out according to Step 5 in the synthesis of the compound (I-A-1).

(Step 6)

It can be carried out according to Step 2, 3 in the synthesis of the compound (I-B-5).

(Step 7)

It can be carried out according to Step 7 in the synthesis of the compound (I-A-1).

The final compound obtained by the above process can be convered to a further compound of the present invention by carrying out a well-known chemical modification to a person skilled in the art. When the functional groups (e.g., hydroxy, amino, carboxy) exist in each reaction before and after, it may be optionally conducted to protecting or deprotecting reaction for the functional groups by well-known reaction to the skilled person in the art (ref: Organic Synthesis, written by T. W. Greene, John Wiley & Sons Inc. (1991)).

The compound of the present invention has an inhibitory effect on HIV replication, thus is useful as a therapeutic agent and/or prophylactic agent of viral infections such as AIDS or the like.

In HIV replication inhibition activity of the compound of the present invention, for example, in the following Experimental Example 1, preferably, EC50 value is 100 nM or less, more preferably 50 nM or less, more preferably 20 nM or less, particularly preferably 10 nM or less. EC90 value is also available in the evaluation of this activity. Also, preferred compound has strong virus mutations resistance. More preferred compound has high C24/EC50 value (C24: blood concentration after administration 24 hours).

Preferably, the compound of the present invention has any or all of excellent characteristics described below.

a) Has a weak inhibitory effect on CYP enzymes (e.g., CYP1A2, CYP2C9, CYP2C19, CYP2D6, CYP3A4, etc.).
b) Shows good pharmacokinetics such as high bioavailability and moderate clearance.
c) Has high metabolic stability.
d) Shows no irreversible inhibitory effect on a CYP enzyme (e.g., CYP3A4) within a concentration range in the measurement conditions described herein.
e) Has no mutagenicity.
f) Has low risk on the cardiovascular system.
g) Shows high solubility.
h) Shows strong efficacy also against resistant viruses.
i) Has high stability in aqueous solution.
j) Has high light stability and/or low or no phototoxicity.
k) It is difficult to develop a resistant virus.

The pharmaceutical composition of the present invention can be administered orally or parenterally. Methods for parenteral administration include dermal, subcutaneous, intravenous, intraarterial, intramusclear, intraperitneal, transmucosal, inhalation, transnasal, ophthalmic, inner ear or vaginal administration and the like.

In case of oral administration, any forms, which are usually used, such as oral solid formulations (e.g., tablets, powder, granyles, capsules, pills, films or the like), oral liquid formulations (e.g., suspension, emulsion, elixir, syrup, lemonade, spirit, aromatic water, extract, decoction, tincture or the like) or the like may prepared. The tablets can be sugar coated tablets, film coated tablets, enteric-coating tablets, sustained-release tablets, troche tablets, sublingual tablets, buccal tablets, chewable tablets or orally dispersing tablets. Powders and granules can be dry syrups. Capsules can be soft capsules, micro capsules or sustained-release capsules.

In the case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) or the like can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, moistening agents, disintegrants, lubricants, diluents or the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, or 12 to 16 years old, or 18 years old. The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

The compound of the present invention can be used in combination with a reverse transcriptase inhibitor, a protease inhibitor, an integrase inhibitor, other anti-HIV drug, or the like (hereinafter, abbreviated as concomitant drug), for the purpose of enhancement of action of the compound, reduction of the dosage amount of the compound, or the like. At this time, the time of administration of the compound of the present invention and the concomitant drug is not limited, and, these may be administered simultaneously, or may be administered with a time difference, to the administration subject. Furthermore, the compound of the present invention and the concomitant drug may be administered as two types of preparations containing each active ingredient, or may be administered as a single preparation containing both active ingredients.

The dosage amount of the concomitant drug can be appropriately selected based on the clinically used dose. In addition, the blending ratio of the compound of the present invention to the concomitant drug can be appropriately selected depending on the administration subject, administration route, target disease, symptoms, combination and the like. For example, when the administration subject in a human, 0.01 to 100 parts by weight of the concomitant dug may be used, based on 1 part by weight of the compound of the present invention.

In addition, the compound of the present invention can be used, in the field of gene therapy, to prevent infection of retroviral vectors from spreading to other parts than the object tissues when using a retroviral vector based on HIV and MLV. In particular, when a vector is transmitted to cells and the like in a test tube and then returned to the body, by administering the compound of the present invention in advance, it is possible to prevent unnecessary infection in the body.

Examples of the reverse transcriptase inhibitor include AZT, 3TC, didanosine, zalcitabine, Sanirubujin, abacavir, tenofovir, emtricitabine, Nebirabin, efavirenz, capravirine, etracirine, delavirdine and the like.

Examples of the protease inhibitor include indinavir, ritonavir, saquinavir, nelfinavir, amprenavir, Atazanavir, lopinavir, fosamprenavir, darunavir, atanazavir, Brecanavir, Tipranavir and the like.

Examples of the integrase inhibitor include raltegravir, Elvitegravir, JTK-656, Dolutegravir (S-349572), S-265744 and the like.

Examples of other anti-HIV drugs include entry inhibitors such as maraviroc and vivriviroc and the like, fusion inhibitors such as enfuvirtide, sifuvirtide, albuvirtide and the like.

Hereinafter, the present invention will be described in more detail with reference to examples and reference examples of the present invention and test examples, but the present invention is not limited by these examples.

(LC/MS Measurement Conditions)

(1) Column: ACQUITY UPLC (Registered trademark) BEH C18 (1.7 μm i.d.2.1×50 mm) (Waters)

Flow rate: 0.8 mL/min; UV detection wavelength: 254 nm;

Mobile phase: [A]: a 0.1% formic acid-containing aqueous solution, [B]: a 0.1% formic acid-containing acetonitrile solution a linear gradient of 5% to 100% solvent [B] was carried out in 3.5 minutes, and 100% solvent [B] was kept for 0.5 minutes.

(2) Column: Shim-pack XR-ODS (2.2 μm, i.d.50×3.0 mm) (Shimadzu)

Flow rate: 1.6 mL/min; UV detection wavelength: 254 nm;

Mobile phase: [A]: a 0.1% formic acid-containing aqueous solution, [B]: a 0.1% formic acid-containing acetonitrile solution Gradient: a linear gradient of 10% to 100% solvent [B] was carried out in 3 minutes, and 100% solvent [B] was kept for 0.5 minutes.

(3) Column: Shim-pack XR-ODS (2.2 μm, i.d.50×3.0 mm) (Shimadzu)

Flow rate: 1.6 mL/min; UV detection wavelength: 254 nm;

Mobile phase: [A]: a 0.1% formic acid-containing aqueous solution, [B]: a 0.1% formic acid-containing acetonitrile solution Gradient: a linear gradient of 10% to 100% solvent [B] was carried out in 8 minutes, and 100% solvent [B] was kept for 0.5 minutes.

(4) Column: ACQUITY UPLC (Registered trademark) BEH C18 (1.7 μm i.d.2.1×50 mm) (Waters)

Flow rate: 0.8 mL/min; UV detection wavelength: 254 nm;

Mobile phase: [A] a 0.1% formic acid-containing aqueous solution, [B] a 0.1% formic acid-containing acetonitrile solution Gradient: a linear gradient of 5% to 100% solvent [B] was carried out in 9.5 minutes, and 100% solvent [B] was kept for 0.5 minutes.

Abbreviation

Ac: Acetyl n-Bu: n-butyl t-Bu: tert-butyl

BINAP: 2,2'-bis(diphenylphosphino)-1,1'-binaphthyl

Bn: benzyl

DMA: N,N-dimethylacetoamide

DME: dimethoxyethane

DMF: N,N-dimethylformamide

DCM: dichloromethane

DMAP: N,N-dimethyl-4-aminopyridine

DMSO: dimethyl suldoxide

DPPA: diphenyl phosphoryl azido dppf: 1,1'-bis(diphenylphosphino)ferrocene dppp: 1,3-bis(diphenylphosphino)propane dtbpf: 1,1'-di-tert-butyl phosphino ferrocene Et: ethyl Fmoc: 9-fluorenylmethyl oxycarbonyl Me: methyl Ms: methyl sulfonyl NBS: N-bromosuccineimide NCS: N-chlorosuccineimide NIS: N-iodesuccineimide Ph: phenyl $Pd_2(dba)_3$: tris(dibenzylideneacetone)dipalladium(0)

SEM: 2-(trimethylsilyl)ethoxymethyl

TBAF: tetra-n-butyl ammonium fluoride

TBS: tert-butyl dimethylsilyl

THF: tetrahydrofuran

Tf: trifluoromethaesulfonyl

TFA: trifluoroacetic acid

TMS: trimethylsilyl

Ts: p-toluenesulfonyl

RuPhos: 2-dicyclohexylphosphino-2',6'-diisopropoxy-1,1'-biphenyl

Reference Example 1

[Chemical formula 107]

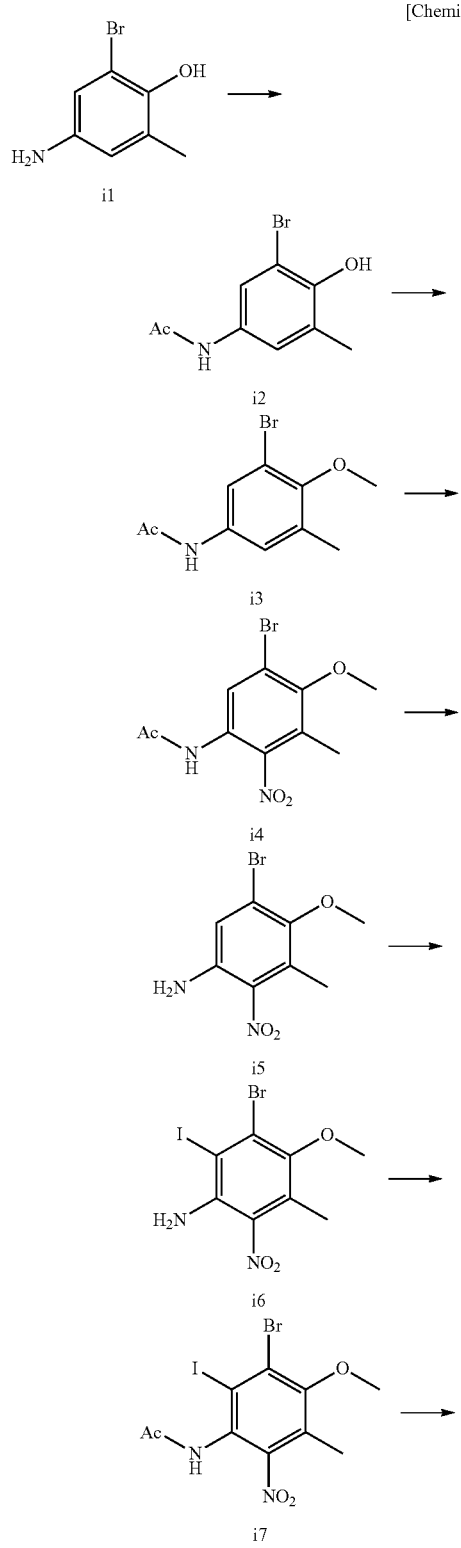

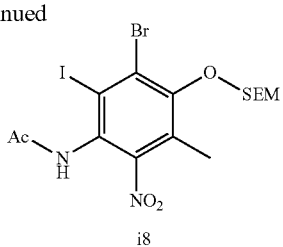

Step 1

To a solution of the compound i1 (7.0 g, 34.6 mmol) in methanol (70 mL) was added dropwise acetic acid anhydride (3.60 mL, 38.1 mmol), and the mixture was refluxed for 0.5 hours. The reaction mixture was concentrated under reduced pressure, the obtained residue was dissolved in ethyl acetate, and the organic layer was washed with water and brine, dried over anhydrous sodium sulfate, and then concentrated under reduced pressure to yield the compound i2 (8.322 g, yield 98%).

$^1$H-NMR (CDCl$_3$) δ: 2.13 (s, 3H), 2.28 (s, 3H), 5.42 (brs, 1H), 6.95 (brs, 1H), 7.09 (s, 1H), 7.60 (s, 1H).

LC/MS (ESI): m/z=243.95, 245.95 [M+H]$^+$.

Step 2

To a suspension of the compound i2 (8.322 g, 34.1 mmol) in acetonitrile (42 mL) was added cesium carbonate (13.33 g, 40.9 mmol) and methyl iodide (2.3 mL, 36.8 mmol), and the mixture was refluxed for 0.5 hours. After cooling to room temperature, water was added to the reaction mixture, and the mixture was extracted with ethyl acetate, the organic layer was washed with aqueous sodium carbonate solution, water and brine, dried over anhydrous sodium sulfate, and then concentrated under reduced pressure to yield the compound i3 (8.68 g, yield 99%).

$^1$H-NMR (CDCl$_3$) δ: 2.15 (s, 3H), 2.31 (s, 3H), 3.78 (s, 3H), 6.97 (brs, 1H), 7.55 (s, 1H).

LC/MS (ESI): m/z=257.95, 259.95 [M+H]$^+$.

Step 3

To a solution of the compound i3 (8.68 g, 33.6 mmol) in concentrated sulfuric acid (86 mL) was added dropwise a solution of concentrated nitric acid (2.25 mL, 35.3 mmol) in concentrated sulfuric acid (4.6 mL) under ice with sodium chloride cooling, and the mixture was stirred for 0.5 hours at room temperature. The reaction mixture was poured into ice water, the precipitate was collected by filtration and washed with water, and dissolved in chloroform and washed with water. The resulting chloroform solution was purified by silica gel column chromatography (ethyl acetate—chloroform) to yield the compound i4 (3.87 g, yield 38%).

$^1$H-NMR (CDCl$_3$) δ: 2.19 (s, 3H), 2.37 (s, 3H), 3.82 (s, 3H), 8.10 (brs, 1H), 8.36 (s, 1H).

LC/MS (ESI): m/z=302.95, 304.90 [M+H]$^+$.

Step 4

To a solution of the compound i4 (3.87 g, 12.77 mmol) in THF (30 mL) and methanol (15 mL) was added 2 mol/L aqueous sodium hydride solution (12.8 mL, 25.5 mmol), the mixture was refluxed for 3 hours. The reaction mixture was cooled to room temperature, aqueous ammonium chloride solution was added, and the mixture was extracted with ethyl acetate. The organic layer was washed with aqueous ammonium chloride solution, water and brine, and dried over anhydrous sodium sulfate, and then concentrated under reduced pressure to yield the compound i5 (3.35 g, yield 100%).

¹H-NMR (CDCl₃) δ: 2.41 (s, 3H), 3.75 (s, 3H), 4.83 (brs, 2H), 6.92 (s, 1H).
LC/MS (ESI): m/z=260.95, 262.95 [M+H]⁺.

Step 5

To a solution of the compound i5 (3.33 g, 12.75 mmol) in ethanol (33 mL) was added silver sulfate solution (6.21 g, 19.93 mmol), and added iodine (4.85 g, 19.14 mmol) under ice-cooling, and the mixture was stirred for 7.5 hours at room temperature. To the reaction mixture was added aqueous sodium bicarbonate carefully, added ethyl acetate, and the mixture was stirred, after that the insoluble materials was filtered out. The resulting filtrate was washed with aqueous sodium thiosulfate solution, aqueous sodium bicarbonate solution and brine, dried over anhydrous sodium sulfate, and concentrated under reduced pressure, to yield a crude product of the compound i6 (5.06 g).
LC/MS (ESI): m/z=386.85, 388.80 [M+H]⁺.

Step 6

To a suspension of the compound i6 (4.94 g, 12.77 mmol) in acetic acid (50 mL) was added acetic anhydride (26.4 mL, 281 mmol), the mixture was refluxed overnight. To the reaction mixture was added water (200 mL), and the mixture was extracted with ethyl acetate. The organic layer was washed with water and brine, dried over anhydrous sodium sulfate, and then concentrated under reduced pressure. The resulting residue was dissolved in THF (20 mL) and methanol (20 mL), aqueous sodium carbonate solution (2 mmol/L, 20 mL) was added, and the mixture was stirred for 1.5 hours at 50° C. The reaction solution was cooled to room temperature, and aqueous citric acid solution was added to the solution, and the mixture was extracted with ethyl acetate. The organic layer was washed with aqueous citric acid solution was brine, dried over anhydrous sodium sulfate, and concentrated under reduced pressure to yield a crude product of the compound i7 (5.54 g).
LC/MS (ESI): m/z=428.85, 430.85 [M+H]⁺.

Step 7

To a suspension of the compound i7 (5.48 g, 12.77 mmol) in dichloromethane (165 mL) cooled in dry ice-acetone bath was added boron tribromide (1 mol/L dichloromethane solution, 38.3 mL, 38.3 mmol) dropwise, and the mixture was stirred overnight while heating to room temperature. The reaction mixture was added aqueous sodium bicarbonate solution under ice-cooling thereto, and the insoluble materials were removed by Celite filtration. The filtrate was extracted with aqueous sodium bicarbonate solution, and washed with chloroform. The aqueous phase was neutralized with aqueous citric acid solution to pH5, and extracted with ethyl acetate. The organic layer was washed with water and brine, dried over anhydrous sodium sulfate, and concentrated under reduced pressure to yield a brown amorphous residue (1.73 g). After the chloroform layer used by washing was dried over anhydrous sodium sulfate and concentrated under reduced pressure to yield a brown amorphous residue (1.29 g).

The combined both residues (3.02 g) were dissolved in THF (60 mL), diisopropylethylamine (2.04 mL, 11.64 mmol), trimethylsilyl ethoxymethoxy chloride (1.74 mL, 9.78 mmol) was added thereto under ice-cooling, and the mixture was stirred for 1 hour. The reaction mixture was added aqueous ammonium chloride solution and ethyl acetate, and the mixture was extracted with ethyl acetate. The organic layer was washed with aqueous ammonium chloride solution, water and brine, dried over anhydrous sodium sulfate, and concentrated under reduced pressure. The resulting residue was purified by silica gel column chromatography (ethyl acetate—chloroform) to yield the compound i8 (2.37 g, yield 60%).
¹H-NMR (CDCl₃) δ: 0.04 (s, 9H), 1.00 (t, 2H, J=8.5 Hz), 2.18 (s, 3H), 2.29 (s, 3H), 3.91 (t, 2H, J=8.5 Hz), 5.14 (s, 2H), 6.96 (brs, 1H).
LC/MS (ESI): m/z=544.95, 546.95 [M+H]⁺.

Reference Example 2

[Chemical formula 108]

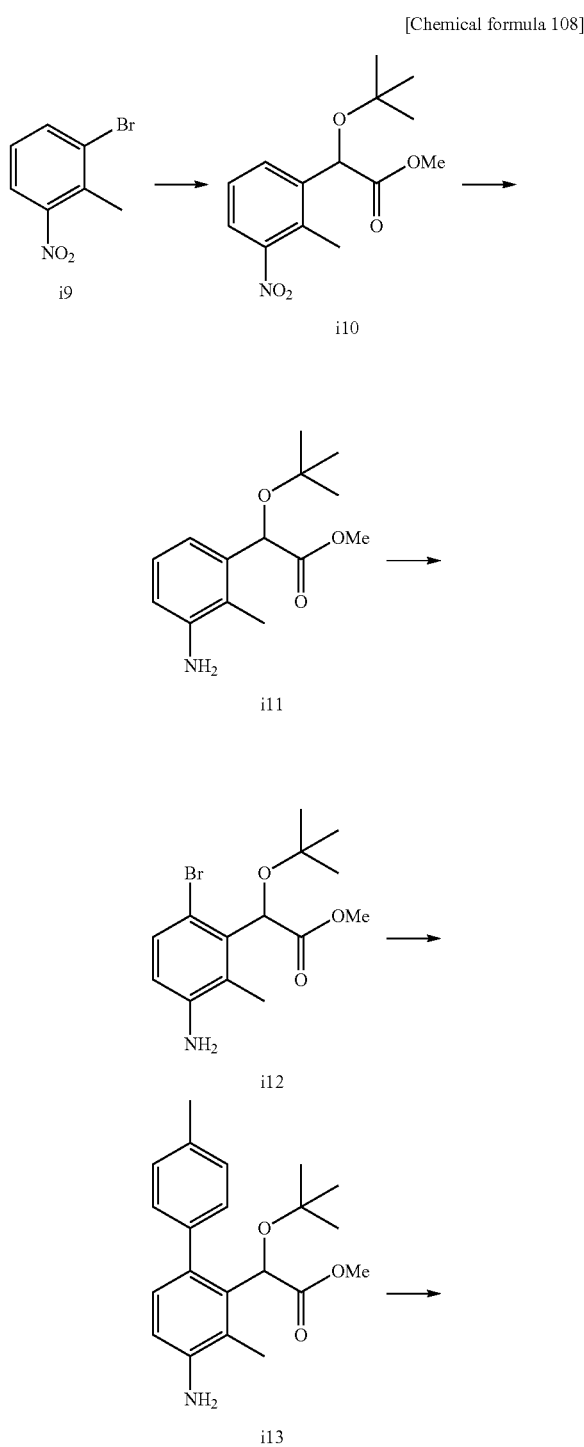

-continued

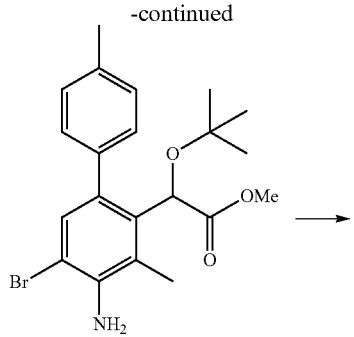

i14

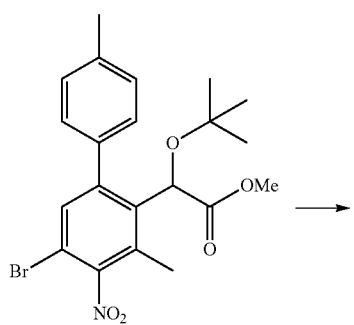

i15

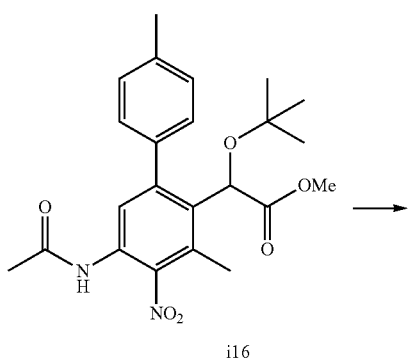

i16

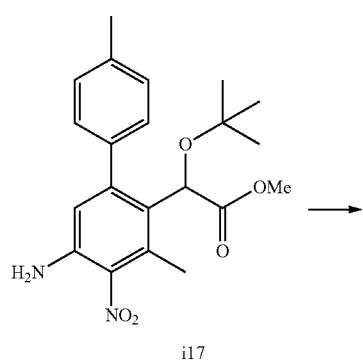

i17

-continued

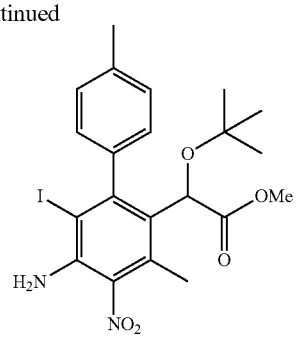

i18

Step 1

To a solution of the compound i9 (10 g, 46.3 mmol) in DMF (100 mL) was added ZnF$_2$ (14.36 g, 139 mmol), t-Bu$_3$P (2.24 mL, 9.26 mmol), Pd(dba)$_2$ (2.66 g, 4.63 mmol), (Z)-((2-(t-butoxy)-1-methoxyvinyl)oxy)trimethylsilane (30.3 g, 139 mmol), the mixture was stirred at 100° C. for 1 hour under nitrogen atmosphere. The reaction solution was added water, extracted with ethyl acetate, the organic layer was washed with water, dried over anhydrous sodium sulfate, and concentrated under reduced pressure. The resulting residue was purified by silica gel column chromatography (hexane—ethyl acetate) to yield a crude product of the compound i10 (16.1 g).

Step 2

To a solution of a crude product i10 (16.1 g) in acetic acid (160 mL) was added Zn (30.3 g, 463 mmol) under ice-cooling, the mixture was stirred at room temperature for 1 hour. The reaction solution was filtered, the filtrate was concentrated under reduced pressure. The resulting residue was purified by silica gel column chromatography (hexane—ethyl acetate) to yield the compound i11 (10.74 g, yield for 2 steps 92%).

$^1$H-NMR (CDCl$_3$) δ: 1.22 (s, 9H), 2.21 (s, 3H), 3.66 (s, 3H), 5.22 (s, 1H), 6.64 (d, 1H, J=7.3 Hz), 6.97-7.04 (m. 2H).

Step 3

To a solution of the compound i11 (10.7 g, 42.6 mmol) in DMF (100 mL) was added NBS (7.2 g, 40.4 mmol) under ice-cooling, the mixture was stirred at room temperature for 10 minutes. The reaction solution was added aqueous sodium bicarbonate solution, aqueous sodium thiosulfate solution, extracted with ethyl acetate, and the organic layer was washed with water, dried over anhydrous sodium sulfate, concentrated under reduced pressure. The resulting residue was purified by silica gel column chromatography (hexane—ethyl acetate) to yield the compound i12 (12.0 g, yield 90%).

LC/MS (ESI): m/z=330.95 [M+H]$^+$.

Step 4

To a solution of the compound i12 (11.9 g, 36 mmol) in DMF (120 mL) was added 2 mol/L aqueous potassium carbonate solution (54.1 mL, 108 mmol), p-tolylboronic acid (7.35 g, 54.1 mmol), and PdCl$_2$(dtbpf) (2.35 g, 3.6 mmol), the mixture was stirred at 100° C. under a nitrogen atmosphere. The reaction solution was added water, extracted with ethyl acetate, the organic layer was washed with water, dried over anhydrous sodium sulfate, and concentrated under reduced pressure. The resulting residue was purified by silica gel column chromatography (hexane—ethyl acetate) to yield the compound i13 (10.8 g, yield 88%).

LC/MS (ESI): m/z=342.15 [M+H]$^+$.

Step 5

The compound i14 (12.8 g, yield 97%) was obtained by reacting the compound i13 (10.7 g, 31.3 mmol) in the same manner as Step 3 of Reference Example 2.

LC/MS (ESI): m/z=420.10 [M+H]$^+$.

Step 6

A solution of the compound i14 (7.5 g, 17.84 mmol) in dichloroethane (80 mL) was added m-CPBA (17.6 g, 71.4 mmol) under ice-cooling, the mixture was refluxed for 2 hours. To the reaction solution was aqueous sodium bicarbonate solution, aqueous sodium thiosulfate solution, and the mixture was extracted with chloroform, the organic layer was washed with water, dried over anhydrous sodium sulfate, and concentrated under reduced pressure. The obtained residue was purified by silica gel column chromatography (hexane—ethyl acetate) to yield the compound i15 (5.81 g, yield 72%).

$^1$H-NMR (CDCl$_3$) δ: 0.89 (s, 9H), 2.36 (s, 3H), 2.43 (s, 3H), 3.78 (s, 3H), 5.26 (s, 1H), 7.24-7.27 (m, 4H), 7.40 (s, 1H).

Step 7

To a solution of the compound i15 (6.2 g, 13.77 mmol) in toluene (60 mL) was added cesium carbonate (13.46 g, 41.3 mmol), acetoamide (2.44 g, 41.3 mmol), BINAP (857 mg, 1.38 mmol), and palladium acetate (309 mg, 1.38 mmol), the mixture was refluxed under nitrogen atmosphere for 2 hours. The reaction solution was filtered, the filtrate was concentrated under reduced pressure, and the obtained residue was purified by silica gel column chromatography (hexane—ethyl acetate) to yield the compound i16 (3.57 g, yield 61%).

LC/MS (ESI): m/z=451.20 [M+Na]$^+$.

Step 8

To a solution of the compound i16 (3.5 g, 8.17 mmol) in methanol (35 mL) was added potassium carbonate (5.64 g, 40.8 mmol), the mixture was refluxed for 5 hours. Water was added to the reaction solution, extracted with chloroform, the organic layer was washed with water, dried over anhydrous sodium sulfate, and concentrated under reduced pressure. The obtained residue was washed with diisopropylether to yield the compound i17 (2.89 g, yield 92%).

LC/MS (ESI): m/z=409.15 [M+Na]$^+$.

Step 9

To a solution of the compound i17 (2.8 g, 7.25 mmol) in ethanol (30 mL) was added silver nitrate (2.46 g, 14.49 mmol) and iodine (3.68 g, 14.49 mmol) under ice-cooling, the mixture was stirred at room temperature for 2.5 hours. The insoluble materials were removed by filtration, aqueous sodium bicarbonate solution and aqueous sodium thiosulfate solution were added to the filtrate, extracted with ethyl acetate, the organic layer was washed with water, dried over anhydrous sodium sulfate, concentrated under reduced pressure. The obtained residue was purified by silica gel column chromatography (hexane—ethyl acetate) to yield the compound i18 (3.51 g, yield 95%).

LC/MS (ESI): m/z=535.00 [M+Na]$^+$.

Reference Example 3

[Chemical formula 109]

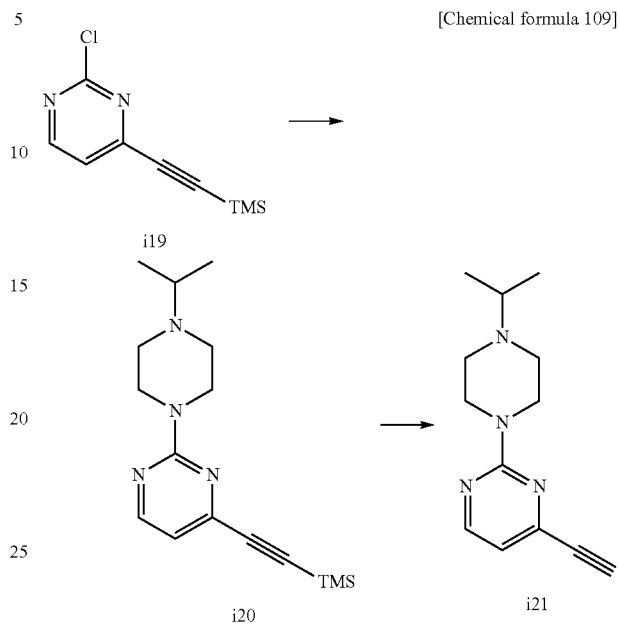

Step 1

To a solution of the compound i19 in DMF (20 mL) was added 1-isopropylpiperazine (4.85 mL, 34.2 mmol), the mixture was stirred at 60° C. for 1 hour. Water was added to the reaction solution, and extracted with ethyl acetate, the organic layer was washed with water, dried over anhydrous sodium sulfate, and concentrated under reduced pressure. The obtained residue was purified by silica gel column chromatography (ethyl acetate) to yield the compound i20 (2.54 g, yield 74%).

LC/MS (ESI): m/z=303.20 [M+H]$^+$.

Step 2

To a solution of the compound i20 in methanol was added potassium hydroxide, the mixture was stirred at room temperature for 30 minutes. The reaction solution was concentrated under reduced pressure, and the obtained residue was purified by silica gel column chromatography (ethyl acetate) to yield the compound i21 (1.17 g, yield 61%).

LC/MS (ESI): m/z=231.05 [M+H]$^+$.

Example 1

[Chemical formula 110]

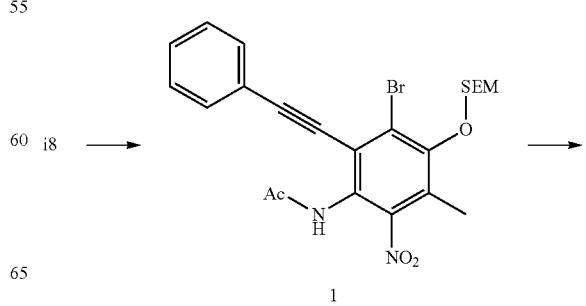

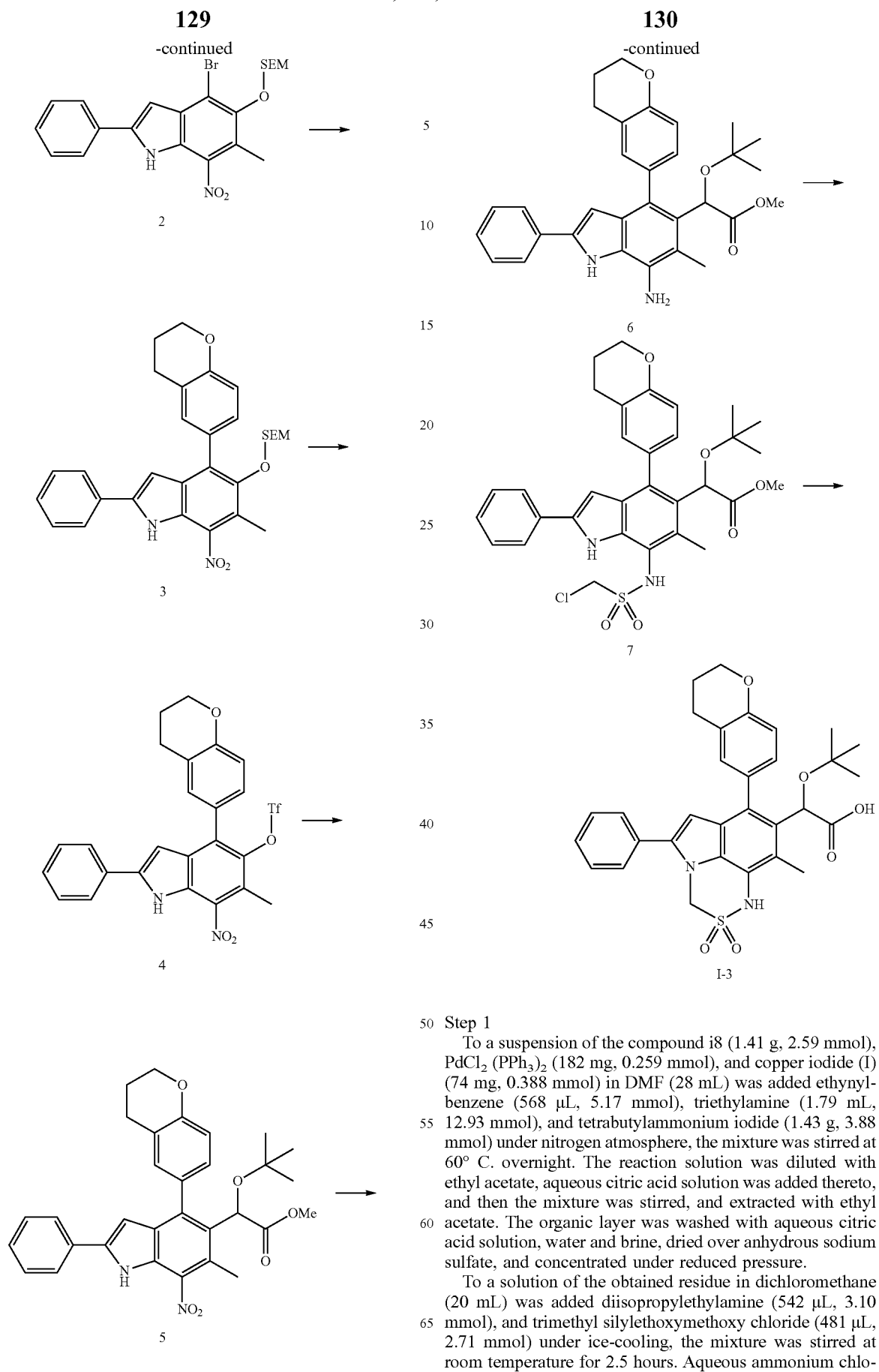

Step 1
To a suspension of the compound i8 (1.41 g, 2.59 mmol), PdCl$_2$(PPh$_3$)$_2$ (182 mg, 0.259 mmol), and copper iodide (I) (74 mg, 0.388 mmol) in DMF (28 mL) was added ethynylbenzene (568 μL, 5.17 mmol), triethylamine (1.79 mL, 12.93 mmol), and tetrabutylammonium iodide (1.43 g, 3.88 mmol) under nitrogen atmosphere, the mixture was stirred at 60° C. overnight. The reaction solution was diluted with ethyl acetate, aqueous citric acid solution was added thereto, and then the mixture was stirred, and extracted with ethyl acetate. The organic layer was washed with aqueous citric acid solution, water and brine, dried over anhydrous sodium sulfate, and concentrated under reduced pressure.
To a solution of the obtained residue in dichloromethane (20 mL) was added diisopropylethylamine (542 μL, 3.10 mmol), and trimethyl silylethoxymethoxy chloride (481 μL, 2.71 mmol) under ice-cooling, the mixture was stirred at room temperature for 2.5 hours. Aqueous ammonium chloride solution was added to the reaction solution, extracted with chloroform, and the organic layer was washed with brine, dried over anhydrous sodium sulfate, and concentrated under reduced pressure. The obtained residue was purified by silica gel column chromatography (ethyl acetate—chloroform) to yield the compound 1 (910 mg, yield 68%).

$^1$H-NMR (CDCl$_3$) δ: 0.05 (s, 9H), 1.01 (t, 2H, J=8.5 Hz), 2.21 (s, 3H), 2.38 (s, 3H), 3.93 (t, 2H, J=8.5 Hz), 5.16 (s, 2H), 7.39-7.42 (m, 3H), 7.53-7.56 (m, 2H).

LC/MS (ESI):m/z=519.10, 521.10 [M+H]$^+$.

Step 2

To a solution of the compound 1 (910 mg, 1.75 mmol) in THF (20 mL) was added tetrabutylammonium bromide/THF solution (1 mol/L, 4.4 mL), the mixture was stirred at 70° C. for 2 hours. The reaction solution was cooled to room temperature, aqueous ammonium chloride solution was added thereto, extracted with ethyl acetate, and then the organic layer was washed with water and brine, dried over anhydrous sodium sulfate, concentrated under reduced pressure. The obtained residue was purified by silica gel column chromatography (ethyl acetate—hexane) to yield the compound 2 (431 mg, yield 52%).

$^1$H-NMR (CDCl$_3$) δ: 0.06 (s, 9H), 1.01-1.08 (m, 2H), 2.81 (s, 3H), 3.96-4.02 (m, 2H), 5.16 (s, 2H), 6.92 (d, 1H, J=2.5 Hz), 7.38-7.43 (m, 1H), 7.50 (t, 2H, J=7.6 Hz), 7.72 (d, 2H, J=7.5 Hz), 10.03 (s, 1H).

LC/MS (ESI): m/z=477.00, 479.05 [M+H]$^+$.

Step 3

To 6-chromanylboronic acid (58 mg, 0.324 mmol), Pd$_2$(dba)$_3$ (7.9 mg, 8.63 μmol), RuPhos (12 mg, 26 μmol), and potassium phosphate (183 mg, 0.863 mmol) were added a solution of the compound 2 (103 mg, 0.216 mg) in dioxane (1 mL) under nitrogen atmosphere, the mixture was stirred at 120° C. for 50 minutes under microwave irradiation. The reaction solution was diluted with ethyl acetate, aqueous ammonium chloride solution was added thereto, extracted with ethyl acetate, and the organic layer was washed with water and brine, dried over anhydrous sodium sulfate, and concentrated under reduced pressure. The obtained residue was purified by silica gel column chromatography (ethyl acetate—hexane) to yield the compound 3 (92.4 mg, yield 81%).

$^1$H-NMR (CDCl$_3$) δ: 0.00 (s, 9H), 0.83 (t, 2H, J=8.5 Hz), 2.07-2.12 (m, 2H), 2.83 (s, 3H), 2.89 (t, 2H, J=6.3 Hz), 3.49 (t, 2H, J=8.5 Hz), 4.28 (t, 2H, J=5.0 Hz), 4.67 (s, 2H), 6.77 (d, 1H, J=1.8 Hz), 6.94 (d, 1H, J=8.3 Hz), 7.32 (s, 1H), 7.34-7.40 (m, 2H), 7.41-7.49 (m, 2H), 7.68 (d, 2H, J=7.7 Hz), 10.10 (s, 1H).

LC/MS (ESI): m/z=531.25 [M+H]$^+$.

Step 4

The compound 4 (114 mg, yield 86%) was obtained by reacting the compound 3 (121 mg, 0.228 mmol) in the same manner as Step 4 in Example 3.

$^1$H-NMR (CDCl$_3$) δ: 2.05-2.13 (m, 2H), 2.85-2.90 (m, 5H), 4.26-4.31 (m, 2H), 6.83 (s, 1H), 6.96 (d, 1H, J=8.5 Hz), 7.22-7.31 (m, 2H), 7.38-7.43 (m, 1H), 7.48 (t, 2H, J=7.4 Hz), 7.69 (d, 2H, J=7.5 Hz), 10.18 (s, 1H).

LC/MS (ESI): m/z=533.10 [M+H]$^+$.

Step 5

The compound 5 (90 mg, yield 80%) was obtained by reacting the compound 4 (113 mg, 0.212 mmol) in the same manner as Step 5 in Example 5.

LC/MS (ESI): m/z=529.15 [M+H]$^+$.

Step 6

To a suspension of the compound 5 (56 mg, 0.106 mmol) and tin chloride (II) (100 mg, 0.53 mmol) in ethanol (5 mL) was refluxed for 6 hours under nitrogen atmosphere. The reaction solution was cooled to room temperature, aqueous sodium bicarbonate solution and ethyl acetate was added thereto, the mixture was filtered by celite. The filtrate was extract with ethyl acetate, and the organic layer was washed with water and brine, dried over anhydrous sodium sulfate, concentrated under reduced pressure. The obtained residue was silica gel column chromatography (ethyl acetate—hexane) to yield the compound 6 (30.4 mg, yield 57%).

$^1$H-NMR (CDCl$_3$) δ: 2.05-2.11 (m, 2H), 2.25 (s, 3H), 2.72-2.93 (m, 2H), 3.54 (br s, 2H), 3.71 (d, 3H, J=9.3 Hz), 4.27 (t, 2H, J=5.0 Hz), 5.43 (d, 1H, J=7.0 Hz), 6.48 (s, 1H), 6.88 (dd, 1H, J=8.1, 5.3 Hz), 7.13-7.30 (m, 3H), 7.35-7.41 (m, 2H), 7.58-7.63 (m, 2H), 8.30 (s, 1H).

LC/MS (ESI): m/z=499.20 [M+H]$^+$.

Step 7

To a solution of the compound 6 (20 mg, 40 μmol) in dichloromethane (1 mL) was added pyridine (8.11 μL, 0.10 mmol), and DMAP (0.5 mg, 4 μmol), then added chloromethane sulfonyl chloride (4.74 μL, 52 μmol), the mixture was stirred at room temperature overnight. To the reaction solution was added aqueous citric acid solution, the mixture was extracted with dichloromethane, and the organic layer was concentrated under reduced pressure, the obtained residue was purified by silica gel column chromatography (ethyl acetate—hexane) to yield the compound 7 (22.7 mg, yield 93%).

LC/MS (ESI): m/z=611.15, 613.15 [M+H]$^+$.

Step 8

To a solution of the compound 7 (22.7 mg, 37 μmol) in DMA was added sodium hydride (60% oil suspension, 8.9 mg, 0.23 mmol) under nitrogen atmosphere, the mixture was stirred at 100° C. The reaction solution was cooled to room temperature, added aqueous citric acid solution and stirred, and then extracted with dichloromethane, concentrated under reduced pressure. The obtained residue was purified by silica gel column chromatography (methanol—chloroform) to yield the compound I-3 (20.2 mg, 74%).

$^1$H-NMR (CDCl$_3$) δ: 0.95 (s, 9H), 1.26 (t, 2H, J=7.0 Hz), 2.35 (d, 3H, J=3.6 Hz), 2.87 (t, 2H, J=6.1 Hz), 4.27 (t, 2H, J=5.0 Hz), 4.90-4.97 (m, 1H), 5.23-5.34 (m, 1H), 5.63 (s, 1H), 6.39 (d, 1H, J=6.3 Hz), 6.91 (t, 1H, J=9.0 Hz), 7.18 (t, 1H, J=8.2 Hz), 7.27-7.45 (m, 7H), 10.15 (s, 1H).

LC/MS (ESI): m/z=561.15 [M+H]$^+$.

[Chemical formula 111]

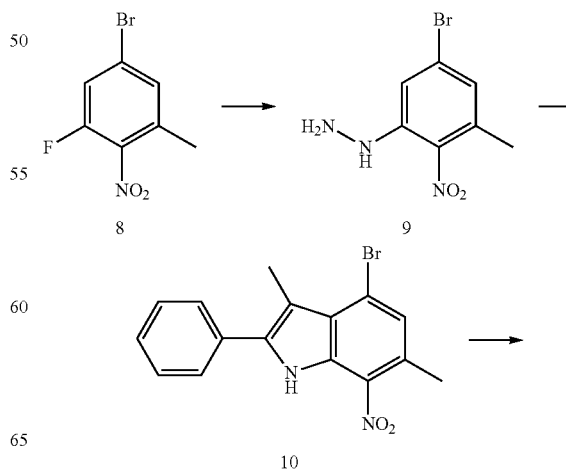

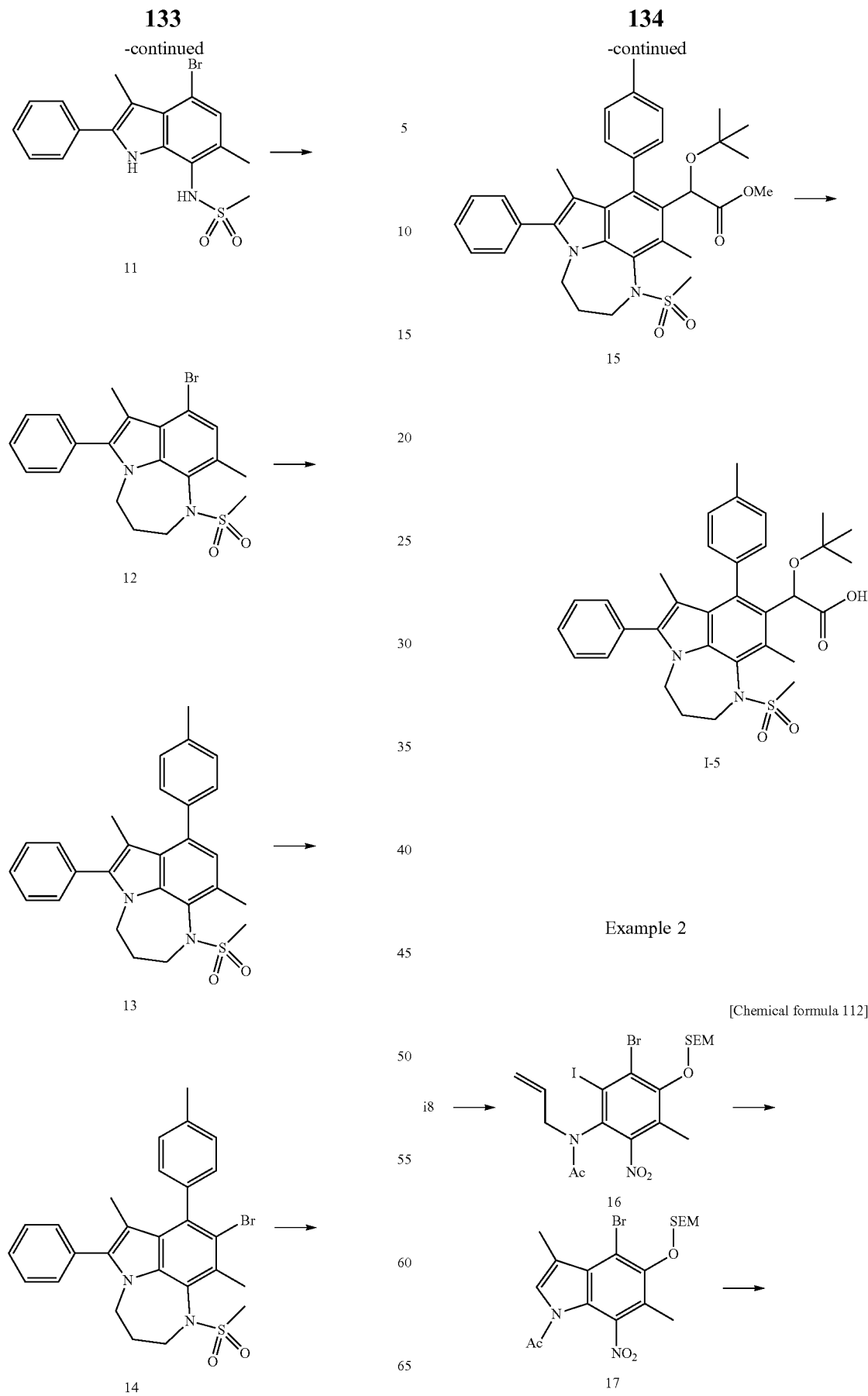

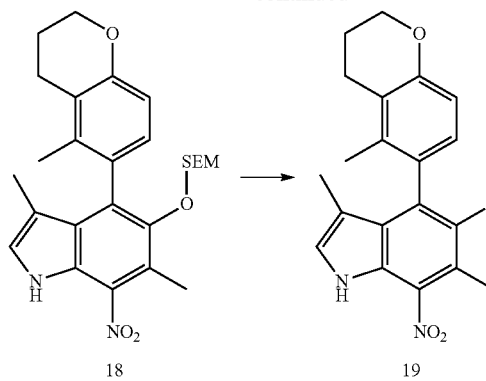

18 → 19

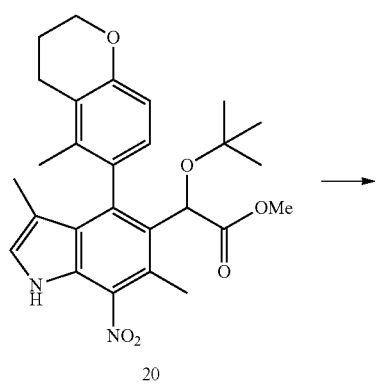

20

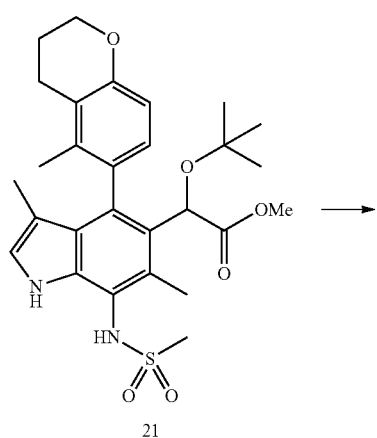

21

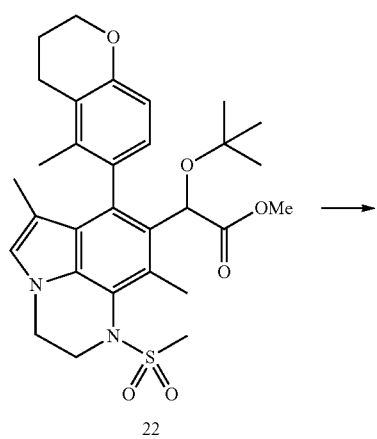

22

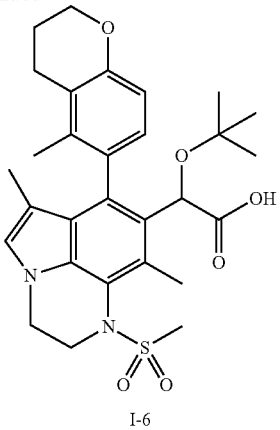

I-6

Step 1

To a suspension of the compound 8 (10 g, 42.7 mmol) in ethanol (50 mL) was added hydrazine monohydrate (6.23 mL, 128 mmol) under ice-cooling, and the mixture was stirred at room temperature overnight. The precipitate was collected by filtration and washed with washing solution to yield a crude product of the compound 9 (10.20 g).

$^1$H-NMR (CDCl$_3$) δ: 2.46 (s, 3H), 3.70 (s, 2H), 6.73 (s, 1H), 7.63 (s, 1H), 7.80 (brs, 1H).

LC/MS (ESI): m/z=245.80, 247.85 [M+H]$^+$.

Step 2

To the compound 9 (3.68 g, 15.0 mmol) was added propiophenone (2.39 mL, 18 mmol), trifluoroacetic acid (23 mL, 299 mmol) under ice-cooling, and the mixture was stirred at 120° C. for 30 minutes in a sealed tube. The reaction solution was added water and hexane, the precipitate was collected by filtration, washed with hexane. The obtained solid was purified by silica gel column chromatography (ethyl acetate—hexane) to yield the compound 10 (2.44 g, yield 47%).

$^1$H-NMR (CDCl$_3$) δ: 2.65 (s, 3H), 2.79 (s, 3H), 7.43-7.49 (m, 1H), 7.50-7.59 (m, 4H), 9.97 (s, 1H).

LC/MS (ESI): m/z=344.90, 346.90 [M+H]$^+$.

Step 3

To a suspension of the compound 10 (1.00 g, 2.90 mmol) in ethanol (200 mL) was added iron powder (1.94 g, 34.8 mmol) and ammonium chloride (6.20 g, 116 mmol), the mixture was refluxed for 7 hours. The reaction solution was cooled to room temperature and filtered through celite, and the residue was washed ethyl acetate and water. The combined filtrate and washing solution was extracted with ethyl acetate, the organic layer was washed with brine, dried over anhydrous sodium sulfate, and concentrated under reduced pressure. To the resulting residue in dichloromethane (180 mL) solution was added pyridine (586 μL, 7.24 mmol), and added methanesulfonic anhydride (555 mg, 3.19 mmol) under ice-cooling, the mixture was stirred at room temperature for 1.5 hours. The reaction solution was added aqueous ammonium chloride solution, extracted with chloroform, and the organic layer was dried over anhydrous sodium sulfate, and concentrated under reduced pressure. The obtained residue was purified by silica gel column chromatography (ethyl acetate—hexane) to yield the compound 11 (792 mg, yield 70%).

$^1$H-NMR (CDCl$_3$) δ: 2.42 (3H, s), 2.64 (3H, s), 3.00 (3H, s), 6.08 (1H, s), 7.17 (1H, s), 7.39 (1H, t, J=7.0 Hz), 7.48 (2H, t, J=7.5 Hz), 7.55 (2H, d, J=7.5 Hz), 9.12 (1H, s).

LC/MS (ESI): m/z=392.90, 394.90 [M+H]$^+$.

Step 4

To a solution of the compound 11 (493 mg, 1.25 mmol) in DMF (5 mL) was added cesium carbonate (1.225 g, 3.76 mmol) and 1,3-dibromopropane (165 μL, 1.63 mmol), and the mixture was stirred at room temperature 10 hours. To the reaction solution was added aqueous ammonium chloride solution, the mixture was extracted with ethyl acetate, the organic layer was washed with aqueous ammonium chloride solution, aqueous sodium bicarbonate solution, water and brine, dried over anhydrous sodium sulfate, and concentrated under reduced pressure. The obtained residue was purified by silica gel column chromatography (ethyl acetate—chloroform) to yield the compound 12 (476 mg, yield 88%).

$^1$H-NMR (CDCl$_3$) δ: 1.87-1.99 (m, 1H), 2.14-2.24 (m, 1H), 2.44 (s, 6H), 3.14 (s, 3H), 3.62-3.71 (m, 1H), 3.78-3.86 (m, 1H), 4.19 (dt, 1H, J=15.0, 7.5 Hz), 4.49 (t, 1H, J=12.8 Hz), 7.16 (s, 1H), 7.35 (d, 2H, J=7.4 Hz), 7.42 (t, 1H, J=7.1 Hz), 7.49 (t, 2H, J=7.4 Hz).

LC/MS (ESI): m/z=433.00, 434.95 [M+H]$^+$.

Step 5

To the compound 12 (100 mg, 0.231 mmol), p-tolylboronic acid (41 mg, 0.30 mmol), Pd$_2$(dba)$_3$ (5.3 mg, 5.8 mmol), and RuPhos (16.2 mg, 0.035 mmol) was added dioxane (2 mL) and aqueous sodium carbonate solution (2 mol/L, 462 μL, 0.923 mmol), and the mixture was stirred at 12° C. for 15 minutes under microwave irradiation. Water was added to the reaction solution, followed by extraction with ethyl acetate, the organic layer was washed with water and brine, dried over anhydrous sodium sulfate, and concentrated under reduced pressure. The obtained residue was purified by silica gel column chromatography (ethyl acetate/hexane) to yield the compound 13 (93 mg, yield 91%).

$^1$H-NMR (CDCl$_3$) δ: 1.75 (s, 3H), 1.96-2.08 (m, 1H), 2.20-2.29 (m, 1H), 2.42 (s, 3H), 2.50 (s, 3H), 3.18 (s, 3H), 3.69-3.78 (m, 1H), 3.79-3.87 (m, 1H), 4.25 (dt, 1H, J=15.0, 7.5 Hz), 4.54 (t, 1H, J=12.5 Hz), 6.84 (s, 1H), 7.21 (d, 2H, J=7.8 Hz), 7.32-7.37 (m, 4H), 7.39 (d, 1H, J=6.4 Hz), 7.43-7.49 (m, 2H).

LC/MS (ESI): m/z=445.10 [M+H]$^+$.

Step 6

The compound 14 (33 mg, yield 61%) was obtained by reacting the compound 13 (46 mg, 0.103 mmol) in the same manner as Step 3 in Reference Example 2.

$^1$H-NMR (CDCl$_3$) δ: 1.45 (s, 3H), 1.54 (s, 3H), 1.92-2.04 (m, 1H), 2.15-2.26 (m, 1H), 2.44 (s, 3H), 2.61 (s, 3H), 3.16 (s, 3H), 3.68-3.77 (m, 1H), 3.77-3.85 (m, 1H), 4.31 (dt, 1H, J=15.0, 7.5 Hz), 4.51 (t, 1H, J=12.8 Hz), 7.19 (t, 1H, J=8.0 Hz), 7.24 (d, 2H, J=8.3 Hz), 7.31 (d, 2H, J=7.3 Hz), 7.38 (t, 1H, J=6.5 Hz), 7.44 (t, 2H, J=7.5 Hz).

LC/MS (ESI): m/z=523.10, 525.10 [M+H]$^+$.

Step 7

The compound 14 (33 mg, 0.063 mmol) was reacted in the same manner as Step 5 in Example 3 to yield a diastereomeric mixture of the compound 15 (24.4 mg, yield 66%) as a yellow amorphous. Although the mixture can be separated, they isomerize at room temperature, therefore they lead to the next step as a diastereomeric mixture.

Both diastereomers: LC/MS (ESI): m/z=589.25 [M+H]$^+$.

Step 8

The compound 15 (33 mg, 0.056 mmol) was reacted in the same manner as Step 8 in Example 3 to yield a diastereomeric mixture of the compound I-5 (13.4 m, yield 42%) as a white solid. Although the mixture can be separated, they isomerize at room temperature, therefore they lead to the next step as a diastereomeric mixture.

Both diastereomer: LC/MS (ESI): m/z=575.20 [M+H]$^+$.

Example 3

Step 1

To a solution of the compound i8 (500 mg, 0.917 mmol) in acetonitrile (10 mL) solution was added cesium carbonate (418 mg, 1.28 mmol) and allyl bromide (95 μL, 1.1 mmol), the mixture was stirred at room temperature overnight. Aqueous ammonium chloride solution was added to the reaction solution, followed by extraction with chloroform and concentration under reduced pressure. The resulting residue was purified by silica gel column chromatography (ethyl acetate—hexane) to yield the compound 16 (398 mg, yield 74%).

LC/MS (ESI): m/z=585.00, 586.95 [M+H]$^+$.

Step 2

To a suspension of the compound 16 (1.354 g, 2.313 mmol) in acetonitrile (27 mL) was added diisopropylethyl amine (1.2 mL, 6.94 mmol) and tetrakistriphenylphosphine palladium (134 mg, 0.116 mmol), the mixture was stirred at room temperature for 6 days. Aqueous ammonium chloride solution was added to the reaction solution, followed by extraction with ethyl acetate, and the organic layer was washed with aqueous ammonium chloride solution, water and brine, dried over anhydrous sodium sulfate, and concentrated under reduced pressure. The obtained residue was purified by silica gel column chromatography (ethyl acetate—hexane) to yield the compound 17 (562 mg, yield 53%).

$^1$H-NMR (CDCl$_3$) δ: 0.04 (s, 9H), 1.02 (t, 2H, J=8.5 Hz), 2.46 (s, 3H), 2.53 (s, 3H), 2.58 (s, 3H), 3.95 (t, 2H, J=8.5 Hz), 5.12 (s, 2H), 7.24 (s, 1H).

LC/MS (ESI): m/z=935.05, 937.05, 939.055 [2M+Na]$^+$.

Step 3

A suspension of the compound 17 (202 mg, 0.442 mmol), (5-methylchromane-6-yl)boronic acid (170 mg, 0.883 mmol), PdCl$_2$(dtbpf) (8.6 mg, 0.013 mmol), dioxane (3 mL), and aqueous sodium carbonate solution (2 mol/L, 0.88 mL, 1.77 mmol) was sealed tube under nitrogen atmosphere and stirred at 150° C. for 30 minutes under microwave irradiation. To the reaction solution was added aqueous ammonium chloride solution and ethyl acetate, the mixture was filtered through celite, and the filtrate was extracted with ethyl acetate. The organic layer was washed with aqueous ammonium chloride solution, aqueous sodium bicarbonate, and brine, dried over anhydrous sodium sulfate, and concentrated under reduced pressure. The obtained residue was purified by silica gel column chromatography (ethyl acetate—hexane) to yield the compound 18 (78 mg, yield 37%).

$^1$H-NMR (CDCl$_3$) δ: 0.02 (s, 9H), 0.83-0.86 (m, 2H), 1.61 (s, 3H), 1.93 (s, 3H), 2.10-2.15 (m, 2H), 2.73 (t, 2H, J=6.4 Hz), 2.81 (s, 3H), 3.30-3.43 (m, 2H), 4.22 (t, 2H, J=5.1 Hz), 4.68 (dd, 2H, J=9.6, 5.2 Hz), 6.76 (d, 1H, J=8.4 Hz), 6.98 (d, 1H, J=8.3 Hz), 7.02 (s, 1H), 9.66 (brs, 1H).

LC/MS (ESI): m/z=481.10 [M−H]$^-$.

Step 4

To a solution of the compound 18 (117 mg, 0.242 mmol) in THF (1 mL) and methanol (1 mL) was added hydrochloric acid (2 mol/L, 0.24 mL, 0.485 mmol), the mixture was stirred at 60° C. for an hour. Water was added to the reaction solution and extracted with chloroform. The organic layer was concentrated under reduced pressure, the obtained residue was purified by silica gel column chromatography (chloroform) to yield a solid (77 mg).

To the solution of the obtained solid (77 mg) in dichloromethane (2 mL) was added pyridine (0.141 mL, 0.568 mmol), and added trifluoromethanesulfonic anhydride (0.1 mL, 0.656 mmol) under ice-cooling, and the mixture was stirred at room temperature for 4 hours. To the reaction mixture was added aqueous ammonium chloride solution followed by extraction with dichloromethane and concentration under reduced pressure. The obtained residue was purified by silica gel chromatography (ethyl acetate—hexane) to yield the compound 19 (104 mg, yield 98%).

LC/MS (ESI): m/z=485.00 [M+H]$^+$.

Step 5

To a suspension of the compound 19 (49 mg, 0.101 mmol), Pd$_2$(dba)$_3$ (14 mg, 0.015 mmol), RuPhos (43 mg, 0.091 mmol), zinc fluoride (II) (52 mg, 0.506 mmol) in DMF (2 mL) was added ((2-(t-butoxy)-1-methoxyvinyl)oxy)trimethylsilane (177 mg, 0.809 mmol), the mixture was stirred at 130° C. for 6 hours under nitrogen atmosphere. The reaction solution was cooled to room temperature, and aqueous ammonium chloride solution and chloroform was added to the mixture, the mixture was extracted with chloroform and concentrated under reduced pressure. The obtained residue was purified by silica gel chromatography (ethyl acetate—hexane) to yield the compound 20 (41 mg, yield 84%).

LC/MS (ESI): m/z=479.10 [M−H]$^-$.

Step 6

To a suspension of the compound 20 (76 mg, 0.158 mmol) in ethanol was added ammonium chloride (169 mg, 3.16 mmol) and iron powder (71 mg, 1.27 mmol), the mixture was refluxed for 4 hours. The reaction solution was filtered through celite, the residue was washed with ethyl acetate and water, and the combined filtrate was extracted with ethyl acetate. The organic layer was washed with brine, dried over anhydrous sodium sulfate, and concentrated under reduced pressure to yield a residue.

To a dichloromethane solution of the resulting residue after addition pyridine (0.0384 mL, 0.475 mmol) was added methanesulfonic anhydride (35.8 mg, 0.206 mmol) under ice-cooling, the mixture was stirred at room temperature for 1 hour. Aqueous ammonium chloride solution was added to the reaction solution, extracted with dichloromethane, and concentrated under reduced pressure. The obtained residue was purified by silica gel chromatography (ethyl acetate—hexane) to yield the compound 21 (42.5 mg, yield 51%).

LC/MS (ESI): m/z=527.10 [M−H]$^-$.

Step 7

To a suspension of the compound 21 (31 mg, 0.059 mmol) and cesium carbonate (86 mg, 264 mmol) in DMF was added 1,2-dicromoethane (9.6 µL, 0.111 mmol), the mixture was stirred at room temperature for 19 hours. The reaction solution was added aqueous ammonium chloride solution and extracted with chloroform, the organic layer was concentrated under reduced pressure. The obtained residue was purified by silica gel chromatography (ethyl acetate—hexane) to yield the compound 22 (30.7 mg, yield 94%).

LC/MS (ESI): m/z=555.25 [M+H]$^+$.

Step 8

To a solution of the compound 22 (30 mg, 0.054 mmol) in THF and methanol (each 0.3 mL) was added aqueous sodium hydrate solution (2 mol/L, 0.54 mL, 1.08 mmol), the mixture was stirred at 65° C. for 9.5 hours. The reaction solution was cooled to room temperature, stirred with aqueous ammonium chloride solution and chloroform and extracted with chloroform, and concentrated under reduced pressure. The obtained residue was purified by silica gel column chromatography (chloroform) to yield the desired compound (27.4 mg, yield 93%) as an atropisomeric mixture. The mixture was purified by preparative TLC to yield the compound I-6 (4.7 mg) as a single isomer.

$^1$H-NMR (CDCl$_3$) δ: 0.79-0.89 (m, 1H), 1.12 (s, 9H), 1.47 (s, 3H), 1.98 (s, 3H), 2.07-2.13 (m, 2H), 2.45 (br s, 3H), 2.66-2.75 (m, 2H), 2.98 (s, 3H), 3.51 (br s, 1H), 4.20 (t, 2H, J=4.9 Hz), 4.37 (br s, 2H), 5.33 (s, 1H), 6.69 (d, 1H, J=8.4 Hz), 6.71 (s, 1H), 6.97-7.02 (m, 1H), 9.92 (br s, 1H).

LC/MS (ESI): m/z=539.15 [M−H]$^-$.

Example 4

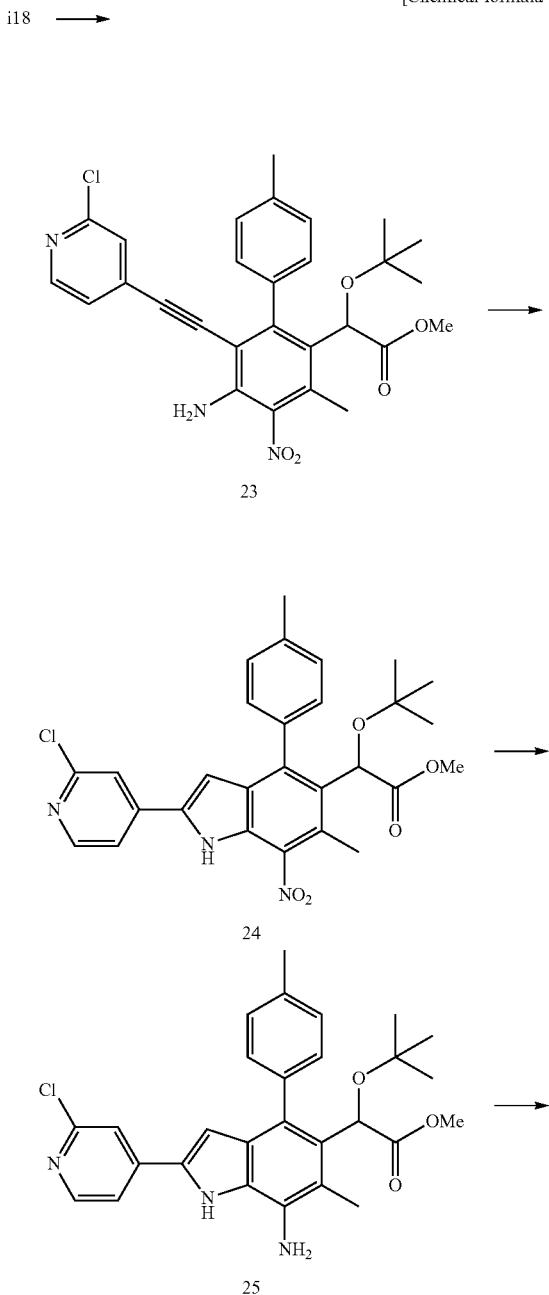

[Chemical formula 113]

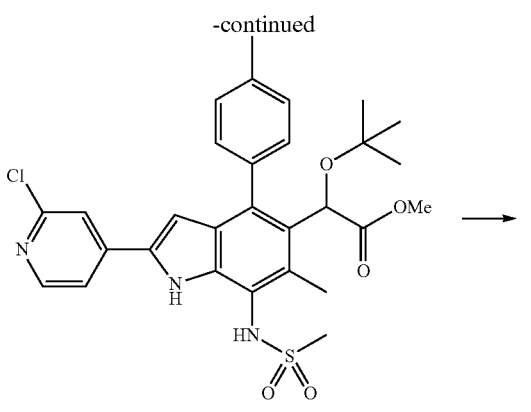

26

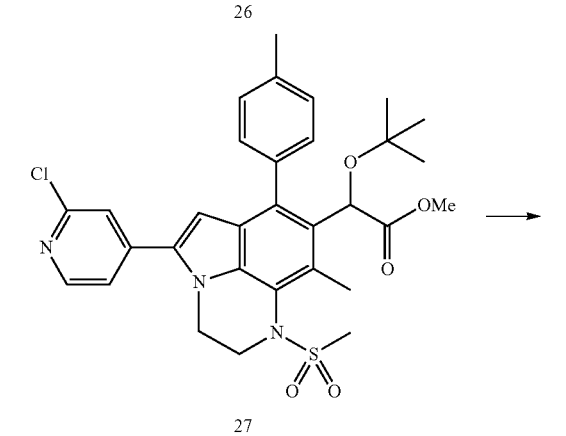

27

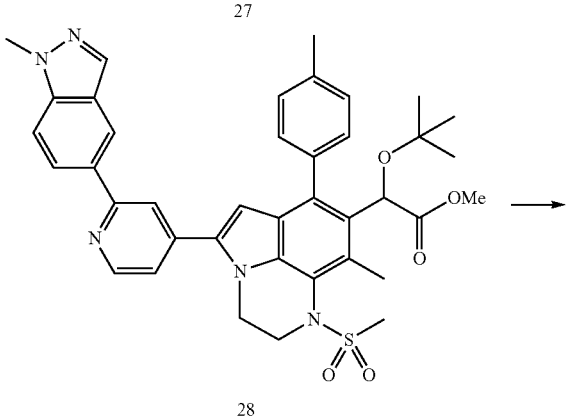

28

I-8

Step 1

To a solution of the compound i18 (1 g, 1.95 mmol) in DMF (10 mL) was added Et₃N (0.812 mL, 5.86 mmol), 2-chloro-4-ethynylpyridine (806 mg, 5.86 mmol), copper iodide (37.2 mg, 0.195 mmol), and PdCl₂(PPh₃)₂ (137 mg, 0.195 mmol), the mixture was stirred under nitrogen atmosphere at 100° C. for 1 hour. Water was added to the reaction solution, extracted with ethyl acetate, and the organic layer was washed water, dried over anhydrous sodium sulfate, concentrated under reduced pressure. The obtained residue was purified by silica gel chromatography (hexane—ethyl acetate) to yield the compound 23 (574 mg, yield 56%).

LC/MS (ESI):m/z=522.20 [M+H]⁺.

Step 2

To a solution of the compound 23 (570 mg, 1.09 mmol) in DMF (6 mL) was added potassium carbonate (1.51 g, 10.92 mmol), the mixture was stirred at 100° C. for 6 hours. Water was added to the reaction solution, and extracted with ethyl acetate, the organic layer was washed with water, dried over anhydrous sodium sulfate, and concentrated under reduced pressure. The obtained residue was purified by silica gel column chromatography (hexane—ethyl acetate) to yield the compound 24 (413 mg, yield 73%).

LC/MS (ESI): m/z=522.15 [M+H]⁺.

Step 3

To a solution of the compound 24 (420 mg, 0.805 mmol) in acetic acid (4 mL) was added zinc (316 mg, 2.82 mmol) under ice-cooling, the mixture was stirred at room temperature for 1 hour. The reaction solution was filtered, the filtrate was concentrated under reduced pressure, the obtained yield was purified by silica gel column chromatography (hexane—ethyl acetate) to yield the compound 25 (388 mg, yield 98%).

LC/MS (ESI): m/z=492.2 [M+H]⁺.

Step 4

To a solution of the compound 25 (375 mg, 0.762 mmol) in dichloromethane (4 mL) was added pyridine (0.123 mL, 1.524 mmol) and methanesulfonyl anhydride (199 mg, 1.143 mmol), the mixture was stirred at room temperature for 10 minutes. Aqueous ammonium chloride solution was added to the reaction solution, extracted with chloroform, washed with water, dried over anhydrous sodium sulfate, and concentrated under reduced pressure. The obtained residue was purified by silica gel column chromatography (hexane—ethyl acetate) to yield the compound 26 (397 mg, yield 91%).

LC/MS (ESI): m/z=570.15 [M+H]⁺.

Step 5

The compound 27 (348 mg, yield 98%) was obtained by reacting the compound 26 (340 mg, 0.596 mmol) in the same manner as Step 7 in Example 3.

LC/MS (ESI): m/z=596.05 [M+H]⁺.

Step 6

To a solution of the compound 27 (100 mg, 0.168 mmol) in DMF (1 mL) was added 2 mol/L aqueous potassium carbonate solution (0.252 mL, 0.503 mmol), (1-methyl-1H-indazole-5-yl) boronic acid (44.3 mg, 0.252 mmol), and PdCl₂ (dtbpf) (10.93 mg, 0.017 mmol), the mixture was stirred at 100° C. under nitrogen atmosphere. Water was added to the reaction solution and extracted with ethyl acetate, and the organic layer was washed with water, dried with anhydrous sodium sulfate, concentrated under reduced pressure. The obtained residue was purified by silica gel column chromatography (hexane—ethyl acetate) to yield the compound 28 (116 mg, yield 100%).

LC/MS (ESI): m/z=692.30 [M+H]⁺.

Step 7
The compound I-8 (105 mg, yield 92%) was obtained by reacting the compound 28 (116 mg, 0.168 mmol) in the same manner as Step 8 in Example 3.
LC/MS (ESI): m/z=678.30 [M+H]$^+$
1H-NMR (CDCl3) δ: 0.95 (s, 9H), 2.47 (s, 3H), 2.49 (s, 3H), 3.25 (s, 3H), 3.42 (br, 1H), 4.12 (s, 3H), 4.31 (br, 2H), 4.82 (br, 1H), 5.57 (s, 1H), 6.60 (s, 1H), 7.20-7.52 (m, 5H), 7.68-7.70 (m, 1H), 7.85 (br, 1H), 8.05-8.14 (m, 1H), 8.36 (br, 1H), 8.68-8.75 (m, 1H).
Example 5
[Chemical formula 114]
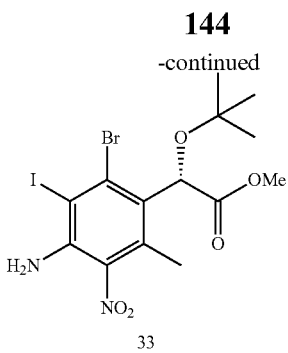
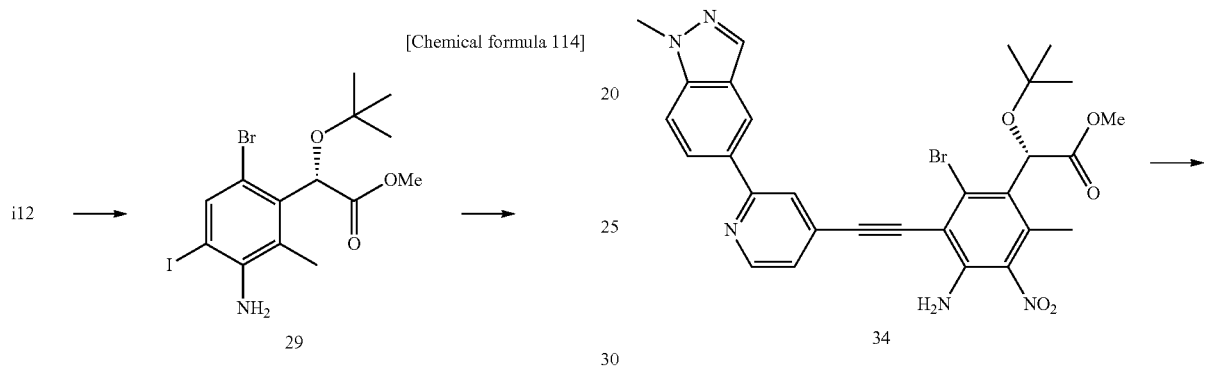
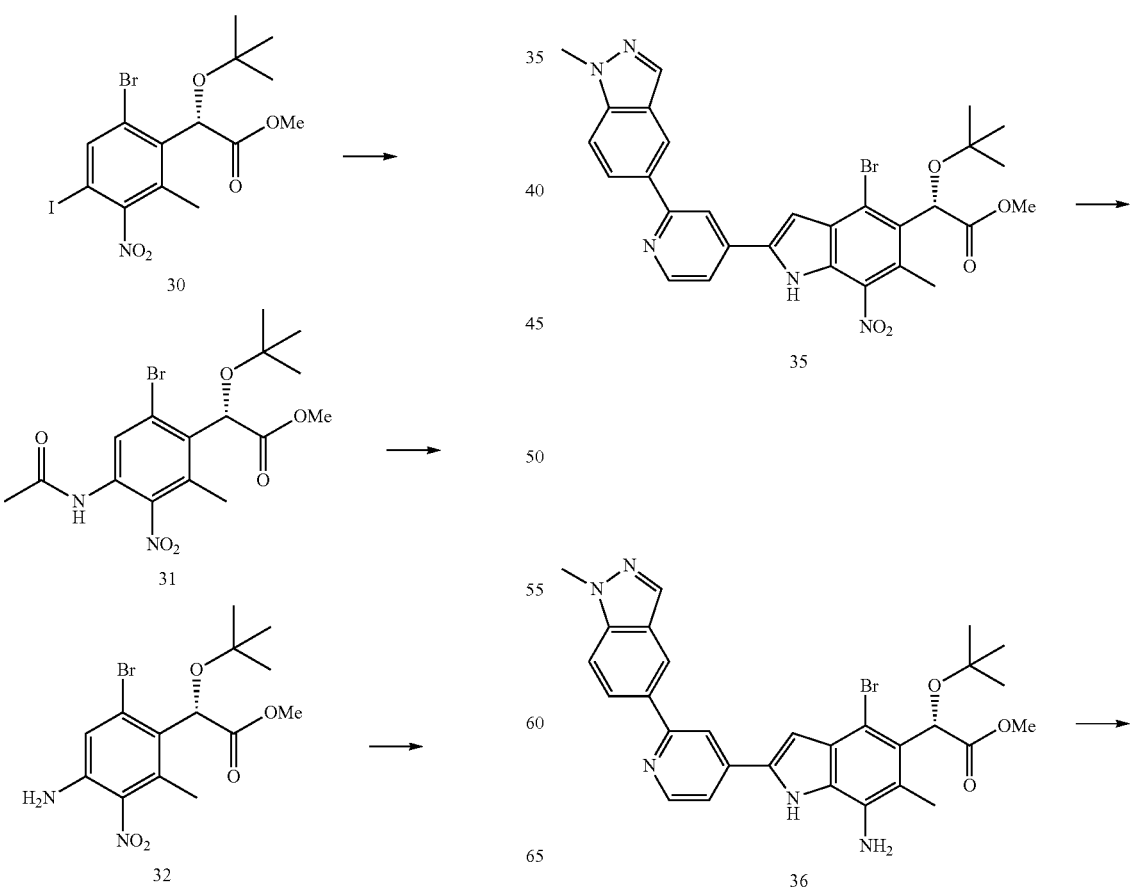

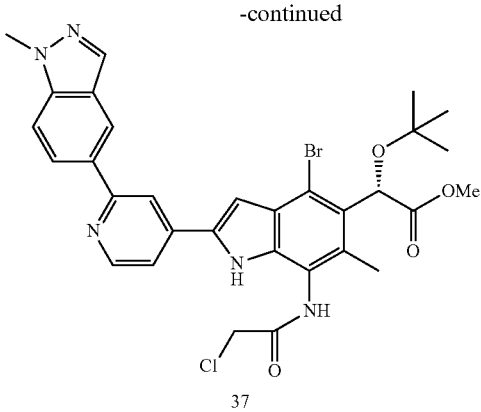

37

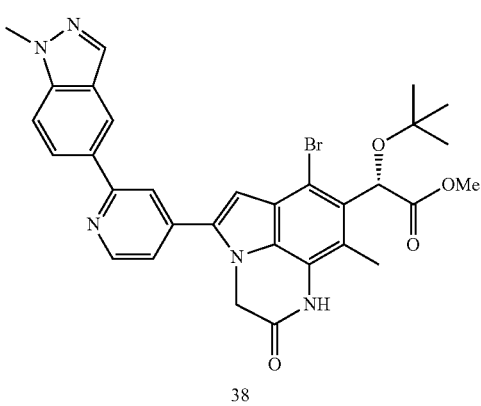

38

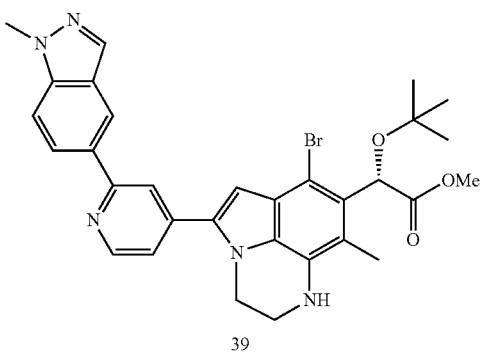

39

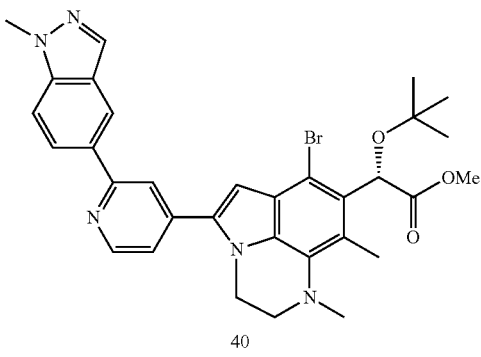

40

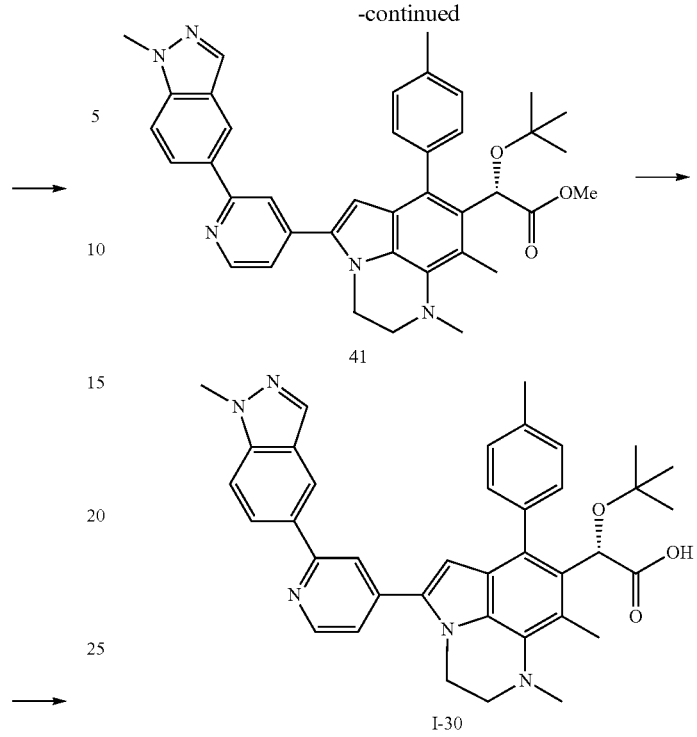

Step 1

To a solution of the compound i12 (30 g, 91 mmol) in ethanol (300 mL) added silver nitrite (30.9 g, 182 mmol) and iodine (46.1 g, 182 mmol) under ice-cooling, the mixture was stirred at room temperature for 4 hours. The insoluble materials were filtered out, to the filtrate was added aqueous sodium bicarbonate solution and aqueous sodium thiosulfate solution, the mixture was extracted with chloroform, washed with water, dried over anhydrous sodium sulfate solution, and concentrated under reduced pressure. The obtained residue was purified by silica gel column chromatography (hexane—ethyl acetate) to yield the compound 29 (24.46 g, yield 59%).

LC/MS (ESI): m/z=455.90 [M+H]$^+$

Step 2

The compound 30 (15.0 g, yield 61%) was obtained by reacting the compound 29 (23.1 g, 50.6 mmol) in the same manner as Step 6 in Reference Example 2.

$^1$H-NMR (CDCl$_3$) δ: 1.22 (s, 9H), 2.37 (s, 3H), 3.71 (s, 3H), 5.77 (s, 1H), 7.98 (s, 1H)

Step 3

The compound 31 (4.2 g, yield 32%) was obtained by reacting the compound 30 (15.5 g, 31.9 mmol) in the same manner as Step 7 in Reference Example 2.

LC/MS (ESI): m/z=438.95 [M+Na]$^+$

Step 4

The compound 32 (2.6 g, yield 48%) was obtained by reacting the compound 31 (6 g, 14.38 mmol) in the same manner as Step 8 in Reference Example 2.

LC/MS (ESI): m/z=374.95 [M+H]$^+$

Step 5

The compound 33 (4.5 g, yield 94%) was obtained by reacting the compound 32 (3.6 g, 9.59 mmol) in the same manner as Step 9 in Reference Example 2.

LC/MS (ESI): m/z=499.10 [M−H]$^+$

Step 6

To a solution of the compound 33 (1 g, 1.99 mmol) in DMF (10 mL) was added Et₃N (1.11 mL, 7.98 mmol), 5-(4-ethynylpyridine-2-yl)-1-methyl-1H-indazole (1.40 g 5.99 mmol), copper iodide (38.0 mg, 0.20 mmol), and PdCl₂(PPh₃)₂ (140 mg, 0.20 mmol), the mixture was stirred at 100° C. under nitrogen atmosphere for 1 hour. Water was added to the reaction solution, extracted with ethyl acetate, and the organic layer was washed with water, dried over anhydrous sodium sulfate, and concentrated under reduced pressure. The obtained residue was purified by silica gel column chromatography (hexane—ethyl acetate) to yield the compound 34 (1.11 g, yield 92%).

LC/MS (ESI): m/z=606.15 [M+H]⁺

Step 7

To a solution of the compound 34 (2.7 g, 4.45 mmol) in THF (27 mL) was added 1 mol/L—TBAF THF solution (6.68 mL, 6.68 mmol), the mixture was refluxed for 1 hour. Water was added to the reaction solution, extracted with ethyl acetate, and the organic layer was washed with water, dried over anhydrous sodium sulfate, concentrated under reduced pressure. The obtained residue was purified by silica gel column chromatography (hexane—ethyl acetate) to yield the compound 35 (2.35 g, yield 87%).

LC/MS (ESI): m/z=606.15 [M+H]⁺

Step 8

To a solution of the compound 35 (2.4 g, 3.96 mmol) in ethanol (24 mL) and water (8 mL) was added ammonium chloride (2.11 g, 39.6 mmol) and iron (1.11 g, 19.8 mmol), the mixture was refluxed for 1.5 hours. The reaction solution was filtered, the filtrate was extracted after addition water, and the organic layer was washed with water, dried over anhydrous sodium sulfate, concentrated under reduced pressure. The obtained residue was purified by silica gel column chromatography (chloroform—methanol) to yield the compound 36 (2.14 g, yield 94%).

LC/MS (ESI): m/z=576.10 [M+H]⁺

Step 9

To a solution of the compound 36 (1.61 g, 2.79 mmol) in dichloromethane (16 mL) was added pyridine (0.452 mL, 5.59 mmol) and chloroacetyl chloride (0.333 mL, 4.19 mmol), the mixture was stirred at room temperature for 30 minutes. Water was added to the reaction solution, the resulting solid was collected by filtration to yield the compound 37 (1.96 g, yield 107%).

LC/MS (ESI): m/z=652.00 [M+H]⁺

Step 10

To a solution of the compound 37 (1.82 g, 2.79 mmol) in DMF (20 mL) was added sodium hydride (279 mg, 6.97 mmol), the mixture was stirred at room temperature for 2 hours. 2 mol/L hydrochloric acid was added to the reaction solution, extracted with ethyl acetate, and the organic layer was washed with water, dried over anhydrous sodium sulfate, concentrated under reduced pressure. The obtained residue was purified by silica gel column chromatography (chloroform—methanol) to yield the compound 38 (528 mg, yield 31%).

LC/MS (ESI): m/z=616.00 [M+H]⁺

Step 11

To a solution of the compound 38 (1.32 g, 2.14 mmol) in THF (14 mL) was added 1 mol/L-borane in THF solution (6.42 mL, 6.42 mmol), the mixture was refluxed for 2 hours under nitrogen atmosphere. To the reaction solution was added methanol and 2 mol/L hydrochloric acid, and the mixture was extracted with ethyl acetate, the organic layer was washed with water, dried over anhydrous sodium sulfate, and concentrated under reduced pressure. The obtained residue was purified by silica gel column chromatography (hexane—ethyl acetate) to yield the compound 39 (800 mg, yield 62%).

LC/MS (ESI): m/z=602.05 [M+H]⁺

Step 12

To a solution of the compound 39 (200 mg, 0.332 mmol) in DMF (2 mL) was added potassium carbonate (92 mg, 0.664 mmol), and methyl iodide (0.042 mL, 0.664 mmol), the mixture was stirred at 60° C. for 1 hour. Water was added to the reaction solution and extracted with ethyl acetate, and the organic layer was washed with water, dried over anhydrous sodium sulfate, concentrated under reduced pressure. The obtained residue was purified by silica gel column chromatography (hexane—ethyl acetate) to yield the compound 40 (126 mg, yield 62%).

LC/MS (ESI): m/z=616.05 [M+H]⁺

Step 13

The compound 41 (122 mg, yield 99%) was obtained by reacting the compound 40 (120 mg, 0.195 mmol) in the same manner as Step 5 in Reference Example 2.

LC/MS (ESI): m/z=628.20 [M+H]⁺

Step 14

The compound I-30 (68.2 mg, yield 58%) was obtained by reacting the compound 41 (120 mg, 0.191 mmol) in the same manner as Step 8 in Example 3.

LC/MS (ESI): m/z=614.15 [M+H]⁺

¹H-NMR (CDCl₃) δ: 0.94 (s, 9H), 2.45 (s, 3H), 2.49 (s, 3H), 2.89 (s, 3H), 3.36-3.53 (m, 2H), 4.12 (s, 3H), 4.23-4.33 (m, 1H), 4.36-4.46 (m, 1H), 5.61 (s, 1H), 6.58 (s, 1H), 7.28-7.47 (m, 4H), 7.49 (d, 2H, J=8.6 Hz), 7.66 (d, 1H, J=7.3 Hz), 7.89 (s, 1H), 8.07 (s, 1H), 8.11 (d, 1H, J=8.6 Hz), 8.36 (s, 1H), 8.71 (d, 1H, J=5.1 Hz)

Example 6

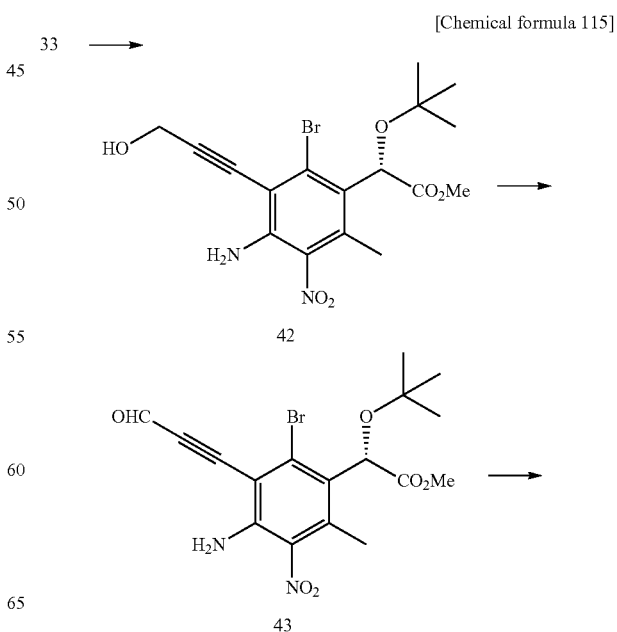

[Chemical formula 115]

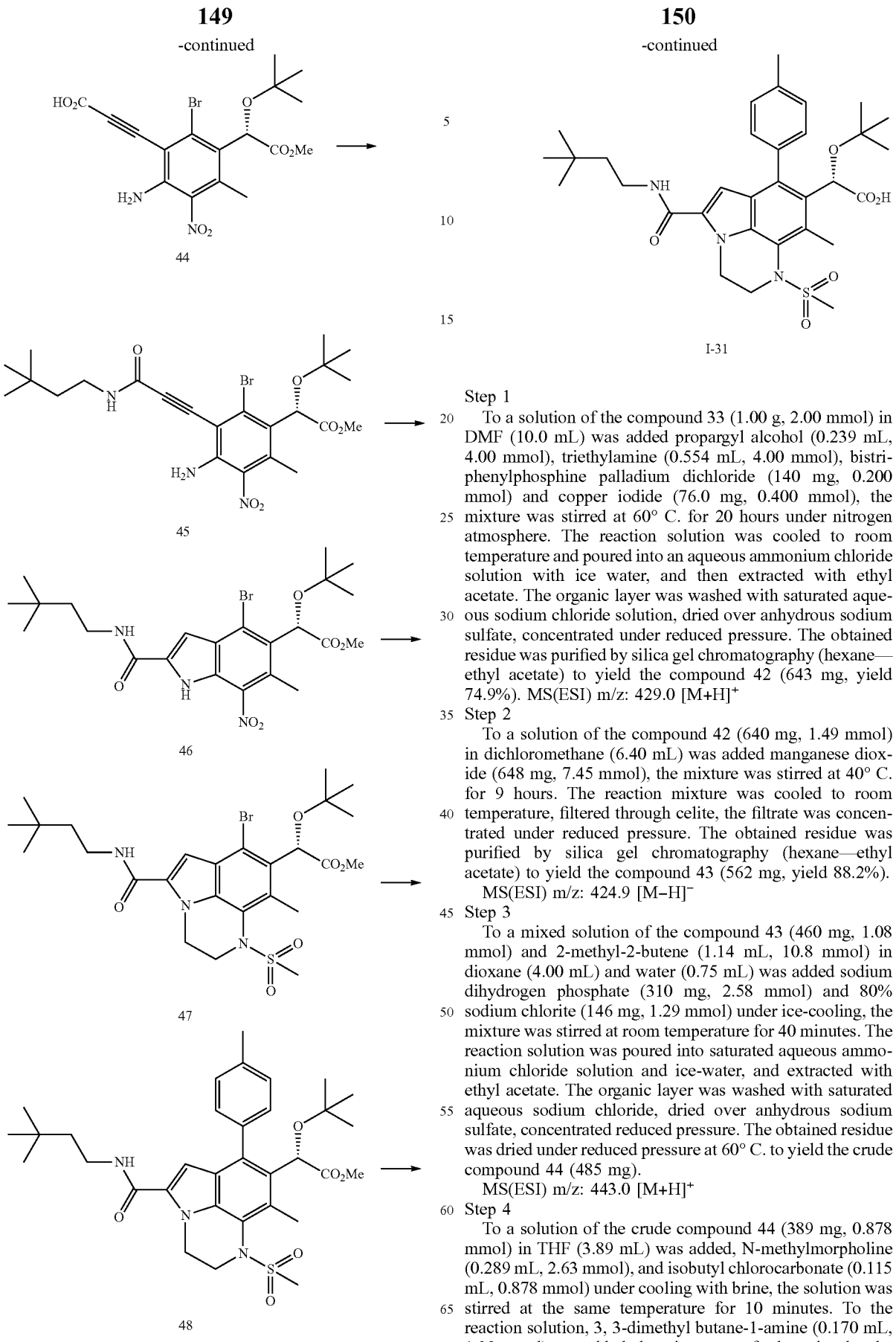

Step 1

To a solution of the compound 33 (1.00 g, 2.00 mmol) in DMF (10.0 mL) was added propargyl alcohol (0.239 mL, 4.00 mmol), triethylamine (0.554 mL, 4.00 mmol), bistriphenylphosphine palladium dichloride (140 mg, 0.200 mmol) and copper iodide (76.0 mg, 0.400 mmol), the mixture was stirred at 60° C. for 20 hours under nitrogen atmosphere. The reaction solution was cooled to room temperature and poured into an aqueous ammonium chloride solution with ice water, and then extracted with ethyl acetate. The organic layer was washed with saturated aqueous sodium chloride solution, dried over anhydrous sodium sulfate, concentrated under reduced pressure. The obtained residue was purified by silica gel chromatography (hexane—ethyl acetate) to yield the compound 42 (643 mg, yield 74.9%). MS(ESI) m/z: 429.0 [M+H]$^+$ Step 2

To a solution of the compound 42 (640 mg, 1.49 mmol) in dichloromethane (6.40 mL) was added manganese dioxide (648 mg, 7.45 mmol), the mixture was stirred at 40° C. for 9 hours. The reaction mixture was cooled to room temperature, filtered through celite, the filtrate was concentrated under reduced pressure. The obtained residue was purified by silica gel chromatography (hexane—ethyl acetate) to yield the compound 43 (562 mg, yield 88.2%). MS(ESI) m/z: 424.9 [M−H]$^-$ Step 3

To a mixed solution of the compound 43 (460 mg, 1.08 mmol) and 2-methyl-2-butene (1.14 mL, 10.8 mmol) in dioxane (4.00 mL) and water (0.75 mL) was added sodium dihydrogen phosphate (310 mg, 2.58 mmol) and 80% sodium chlorite (146 mg, 1.29 mmol) under ice-cooling, the mixture was stirred at room temperature for 40 minutes. The reaction solution was poured into saturated aqueous ammonium chloride solution and ice-water, and extracted with ethyl acetate. The organic layer was washed with saturated aqueous sodium chloride, dried over anhydrous sodium sulfate, concentrated reduced pressure. The obtained residue was dried under reduced pressure at 60° C. to yield the crude compound 44 (485 mg).

MS(ESI) m/z: 443.0 [M+H]$^+$

Step 4

To a solution of the crude compound 44 (389 mg, 0.878 mmol) in THF (3.89 mL) was added, N-methylmorpholine (0.289 mL, 2.63 mmol), and isobutyl chlorocarbonate (0.115 mL, 0.878 mmol) under cooling with brine, the solution was stirred at the same temperature for 10 minutes. To the reaction solution, 3, 3-dimethyl butane-1-amine (0.170 mL, 1.32 mmol) was added, the mixture was further stirred at the same temperature for 20 minutes. The reaction solution was poured into 2 mol/L hydrochloric acid solution and ice-water, and extracted with ethyl acetate. The organic layer was washed with saturated aqueous sodium hydrocarbonate solution and saturated aqueous sodium chloride solution, dried over anhydrous sodium sulfate, concentrated under reduced pressure. The obtained residue was purified by silica gel chromatography (hexane—ethyl acetate) to yield the compound 45 (271 mg, yield 58.7%).

MS(ESI) m/z: 526.1 [M+H]$^+$

Step 5

The compound 46 (231 mg, yield 85.9%) was obtained by reacting the compound 45 (269 mg, 0.511 mmol) in the same manner as Step 7 in Example 5.

MS(ESI) m/z: 526.1 [M+H]$^+$

Step 6

The compound 47 (208 mg, yield for 3 steps 79.6%) was obtained by reacting the compound 46 (229 mg, 0.435 mmol) in the same manner as Step 6, 7 in Example 3.

MS(ESI) m/z: 617.1 [M+NH$_4$]$^+$

Step 7

The compound 48 (199 mg, yield 87.6%) was obtained by reacting the compound 47 (223 mg, 0.371 mmol) in the same manner as Step 5 in Reference Example 2.

MS(ESI) m/z: 612.2 [M+H]$^+$

Step 8

The compound I-31 (173 mg, yield 89.9%) was obtained by reacting the compound 48 (197 mg, 0.322 mmol) in the same manner as Step 8 in Example 3.

MS(ESI) m/z: 598.2 [M+H]$^+$

[Chemical formula 116]

33 →

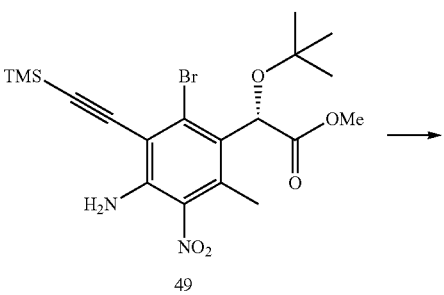

49

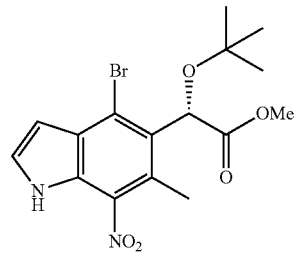

50

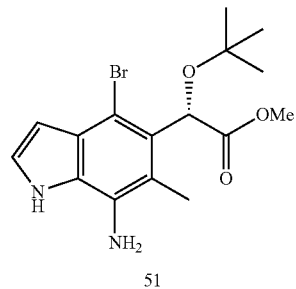

51

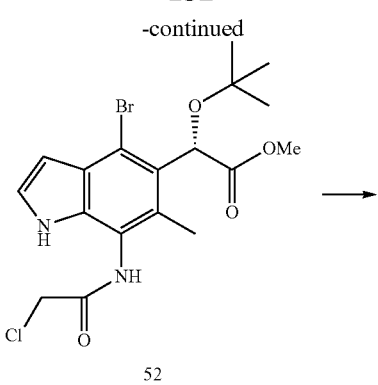

52

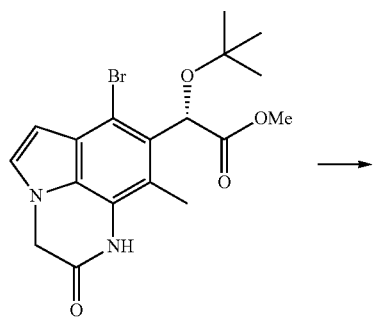

53

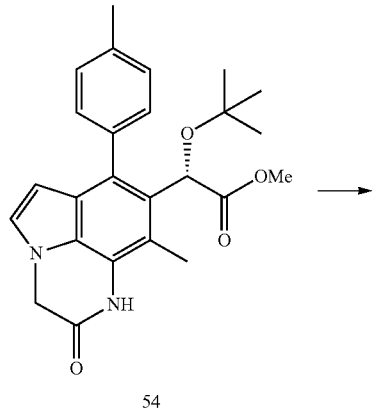

54

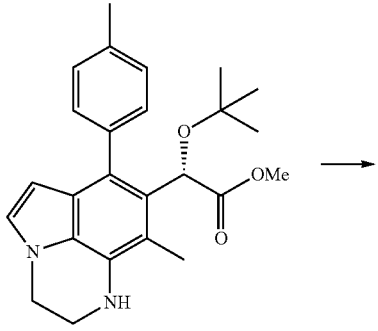

55

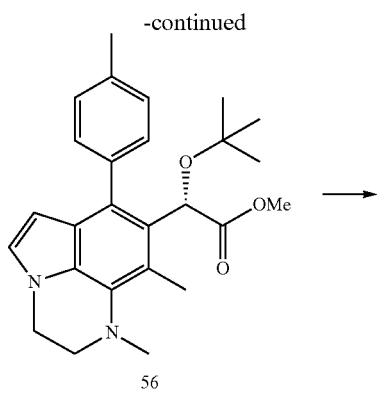

56

↓

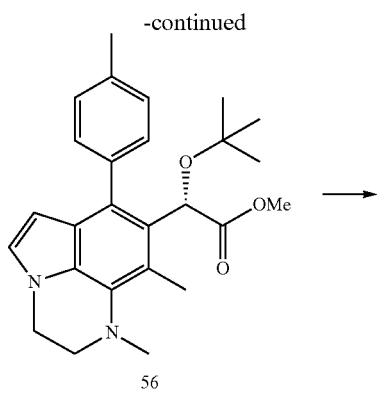

I-36

Example 7

Step 1

To a solution of the compound 33 (5 g, 9.98 mmol) in DMF (50 mL) was added Et₃N (5.53 mL, 39.9 mmol), trimethylsilylacetylene (4.23 mL, 29.9 mmol), copper iodide (190 mg, 0.99 mmol), and PdCl₂(PPh₃)₂ (700 mg, 0.99 mmol), the mixture was stirred at 100° C. for 1 hour under nitrogen atmosphere. Water was added to the reaction solution, and extracted with ethyl acetate, and the organic layer was washed with water, dried over anhydrous sodium sulfate, concentrated under reduced pressure. The obtained residue was purified by silica gel column chromatography (hexane—ethyl acetate) to yield the compound 49 (4.0 g, yield 85%).

LC/MS (ESI): m/z=396.8 [de-TMS body+H]⁺

Step 2

The compound 50 (2.37 g, yield 70%) was obtained by reacting the compound 49 (4 g, 8.48 mmol) in the same manner as Step 7 in Example 5.

LC/MS (ESI): m/z=396.9 [M−H]⁻

Step 3

The compound 51 (1.89 g, yield 86%) was obtained by reacting the compound 50 (2.37 g, 5.94 mmol) in the same manner as Step 8 in Example 5.

LC/MS (ESI): m/z=369.00 [M+H]⁺

Step 4

The compound 52 (2.23 g, yield 98%) was obtained by reacting the compound 51 (1.89 g, 5.12 mmol) in the same manner as Step 9 in Example 5.

LC/MS (ESI): m/z=444.90 [M+H]⁺

Step 5

To a solution of the compound 52 (750 mg, 1.68 mmol) in DMF (7.5 mL) was added sodium hydride (202 mg, 3.37 mmol) and sodium iodide (504 mg, 3.37 mmol) under ice-cooling, the mixture was stirred at room temperature for 30 minutes. The reaction solution was extracted with ethyl acetate after addition of 2 mol/L hydrochloric acid under ice-cooling, the organic layer was washed with water, dried over anhydrous sodium sulfate, concentrated under reduced pressure. The obtained residue was purified by silica gel column chromatography (hexane—ethyl acetate) to yield the compound 53 (576 mg, yield 84%).

LC/MS (ESI): m/z=430.85 [M+Na]⁺

Step 6

To a solution of the compound 53 (896 mg, 2.19 mmol) in DMF (9 mL) was added 2 mol/L aqueous potassium carbonate solution (3.28 mL, 6.57 mmol), p-tolylboronic acid (446 mg, 3.28 mmol), and PdCl₂ (dtbpf) (143 mg, 0.219 mmol), the mixture was stirred at 100° C. under nitrogen atmosphere for 1 hour. The reaction solution was extracted with ethyl acetate after addition of water, and the organic layer was washed with water, dried over anhydrous sodium sulfate, concentrated under reduced pressure. The obtained residue was purified by silica gel column chromatography (hexane—ethyl acetate) to yield the compound 54 (759 mg, yield 82%).

LC/MS (ESI): m/z=442.95 [M+Na]⁺

Step 7

The compound 55 (250 mg, yield 74%) was obtained by reacting the compound 54 (350 mg, 0.832 mmol) in the same manner as Step 11 in Example 5.

LC/MS (ESI): m/z=407.05 [M+H]⁺

Step 8

The compound 56 (222 mg, yield 86%) was obtained by reacting the compound 55 (250 mg, 0.615 mmol) in the same manner as Step 12 in Example 5.

LC/MS (ESI): m/z=421.05 [M+H]⁺

Step 9

The compound I-36 (22 mg, yield 57%) was obtained by reacting the compound 56 (40 mg, 0.095 mmol) in the same manner as Step 8 in Example 3.

LC/MS (ESI): m/z=407.90 [M+H]+

1H-NMR (CDCl3) δ: 0.91 (s, 9H), 2.43 (s, 3H), 2.45 (s, 3H), 2.79 (s, 3H), 3.39-3.46 (m, 2H), 4.07-4.15 (2H, m), 5.61 (1H, s), 6.19 (1H, d, J=3.0 Hz), 6.99 (1H, d, J=3.0 Hz), 7.26-7.27 (2H, m), 7.41 (1H, d, J=7.5 Hz), 7.60 (1H, d, J=7.5 Hz), 10.0 (1H, brs)

Example 8

[Chemical formula 117]

33 ⟶

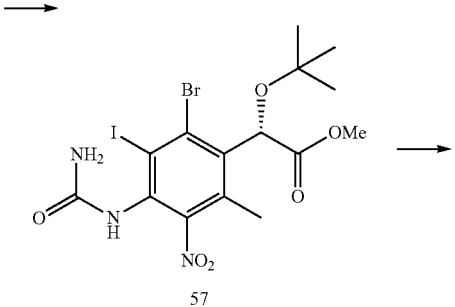

57 ⟶

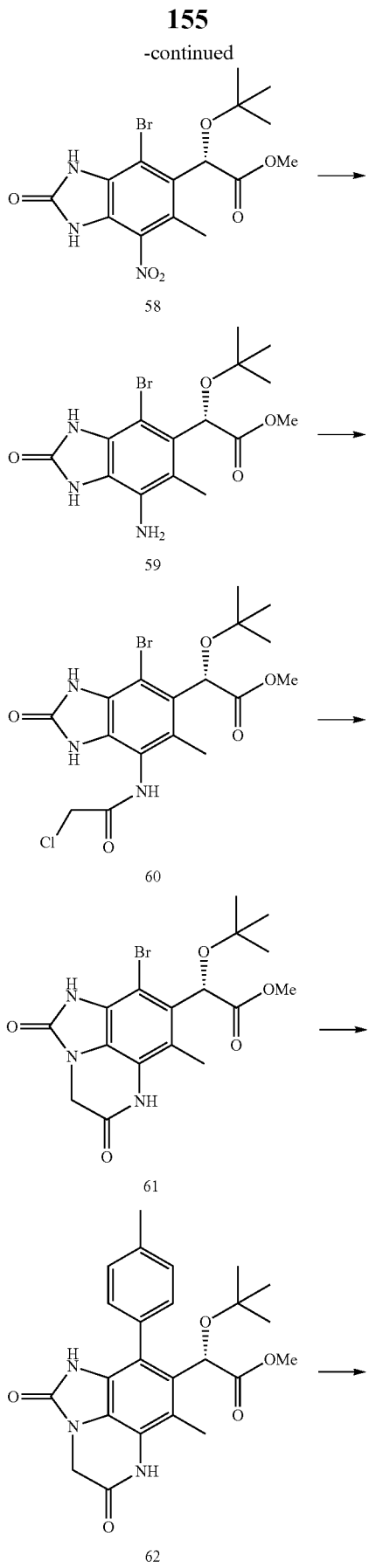

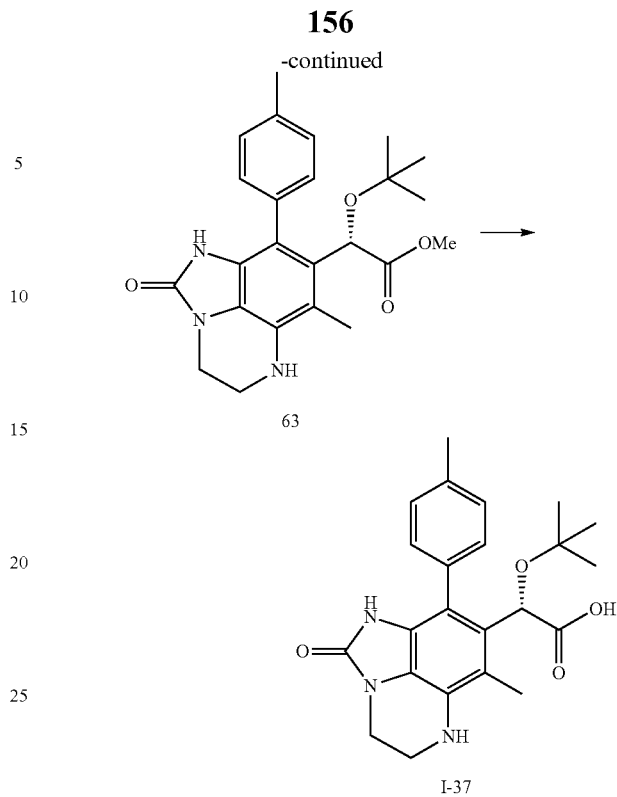

Step 1

To a solution of the compound 33 (2.5 g, 4.99 mmol) in THF (25 mL) was added sodium hydride (599 mg, 15.0 mmol) under ice-cooling, the mixture was stirred at room temperature for 10 minutes under nitrogen atmosphere. Then carbonyldiimidazole (2.43 g, 15.0 mmol) was added to the reaction mixture, the mixture was stirred at room temperature for 1 hour, 28% aqueous ammonia solution (3.37 mL, 49.9 mmol) was added to the mixture, and the mixture was stirred at room temperature for 2 hours. The reaction solution was extracted with chloroform after addition of 2 mol/L hydrochloric acid, the organic layer was washed with water, dried over anhydrous sodium sulfate, concentrated under reduced pressure. The obtained residue was purified by silica gel column chromatography (hexane—ethyl acetate) to yield the compound 57 (2.2 g, yield 81%).

LC/MS (ESI): m/z=541.90 [M−H]$^-$

Step 2

To a solution of the compound 57 (1.88 g, 3.45 mmol) in DMF (19 mL) was added DBU (1.04 mL, 6.91 mmol) and copper iodide (6.58 g, 34.5 mmol), the mixture was stirred at 80° C. under nitrogen atmosphere for 3.5 hours. The insoluble materials were filtered through celite, the filtrate was extracted with ethyl acetate after addition of 2 mol/L hydrochloric acid, the organic layer was washed with water, dried over anhydrous sodium sulfate, concentrated under reduced pressure. The obtained residue was purified by silica gel column chromatography (hexane—ethyl acetate) to yield the compound 58 (1.19 g, yield 83%).

LC/MS (ESI): m/z=414.00 [M−H]$^-$

Step 3

The compound 59 (1.17 g, yield 99%) was obtained by reacting the compound 58 (1.28 g, 3.08 mmol) in the same manner as Step 8 in Example 5.

LC/MS (ESI): m/z=384.00 [M−H]$^-$

Step 4

The compound 60 (2.23 g, yield 98%) was obtained by reacting the compound 59 (1.15 g, 2.98 mmol) in the same manner as Step 9 in Example 5.

LC/MS (ESI): m/z=461.95 [M−H]−

Step 5

The compound 61 (576 mg, yield 84%) was obtained by reacting the compound 60 (1.12 g, 2.42 mmol) in the same manner as Step 10 in Example 5.

LC/MS (ESI): m/z=424.00 [M−H]−

Step 6

The compound 62 (165 mg, yield 87%) was obtained by reacting the compound 61 (185 mg, 0.434 mmol) in the same manner as Step 6 in Example 7.

LC/MS (ESI): m/z=436.10 [M−H]−

Step 7

The compound 63 (138 mg, yield 86%) was obtained by reacting the compound 62 (165 mg, 0.377 mmol) in the same manner as Step 11 in Example 5.

LC/MS (ESI): m/z=424.00 [M+H]+

Step 8

The compound I-37 (22 mg, yield 57%) was obtained by reacting the compound 63 (30 mg, 0.071 mmol) in the same manner as Step 8 in Example 3.

LC/MS (ESI): m/z=408.15 [M−H]−

1H-NMR (CDCl3) δ: 0.93 (9H, s), 2.17 (3H, s), 2.42 (3H, s), 3.52-3.64 (2H, m), 3.93-3.98 (2H, m), 5.30 (1H, s), 5.43 (1H, s), 7.15-7.31 (3H, m), 7.51 (1H, d, J=7.6 Hz)

The following compounds were synthesized using commercially available compounds or the above intermediates according to the above Examples or the above General methods. In the table, "Comp. No." means a compound number, "Struct" means chemical structure formula, "Ms cond." means the above measurement condition of LC/MS (liquid chromatography/mass spectrometry), "RT (min)" means retention time (minute).

TABLE 1

| Comp. No. | Struct | Ms cond. | RT(min) | MS |
|---|---|---|---|---|
| I-001 | | (2) | 2.15 | 469.05 [M − H]− |
| I-002 | | (2) | 2.35 | 575.2 [M + H]+ |

TABLE 1-continued

| Comp. No. | Struct | Ms cond. | RT(min) | MS | |
|---|---|---|---|---|---|
| I-003 | | (2) | 2.39 | 561.15 | [M + H]+ |
| I-004 | | (2) | 2.05 | 511.1 | [M − H]− |
| I-005 | | (2) | 2.65<br>2.79 | 575.2 | [M + H]+ |

TABLE 2

| Comp. No. | Struct | Ms cond. | RT(min) | MS | |
|---|---|---|---|---|---|
| I-006 | | (2) | 2.29 | 539.15 | [M − H]− |
| I-007 | | (2) | 2.69 | 561.25 | [M + H]+ |
| I-008 | | (2) | 2.25 | 678.3 | [M + H] |
| I-009 | | (2) | 1.65 | 675.76 | [M + H] |

TABLE 2-continued

| Comp. No. | Struct | Ms cond. | RT(min) | MS | |
|---|---|---|---|---|---|
| I-010 | | (2) | 2.48 | 582.11 | [M + H] |

TABLE 3

| Comp. No. | Struct | Ms cond. | RT(min) | MS | |
|---|---|---|---|---|---|
| I-011 | | (2) | 2.26 | 678.55 | [M + H]+ |
| I-012 | | (2) | 2.29 | 642.2 | [M + H]+ |

TABLE 3-continued
| Comp. No. | Struct | Ms cond. | RT(min) | MS | |
|---|---|---|---|---|---|
| I-013 | 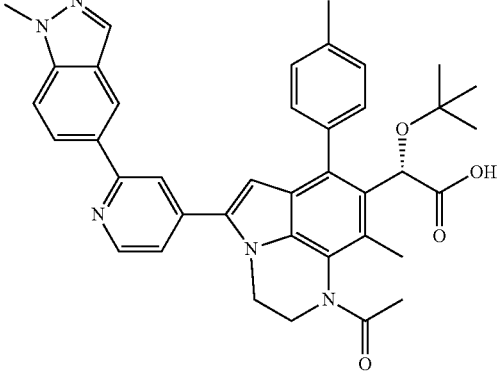 | (2) | 2.29 | 642.2 | [M + H]+ |
| I-014 | 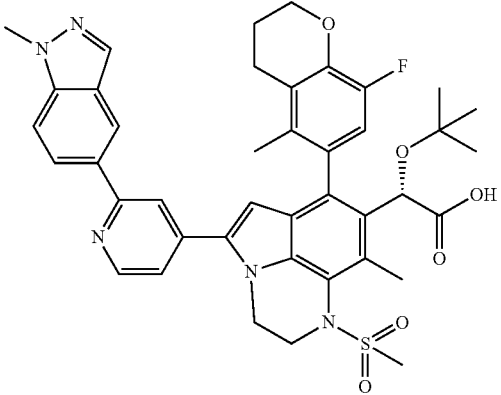 [SMILES: Cc1c(-c2c([C@H](OC(C)(C)C)C(=O)O)c(C)c3c4c2cc(-c2ccnc(-c5ccc6c(cnn6C)c5)c2)n4CCN3S(C)(=O)=O)cc(F)c2c1CCCO2] | (2) | 2.16 | 752.6 | [M + H]+ |
| I-015 | 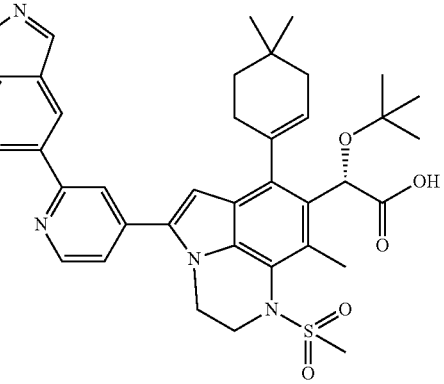 | (2) | 2.48 | 696.9 | [M + H]+ |

TABLE 4

| Comp. No. | Struct | Ms cond. | RT(min) | MS |
|---|---|---|---|---|
| I-016 | | (2) | 2.29 | 698.2 [M + H]+ |
| I-017 | | (2) | 1.61 | 674.3 [M + H]+ |
| I-018 | | (2) | 2.14 | 716.5 [M + H]+ |
| I-019 | | (2) | 2.15 | 614.25 [M + H]+ |

TABLE 4-continued

| Comp. No. | Struct | Ms cond. | RT(min) | MS | |
|---|---|---|---|---|---|
| I-020 | | (2) | 2.33 | 628.25 | [M + H]+ |

TABLE 5

| Comp. No. | Struct | Ms cond. | RT(min) | MS | |
|---|---|---|---|---|---|
| I-021 | | (2) | 1.62 | 685.2 | [M + H]+ |
| I-022 | | (2) | 1.87 | 735.25 | [M + H]+ |

TABLE 5-continued
| Comp. No. | Struct | Ms cond. | RT(min) | MS | |
|---|---|---|---|---|---|
| I-023 | 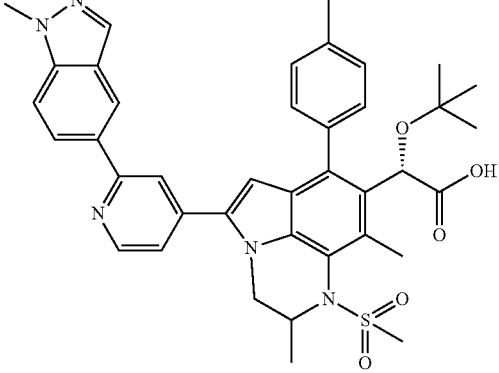 | (2) | 2.27 | 692.8 | [M + H]+ |
| I-024 | 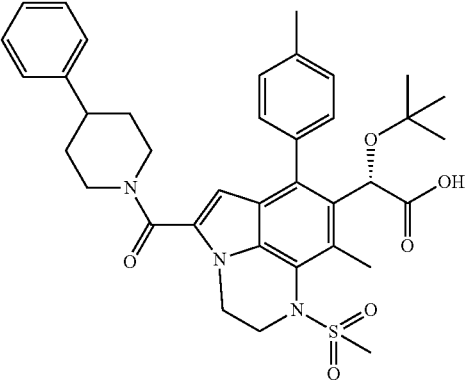 [SMILES: Cc1ccc(-c2c([C@H](OC(C)(C)C)C(=O)O)c(C)c3c4c2cc(C(=O)N2CCC(c5ccccc5)CC2)n4CCN3S(C)(=O)=O)cc1] | (2) | 2.75 | 658.2 | [M + H]+ |
| I-025 | 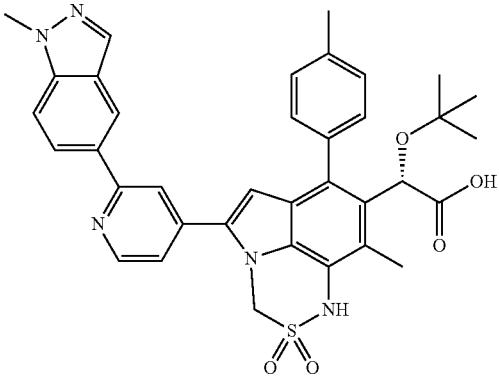 [SMILES: Cc1ccc(-c2c([C@H](OC(C)(C)C)C(=O)O)c(C)c3c4c2cc(-c2ccnc(-c5ccc6c(cnn6C)c5)c2)n4CS(=O)(=O)N3)cc1] | (2) | 2.25 | 650.15 | [M + H]+ |

TABLE 6
| Comp. No. | Struct | Ms cond. | RT(min) | MS | |
|---|---|---|---|---|---|
| I-026 | 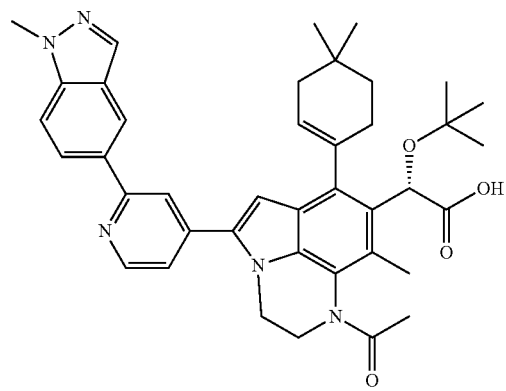 [SMILES: CC(=O)N1CCn2c(-c3ccnc(-c4ccc5c(cnn5C)c4)c3)cc3c(C4=CCC(C)(C)CC4)c([C@H](OC(C)(C)C)C(=O)O)c(C)c1c32] | (2) | 2.49 | 660.3 | [M + H]+ |
| I-027 | 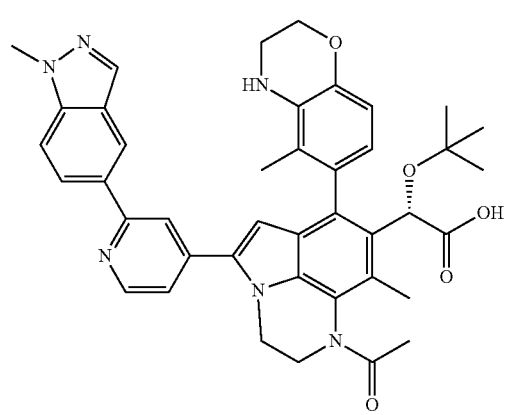 | (2) | 1.91 | 699.05 | [M + H]+ |
| I-028 | 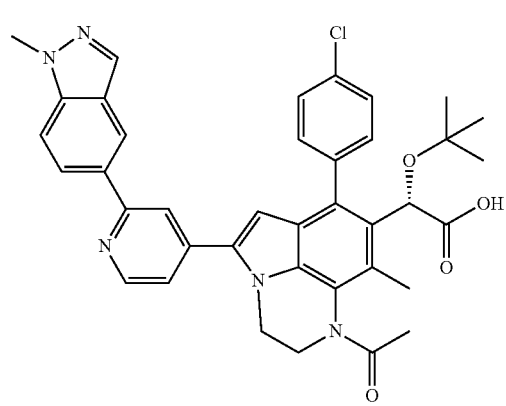 [SMILES: CC(=O)N1CCn2c(-c3ccnc(-c4ccc5c(cnn5C)c4)c3)cc3c(-c4ccc(Cl)cc4)c([C@H](OC(C)(C)C)C(=O)O)c(C)c1c32] | (2) | 2.26 | 662.2 | [M + H]+ |
| I-029 | 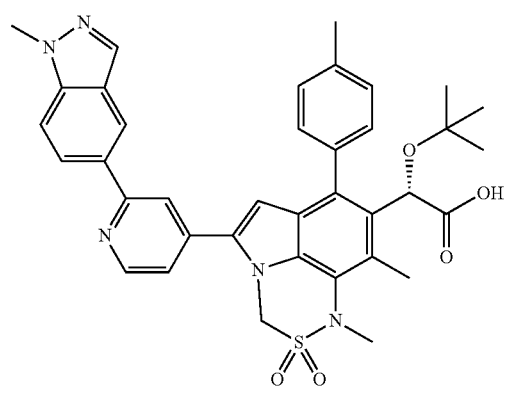 | (2) | 2.38 | 664.2 | [M + H]+ |

TABLE 6-continued

| Comp. No. | Struct | Ms cond. | RT(min) | MS |
|---|---|---|---|---|
| I-030 | | (2) | 2.35 | 614.15 [M + H]+ |

TABLE 7

| Comp. No. | Struct | Ms cond. | RT(min) | MS |
|---|---|---|---|---|
| I-031 | | (1) | 2.72 | 598.2 [M + H]+ |
| I-032 | | (1) | 2.48 | 604.1 [M + H]+ |

TABLE 7-continued

| Comp. No. | Struct | Ms cond. | RT(min) | MS |
|---|---|---|---|---|
| I-033 | | (2) | 2.4 | 618.1 [M + H]+ |

TABLE 8

| Comp. No. | Struct | MS cond. | RT(min) | MS |
|---|---|---|---|---|
| I-034 | | (2) | 1.69 | 671.25 [M + H]+ |
| I-035 | | (1) | 2.74 | 534.3 [M + H]+ |
| I-036 | | (2) | 1.63 | 408.15 [M − H]− |

TABLE 8-continued
| Comp. No. | Struct | MS cond. | RT(min) | MS | |
|---|---|---|---|---|---|
| I-037 | 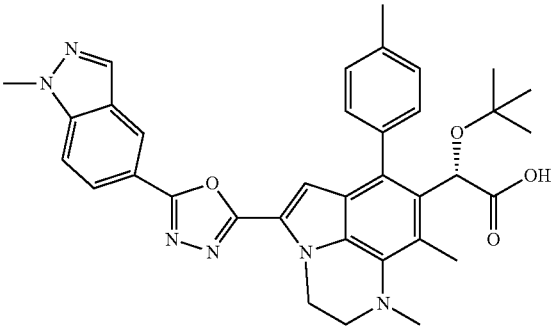 [SMILES: Cc1ccc(-c2c([C@H](OC(C)(C)C)C(=O)O)c(C)c3c4c2cc(-c2nnc(-c5ccc6c(cnn6C)c5)o2)n4CCN3C)cc1] | (2) | 2.61 | 605.15 | [M + H]+ |
| I-038 | 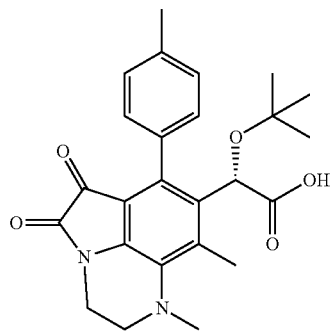 [SMILES: Cc1ccc(-c2c3c4c(c(C)c2[C@H](OC(C)(C)C)C(=O)O)N(C)CCN4C(=O)C3=O)cc1] | (2) | 1.98 | 437 | [M + H]+ |
| I-039 | 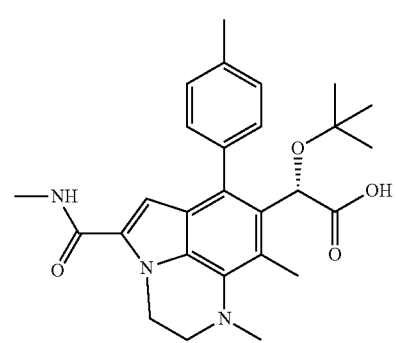 [SMILES: CNC(=O)c1cc2c(-c3ccc(C)cc3)c([C@H](OC(C)(C)C)C(=O)O)c(C)c3c2n1CCN3C] | (1) | 2.17 | 465.1 | [M + H]+ |
TABLE 9
| Comp. No. | Struct | MS cond. | RT(min) | MS | |
|---|---|---|---|---|---|
| I-040 | 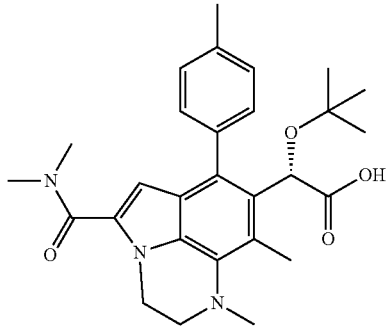 [SMILES: Cc1ccc(-c2c([C@H](OC(C)(C)C)C(=O)O)c(C)c3c4c2cc(C(=O)N(C)C)n4CCN3C)cc1] | (1) | 2.3 | 478.2 | [M + H]+ |

TABLE 9-continued

| Comp. No. | Struct | MS cond. | RT(min) | MS |
|---|---|---|---|---|
| I-041 | | (2) | 2.31 | 489 [M + H]+ |
| I-042 | | (2) | 1.68 | 507.1 [M + H]+ |
| I-043 | | (1) | 2.03 | 423.2 [M + H]+ |
| I-044 | | (1) | 1.88 | 450.4 [M + H]+ |

The present invention further provides the following compounds.
Example X1
[Chemical formula 118]
(I-A-1-2-1)
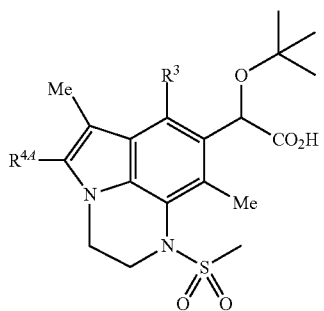
(I-A-3-2-1)
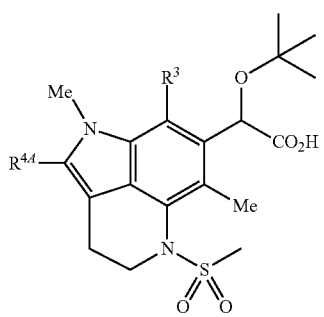
(I-B-1-2-1)
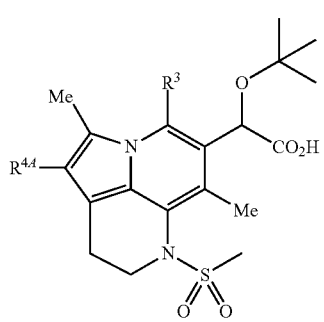
(I-C-1-2-1)
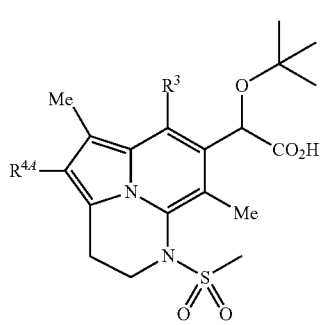
(I-A-1-1-1)
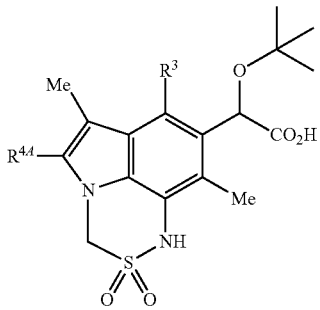
(I-A-3-1-1)
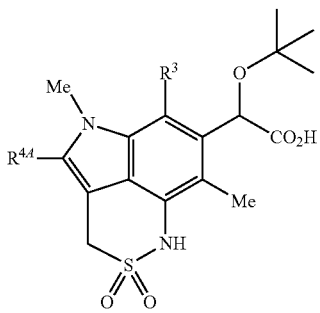
(I-B-1-1-1)
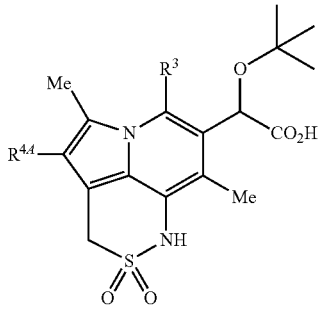
(I-C-1-1-1)
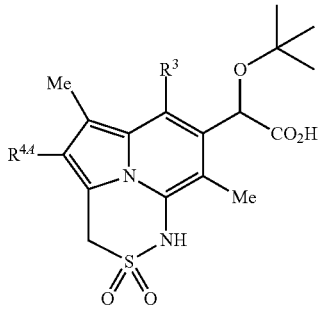
(I-A-1-1-2)
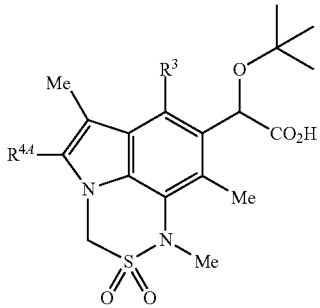

(I-A-3-1-2)
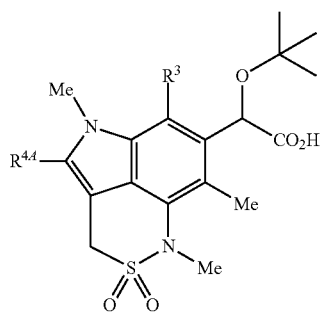
(I-B-1-1-2)
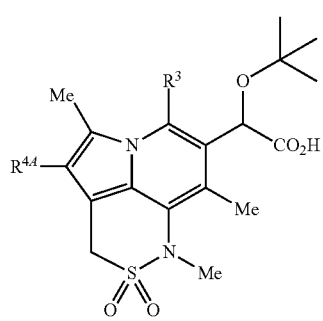
(I-C-1-1-2)
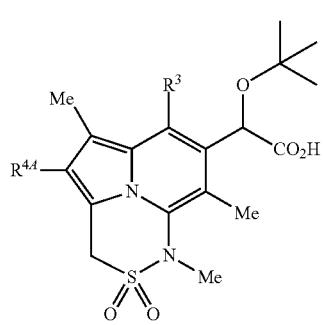
[Chemical formula 119]
(I-A-1-2-2)
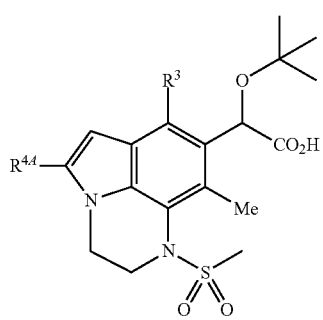
(I-A-3-2-2)
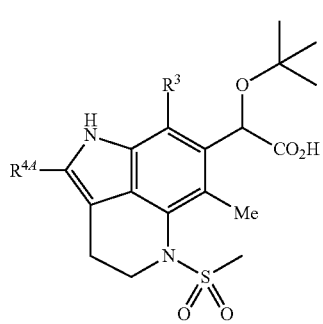
(I-B-1-2-2)
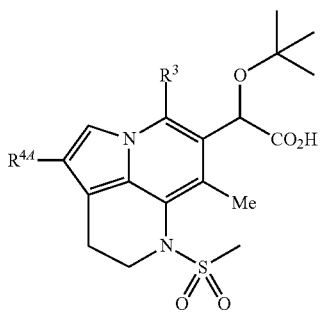
(I-C-1-2-2)
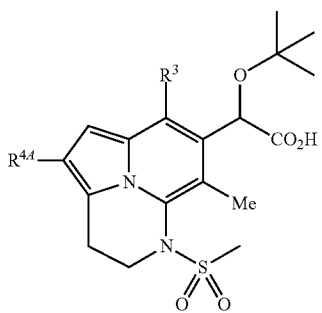
(I-A-1-1-3)
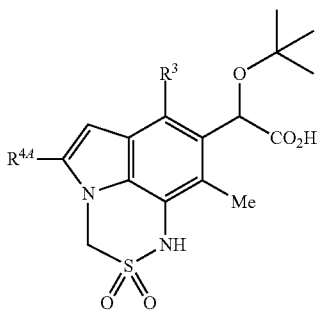
(I-A-3-1-3)
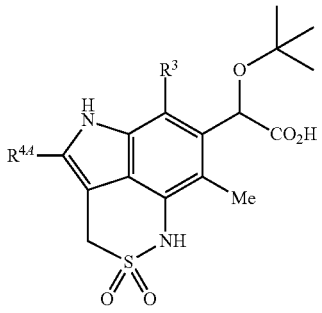
(I-B-1-1-3)
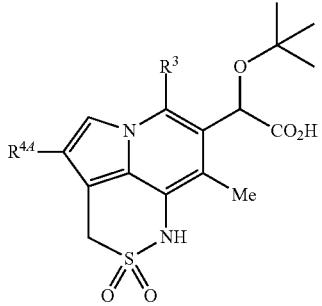

(I-C-1-1-3) 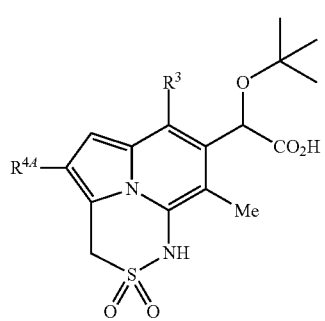
(I-A-1-1-4) 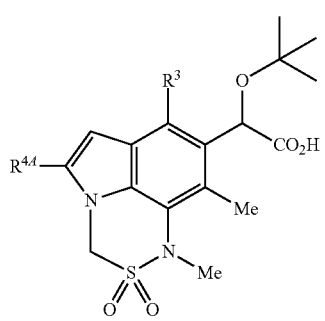
(I-A-3-1-4) 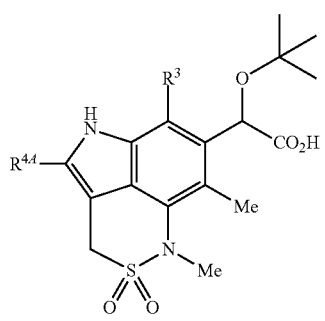
(I-B-1-1-4) 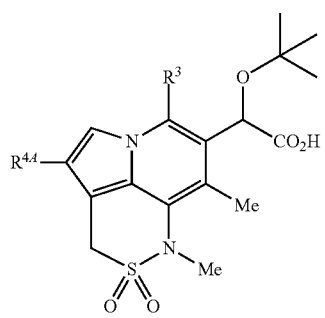
(I-C-1-1-4) 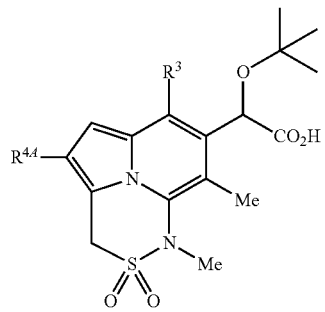
[Chemical formula 120]
(I-B-4-2-1) 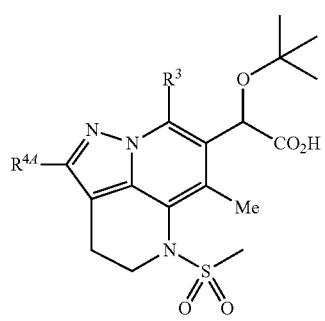
(I-A-4-2-1) 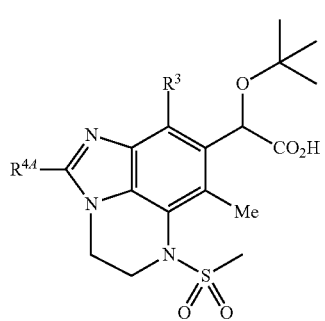
(I-C-5-2-1) 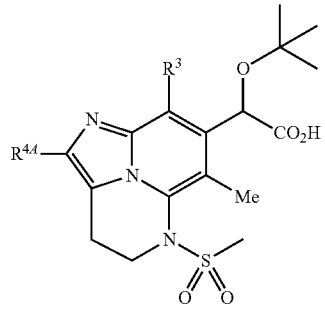
(I-A-8-2-1) 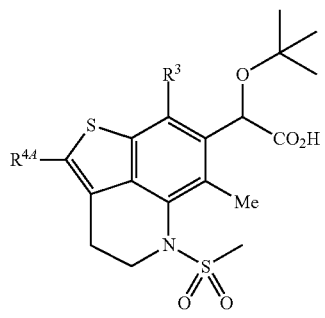

-continued
(I-B-4-1-1)
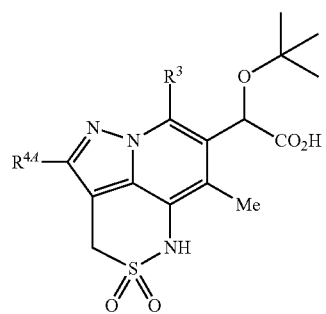
(I-A-4-1-1)
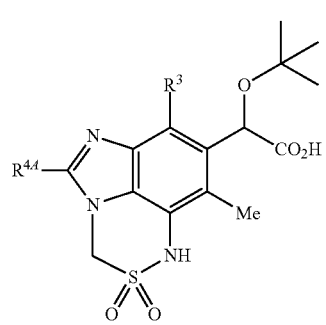
(I-C-5-1-1)
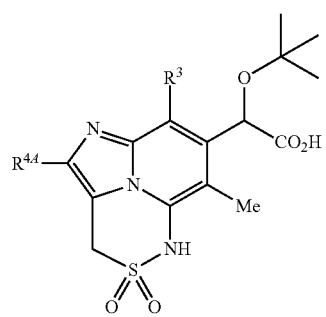
(I-A-8-1-1)
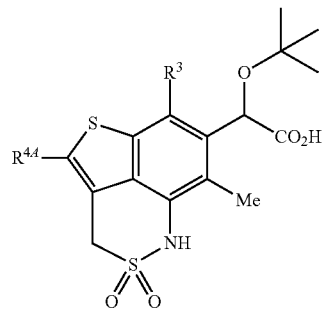
(I-B-4-1-2)
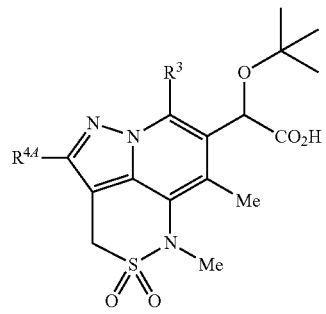
(I-A-4-1-2)
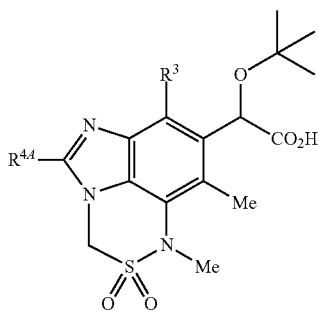
(I-C-5-1-2)
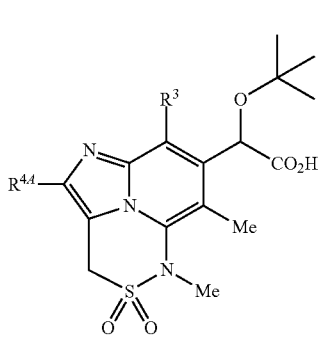
(I-A-8-1-2)
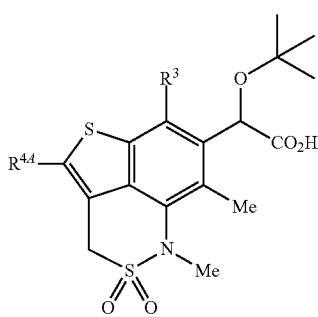
(I-A-7-2-1)
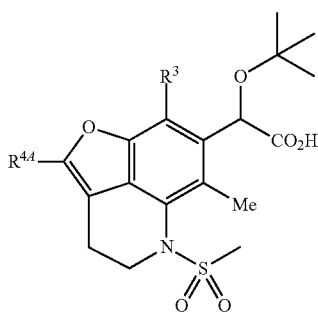
(I-A-7-1-1)
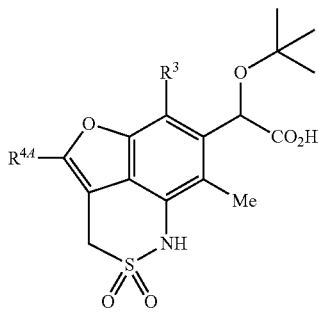

-continued
(I-A-7-1-2)
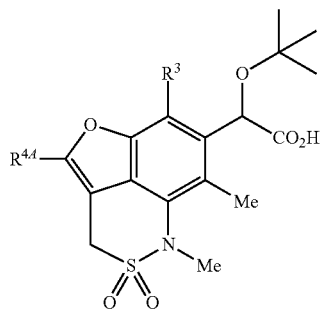
wherein each substituents is independently selected from the following.
[Chemical formula 121]
$R^3 =$
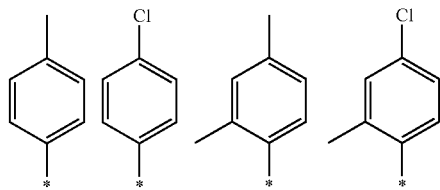
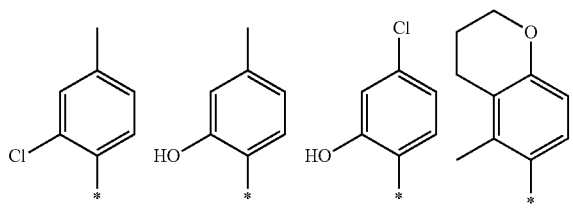
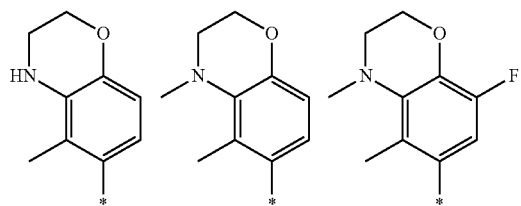
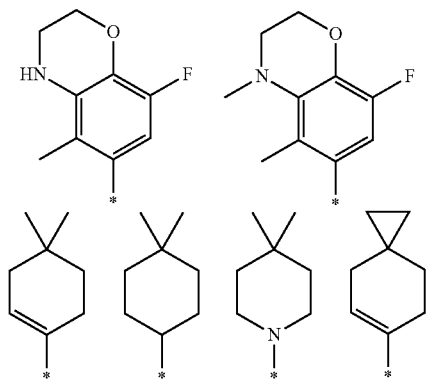
-continued
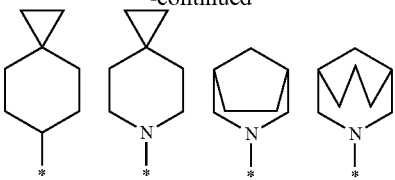
[Chemical formula 122]
$R^{4A} =$
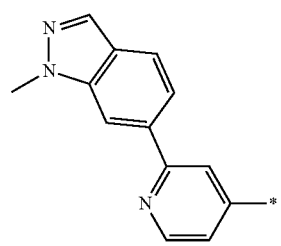
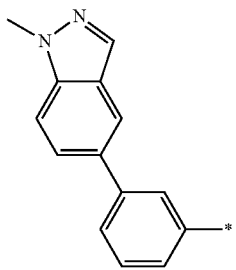
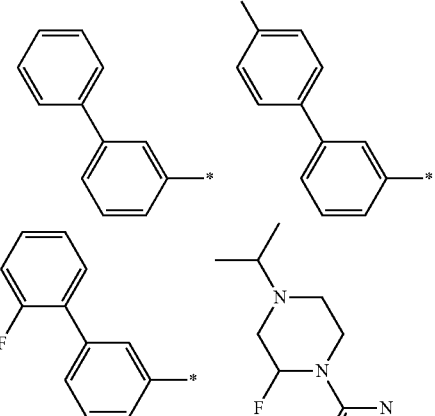
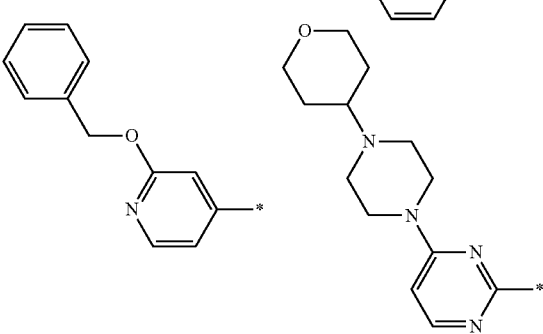

Example X2
[Chemical formula 123]
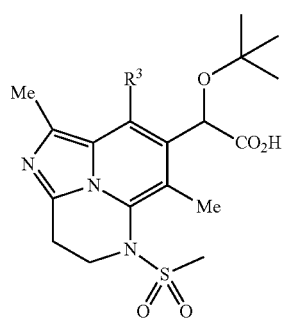
(I-C-6-2-1)
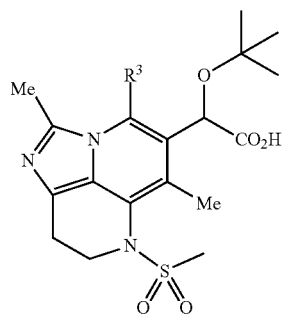
(I-B-5-2-1)
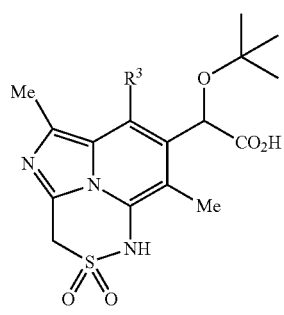
(I-C-6-1-1)
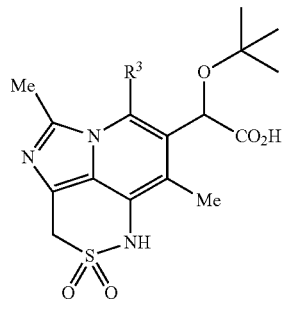
(I-B-5-1-1)
-continued
(I-C-6-1-2)
(I-B-5-1-2)
[Chemical formula 124]
(I-C-6-1-2)
(I-B-5-1-2)
(I-C-6-1-3)

-continued
(I-B-5-1-3)
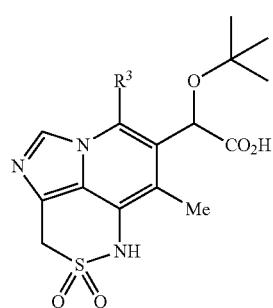
(I-B-5-1-4)
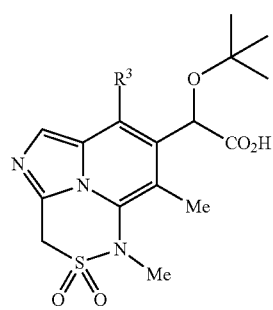
(I-B-5-1-4)
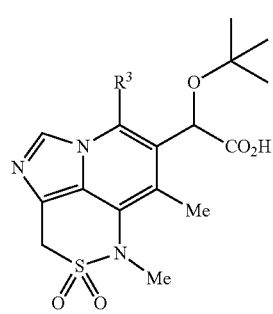
wherein $R^3$ is each independently selected from the following.
[Chemical formula 125]
$R^3 =$
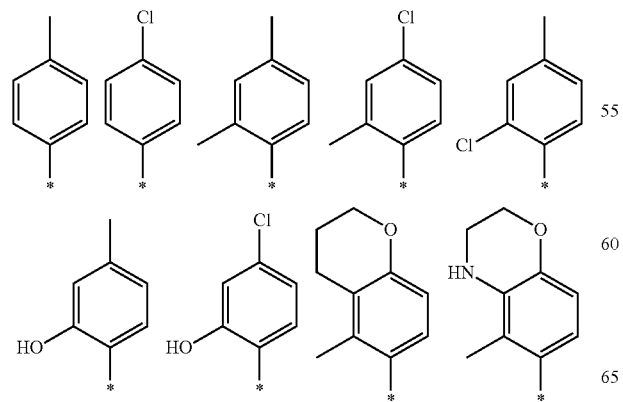
-continued
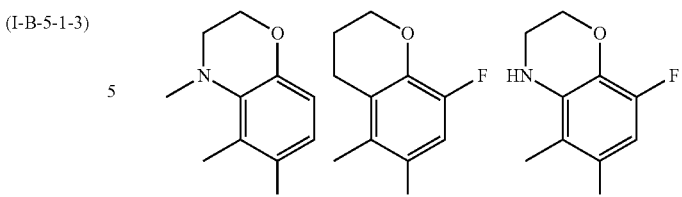
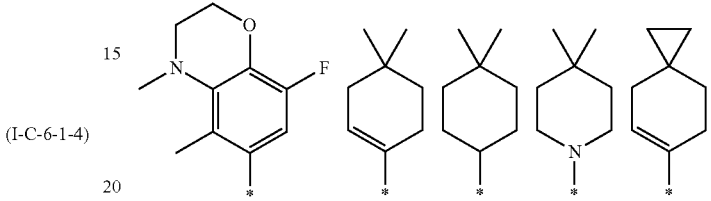
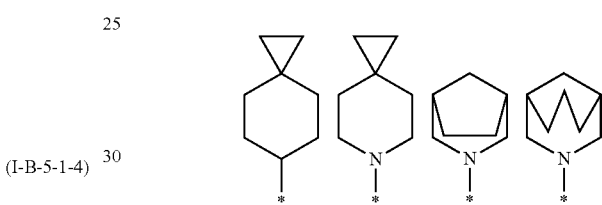
Example X3
[Chemical formula 126]
(I-A-1-2-3)
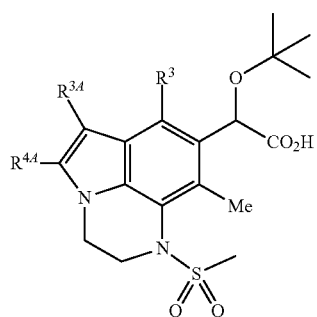
(I-A-3-2-3)
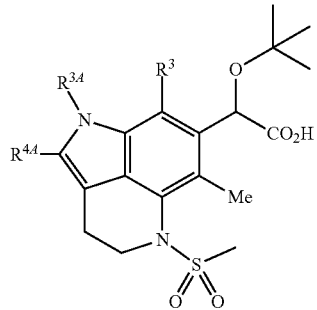

(I-B-1-2-3)
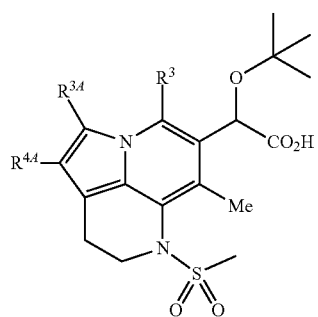
(I-C-1-2-3)
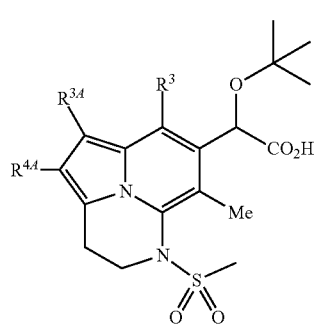
(I-A-1-1-5)
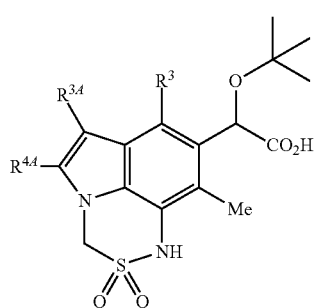
(I-A-3-1-5)
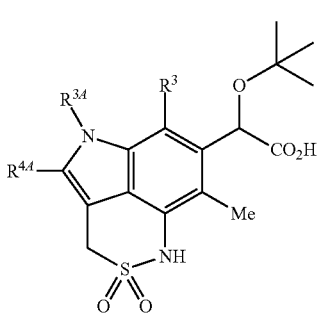
(I-B-1-1-5)
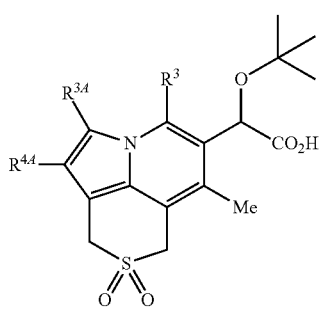
(I-C-1-1-5)
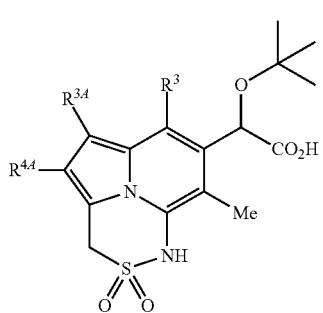
(I-A-1-1-6)
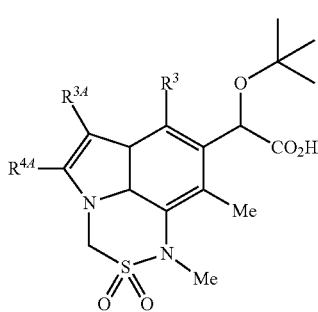
(I-A-3-1-6)
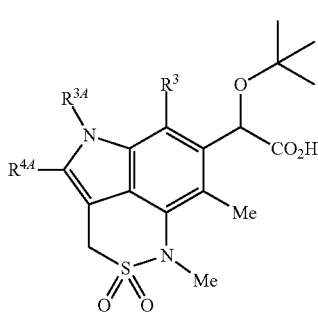
(I-B-1-1-6)
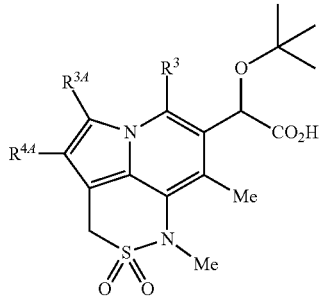

(I-C-1-1-6)

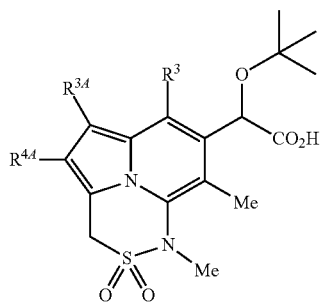

wherein R³ is each independently selected from the following.

[Chemical formula 127]

R³ =

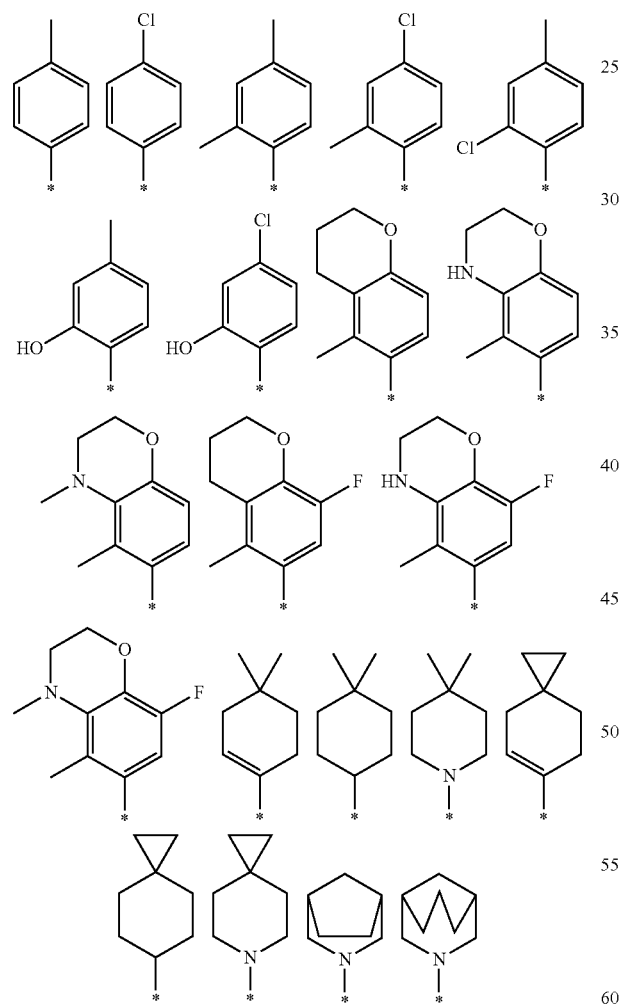

wherein $R^{3A}$ and $R^{4A}$ are taken together to form a divalent group shown below each independently. That is, these groups are taken together with an adjacent atom of $R^{3A}$ and $R^{4A}$ to form a T² ring of the compound of the present invention.

[Chemical formula 128]

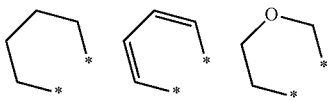

*—$R^{3A}$—$R^{4A}$—*

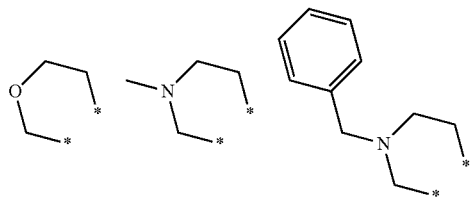

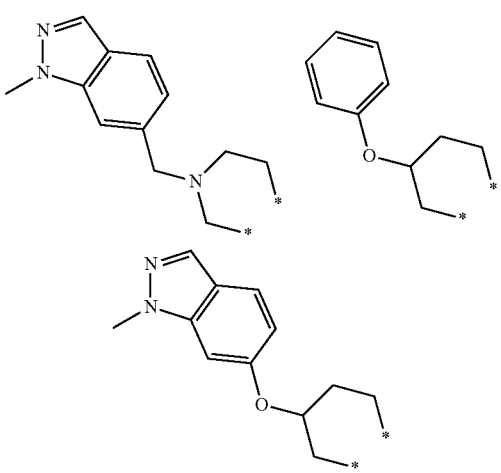

The present invention further provides the following compounds.

Example X4

[Chemical formula 129]

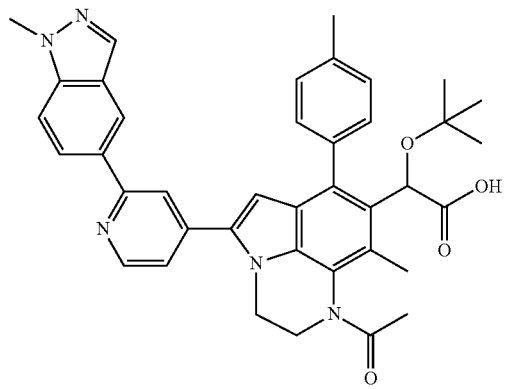

201
-continued
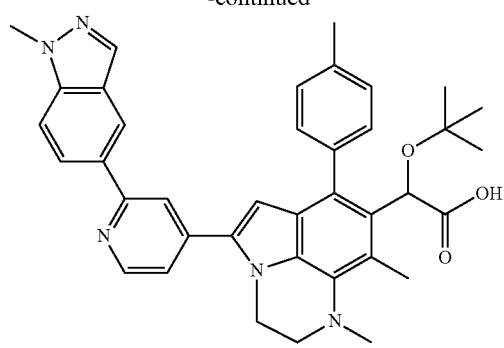
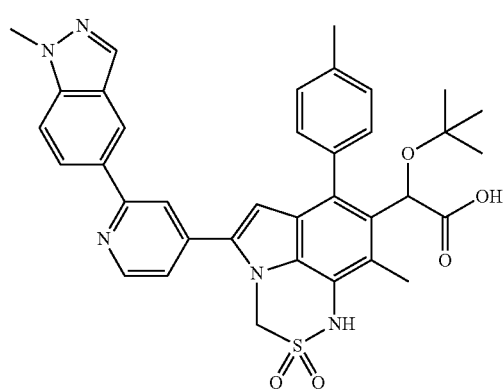
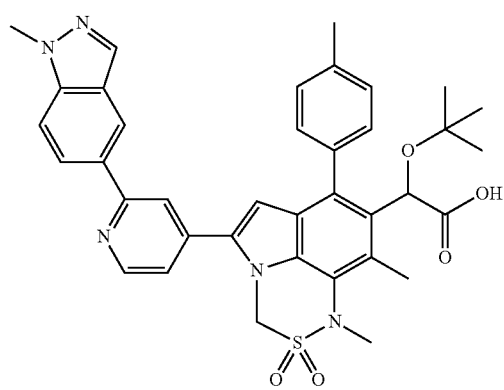
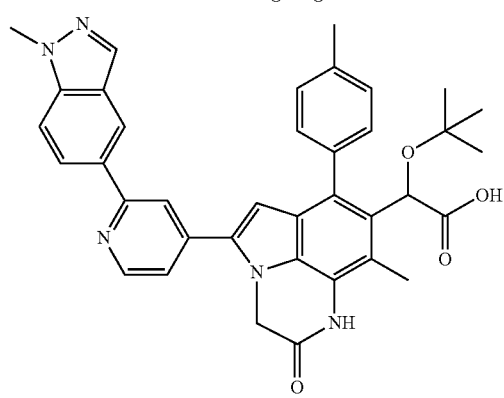
202
-continued
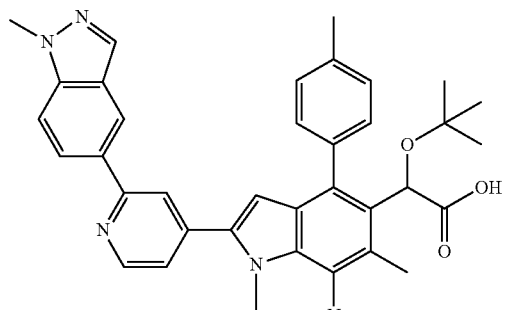
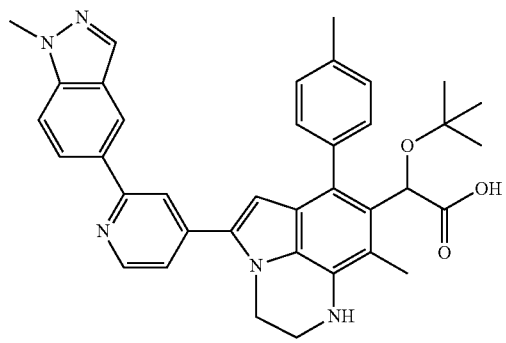
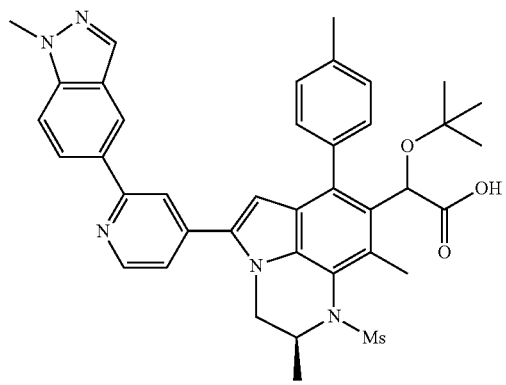
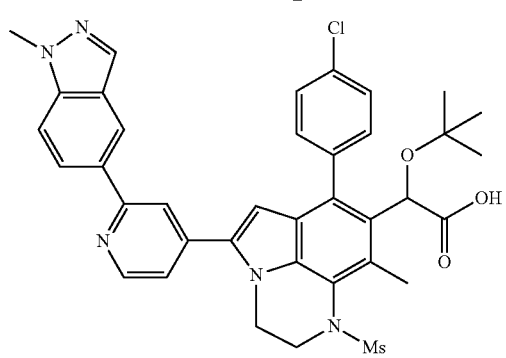

203
-continued
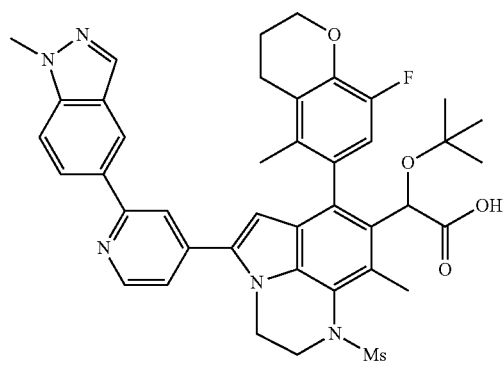
[Chemical formula 130]
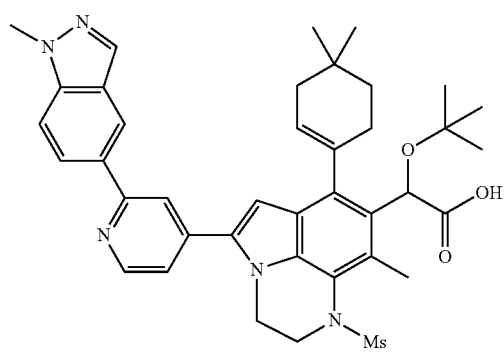
[Chemical formula 131]
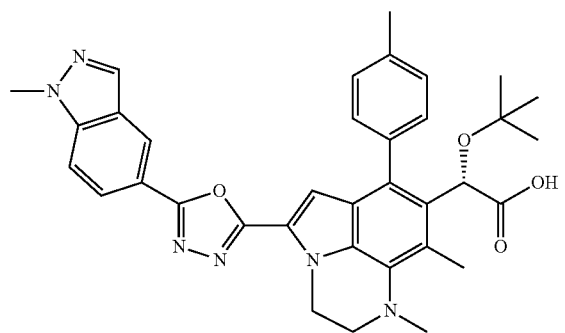
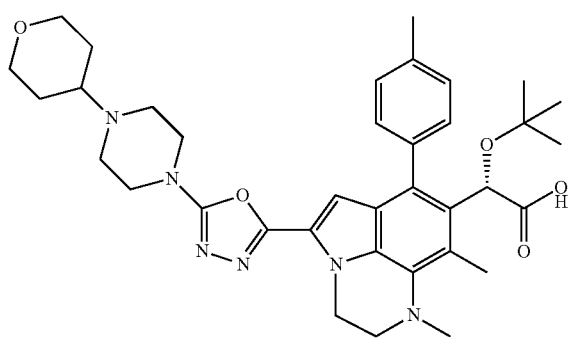
204
-continued
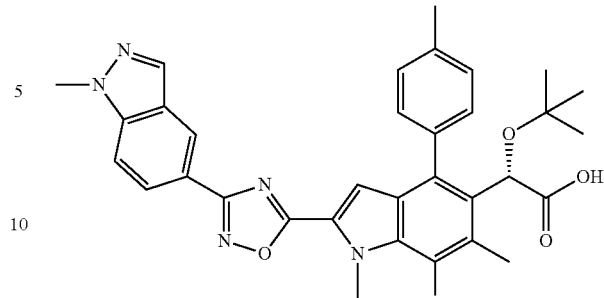
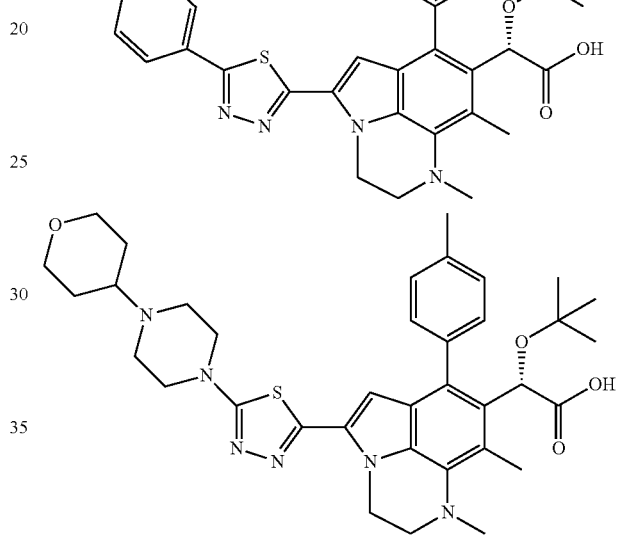
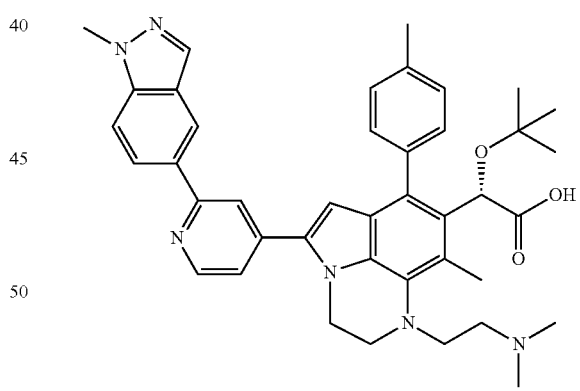
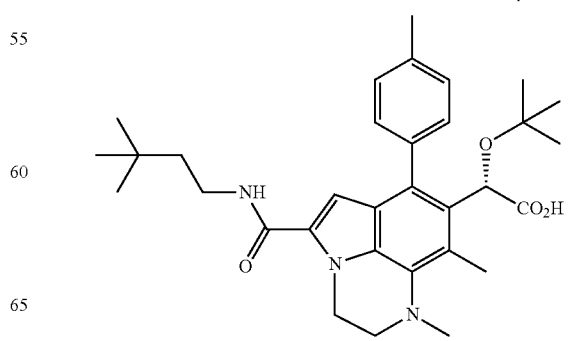

-continued

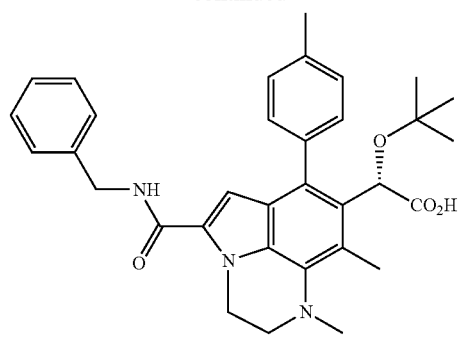 [SMILES: Cc1ccc(-c2c([C@H](OC(C)(C)C)C(=O)O)c(C)c3c4c2cc(C(=O)NCCC(C)C)n4CCN3C)cc1]

[Chemical formula 132]

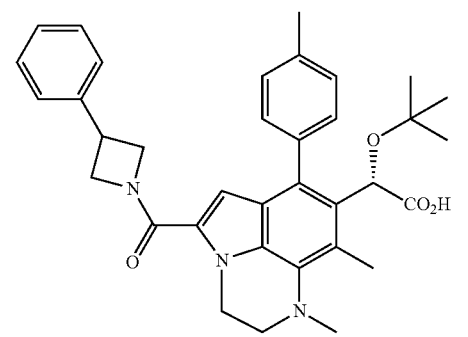

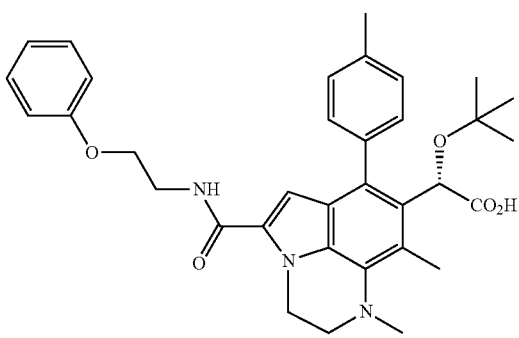

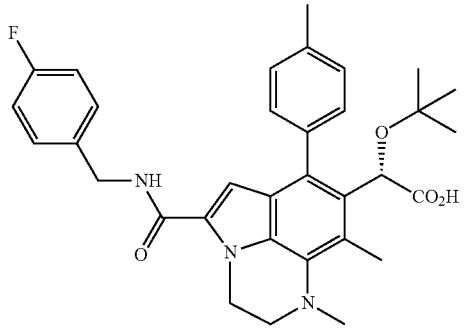

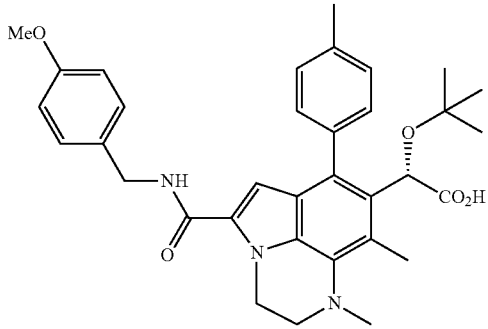

-continued

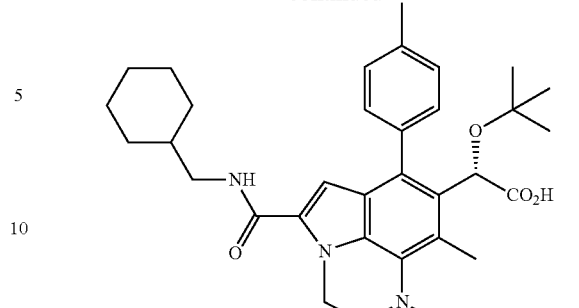

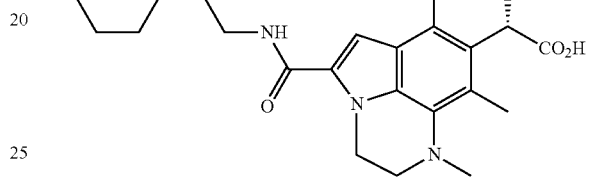

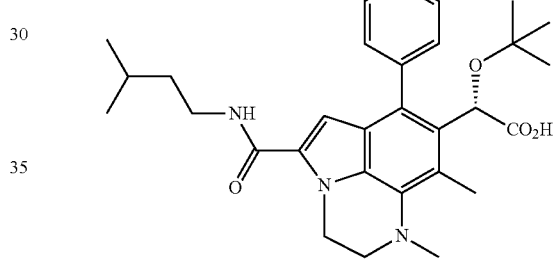

The biology assay of the compound of the present invention is described below.

Test Example 1: HIV Replication Inhibition Assay

HIV (HTLV-IIIB strain) persistent infected human T cell strain Molt-4 clone 8 was cultured in 10% Fetal Bovine Serum-containing RPMI-1640 medium and the supernatant was filtered, then the virus titer was measured and the solution was stored at −80° C. Each anti-human immunodeficiency virus active substance was diluted with the above cultured medium to the designated concentration, which was dispensed into 96 well micro plate by 50 μL. Next, a MT-4 cell suspended liquid was dispensed by 100 μL ($2.5 \times 10^4$ cells), then the above HIV-containing supernatant diluted with the above cultured medium was added thereto by 50 μl (60 pfu (plaque forming unit)).

The obtained mixture was cultured at 37° C. in $CO_2$ incubator for four days, then 3-(4,5-dimethylthiazole-2-yl)-2,5-diphenyltetrazolynium bromide (MTT) 5 mg/mL in PBS was added to each well by 30 μL, followed by 1 hr-cultivation. In this step, as formazan was precipitated by reduction of MTT in living cells, the cell supernatant was removed from all was by 150 μL, then a 150 μL of solution (10% Triton X-100 and 0.4% (v/v)-HCl containing isopropanol) was added thereto, followed by shaking with a plate mixer, to elute formazan. The formazan was measured with a microreader at OD: 560 nm and 690 nm (reference wavelength) and the result was compared with the reference. EC50 means the compound concentration at which cell cytotoxicity by virus is inhibited 50%.
(Result)

TABLE 10

| Comp. No. | EC50(nM) |
|---|---|
| I-006 | 14 |
| I-008 | 5.9 |
| I-009 | 32 |
| I-010 | 16 |
| I-011 | 2.3 |
| I-012 | 3.7 |
| I-013 | 3.4 |
| I-014 | 1.3 |
| I-015 | 4 |
| I-016 | 3.9 |
| I-017 | 9.1 |
| I-018 | 1.1 |
| I-019 | 6 |
| I-020 | 3.6 |
| I-021 | 3.8 |
| I-022 | 4 |
| I-023 | 0.82 |
| I-024 | 4.2 |
| I-025 | 89 |
| I-026 | 3.7 |
| I-027 | 1.7 |
| I-028 | 3.3 |
| I-029 | 2.4 |
| I-030 | 1.9 |
| I-031 | 2.9 |
| I-032 | 5.2 |

TABLE 11

| Comp. No. | EC50(nM) |
|---|---|
| I-034 | 2.4 |
| I-035 | 5.2 |
| I-037 | 0.4 |
| I-039 | 53 |
| I-040 | 67 |
| I-041 | 4.6 |
| I-044 | 44 |

Test Example 2: CYP Inhibition Assay

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenadine hydroxylation (CYP3A4) as typical substrate metabolism reactions of human main five CYP enzyme forms (CYP1A2, 2C9, 2C19, 2D6, 3A4) an inhibitory degree of each metabolite production amount by a test compound was assessed.

The reaction conditions were as follows: substrate, 0.5 μmol/L ethoxyresorufin (CYP1A2), 100 μmol/L tolbutamide (CYP2C9), 50 μmol/L S-mephenytoin (CYP2C19), 5 μmol/L dextromethorphan (CYP2D6), 1 μmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 μmol/L (four points).

Each five kinds of substrates, human hepatic microsome, and a test drug in 50 mmol/L Hepes buffer as a reaction solution was added to a 96-well plate as the composition ad described above, NADPH, as a coenzyme was added to initiate metabolism reactions as markers and, after the incubation at 37° C. for 15 minutes, a methanol/acetonitrile=1/1 (V/V) solution was added to stop the reaction. After the centrifugation at 3000 rpm for 15 minutes, resorufin (CYP1A2 metabolite) in the supernatant was quantified by a fluorescent multilabel counter and tolbutamide hydroxide (CYP2C9 metabolite), mephenytoin 4' hydroxide (CYP2C19 metabolite), dextrorphan (CYP2D6 metabolite), and terfenadine alcohol (CYP3A4 metabolite) were quantified by LC/MS/MS.

A reaction system containing only DMSO which is a solvent for dissolving a drug was adopted as a control (100%), and the remaining activity (%) was calculated, then $IC_{50}$ was calculated by reverse presumption with a logistic model using a concentration and an inhibition rate.
(Result)
Compound No. I-34: five 5 species>20 μmol/L Test Example 3-1: CYP3A4 Fluorescent MBI Test The CYP3A4 fluorescent MBI test is to investigate the enhancement of CYP3A4 inhibition of a compound by a metabolism reaction. 7-Benzyloxytrifluoromethylcoumarin (7-BFC) is debenzylated by the CYP3A4 enzyme to produce 7-hydroxytrifluoromethylcoumarin (HFC), a metabolite emitting fluorescent light. The test was performed using 7-HFC-producing reaction as an index.

The reaction conditions were as follows: substrate 5.6 μmol/L 7-BFC; pre-reaction time, 0 or 30 minutes; reaction time, 15 minutes; reaction temperature, 25° C. (room temperature); CYP3A4 content (expressed in *Eschericha coli*), at pre-reaction 62.5 μmol/mL, at reaction 6.25 μmol/mL (at 10-fold dilution); test drug concentration, 0.625, 1.25, 2.5, 5, 10, 20 μmol/L (six points).

An enzyme in a K-Pi buffer (pH 7.4) and a test drug solution as a pre-reaction solution were added to a 96-well plate so that it was 1/10 diluted by a substrate in a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1(V/V) was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)=4/1 was added to stop the reaction. For the plate on which each index reaction had been performed, a fluorescent value of 7-HFC which is a metabolite was measured with a fluorescent plate reader. (Ex=420 nm, Em=535 nm)

Addition of only DMSO which is a solvent dissolving a drug to a reaction system was adopted as a control (100%), remaining activity (%) was calculated at each concentration of a test drug added as the solution, and $IC_{50}$ was calculated by reverse-presumption by a logistic model using a concentration and an inhibition rate. A case where the difference of $IC_{50}$ values was 5 μmol/L or more was defined as (+) and, a case where the difference was 3 μmol/L or less was defined as (−).

Test Example 3-2: CYP3A4 (MDZ) MBI Test

CYP3A4 (MDZ) MBI test is a test of investigating mechanism based inhibition (MBI) ability on CYP3A4 inhibition of a compound by enhancement of a metabolism reaction. CYP3A4 inhibition is evaluated using 1-hydroxylation reaction of midazolam (MDZ) by pooled human liver microsomes as an index.

The reaction conditions are as follows: substrate, 10 µmol/L MDZ; pre-reaction time, 0 or 30 minutes; substrate reaction time, 2 minutes; reaction temperature, 37° C.; protein content of pooled human liver microsomes, at pre-reaction time 0.5 mg/mL, at reaction time 0.05 mg/mL (at 10-fold dilution); concentrations of the compound of the present invention, 1, 5, 10, 20 µmol/L (four points).

Pooled human liver microsomes in K-Pi buffer (pH 7.4) and a solution of the compound of the present invention as a pre-reaction solution were added to a 96-well plate at the composition of the pre-reaction. A part of pre-reaction solution was transferred to another 96-well plate, and 1/10 diluted by a substrate in K-Pi buffer NADPH as a co-factor was added in order to initiate a reaction as an index (without preincubation). After a predetermined time of a reaction, methanol/acetonitrile=1/1 (V/V) solution was added in order to stop the reaction. On the other hand, NADPH was also added to a remaining pre-reaction solution in order to initiate a preincubation (with preincubation). After a predetermined time of a preincubation, a part was transferred to another 96-well plate, and 1/10 diluted by a substrate in K-Pi buffer in order to initiate a reaction as an index. After a predetermined time of a reaction, methanol/acetonitrile=1/1 (V/V) solution was added in order to stop the reaction. After centrifuged at 3000 rpm for 15 minutes, 1-hydroxymidazolam in the supernatant was quantified by LC/MS/MS.

The sample adding DMSO to a reaction system instead of a solution of the compound of the present invention is adopted as a control (100%) because DMSO is used as a solvent to dissolve the compound of the present invention. Remaining activity (%) is calculated at each concentration of the compound of the present invention added as the solution, and IC-value is calculated by reverse-presumption by a logistic model using a concentration and an inhibition rate. Shifted IC value is calculated as "IC of preincubation at 0 min/IC of preincubation at 30 min". When a shifted IC is 1.5 or more, this is defined as positive. When a shifted IC is 1.0 or less, this is defined as negative.
(Result)
Compound No. I-34: (−)

Test Example 4: Metabolism Stability Test

Commercially available pooled human hepatic microsomes and a test compound were reacted for a constant time, then a remaining rate was calculated by comparing a reacted sample and an unreacted sample, thereby a degree of metabolism of the test compound in liver was assessed.

A reaction was performed (oxidative reaction) at 37° C. for 0 minute or 30 minutes in the presence of 1 mmol/L NADPH in 0.2 mL of a buffer (50 mmol/L Tris-HCl, pH 7.4, 150 mmol/L potassium chloride, 10 mmol/L magnesium chloride) containing 0.5 mg protein/mL of human liver microsomes. After the reaction, 50 µL of the reaction solution was added to 100 µL of a methanol/acetonitrile=1/1 (v/v), mixed and centrifuged at 3000 rpm for 15 minutes. The test compound in the supernatant was quantified by LC/MS/MS, and a remaining amount of the test compound after the reaction wad calculated, letting a compound amount at 0 minute reaction time to be 100%. Hydrolysis reaction was performed in the absence of NADPH and glucuronidation reaction was in the presence of 5 mM UDP-glucuronic acid in place of NADPH, followed by similar operations.
(Result) The residual rate of the compound concentration 0.5 µmol/L in the oxidation reaction was shown below.
Compound No. I-34: >99.9%

Test Example 5: Solubility Test

The solubility of the compound of the present invention was determined under 1% DMSO addition conditions. A 10 mmol/L solution of the compound was prepared with DMSO, and 6 µL of the solution was added to 594 µL of an artificial intestinal juice (: water and a 118 mL solution of 0.2 mol/L NaOH reagent are added to 250 mL of 0.2 mol/L potassium dihydrogen phosphate reagent to reach 1000 mL) with a pH of 6.8. The mixture was left standing for 16 hours at 25° C., and the mixture was vacuum-filtered. The filtrate was two-fold diluted with methanol/water=1/1(v/v), and the compound concentration in the filtrate was measured with HPLC or LC/MS/MS by the absolute calibration method.
(Result)
Compound No. I-17: >50 µmol/L Test Example 6: Fluctuation Ames Test The mutagenicity of the compound of the present invention was assaied.

20 µL of freezing-stored rat typhoid *bacillus* (*Salmonella typhimurium* TA98 strain, TA 100 strain) was inoculated on 10 mL of a liquid nutrient medium (2.5% Oxoid nutrient broth No. 2), and this was cultured before shaking at 37° C. for 10 hours. 9 mL of a bacterial solution of the TA98 strain was centrifuged (2000×g, 10 minutes) to remove a culturing solution. The bacteria was suspended in F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4.7H_2O$: 0.1 g/L), and the suspension was added to 110 mL of an Exposure medium (Micro F buffer containing Biotin: 8 µg/mL, histidine: 0.2 µg/mL, glucose: 8 mg/mL). The TA100 strain was added to 120 mL of the Exposure medium per 3.16 mL of the bacterial solution to prepare a test bacterial solution. Each 12 µL of a test substance DMSO solution (several stage dilution from maximum dose 50 mg/mL at 2 to 3-fold ratio), DMSO as a negative control, 50 µg/mL of 4-nitroquinoline-1-oxide DMSO solution for the TA98 strain, 0.25 µg/mL of 2-(2-furyl)-3-(5-nitro-2-furyl)acrylamide DMSO solution for the TA100 strain each under the non-metabolism activating condition, 40 µg/mL of 2-aminoanthracene DMSO solution for the TA98 strain, 20 µg/mL of 2-aminoanthracene DMSO solution for the TA100 strain each under the metabolism condition all as a positive control, and 588 µL of the test bacterial solution (a mixed solution of 498 µl of the test bacterial solution and 90 µL of S9 mix under the metabolism activating condition) were mixed, and this was shaking-cultured at 37° C. for 90 minutes. 460 µL of the bacterial solution exposed to the test substance was mixed with 2300 µL of an Indicator medium (Micro F buffer containing biotin: 8 µg/mL, histidine: 0.2 µg/mL, glucose: 8 mg/mL, Bromo Cresol Purple: 37.5 µg/mL), each 50 µL was dispensed into microplate 48 wells/dose, and this was subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turner to yellow in 48 wells per dose is counted, and was assessed by comparing with a negative control group. (−) means that mutagenicity is negative and (+) is positive.
(Result)
Compound No. I-30: (−)

Test Example 7: BA Test

Materials and methods for studies an oral absorption
(1) Animal: mouse or SD rats are used.
(2) Breeding conditions: mouse or SD rats were allowed to freely take solid feed and sterilized tap water.
(3) Dose and grouping: orally or intravenously administered at a predetermined dose; grouping is as follows (Dose depends on the compound)
  Oral administration: 1 to 30 mg/kg (n=2 to 3)
  Intravenous administration: 0.5 to 10 mg/kg (n=2 to 3)
(4) Preparation of dosing solution: for oral administration, in a solution or a suspension state; for intravenous administration, in a solubilized state.
(5) Administration method: in oral administration, forcedly administer into ventriculus with oralprobe; in intravenous administration, administer from caudal vein with a needle-equipped syringe.
(6) Evaluation items: blood is collected over time, and the plasma concentration of drug is measured by LC/MS/MS.
(7) Statistical analysis: regarding the transition of the plasma concentration, the area under the plasma concentration-time curve (AUC) is calculated by non-linear least squares program WinNonlin (Registered trademark), and the bioavailability (BA) is calculated from the AUCs of the oral administration group and intravenous administration group.
(Result)
Compound No. I-30: 45.2%

Experimental Example 8: hERG Test

For the purpose of assessing risk of an electrocardiogram QT interval prolongation, effects on delayed rectifier K+ current ($I_{Kr}$), which plays an important role in the ventricular repolarization process of the compound of the present invention, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, $NaH_2 PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazineethanesulfonic acid, 4-(2-hydroxyethyl)-1-piperazine ethanesulfonic acid): 10 mmol/L, pH=7.4) in which the test compound had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver. 1, Molecular Devices Corporation). Further, the inhibition relative to the tail peak current before application of the test substance was calculated, and compared with the vehicle-applied group (0.1% dimethyl sulfoxide solution) to access influence of the test substance on $I_{Kr}$.

(Result) The inhibition ratio in the compound concentration 5 μmol/L was shown.

Compound No. I-30: 11.7%

Test Example 9: Powder Solubility Test

Appropriate amounts of the test substances are put into appropriate containers. To the respective containers are added 200 μL of JP-1 fluid (sodium chloride 2.0 g, hydrochloric acid 7.0 mL and water to reach 1000 mL), 200 μL of JP-2 fluid (phosphate buffer (pH 6.8) 500 mL and water 500 mL), and 200 μL of 20 mmol/L TCA (sodium taurocholate)/JP-2 fluid (TCA 1.08 g and JP-2 fluid to reach 100 μL). IN the case that all amount of the test compound is dissolved after the addition of the test fluid, the test compound is added as appropriate. The containers are sealed, and shaken for 1 hour at 37° C. The mixtures are filtered, and 100 μL of methanol is added to each of he filtrate (1001 μL) so that the filtrates are two-fold diluted. The dilution ratio may be changed if necessary. The dilutions are observed for bubbles and precipitates, and then the containers are sealed and shaken. Quantification is performed by HPLC with an absolute calibration method.

(Result)
Compound No. I-34: JP-1 fluid; >1000 μg/mL, JP-2 fluid; 0.603 μg/mL, 20 mmol/L TCA/JP-2 fluid >1000 μg/mL Test Example 10: Light Hemolysis Test The compound of the present invention is dissolved at the target concentration, and is mixed with the red blood cell suspension on a microplate. The mixture is irradiated with fluorexcent UV lamps under the condition of 10 J/cm$^2$ in the UVA and UVB. After the irradiation, a supernatant of the mixture is collected and is transferred to a microplate. Absorbance of the supernatants is measured at 540 nm and 630 nm, and phototoxicity of the compound is determined based on the optical density. In the study, two endpoints of 540 nm and 630 nm are indicated of lipid membrane (met-hemoglobin formation), respectively.

(Result)
Compound No. I-17: (−)

INDUSTRIAL APPLICABILITY

The compound of the present invention is useful as a medicament used as a therapeutic or prophylactic agent for virus infection disease such as AIDS, or an intermediate thereof.

The invention claimed is:

1. A compound of formula (I):

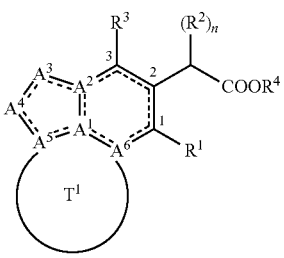

or a pharmaceutically acceptable salt thereof,
wherein
$A^1$ is C, $CR^{1A}$, or N;
$A^2$ is C, $CR^{2A}$, or N;
$A^3$ is $CR^{3A}$, $CR^{3A}R^{3B}$, N, $NR^{3C}$, O, S, SO, or $SO_2$;
$A^4$ is $CR^{4A}$, $CR^{4A}R^{4B}$, N, $NR^{4C}$, O, S, SO, or $SO_2$;
$A^5$ is C, $CR^{5A}$, or N;
$A^6$ is C, $CR^{6A}$, or N;
$R^{1A}$, $R^{2A}$, $R^{3A}$, $R^{3B}$, $R^{4A}$, $R^{4B}$, $R^{5A}$, and $R^{6A}$ are each independently hydrogen, halogen, hydroxy, substituted or unsubstituted alkyl, substituted or unsubstituted alkenyl, substituted or unsubstituted alkynyl, substituted or unsubstituted alkyl oxy, substituted or unsubstituted alkenyloxy, substituted or unsubstituted alkynyloxy, substituted or unsubstituted alkyl carbonyl, substituted or unsubstituted alkenyl carbonyl, substituted or unsubstituted alkynyl carbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocycle oxy, substituted or unsubstituted non-aromatic carbocycle oxy, substituted or unsubstituted aromatic heterocycle oxy, substituted or unsubstituted non-aromatic heterocycle oxy, substituted or unsubstituted aromatic carbocycle thio, substituted or unsubstituted non-aromatic carbocycle thio, substituted or unsubstituted aromatic heterocycle thio, substituted or unsubstituted non-aromatic heterocycle thio, substituted or unsubstituted aromatic carbocycle amino, substituted or unsubstituted non-aromatic carbocycle amino, substituted or unsubstituted aromatic heterocycle amino, substituted or unsubstituted non-aromatic heterocycle amino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylalkylcarbonyl, substituted or unsubstituted non-aromatic carbocyclylalkylcarbonyl, substituted or unsubstituted aromatic heterocyclylalkyl carbonyl, substituted or unsubstituted non-aromatic heterocyclylalkylcarbonyl, substituted or unsubstituted amino, or substituted or unsubstituted carbamoyl;
$R^{3C}$ and $R^{4C}$ are each independently hydrogen, substituted or unsubstituted alkyl, substituted or unsubstituted alkenyl, substituted or unsubstituted alkynyl, substituted or unsubstituted alkyl oxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; or,
$R^{3A}$ and $R^{3B}$ may be taken together to form oxo, $R^{4A}$ and $R^{4B}$ may be taken together to form oxo;
$R^{3A}$ and $R^{4A}$ may be taken together with an adjacent atom to form substituted or unsubstituted monocyclic carbocycle, or substituted or unsubstituted monocyclic heterocycle, the carbocycle or heterocycle may be further fused to;
$R^{3A}$ and $R^{4C}$ may be taken together with an adjacent atom to form substituted or unsubstituted monocyclic heterocycle, the heterocycle may be further fused to;
$R^{3C}$ and $R^{4A}$ may be taken together with an adjacent atom to form substituted or unsubstituted monocyclic heterocycle, the heterocycle may be further fused to;
$R^{3C}$ and $R^{4C}$ may be taken together with an adjacent atom to form substituted or unsubstituted monocyclic heterocycle, the heterocycle may be further fused to;
$R^{3A}$ and $R^{3B}$ may be taken together with an adjacent atom to form substituted or unsubstituted spiro ring, the spiro ring may be further fused to;
$R^{4A}$ and $R^{4B}$ may be taken together with an adjacent atom to form substituted or unsubstituted spiro ring, the spiro ring may be further fused to;
$R^{4B}$ may be taken together with an atom on the circular arc of $T^1$ ring to form substituted or unsubstituted monocyclic carbocycle, or substituted or unsubstituted monocyclic heterocycle, the carbocycle or heterocycle may be further fused to;
$R^{4C}$ may be taken together with an atom on the circular arc of T1 ring to form substituted or unsubstituted monocyclic heterocycle, the heterocycle may be further fused to;
the broken line means the presence or absence of bond, the adjacent broken lines do not exist at the same time, the carbon atoms on 1st, 2nd, and 3rd position are $sp^2$ carbon;
$T^1$ ring is substituted or unsubstituted monocyclic carbocycle or substituted or unsubstituted monocyclic heterocycle, (1) the carbocycle or heterocycle may be fused with the other substituted or unsubstituted carbocycle or substituted or unsubstituted heterocycle, and/or (2) two atoms which are not adjacent to one another constituting the carbocycle or heterocycle may be bridged by substituted or unsubstituted alkylene, substituted or unsubstituted alkenylene or substituted or unsubstituted alkynylene;
$R^1$ is halogen, cyano, nitro or $-X^1-R^{11}$,
$X^1$ is a bond, $-O-$, $-S-$, $-NR^{12}-$, $-CO-$, $-SO-$, $-SO_2-O-CO-$, $-CO-O-$, $-NR^{12}-CO-$, $-CO-NR^{12}-$, $-NR^{12}-CO-O-$, $-NR^{12}-CO-NR^{13}$, $-NR^{12}-SO_2-$ or $-SO_2-NR^{12}-$,
$R^{11}$ is hydrogen atom, substituted or unsubstituted alkyl, substituted or unsubstituted alkenyl, substituted or unsubstituted alkynyl, substituted or unsubstituted carbocyclyl, or substituted or unsubstituted heterocyclyl,
$R^{12}$ and $R^{13}$ are each independently hydrogen atom, substituted or unsubstituted alkyl, substituted or unsubstituted alkenyl or substituted or unsubstituted alkynyl, when $X^1$ is —$NR^{12}$—, —CO—$NR^{12}$— or —$SO_2$—$NR^{12}$—, $R^{11}$ and $R^{12}$ may be taken together with an adjacent nitrogen atom to form substituted or unsubstituted heterocyclyl, $X^1$ is —$NR^{12}$—CO—$NR^{13}$—, $R^{11}$ and $R^{13}$ may be taken together with an adjacent nitrogen atom to form substituted or unsubstituted heterocyclyl, $R^1$ may be taken together with a carbon atom or a nitrogen atom on the circular arc of $T^1$ ring to form substituted or unsubstituted monocyclic carbocycle, or substituted or unsubstituted monocyclic heterocycle, the carbocycle or heterocycle may be further fused to;

$R^2$ is each substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyloxy, or substituted or unsubstituted cycloalkenyloxy;

n is 1 or 2;

$R^3$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocycle alkenyl, substituted or unsubstituted non-aromatic carbocycle alkenyl, substituted or unsubstituted aromatic heterocycle alkenyl, substituted or unsubstituted non-aromatic heterocycle alkenyl, substituted or unsubstituted aromatic carbocycle alkynyl, substituted or unsubstituted non-aromatic carbocycle alkynyl, substituted or unsubstituted aromatic heterocycle alkynyl, or substituted or unsubstituted non-aromatic heterocycle alkynyl; and $R^4$ is hydrogen or a carboxy protecting group.

2. The compound or pharmaceutically acceptable salt thereof according to claim 1, wherein the formula (I) is one of formulas (I-A), (I-B) and (I-C):

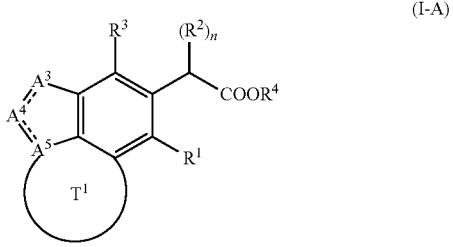

(I-A)

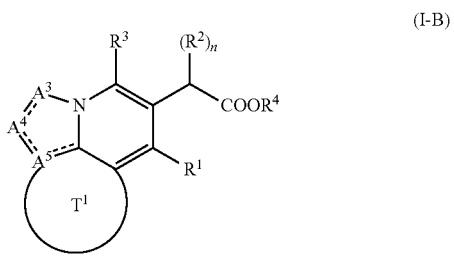

(I-B)

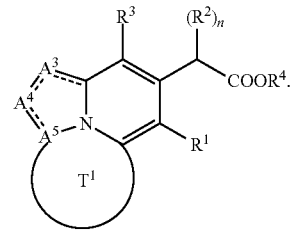

(I-C)

3. The compound or pharmaceutically acceptable salt thereof according to claim 1, wherein at least one of conditions 1) to 3) is fulfilled:

1) $A^3$ is N, $NR^{3C}$, O, S, SO, or $SO_2$;
2) $A^4$ is N, $NR^{4C}$, O, S, SO, or $SO_2$; and
3) $A^5$ is N.

4. The compound or pharmaceutically acceptable salt thereof according to claim 1, wherein $A^3$ is $CR^{3A}$; $A^4$ is $CR^{4A}$; and $A^5$ is N.

5. The compound or pharmaceutically acceptable salt thereof according to claim 1, wherein $A^3$ is N or $NR^{3C}$; $A^4$ is $CR^{4A}$; and $A^5$ is C.

6. The compound or pharmaceutically acceptable salt thereof according to claim 1, wherein $A^3$ is N or $NR^{3C}$; $A^4$ is $CR^{4A}$; and $A^5$ is C or N.

7. The compound or pharmaceutically acceptable salt thereof according to claim 1, wherein $A^3$ is O or S; $A^4$ is $CR^{4A}$ or N; and $A^5$ is C.

8. The compound or pharmaceutically acceptable salt thereof according to claim 1, wherein the formula (I) is formula (I-A):

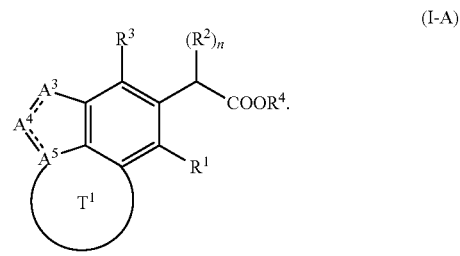

(I-A)

9. The compound or pharmaceutically acceptable salt thereof according to claim 8, wherein the formula (I) is one of formulas (I-A-1), (I-A-2), (I-A-3), (I-A-4), (I-A-5), (I-A-6), (I-A-5'), (I-A-6'), (I-A-7), (I-A-8), (I-A-9), and (I-A-10):

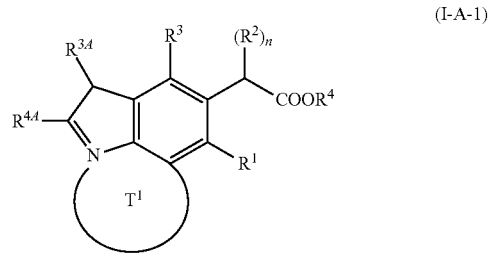

(I-A-1)

(I-A-2)
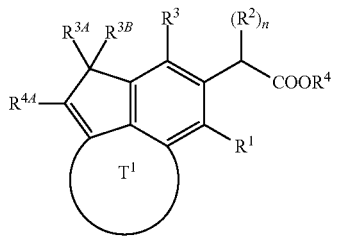
(I-A-3)
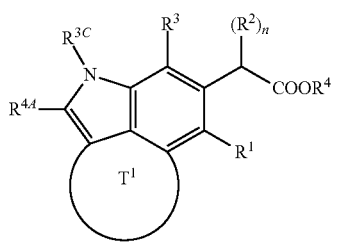
(I-A-4)
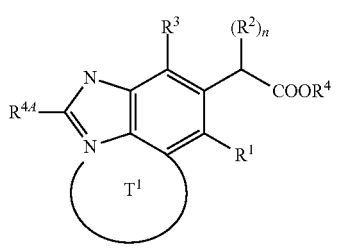
(I-A-5)
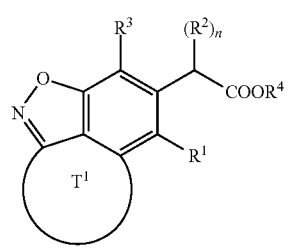
(I-A-6)
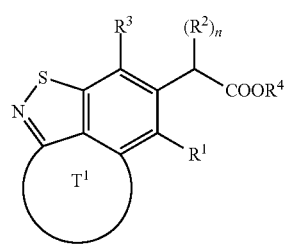
(I-A-5')
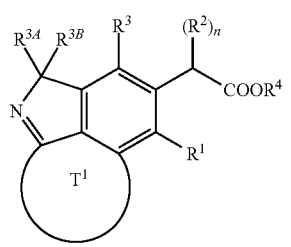
(I-A-6')
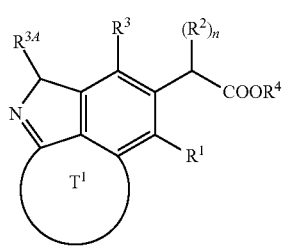
(I-A-7)
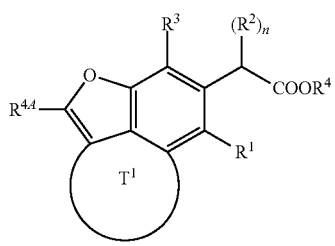
(I-A-8)
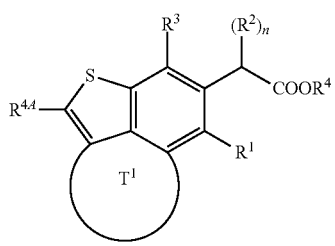
(I-A-9)
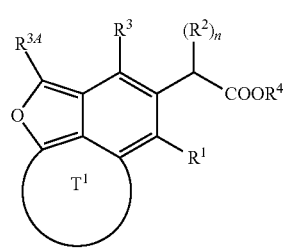
(I-A-10)
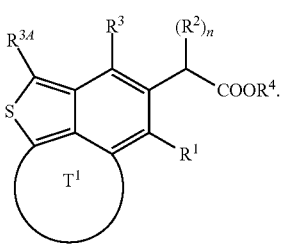
10. The compound or pharmaceutically acceptable salt thereof according to claim 8, wherein $T^1$ ring is one of structures ($T^1$-2-1), ($T^1$-2-2) and ($T^1$-2-3):
($T^1$-2-1)
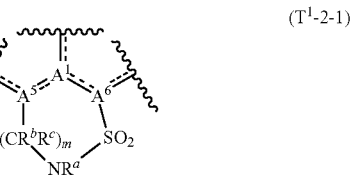

-continued

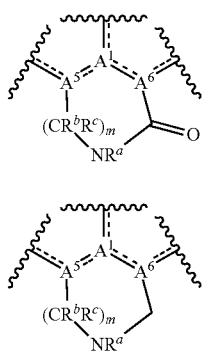
(T¹-2-2)

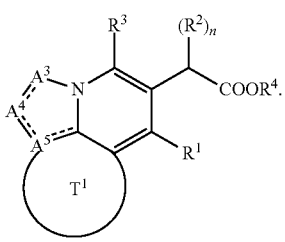
(T¹-2-3)

where R$^a$ is hydrogen, substituted or unsubstituted alkyl, substituted or unsubstituted alkenyl, substituted or unsubstituted carbocyclyl, substituted or unsubstituted heterocyclyl, —COR$^{a1}$, —SOR$^{a2}$, or —SO$_2$R$^{a3}$ (R$^{a1}$, R$^{a2}$, and R$^{a3}$ are each independently hydrogen, substituted or unsubstituted alkyl, substituted or unsubstituted alkenyl, substituted or unsubstituted carbocyclyl, or substituted or unsubstituted heterocyclyl);

m is an integer of 0 to 5;

L is —SO$_2$—, —SO—, —CO—, or —CR$^b$R$^c$—; and

R$^b$ and R$^c$ are each independently hydrogen, substituted or unsubstituted alkyl, substituted or unsubstituted alkenyl, substituted or unsubstituted carbocyclyl, substituted or unsubstituted heterocyclyl, or R$^b$ and R$^c$ may be taken together to form oxo.

11. The compound or pharmaceutically acceptable salt thereof according to claim 1, wherein the formula (I) is formula (I-B):

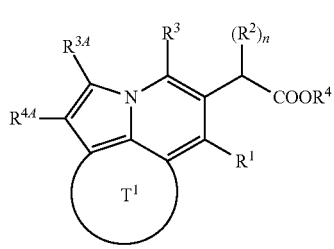
(I-B)

12. The compound or pharmaceutically acceptable salt thereof according to claim 11, wherein the formula (I) is one of formulas (I-B-1), (I-B-2), (I-B-3), (I-B-4), (I-B-5), (I-B-6), (I-B-7), (I-B-8), and (I-B-9):

(I-B-1)

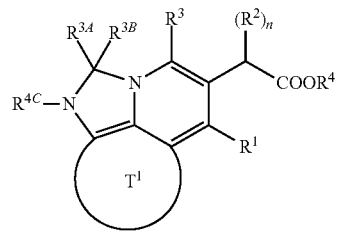
(I-B-2)

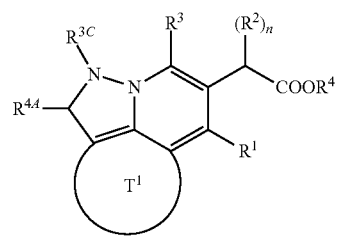
(I-B-3)

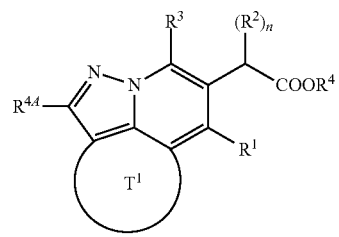
(I-B-4)

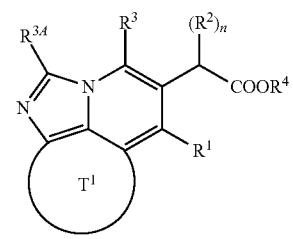
(I-B-5)

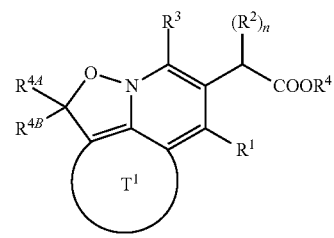
(I-B-6)

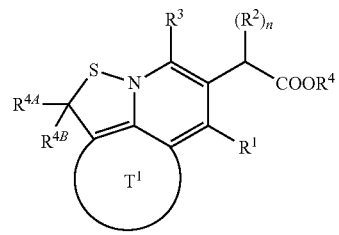
(I-B-7)

(I-B-8)

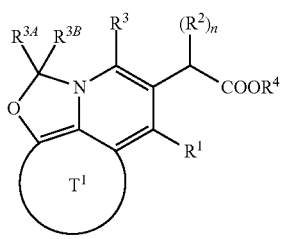

(I-B-9)

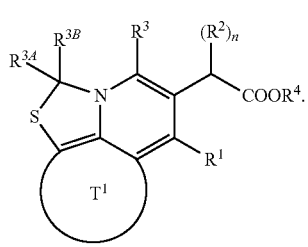

(I-C-3)

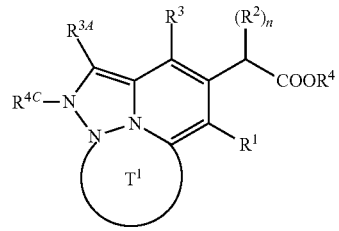

(I-C-4)

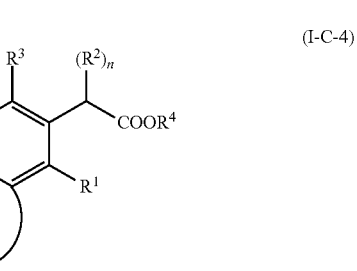

13. The compound or pharmaceutically acceptable salt thereof according to claim 1, wherein the formula (I) is formula (I-C):

(I-C)

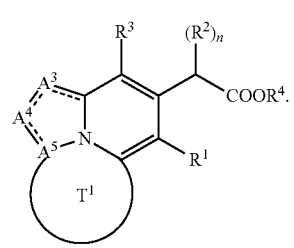

(I-C-5)

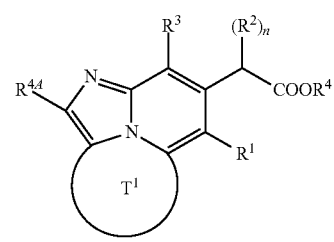

(I-C-6)

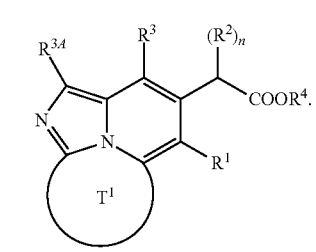

14. The compound or pharmaceutically acceptable salt thereof according to claim 13, wherein the formula (I) is one of formulas (I-C-1), (I-C-2), (I-C-3), (I-C-4), (I-C-5), and (I-C-6):

(I-C-1)

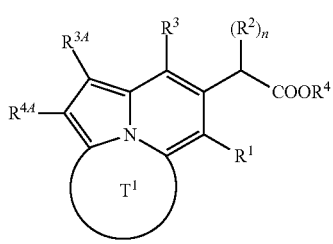

15. The compound or pharmaceutically acceptable salt thereof according to claim 1, wherein $T^1$ ring is one of structures ($T^1$-1) and ($T^1$-2):

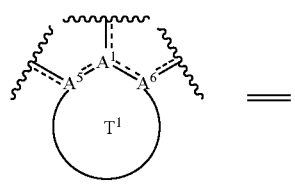

(I-C-2)

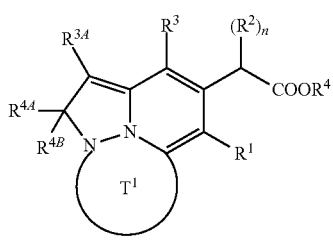

($T^1$-1)

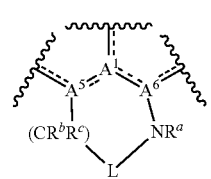

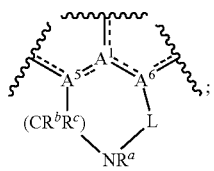

(T¹-2)

where $R^a$ is hydrogen, substituted or unsubstituted alkyl, substituted or unsubstituted alkenyl, substituted or unsubstituted carbocyclyl, substituted or unsubstituted heterocyclyl, —$COR^{a1}$, —$SOR^{a2}$, or —$SO_2R^{a3}$ ($R^{a1}$, $R^{a2}$, and $R^{a3}$ are each independently hydrogen, substituted or unsubstituted alkyl, substituted or unsubstituted alkenyl, substituted or unsubstituted carbocyclyl, or substituted or unsubstituted heterocyclyl;

m is an integer of 0 to 5;

L is —$SO_2$—, —SO—, —CO—, or —$CR^bR^c$—; and $R^b$ and $R^c$ are each independently hydrogen, substituted or unsubstituted alkyl, substituted or unsubstituted alkenyl, substituted or unsubstituted carbocyclyl, substituted or unsubstituted heterocyclyl, or $R^b$ and $R^c$ may be taken together to form oxo.

16. The compound or pharmaceutically acceptable salt thereof according to claim 15, wherein $R^1$ is alkyl; n is 1, $R^2$ is alkyloxy; $R^4$ is hydrogen; $R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl; m is an integer of 1 to 3; and $R^b$ and $R^c$ are each independently hydrogen or alkyl.

17. The compound or pharmaceutically acceptable salt thereof according to claim 1, wherein $T^1$ ring is one of structures (T¹-1-1), (T¹-1-2), (T¹-1-3), (T¹-1-4), (T¹-1-5), (T¹-2-1), (T¹-2-2) and (T¹-2-3):

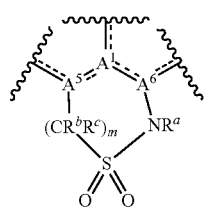

(T¹-1-1)

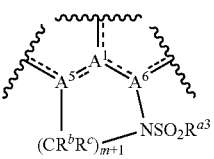

(T¹-1-2)

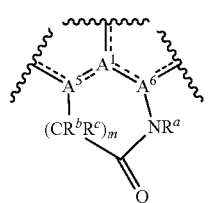

(T¹-1-3)

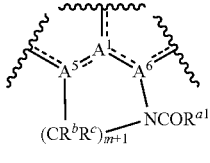

(T¹-1-4)

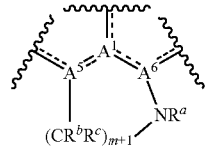

(T¹-1-5)

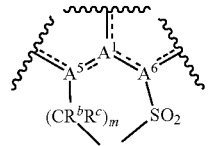

(T¹-2-1)

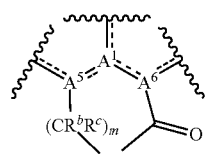

(T¹-2-2)

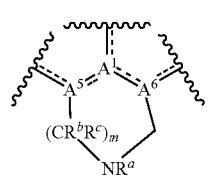

(T¹-2-3)

where $R^a$ is hydrogen, substituted or unsubstituted alkyl, substituted or unsubstituted alkenyl, substituted or unsubstituted carbocyclyl, substituted or unsubstituted heterocyclyl, —$COR^{a1}$, —$SOR^{a2}$, or —$SO_2R^{a3}$ ($R^{a1}$, $R^{a2}$, and $R^{a3}$ are each independently hydrogen, substituted or unsubstituted alkyl, substituted or unsubstituted alkenyl, substituted or unsubstituted carbocyclyl, or substituted or unsubstituted heterocyclyl);

m is an integer of 0 to 5;

L is —$SO_2$—, —SO—, —CO—, or —$CR^bR^c$—; and $R^b$ and $R^c$ are each independently hydrogen, substituted or unsubstituted alkyl, substituted or unsubstituted alkenyl, substituted or unsubstituted carbocyclyl, substituted or unsubstituted heterocyclyl, or $R^b$ and $R^c$ may be taken together to form oxo.

18. The compound or pharmaceutically acceptable salt thereof according to claim 1, wherein the formula (I) is one of formulas (I-A-1-1), (I-A-1-2), (I-A-1-3), (I-A-1-4), (I-A-1-5), (I-A-2-1), (I-A-2-2), (I-A-2-3), (I-A-2-4), (I-A-3-1), (I-A-3-2), (I-A-3-3), (I-A-3-4), (I-A-4-1), (I-A-4-2), (I-A-4-3), (I-A-4-4), (I-A-5-1), (I-A-5-2), (I-A-5-3), (I-A-5-4), (I-A-5'-1), (I-A-5'-2), (I-A-5'-3), (I-A-5'-4), (I-A-6-1), (I-A-6-2), (I-A-6-3), (I-A-6-4), (I-A-6'-1), (I-A-6'-2), (I-A-6'-3), (I-A-6'-4), (I-A-7-1), (I-A-7-2), (I-A-7-3), (I-A-7-4), (I-A-8-1), (I-A-8-2), (I-A-8-3), (I-A-8-4), (I-A-9-1), (I-A-9-2), (I-A-9-3), (I-A-9-4), (I-A-10-1), (I-A-10-2), (I-A-10-3), and (I-A-10-4):

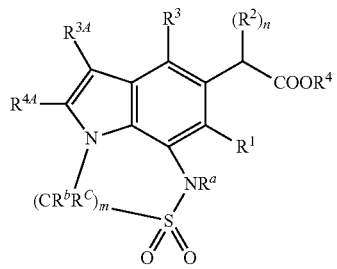
(I-A-1-1)
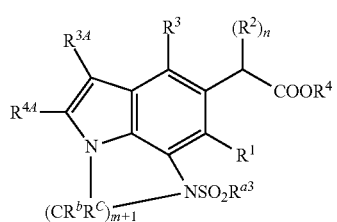
(I-A-1-2)
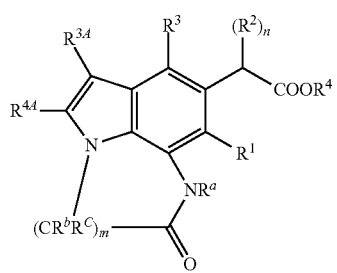
(I-A-1-3)
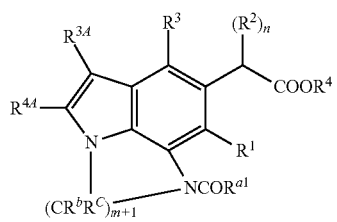
(I-A-1-4)
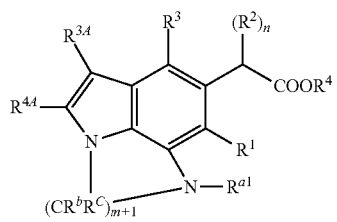
(I-A-1-5)
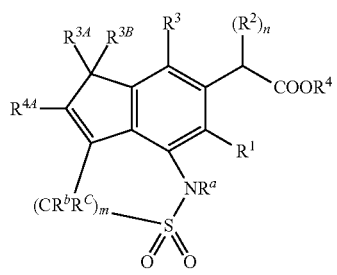
(I-A-2-1)
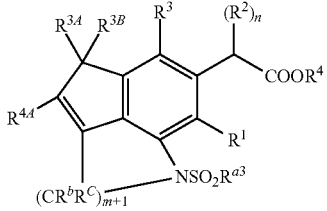
(I-A-2-2)
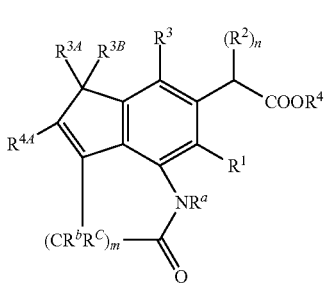
(I-A-2-3)
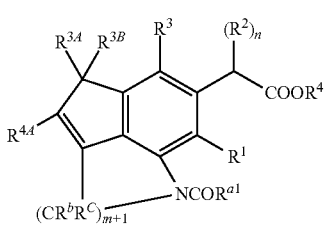
(I-A-2-4)
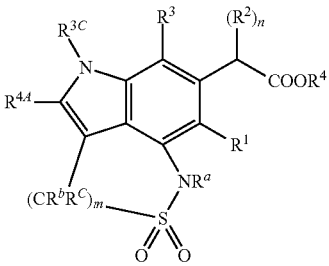
(I-A-3-1)
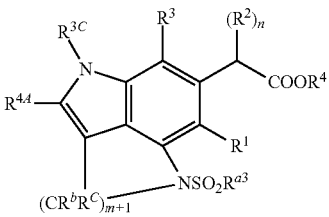
(I-A-3-2)
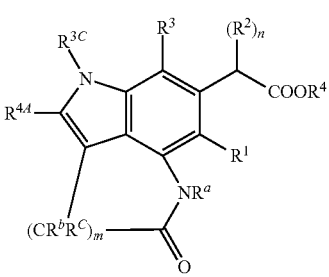
(I-A-3-3)

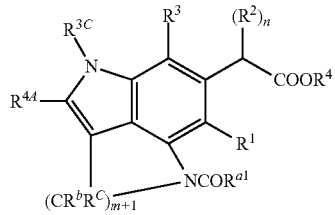 (I-A-3-4)
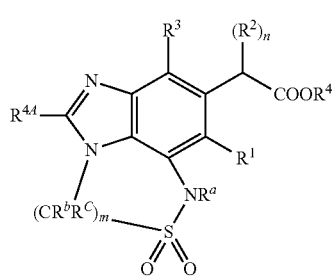 (I-A-4-1)
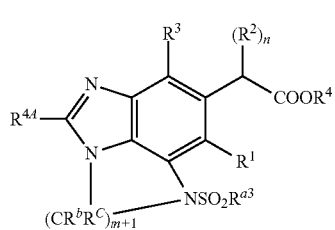 (I-A-4-2)
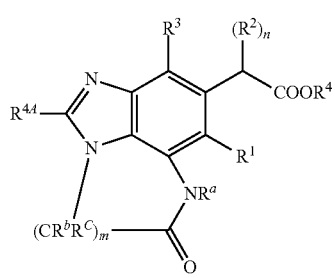 (I-A-4-3)
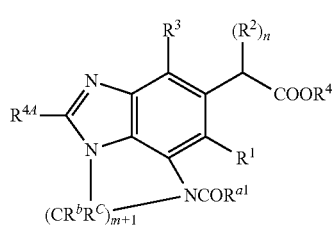 (I-A-4-4)
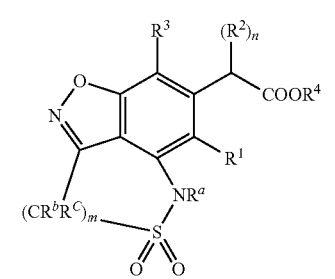 (I-A-5-1)
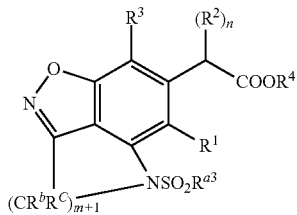 (I-A-5-2)
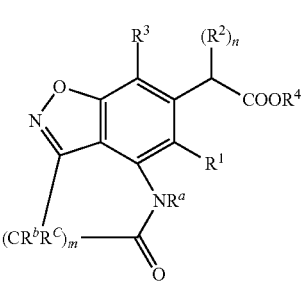 (I-A-5-3)
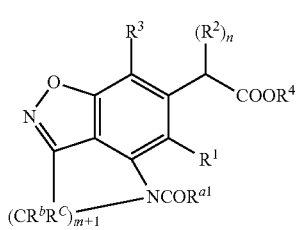 (I-A-5-4)
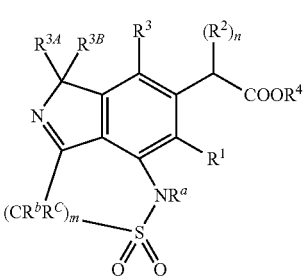 (I-A-5′-1)
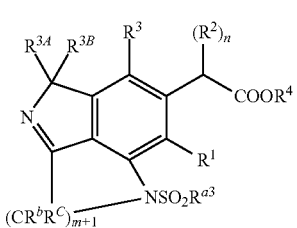 (I-A-5′-2)
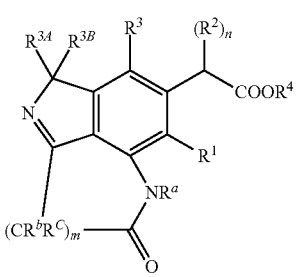 (I-A-5′-3)

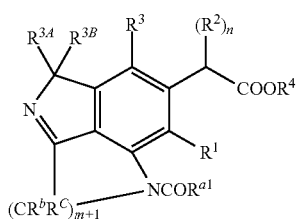 (I-A-5'-4)
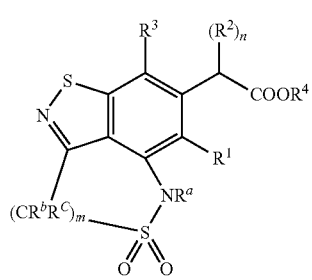 (I-A-6-1)
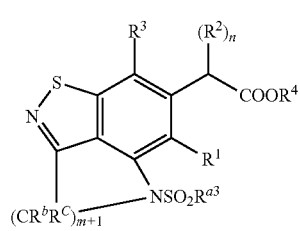 (I-A-6-2)
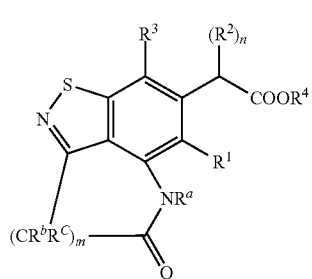 (I-A-6-3)
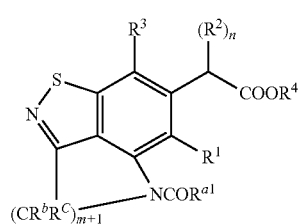 (I-A-6-4)
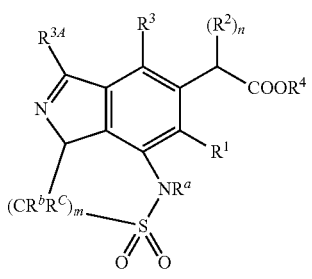 (I-A-6'-1)
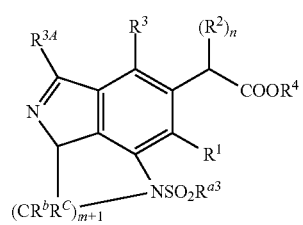 (I-A-6'-2)
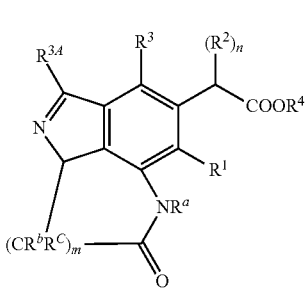 (I-A-6'-3)
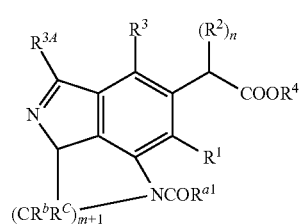 (I-A-6'-4)
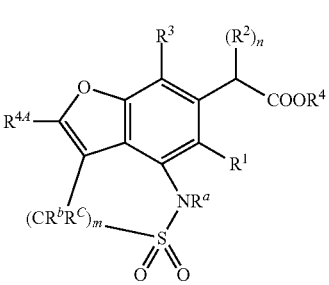 (I-A-7-1)
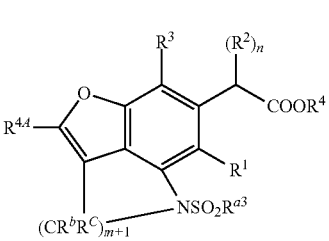 (I-A-7-2)
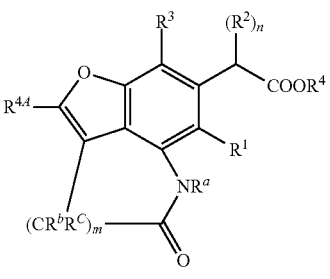 (I-A-7-3)

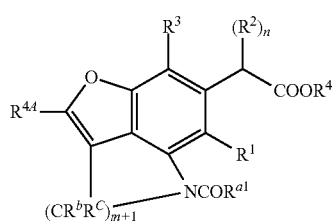 (I-A-7-4)
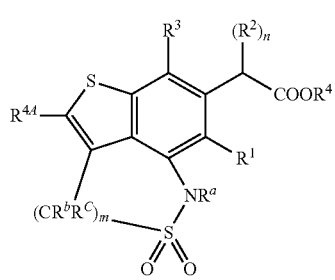 (I-A-8-1)
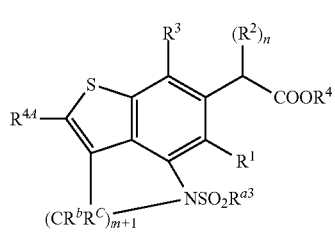 (I-A-8-2)
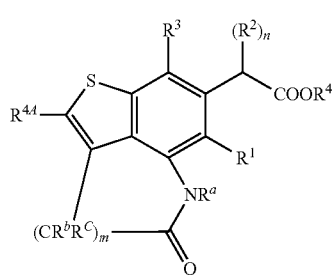 (I-A-8-3)
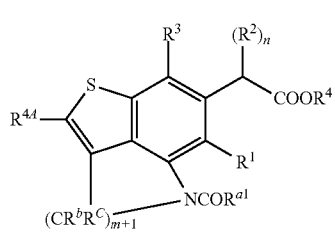 (I-A-8-4)
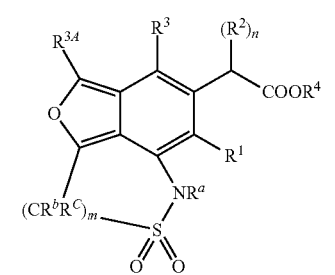 (I-A-9-1)
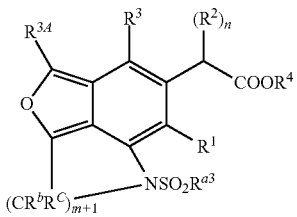 (I-A-9-2)
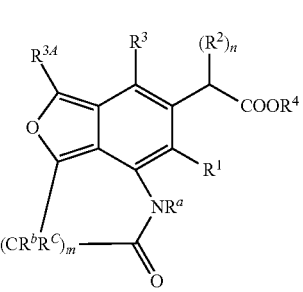 (I-A-9-3)
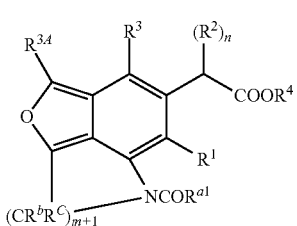 (I-A-9-4)
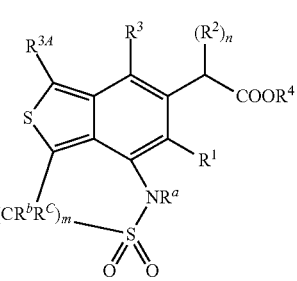 (I-A-10-1)
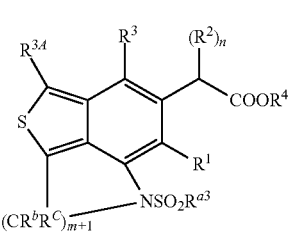 (I-A-10-2)
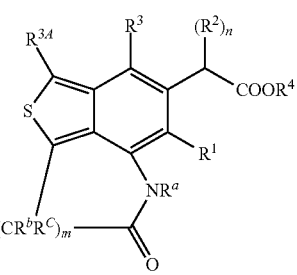 (I-A-10-3)

-continued (I-A-10-4)

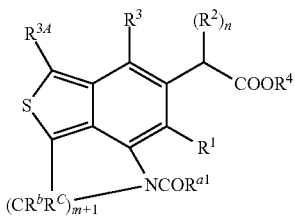

where R$^a$ is hydrogen, substituted or unsubstituted alkyl, substituted or unsubstituted alkenyl, substituted or unsubstituted carbocyclyl, substituted or unsubstituted heterocyclyl, —COR$^{a1}$, —SOR$^{a2}$, or —SO$_2$R$^{a3}$ (R$^{a1}$, R$^{a2}$, and R$^{a3}$ are each independently hydrogen, substituted or unsubstituted alkyl, substituted or unsubstituted alkenyl, substituted or unsubstituted carbocyclyl, or substituted or unsubstituted heterocyclyl);

m is an integer of 0 to 5;

L is —SO$_2$—, —SO—, —CO—, or —CR$^b$R$^c$—; and

R$^b$ and R$^c$ are each independently hydrogen, substituted or unsubstituted alkyl, substituted or unsubstituted alkenyl, substituted or unsubstituted carbocyclyl, substituted or unsubstituted heterocyclyl, or R$^b$ and R$^c$ may be taken together to form oxo.

19. The compound or pharmaceutically acceptable salt thereof according to claim 1, wherein the formula (I) is one of formulas (I-B-1-1), (I-B-1-2), (I-B-1-3), (I-B-1-4), (I-B-2-1), (I-B-2-2), (I-B-2-3), (I-B-2-4), (I-B-3-1), (I-B-3-2), (I-B-3-3), (I-B-3-4), (I-B-4-1), (I-B-4-2), (I-B-4-3), (I-B-4-4), (I-B-5-1), (I-B-5-2), (I-B-5-3), (I-B-5-4), (I-B-6-1), (I-B-6-2), (I-B-6-3), (I-B-6-4), (I-B-7-1), (I-B-7-2), (I-B-7-3), (I-B-7-4), (I-B-8-1), (I-B-8-2), (I-B-8-3), (I-B-8-4), (I-B-9-1), (I-B-9-2), (I-B-9-3), and (I-B-9-4):

(I-B-1-1)

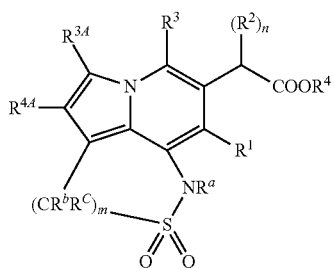

(I-B-1-2)

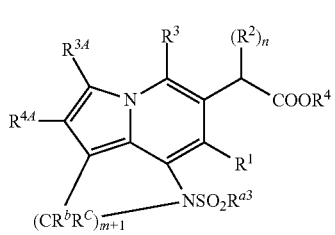

(I-B-1-3)

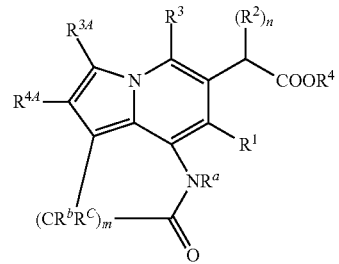

(I-B-1-4)

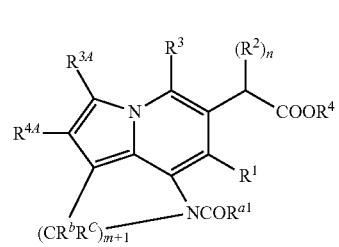

(I-B-2-1)

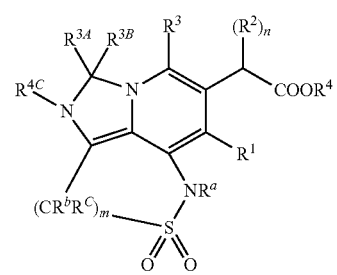

(I-B-2-2)

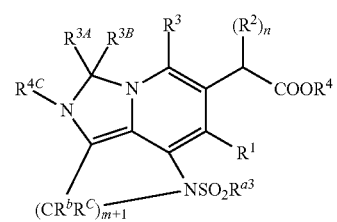

(I-B-2-3)

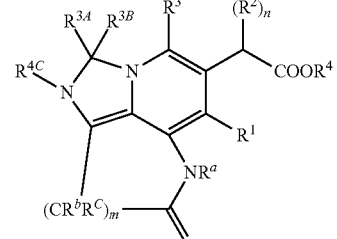

(I-B-2-4)

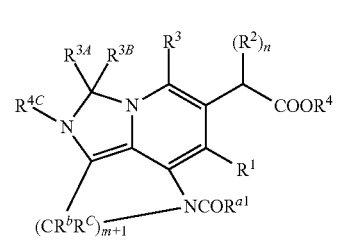

(I-B-3-1)
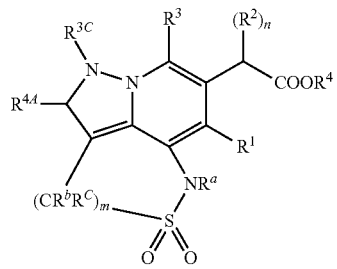
(I-B-3-2)
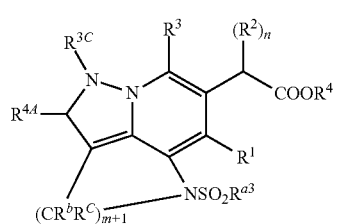
(I-B-3-3)
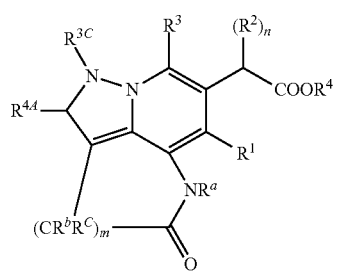
(I-B-3-4)
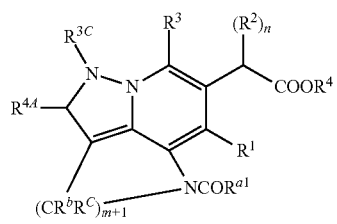
(I-B-4-1)
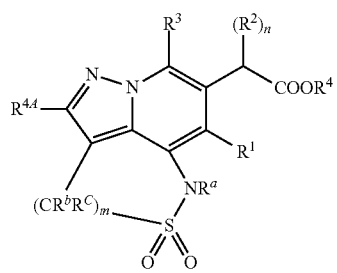
(I-B-4-2)
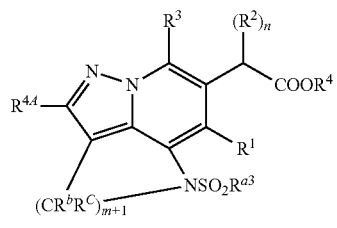
(I-B-4-3)
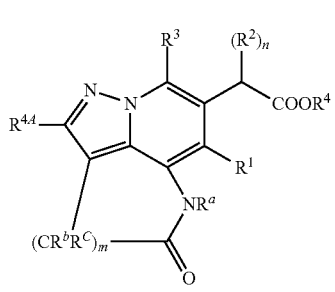
(I-B-4-4)
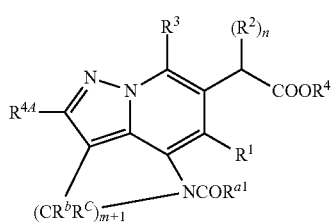
(I-B-5-1)
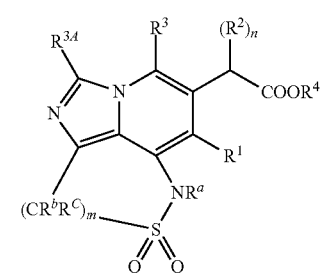
(I-B-5-2)
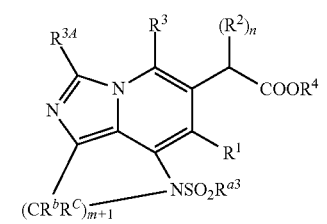
(I-B-5-3)
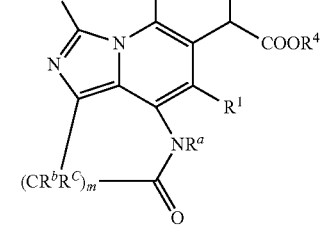
(I-B-5-4)
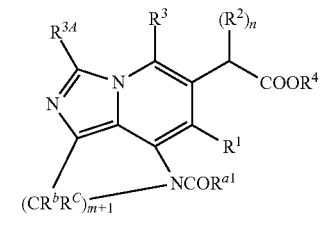

(I-B-6-1)
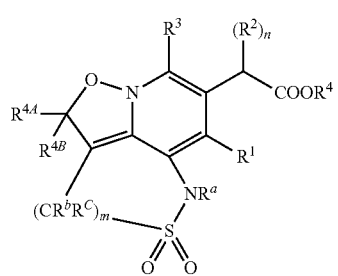
(I-B-6-2)
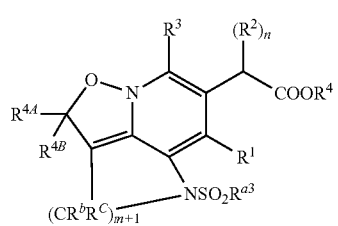
(I-B-6-3)
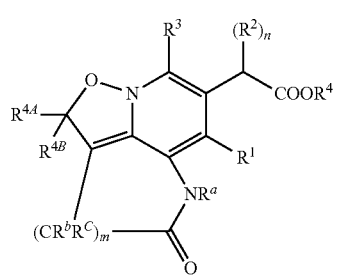
(I-B-6-4)
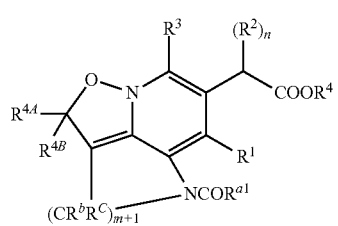
(I-B-7-1)
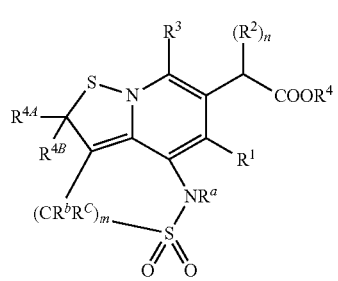
(I-B-7-2)
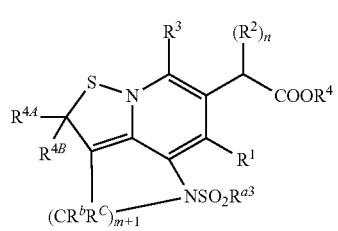
(I-B-7-3)
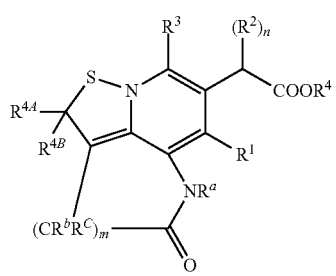
(I-B-7-4)
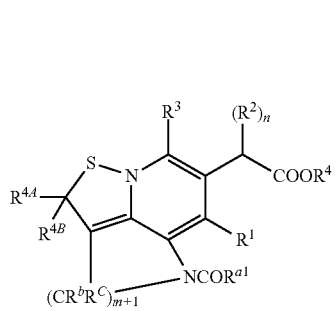
(I-B-8-1)
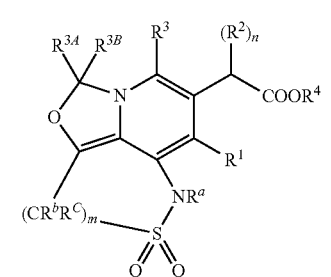
(I-B-8-2)
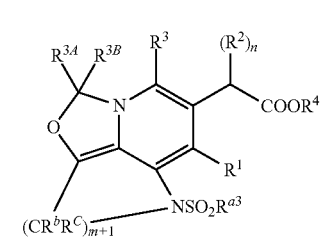
(I-B-8-3)
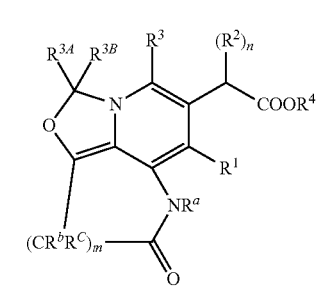
(I-B-8-4)
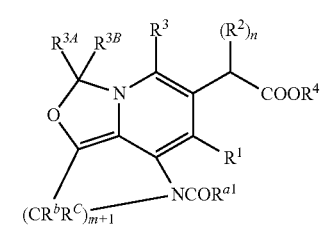

-continued

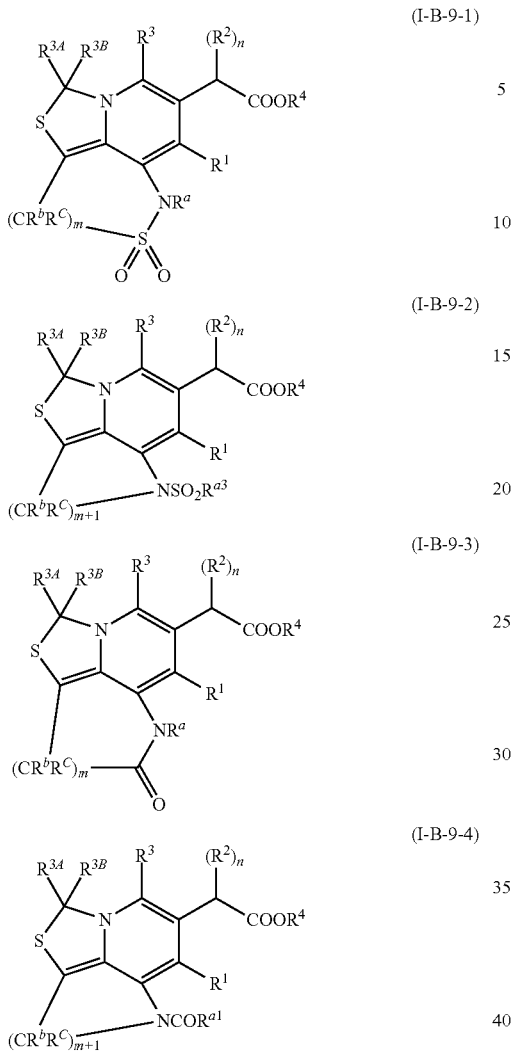

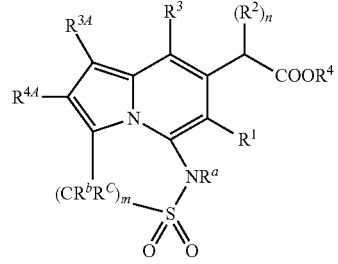

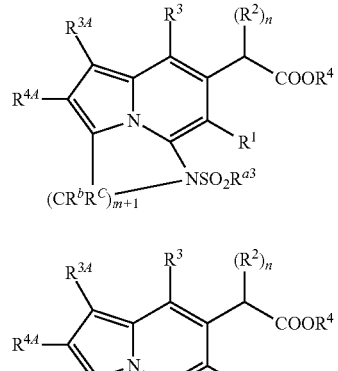

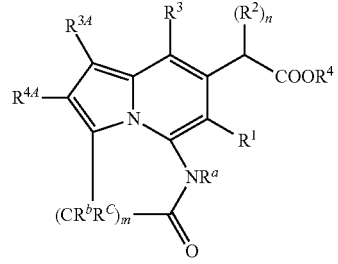

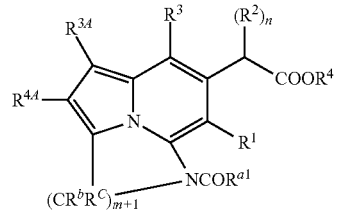

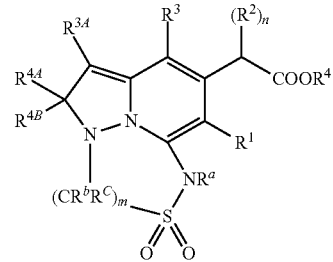

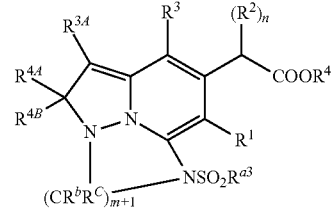

where $R^a$ is hydrogen, substituted or unsubstituted alkyl, substituted or unsubstituted alkenyl, substituted or unsubstituted carbocyclyl, substituted or unsubstituted heterocyclyl, —COR$^{a1}$, —SOR$^{a2}$, or —SO$_2$R$^{a3}$ (R$^{a1}$, R$^{a2}$, and R$^{a3}$ are each independently hydrogen, substituted or unsubstituted alkyl, substituted or unsubstituted alkenyl, substituted or unsubstituted carbocyclyl, or substituted or unsubstituted heterocyclyl);

m is an integer of 0 to 5;

L is —SO$_2$—, —SO—, —CO—, or —CR$^b$R$^c$—; and

R$^b$ and R$^c$ are each independently hydrogen, substituted or unsubstituted alkyl, substituted or unsubstituted alkenyl, substituted or unsubstituted carbocyclyl, substituted or unsubstituted heterocyclyl, or R$^b$ and R$^c$ may be taken together to form oxo.

20. The compound or pharmaceutically acceptable salt thereof according to claim 1, wherein the formula (I) is one of formulas (I-C-1-1), (I-C-1-2), (I-C-1-3), (I-C-1-4), (I-C-2-1), (I-C-2-2), (I-C-2-3), (I-C-2-4), (I-C-3-1), (I-C-3-2), (I-C-3-3), (I-C-3-4), (I-C-4-1), (I-C-4-2), (I-C-4-3), (I-C-4-4), (I-C-5-1), (I-C-5-2), (I-C-5-3), (I-C-5-4), (I-C-6-1), (I-C-6-2), (I-C-6-3), and (I-C-6-4):

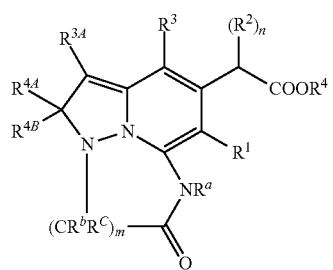
(I-C-2-3)
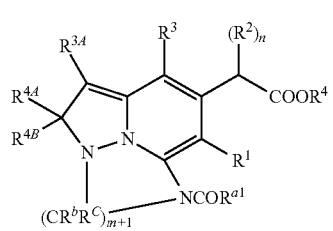
(I-C-2-4)
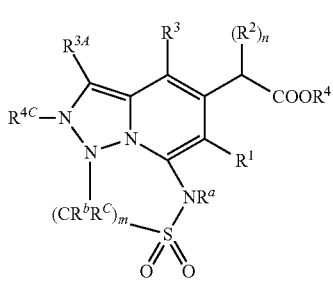
(I-C-3-1)
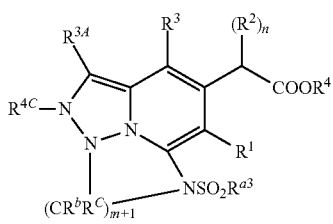
(I-C-3-2)
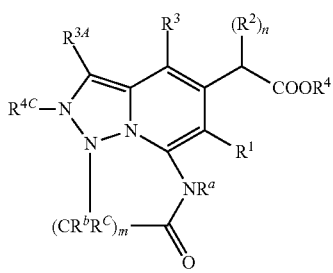
(I-C-3-3)
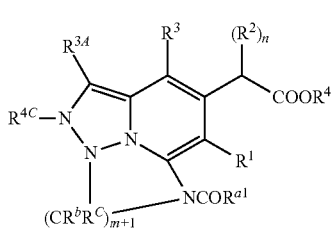
(I-C-3-4)
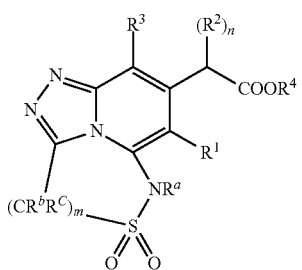
(I-C-4-1)
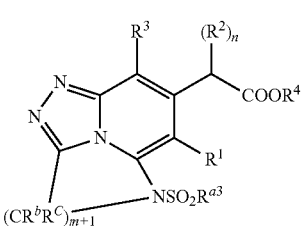
(I-C-4-2)
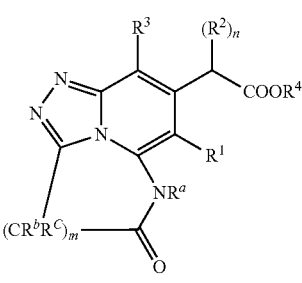
(I-C-4-3)
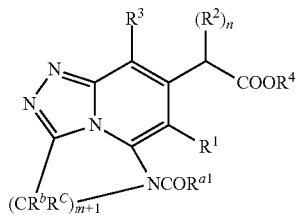
(I-C-4-4)
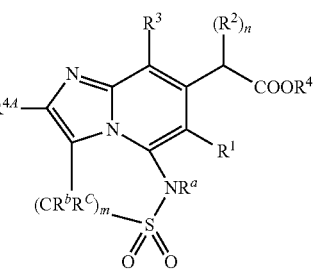
(I-C-5-1)
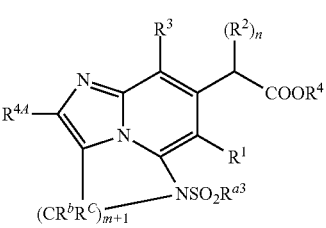
(I-C-5-2)

-continued (I-C-5-3)
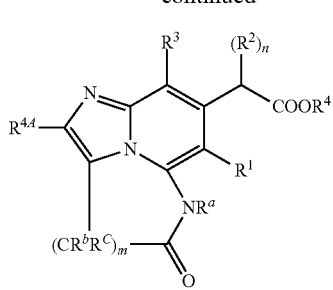

(I-C-5-4)
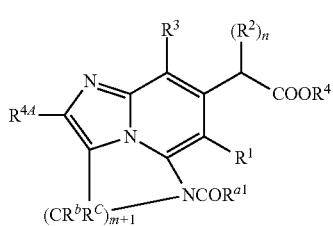

(I-C-6-1)
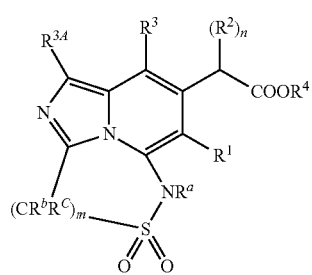

(I-C-6-2)
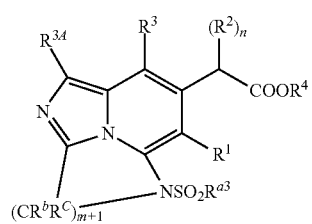

(I-C-6-3)
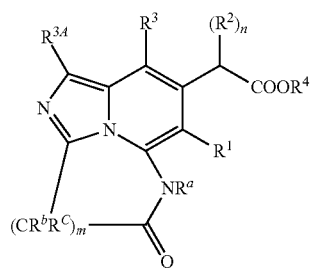

(I-C-6-4)
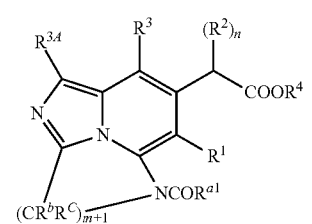

where $R^a$ is hydrogen, substituted or unsubstituted alkyl, substituted or unsubstituted alkenyl, substituted or unsubstituted carbocyclyl, substituted or unsubstituted heterocyclyl, —COR$^{a1}$, —SOR$^{a2}$, or —SO$_2$R$^{a3}$ (R$^{a1}$, R$^{a2}$, and R$^{a3}$ are each independently hydrogen, substituted or unsubstituted alkyl, substituted or unsubstituted alkenyl, substituted or unsubstituted carbocyclyl, or substituted or unsubstituted heterocyclyl);

m is an integer of 0 to 5;

L is —SO$_2$—, —SO—, —CO—, or —CR$^b$R$^c$—; and $R^b$ and $R^c$ are each independently hydrogen, substituted or unsubstituted alkyl, substituted or unsubstituted alkenyl, substituted or unsubstituted carbocyclyl, substituted or unsubstituted heterocyclyl, or $R^b$ and $R^c$ may be taken together to form oxo.

21. The compound or pharmaceutically acceptable salt thereof according to claim 1, wherein $R^1$ is alkyl.

22. The compound or pharmaceutically acceptable salt thereof according to claim 1, wherein n is 1, and $R^2$ is alkyloxy.

23. The compound or pharmaceutically acceptable salt thereof according to claim 1, wherein $R^4$ is hydrogen.

24. The compound or pharmaceutically acceptable salt thereof according to claim 1, wherein $R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

25. The compound or pharmaceutically acceptable salt thereof according to claim 1, wherein $R^1$ is alkyl; n is 1, $R^2$ is alkyloxy; $R^4$ is hydrogen; and $R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

26. The compound or pharmaceutically acceptable salt thereof according to claim 1, wherein the formula (I) is formula (I-A-1-1):

(I-A-1)
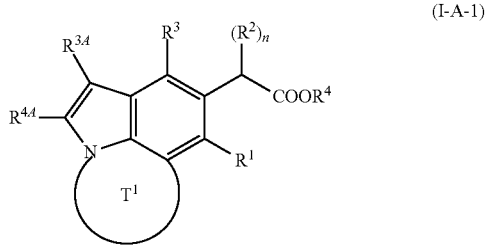

where $R^1$ is alkyl; n is 1, $R^2$ is alkyloxy; $R^4$ is hydrogen; $R^3$ is substituted or unsubstituted aromatic carbocyclyl or substituted or unsubstituted non-aromatic carbocyclyl, $R^{3A}$ is hydrogen, $R^{4A}$ is substituted or unsubstituted aromatic heterocyclyl, and $T^1$ ring is substituted or unsubstituted monocyclic heterocycle.

27. The compound or pharmaceutically acceptable salt thereof according to claim 26, wherein the formula (I) is formula (I-A-1-1):

(I-A-1-1)

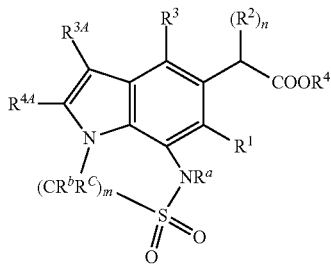

where $R^1$ is alkyl; n is 1, $R^2$ is alkyloxy; $R^4$ is hydrogen; $R^3$ is substituted or unsubstituted aromatic carbocyclyl or substituted or unsubstituted non-aromatic carbocyclyl, $R^{3A}$ is hydrogen, $R^{4A}$ is substituted or unsubstituted aromatic heterocyclyl, m is 1, $R^b$ and $R^c$ are hydrogen, and $R^a$ is hydrogen or alkyl.

28. The compound or pharmaceutically acceptable salt thereof according to claim 26, wherein the formula (I) is formula (I-A-1-2):

(I-A-1-2)

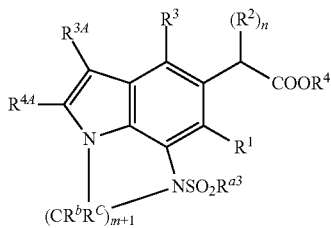

where $R^1$ is alkyl; n is 1, $R^2$ is alkyloxy; $R^4$ is hydrogen; $R^3$ is substituted or unsubstituted aromatic carbocyclyl or substituted or unsubstituted non-aromatic carbocyclyl, $R^{3A}$ is hydrogen, $R^{4A}$ is substituted or unsubstituted aromatic heterocyclyl, m is 1, $R^b$ is each independently hydrogen or alkyl, $R^C$ is hydrogen, and $R^{a3}$ is alkyl.

29. The compound or pharmaceutically acceptable salt thereof according to claim 26, wherein the formula (I) is formula (I-A-1-3):

(I-A-1-3)

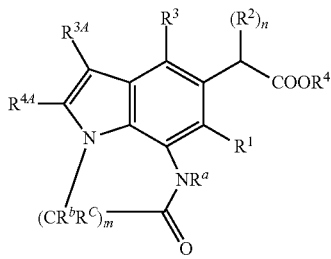

where $R^1$ is alkyl; n is 1, $R^2$ is alkyloxy; $R^4$ is hydrogen; $R^3$ is substituted or unsubstituted aromatic carbocyclyl or substituted or unsubstituted non-aromatic carbocyclyl, $R^{3A}$ is hydrogen, $R^{4A}$ is substituted or unsubstituted aromatic heterocyclyl, m is 1, and $R^a$ is hydrogen or alkyl.

30. The compound or pharmaceutically acceptable salt thereof according to claim 26, wherein the formula (I) is formula (I-A-1-4):

(I-A-1-4)

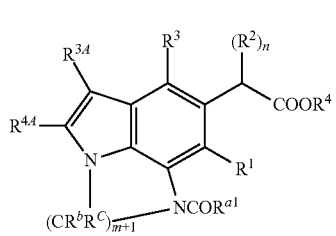

where $R^1$ is alkyl; n is 1, $R^2$ is alkyloxy; $R^4$ is hydrogen; $R^3$ is substituted or unsubstituted aromatic carbocyclyl or substituted or unsubstituted non-aromatic carbocyclyl, $R^{3A}$ is hydrogen, $R^{4A}$ is substituted or unsubstituted aromatic heterocyclyl, m is 1, and $R^a$ is hydrogen or alkyl.

31. The compound or pharmaceutically acceptable salt thereof according to claim 26, wherein the formula (I) is formula (I-A-1-5):

(I-A-1-5)

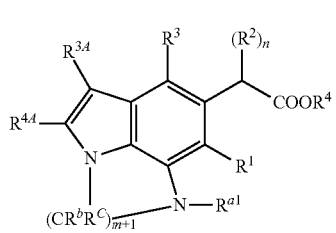

where $R^1$ is alkyl; n is 1, $R^2$ is alkyloxy; $R^4$ is hydrogen; $R^3$ is substituted or unsubstituted aromatic carbocyclyl or substituted or unsubstituted non-aromatic carbocyclyl, $R^{3A}$ is hydrogen, $R^{4A}$ is substituted or unsubstituted aromatic heterocyclyl, m is 1, and $R^{a1}$ is hydrogen or alkyl.

32. A pharmaceutical composition, comprising:
the compound or pharmaceutically acceptable salt thereof according to claim 1.

33. A method of treating a HIV infectious disease, comprising:
administering the compound or pharmaceutically acceptable salt thereof according to claim 1.

* * * * *